US008877210B2

(12) United States Patent
Yang et al.

(10) Patent No.: US 8,877,210 B2
(45) Date of Patent: Nov. 4, 2014

(54) INFLUENZA HEMAGGLUTININ AND NEURAMINIDASE VARIANTS

(71) Applicant: Medimmune, LLC, Gaithersburg, MD (US)

(72) Inventors: Chin-Fen Yang, Zhubei (TW); George Kemble, Saratoga, CA (US); Chongguang Liu, Fremont, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/156,284

(22) Filed: Jan. 15, 2014

(65) Prior Publication Data

US 2014/0242102 A1    Aug. 28, 2014

Related U.S. Application Data

(60) Division of application No. 13/767,749, filed on Feb. 14, 2013, now Pat. No. 8,685,410, which is a continuation of application No. 13/538,972, filed on Jun. 29, 2012, now Pat. No. 8,404,248, which is a continuation of application No. 13/247,903, filed on Sep. 28, 2011, now abandoned, which is a division of application No. 12/877,000, filed on Sep. 7, 2010, now Pat. No. 8,048,430, which is a continuation of application No. 12/399,077, filed on Mar. 6, 2009, now abandoned, which is a division of application No. 10/870,690, filed on Jun. 16, 2004, now Pat. No. 7,566,458.

(60) Provisional application No. 60/479,078, filed on Jun. 16, 2003.

(51) Int. Cl.
A61K 39/145    (2006.01)
C12N 7/02    (2006.01)
C12Q 1/70    (2006.01)
C07K 14/005    (2006.01)
C12N 9/24    (2006.01)

(52) U.S. Cl.
CPC ............ C07K 14/005 (2013.01); C12N 9/2402 (2013.01)
USPC ............. 424/206.1; 424/209.1; 435/239; 435/235.1; 435/5

(58) Field of Classification Search
None
See application file for complete search history.

(56) References Cited

U.S. PATENT DOCUMENTS

| 3,992,522 A | 11/1976 | Chanock et al. |
| 4,071,618 A | 1/1978 | Konobe et al. |
| 4,634,666 A | 1/1987 | Engelmann et al. |
| 4,659,569 A | 4/1987 | Mitsuhashi et al. |
| 5,166,057 A | 11/1992 | Palese et al. |
| 5,690,937 A | 11/1997 | Parkin |
| 5,716,821 A | 2/1998 | Wertz et al. |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,922,326 A | 7/1999 | Murphy |
| 6,001,634 A | 12/1999 | Palese et al. |
| 6,033,886 A | 3/2000 | Conzelmann |
| 6,090,391 A | 7/2000 | Parkin |
| 6,146,642 A | 11/2000 | Garcia-Sastre et al. |
| 6,146,873 A | 11/2000 | Kistner et al. |
| 6,168,943 B1 | 1/2001 | Rose |
| 6,951,754 B2 | 10/2005 | Hoffmann |
| 7,037,707 B2 | 5/2006 | Webster et al. |
| 7,459,162 B2 | 12/2008 | Yang |
| 7,566,458 B2 | 7/2009 | Yang |
| 8,048,430 B2 | 11/2011 | Yang |
| 8,333,975 B2 | 12/2012 | Yang |
| 8,404,248 B2 | 3/2013 | Yang |
| 2002/0119445 A1 | 8/2002 | Parkin et al. |
| 2002/0164770 A1 | 11/2002 | Hoffmann |
| 2003/0035814 A1 | 2/2003 | Kawaoka et al. |
| 2003/0147916 A1 | 8/2003 | Ferko |
| 2004/0029251 A1 | 2/2004 | Hoffman et al. |
| 2004/0071734 A1 | 4/2004 | Garcon et al. |
| 2004/0137013 A1 | 7/2004 | Katinger |
| 2004/0265987 A1 | 12/2004 | Trager et al. |
| 2005/0042229 A1 | 2/2005 | Yang |
| 2005/0266026 A1 | 12/2005 | Hoffmann |
| 2006/0188977 A1 | 8/2006 | Schwartz et al. |
| 2006/0252132 A1 | 11/2006 | Yang et al. |
| 2007/0253982 A1 | 11/2007 | Song et al. |
| 2009/0004222 A1 | 1/2009 | O'Hagan |
| 2009/0017052 A1 | 1/2009 | Bogoch et al. |
| 2009/0175898 A1 | 7/2009 | Yang |
| 2009/0175908 A1 | 7/2009 | Yang |

(Continued)

FOREIGN PATENT DOCUMENTS

| CN | 1536077 | 10/2004 |
| EP | 0702085 | 3/1996 |

(Continued)

OTHER PUBLICATIONS

Bragstad et al., New avian influenza A virus subtype combination H5N7 identified in Danish mallard ducks, 2005, Virus Research, vol. 109, pp. 181-190.*

(Continued)

*Primary Examiner* — Benjamin P Blumel
(74) *Attorney, Agent, or Firm* — Grant IP, Inc.

(57) ABSTRACT

Polypeptides, polynucleotides, methods, compositions, and vaccines comprising influenza hemagglutinin and neuraminidase variants are provided.

19 Claims, 35 Drawing Sheets

(56) References Cited

U.S. PATENT DOCUMENTS

| | | |
|---|---|---|
| 2010/0239610 A1 | 9/2010 | D'Aoust et al. |
| 2011/0002960 A1 | 1/2011 | Yang |
| 2011/0070263 A1 | 3/2011 | Yang |
| 2011/0212117 A1 | 9/2011 | Yang |
| 2012/0135023 A1 | 5/2012 | Yang |
| 2013/0156810 A1 | 6/2013 | Yang et al. |
| 2013/0243816 A1 | 9/2013 | Yang et al. |

FOREIGN PATENT DOCUMENTS

| | | |
|---|---|---|
| EP | 0863202 | 9/1998 |
| EP | 0864645 | 9/1998 |
| EP | 0780475 | 6/1999 |
| EP | 1826269 | 8/2007 |
| JP | 2008-500042 | 10/2008 |
| WO | WO 91/03552 | 3/1991 |
| WO | WO 93/21306 | 10/1993 |
| WO | WO 96/10632 | 4/1996 |
| WO | WO 96/34625 | 11/1996 |
| WO | WO 96/37624 | 11/1996 |
| WO | WO 97/06270 | 2/1997 |
| WO | WO 97/12032 | 4/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/53786 | 9/2000 |
| WO | WO 00/60050 | 10/2000 |
| WO | WO 2005/018539 | 3/2005 |
| WO | WO 2005/116260 | 12/2005 |
| WO | WO 2006/098901 | 9/2006 |
| WO | WO 2010/006144 | 1/2010 |

OTHER PUBLICATIONS

GenBank Accession # AAT08000, hemagglutinin [Influenza A virus (A/Wyoming/03/2003(H3N2))], 2005.*
GenBank Accession # ABX10525, hemagglutinin [Influenza A virus (A/Wyoming/03/2003(H3N2))], 2008.*
GenBank Accession # AFN11856, hemagglutinin, partial [Influenza A virus (A/Wyoming/03/2003(H3N2))], 2012.*
Alignment sequence between SEQ 10 No. 53 and 8 of U.S. Appl. No. 10/870,690 and U.S. Appl. No. 60/479,078, respectively-Appendix A.
Andreas et al., "A host restriction-based selection system for influenza haemagglutinin transfectant viruses," Journal of General Virology, vol. 79, No. 6, Jun. 1998, pp. 1405-1409.
Anwar et al., "In silico analysis of genes nucleoprotein, neuraminidase and hemagglutinin: A comparative study on different strains of influenza A (Bird Flu) virus sub-type H5N1," In Silico Biology 6, 0015 (2006) 161-168.
Banerjee and Bark, 1992, "Gene expression of vesicular stomatitis virus genome RNA", Virology. 188(2):417-28.
Baron and Barrett, 1997, "Rescue of Rinderpest Virus from Cloned cDNA", J. Virol. 71:1265-1271.
Basler et al., Mutation of Neuraminidase Cysteine Residues Yields Temperature-Sensitive Influenza Viruses, Journal of Virology, Oct. 1999, vol. 73, No. 10, p. 8095-8103.
Beare et al., 1975, "Trials in Man with Live Recombinants Made from A/NPR/8/34 (HO N1) and Wild H3 N2 Influenza Viruses", Lancet 2(7938):729-732.
Belshe, 1995 "A Review of Attenuation of Influenza Viruses by Genetic manipulation," American Journal of Respiratory and Critical Care Medicine 152[4 Pt 2], 572-575. 1995.
Belshe, et al., "The Efficacy of live attenuated, cold-adapted, trivalent intranasal influenza virus vaccine in children," (1998) A128N Eng J Med 338:1405-1412.
Bender et al., 1999, "Characterization of the surface proteins of influenza A (H5NI) viruses . . . ", Virology 254(1):115-23.
Bergmann, el al., "The relative amount of an influenza A virus segment present in the viral particle is not affected by a reduction in replication of that segment,". Journal of General Virology, 1995,76:3211-3215.
Boyce et al., 2001, "Safety and immunogonicity of adjuvanted and unadjuvanted subunit influenza vaccines administered intranasally to healthy adults", Vaccine 19:217-226.
Boyer et al., 1994, "Infectious transcripts and cDNA clones of RNA viruses", Virology. 198(2):415-26.
Brandt et al., 2001, "Molecular Determinants of Virulence, Cell Tropism. and Pathogenic Phenotype of Infectious Bursal Disease Virus". Journal of Virology 75(24):11974-11982.
Brigden and Elliott. 1996, "Rescue of a Segmented Negative-Strand RNA Virus Entirely from Cloned Complementary DNAS", Proc. Natl. Acad. Sci. USA 93:15400-15404.
Buchholz et al., 1999 "Generation of Bovine Respiratory Syncytial Virus (BRSV) from cDNA: BRSV NS2 is Not Essential for Virus Replication in Tissue Culture. and the Human RSV Leader Region Acts as a Functional BRSV Genome Promoter". J. Virol. 73:251-259.
Bukreyev et al., 1996, "Recovery of infectious respiratory syncytial virus expressing an additional, foreign gene", J Virol. 70(10):6634-6641.
Castrucci et al., 1995, "Reverse genetics system for generation of an influenza A virus mutant containing a deletion of the carboxyl-terminal residue of M2 protein", J Virol. 69(5):2725-2728.
Caton et al., Dec. 1982, "The antigenic structure of the influenza virus AIPR/8/34 hemagglutinin (H1 subtype)", Cell, 31(2 Pt 1):417-27.
Chen et al., 1999, "Influenza A virus NS1 protein targets poly (A)-binding protein II of the cellular 3'-end processing machinery", EMBO 18: 2273-2283.
Chen et al., Generation and Evaluation of a high-growth reassortant H9N2 influenza A Virus as a pandemic vaccine candidate, (2003) Vaccine,vol. 21, pp. 1974-1979.
Chen et al., "Generation and evaluation of a high-growth reassortant H9N2 influenza A virus as a pandemic vaccine candidate," Vaccine 21 (2003) pp. 1983-1988.
Chutinimithul et al., "Molecular 1-13 characterization and phylogenetic analysis of H1N1 and H3N2 human influenza A viruses among infants and children in Thailand", Virus Research, Amsterdam, NL, vol. 132, No. 1-2, Dec. 21, 2007, pp. 122-131.
Clarke et al., 2000, "Rescue of mumps virus from cDNAJ", J Virol. 74(10):4831-8.
Clements et al., Evaluation of the infectivity and Efficacy of Live Cold-Adapted Influenza B/Ann Arbor/1/86 Reassortant Virus Vaccine in Adult Volunteers 1990, Journal of Infectious diseases, vol. 161, No. 5, pp. 869-877.
Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663 9657.
Collins et al., 1995, "Production of infectious human respiratory syncytial virus from cloned cDNA confirms an essential role . . . " PNAS 92: 11563-7.
Collins et al., 1996, "Parainfluenza Viruses", Fields Virology, Lippincott-Raven Publishers, Phila., Chapter 41, pp. 1205-1241.
Conzelmann et al., 1994, "Rescue of synthetic genomic RNA analogs of rabies virus by plasmid-encoded proteins", J Virol. 68(2):713-9.
Conzelmann et al., 1996, "Genetic engineering of animal RNA viruses", Trends Microbiol. 4(10):386-93.
Conzelmann et al., 1996, "Genetic manipulation of non-segmented negative-strand RNA viruses", J Gen Virol. 77 (Pt 3):381-389.
Conzelmann et al., 1998, "Nonsegmented negative-strand RNA viruses: genetics and manipulation of viral genomes", Annu Rev Genet. 32:123-62.
Cox. NJ et al., "Identification of sequence changes in the cold-adapted, live attenuated influenza vaccine strain . . . ". Virology. Dec. 1988; 167(2)554-567.
Database Caplus on NCBI, Accession No. AY553802, Influenza A Virus (A/little grebe/Thailand/Phichit-01/2004(H5N1) hemagglutinin (HA) gene, partial cds. May 21, 2004.
Database EMBL [Online] 1-13 E.B.I. Hinxton U.K.; Sep. 11, 2007, Komadina N and Deed N: "Influenza A virus (A/Solomon Islands/3/

(56) References Cited

OTHER PUBLICATIONS

2006(H1N1)) segment 6 neuraminidase (NA) gene, partial cds.", XP002692397, Database accession No. EU124136.
Database EMBL [Online] E. B. I. Hinxton U. K. ; May 29, 2007, Li D et al: "Influenza A virus (A/Hanoi/BM344/2006(H1N1)) genomic RNA, segment 6, complete sequence", XP002692398, Database accession No. AB286007.
Database EMBL [Online] E.B.I. Hinxton U.K.; May 15, 2008, Garten R et al: "Influenza A virus (A/Uruguay/716/2007(H3N2)) segment 4 hemagglutinin (HA) gene, complete cds.", XP002665732, A198Database accession No. EU716426.
Database EMBL [Online] E.B.I. Hinxton U.K.; May 15, 2008, Garten R et al: "Influenza A virus (A/Uruguay/716/2007(H3N2)) segment 6 neuraminidase (NA) gene, complete cds.", XP002665734, Database accession No. EU716427.
Database EMBL [Online] E.B.I. Hinxton U.K.; Jul. 1, 2008, Garten R et al: "Neuraminidase; Influenza A virus (A/Uruguay/716/2007(H3N2).", XP002665733, Database accession No. B2ZV33.
Database EMBL [Online] EBI; Nov. 5, 1999 "Influenza A Virus (A/Nagasaki/97/95(H3N2) HA gene for Hemagglutinin", Database accession No. AB019357.
Database EMBL [Online] EBI; Sep. 23, 1997, "Influenza A virus (A/Vienna/47/96v(H3N2) hemagglutinin mRNA," Database accession No. AF017272.
Database Geneseq [Online] Jun. 2, 2005, "Influenza B virus DNA sequence, SEQ ID 4." XP002544304 retrieved from EBI accession No. GSN:ADY93069 Database accession No. ADY93069.
Database UniProt [Online] Nov. 1, 1999, "SubName: Full=Pre-hemagglutinin;" XP002544292 retrieved from EBI accession No. UNIPROT:Q9WPM8 Database accession No. Q9WPM8.
Database UniProt [Online] 1-13 E.B.I. Hinxton U.K.; Oct. 2, 2007, Garten R et al: "Hemagglutinin; A/Solomon Islands/3/2006 (H1N1)", XP002692396, Database accession No. A7UPX0.
Database UniProt [Online] Dec. 7, 2004, "SubName: Full=Pre-hemagglutinin;" XP002544291 retrieved from EBI accession No. Uniprot:Q5V9D2 Database accession No. Q5V9D2.
Database UniProt [Online] EBI Nov. 1, 1996 "Influenza A Virus (A/Beijing/32/1992 (H3N2)" Database accession No. Q82525.
Database Uniprotkb E.B.I. Hinxton U.K.; Jul. 1, 2008, Garten R et al: "Hemagglutinin; Influenza A virus (A/Uruguay/716/2007(H3N2)).", XP002665731, Database accession No. B2ZV32.
Database USPTO Proteins [Online] Sep. 29, 1999, "Sequence 19 from patent US 5858368." XP002544293 retrieved from EBI accession No. USPOP:AAE01218 Database accession No. AAE01218.
Daum et al., Genetic and Antigenic Analysis of the First A/New Caledonia/20/99-like H1N1 Influenza Isolates Reported in the Americas, 2002, Emerging Infectious Diseases, vol. 8, No. 4, pp. 408-412.
Daum et al., Influenza A (H3N2) Outbreak, Nepal, 2005, Emerging Infectious Diseases, vol. 11, No. 8, pp. 1186-1191.
De and Banerjee, 1985, "Requirements and Functions of Vesicular Stomatitis Virus Land NS Proteins in the Transcription Process in vitro", Biochem. Biophys. Res. Commun. 126:40-49.
De and Banerjee, 1993, "Rescue of synthetic analogs of genome RNA of human parainfluenza virus type 3", Virology, 96(1):344-8.
De and Banerjee, 1994, "Reverse genetics of negative strand RNA viruses", Indian J Biochem Biophys. 31(5):367-76.
De et al., "Complete sequence of a cDNA clone of the hemagglutinin gene of influenza A/Chicken/Scotland/59 (H5NI) virus: comparison with contemporary North American and European strains," Nucleic Acids Research, 1988. vol. 16, No. 9, pp. 4181-4182.
De et al., "Protection against virulent H5 avian influenza virus infection in chickens by an inactivated vaccine produced with recombinant vaccine virus", Jun. 1988 Vaccine vol. 6, pp. 257-261.
De la Luna et al., 1993. "Influenza virus naked RNA can be expressed upon transfection into cells co-expressing the three subunits of the polymerase and the nucleoprotein from simian virus 40 recombinant viruses", J Gen Virol. 74 (Pt 3):535-9.

De La Luna et al., 1995, "Influenza virus NS1 Protein Enhances the Rate of Translation Initiation of Viral mRNAs", J. of Virol. 69: 2427-2433.
di Bernardi di Valserra et al., An Open Label Comparison of the Immunogenicity and Tolerability if Intranasal and intramuscular Formulations of Virosomal Influenza Vaccine in Healthy Adults, 2002, Clinical Therapeutics, vol. 24, pp. 100-111.
Dimock et al., 1993, Rescue of synthetic analogs of genomic RNA and replicative-intermediate RNA of human parainfluenza virus type 3 . . . J Virol. 67(5):2772-8.
Dreher and Hall, 1988, "Mutational Analysis of the Sequence and Structural Requirements in Brome Mosaic Virus RNA for Minus Strand Promoter Activity", J. Mol. Biol. 201:31-40.
Dreher et al., 1984, "Mutant Viral RNAs Synthesized in vitro Show Altered Aminoacylation and Replicase Template Activities", Nature 311:171-175.
Dunn et al., 1995, "Transcription of a recombinant bunyavirus RNA template by transiently expressed bunyavirus proteins", Virology, 211 (1): 133-43.
Durbin et al., 1997, "Recovery of infectious Human Parainfluenza Virus Type 3 from cDNA", Virol. 235:323-332.
Edwards et al.. 1994. "A randomized controlled trial of cold adapted and inactivated vaccines for the prevention of influenza A disease", J Infect Dis 169:68-76.
Egorov et al., Transfectant Influenza A Viruses with Long Deletions in the NS1 Protein Grow Efficiently in Vero Cells, Journal of Virology, Aug. 1998, vol. 72, No. 8, p. 6437-6441.
Elliot et al., 1997, Abstract # 96 10.sup.th International conference on Negative Strand Viruses.
Elliott et al., 1991, "Some highlights of virus research in 1990", J Gen Virol.72 (Pt 8):1761-79. Review. No abstract available.
Ellis and Zambon, Molecular analysis of an outbreak of influenza in the United Kingdom, 1997, European Journal of Epidemiology, vol. 13, pp. 369-372.
Emerson and Yu, 1975, "Both NS and L Proteins are Required for in vitro RNA Synthesis by Vesicular Stomatitis Virus", J. Virol. 15:1348-1356.
Enami and Palese, 1991, "High-Efficiency Formation of Influenza Virus Transfectants", J. Virol. 65:2711-2713.
Enami et al., 1991, "An influenza virus containing nine different RNA segments", Virology. 185(1):291-8.
Enami et al., 1990, "Introduction of Site Specific Mutations into the Genome of Influenza Virus", Proc Natl Acad Sci USA 87: 3802-3805.
Enami et al., "Characterization of Influenza Virus NS1 Protein by Using a Novel Helper-Virus-Free Reverse Genetic System" Journal of Virology, 2000, 74(12):5556-5561.
Extended European Search Report dated: Dec. 29, 2011 in European Patent Application No. EP 09795168 filed on Jul. 9, 2009 based on International Application No. PCT/US2009/050070.
Extended European Search Report dated: Jun. 4, 2012 in European Patent Application No. EP 12162668 filed on Mar. 6, 2006 based on International Application No. PCT/US2009/050070.
Extended European Search Report dated: Mar. 15, 2012 in European Patent Application No. EP 11008240 filed on Mar. 6, 2006 based on International Application No. PCT/US2009/050070.
Extended European Search Report dated: Mar. 18, 2013 in European Patent Application No. EP 12193604 filed on Jun. 16, 2004.
Extended European Search Report dated: Mar. 5, 2013 in European Patent Application No. EP 12177899 filed on Jun. 9, 2009.
Fahey and Schooley, 1992, "Status of Immune-Based Therapies in HIV Infection and AIDS", Clin. Exp. Immunol. 88:1-5.
Flandorfer et al., 2003, Chimeric Influenza A Viruses with a Functional Influenza B Virus Neuraminidase or Hemagglutinin, J. of Virology—77(17):9116-9123.
Flick. et al., "Promoter elements in the influenza vRNA terminal structure," RNA, 1996: 2(10):1046-1057.
Fodor et al., "Rescue of Influenza A Virus from Recombinant DNA". J. of Virology, Am. Society for Microbiology. Nov. 1999, vol. 73, No. 11, pp. 9679-9682.
Fortes et al., 1994, "Influenza virus NS 1 protein inhibits pre-mRNA splicing and blocks mRNA nucleocytoplasmic transport", EMBO 13: 704-712.

(56) References Cited

OTHER PUBLICATIONS

Furminger, "Vaccine Production," Textbook of Influenza, pp. 324-332 (1996).
Garcia-Sastre A, Palese p, 1993. "Genetic manipulation of negative-strand RNA virus genomes", Annu Rev Microbiol. :47:765-90.
Garcin et al., 1995, A highly recombinogenic system for the recovery of infectious *Sendai paramyxovirus* from cDNA: generation of a novel copy-back nondefeclive interfering virus*, EMBO J. 14: 6087-6094.
GenBank Accession No. AAB63711, Nov. 17, 1999.
GenBank Accession No. AAK70453, Mar. 11, 2003.
GenBank Accession No. AAK70456, Mar. 11, 2003.
GenBank Accession No. AAK70457, Mar. 11, 2003.
GenBank Accession No. AAP34324, Sep. 3, 2003.
GenBank Accession No. AAT12657 Mar. 26, 2005.
GenBank Accession No. AAT12674 Mar. 26, 2005.
GenBank Accession No. AJ344014, Published Apr. 15, 2005.
GenBank Accession No. CAC86622, Apr. 15, 2005.
GenBank Accession No. AAX11495 Oct. 12, 2006.
GenBank: AAA87553.1, "hemagglutinin [Influenza A virus (A/Beijing/32/1992(H3N2))]" Direct submission, May 11, 1995.
GenBank: AAD42311.2, "pre-hemagglutinin [Influenza B virus (B/Memphis/18/95)]," Updated Sequence Submitted Dec. 6, 2004.
GenBank: AAD44192.2, "pre-hemagglutinin [Influenza B virus (B/Nanchang/5/97)]," Updated Sequence Submitted, Dec. 6, 2004.
GenBank: AAK52912.1, "hemagglutinin [Influenza A virus (A/Paris/908/97(H3N2))]," Direct submission, Mar. 23, 2001.
GenBank: AAK63816.1, "hemagglutinin [Influenza A virus (A/Switzerland/7729/98(H3N2))]," Direct submission, May 21, 2001.
GenBank: AAK63822.1, "hemagglutinin [Influenza A virus (A/Hong Kong/1179/1999(H3N2))]," Direct Submission, May 21, 2001.
GenBank: AAP22117.1, "HA protein [Influenza B virus (B/Memphis/12/97-MA)]," Direct Submission, Mar. 24, 2003.
GenBank: AAP34322.1, "hemagglutinin [Influenza A virus (A/Texas/36/1991(H1N1))]," Direct Submission, May 1, 2003.
GenBank: AAP34323.1, "hemagglutinin [Influenza A virus (A/Beijing/262/1995(H1N1))]," Direct Submission, May 1, 2003.
GenBank: ABL77024.1, "hemagglutinin [Influenza B virus (B/Paris/549/1999)]," Direct submission, Dec. 29, 2006.
GeneBank ABF21273.1, hemagglutinin [Influenza A virus (A/Panama/2007/1999(H3N2))], May 3, 2006.
GeneBank Accession No. CAH04474, Jul. 11, 2005.
GeneBank accession No. CY027571.1, Nov. 27, 2007.
GeneBank Accession No. CY000025, Feb. 20, 2005.
Ghendon, "Cold-Adapted, Live Influenza Vaccines Developed in Russia," Textbook of Influenza, Chapter 29, pp. 391-399 (1998).
Goto et al., 1997, "Mutations Affecting the Sensitivity of the Influenza Virus Neuraminidase to 4-Guanidino-2,4-Dideoxy-2,3 Dehydro-N-Acetyineuraminic Acid", Virol. 238:265-272.
Govorkova, et al., "African Green Monkey Kidney (Vero) Cells Provide an Alternative Host Cell System for Influenza A and B Viruses". Journal of Virology. American Society for Microbiology. Aug. 1996. vol. 70. No. 8, pp. 5519-5524.
Grosfeld et al., 1995, RNA replication by respiratory syncytial virus (RSV) is directed by the N. P. and L proteins: transcription also occurs under these conditions but requires RSV superinfection for efficient synthesis of full-length mRNA. J Virol. 69(9):5677-86.
Guan, Vi, et al., "Molecular Characterization of H9N2 Influenza Viruses: Were They the Donors of the "Internal" Genes of H5N1 Viruses in Hong Kong?" Proc. Nail. Acad. Sci., U.S.A., Aug. 1999, vol. 96, pp. 9363-9367.
Hatada and Fukudo, 1992, "Binding of influenza A virus NS1 protein to dsRNA in vitro", J. of Gen. Virol. 73: 3325-3329.
He et al., 1997, "Recovery of Infectious SV5 from Cloned DNA and Expression of a Foreign Gene", Virol. 237:249-260.
Herlocher et al., "Sequence Comparisons of AIAAJ6/60 Influenza Viruses: Mutations Which May Contribute to Attenuation", Virus Research, 42:11-25; (1996).

Hillman Maurice R., 2000, "Vaccines in historic evolution and perspective: a narrative of vaccine discoveries", Vaccine 18:1436-1447.
Hiromoto et al., 2000,. "Evolutionary characterization of the six internal genes of H5N1 human influenza A virus", J. Gen. Virol. 81(Pt5):1293-303.
Hoffman and Banerjee, 1997. "An Infectious Clone of a Human Parainfluenza Virus Type 3", J. Virol. 71:4272-4277.
Hoffman et al., "A DNA transfection system for generation of influenza A virus from eight plasmids", PNAS, May 23, 2000, vol. 97, No. 11, pp. 6108-6113.
Hoffman et al., 2002, "Rescue of influenza B virus from eight plasmids", PNAS 99: 11411-11416.
Hoffman et al., "Unidirectional RNA polymerase I-polymerase II transcription system for generation of influenza A virus from eight plasmids", J. of Gen Vir, 2000, 61, 2843-2847.
Hoffman et al.. "Eight-Plasmid Rescue System for Influenza A Virus". International Congress Series. 1219:1007-1013; (2001).
Hoffman et al.. "Eight-Plasmid Rescue System for Rapid Generation of Influenza Virus Vaccines", Vaccine, 20:3165-3170; (2002).
Hoffman et al.. 2000. "Ambisense approach for the generation of influenza A virus: vRNA and mRNA synthesis from one template", Virology 267:310-7.
Hoffmann et al., "Characterization of the Influenza A Virus Gene Pool in Avian Species in Southern China: Was H6N1 a Derivative or a Precursor of H5N1?" J. Virology. 2000. vol. 74. No. 14. pp. 6309-6315.
Hoffmann et al., 2005, "Role of specific hemagglutinin amino acids in the immunogenicity" Proc. Natl. Acad. Sci. U.S.A. 102(36):12915-20. Epub Aug. 23, 2005.
Hoffmann et al., "Eight-plasmid system for rapid generation of influenza virus vaccines," Vaccine 20(2002); pp. 3165-3170.
Hoffmann et al., "Universal primer set for the full-length amplification of all Influenza A viruses." Arch Virol. Dec. 2001; 146(12):2275-89.
Hoffmann, Erich, Aufbau eines RNA-Polymerase I-Vektorsystems zur gezlelten Mutagenese von Influenza A Viren, Glessen 1997 (Doctoral Dissertation).With translation (Generation of an RNA-Polymerase Vector System for the Selective Mutagenesis of Influenza A).
Huang et al.. 1990, "Determination of Influenza virus proteins required for genome replication". J Virol. 64(11):5669-5673.
International Preliminary Report on Patentability mailed on: Jan. 11, 2011 in International Application No. PCT/US2009/050070 filed on Jul. 9, 2009 and published as WO 2010/005144 on Jan. 14, 2010.
International Preliminary Report on Patentability mailed on: Sep. 9, 2008 in International Application No. PCT/US2004/19372 filed on Jun. 16, 2004 and published as: WO 2005/018539 on Mar. 3, 2005.
International Preliminary Report on Patentability mailed on: Mar. 10, 2009, in International Application No. PCT/US2006/007630 filed on Jun. 3, 2006 and published as: WO2006/098901 on Sep. 21, 2006.
International Search Report and Written Opinion mailed on: Dec. 29, 2009 in International Application No. PCT/US2009/050070 filed on Jul. 9, 2009 and published as WO 2010/005144 on Jan. 14, 2010.
International Search Report and Written Opinion mailed on: Aug. 13, 2008, in International Application No. PCT/US2006/007630 filed on Jun. 3, 2006 and published as: WO 2006/098901 on Sep. 21, 2006.
Kaplan et al.. 1985. "In vitro Synthesis of Infectious Poliovirus RNA". Proc. Natl. Acad. Sci. USA 82:8424-8428.
Katinger et al., "Attenuated Influenza Virus as a Vector for Mucosal Immunization against HIV-1", Vaccines, pp. 315-319, (1997).
Kato et al., 1996, "Initiation of Sendai Virus Multiplication from Transfected cDNA or RNA with Negative or Positive Sense", Genes Cells 1 :569-579.
Keitel. et al., "Live Cold-Adapted, Reassortant Influenza Vaccines (USA)," Textbook of Influenza, Chapter 28, pp. 373-390 (1998).
Kimura et al., 1993, "An in vivo study of the replication origin in the influenza virus complementary RNA". J Biochem (Tokyo) 113(1):88-92.
Kimura et al., 1992, Transcription of a recombinant influenza virus RNA in cells that can express the influenza virus RNA polymerase and nucleoprotein genes*, J Gen Virol. 73 (Pt 6):1321-1328.

(56) References Cited

OTHER PUBLICATIONS

Kobayashi, 1992, Reconstitution of influenza virus RNA polymerase from three subunits expressed using recombinant baculovirus system. Virus Res. 22(3):235-245.
Konarska et al., 1990, "Structure of RNAs replicated by the DNA-dependent T7 RNA polymerase", Cell. 63(3):609-18.
Krystal et al., 1986, Expression of the Three Influenza Virus Polymerase Proteins in a Single Cell Allows Growth Complementation of Viral Mutants, Proc. Nail. Acad. Sci. USA 83:2709-2713.
Kunkel, 1985. "Rapid and Efficient Site-Specific Mutagenesis without Phenotypic Selection", Proc. Natl. Acad. Sci. USA 82:488.492.
Lamb et al., 1996, Fundamental Virology 3.sup.rd ed. Chapters 20 and 21.
Lawson et al., 1995, "Recombinant vesicular stomatitis viruses from DNA", Proc Natl Acad Sci U S A.92(1 0):4477-81.
Lee et al., Cross-reactive H1N1 antibody responses to a live attenuated influenza vaccine in children: implication for selection of vaccine strains. J Infect Dis. Nov. 1, 2003;188(9):1362-6. Epub Oct. 16, 2003.
Lehringer's Principles of Biochemistry, 4th Edition, Nelson and Cox, pp. 86 and 87 Alignment sequence between SEQ 10 No. 53 and 8 of U.S. Appl. No. 10/870,690 and U.S. Appl. No. 60/479,078, respectively-Appendix A.
Levis et al., 1986, "Deletion Mapping of Sindbis Virus 01 RNAs Derived from cDNAs Defines the Sequences Essential for Replication and Packaging", Cell 44:137-145.
Li et al, Recombinant influenza A virus vaccines for the pathogenic human A/Hong Kong/97 (H5N1) viruses, Journal of Infectious Diseases, vol. 179, No. May 5, 1999, pp. 1132-1138.
Li et al.. 1999, "Recombinant influenza A virus vaccines for the pathogenic human A/Hong Kong/97 (H5N1) viruses," J. of Infectious Diseases. 179:1132-8.
Luytjes et al., "Amplification, expression, and packaging of foreign gene by influenza virus," 1989, Cell, 59:1107-1113.
Maassab et al., The Development of Live Attenuated Cold-Adapted Influenza Virus Vaccine for Humans, Reviews in Medical Virology, 1999, vol. 9, pp. 237-244.
Maassab et al.. "Evaluation of a Cold-Recombinant Influenza Virus Vaccine in Ferrets", J. of Infectious Diseases. 146:780-790; (1982).
Maassab, Adaptation and growth characteristics of influenza virus at 25 degrees C Nature. 213:612-614 (1967).
Marozin et al., Antigenic and genetic diversity among swine influenza A HINI and HIN2 viruses in Europ J Gen Virol Apr. 2002;83 (Pt 4):735-745.
Martin at al., 1998, "Studies of the Binding Properties of Influenza Hemagglutinin Receptor-Site Mutants", Virology 241:101-111.
McCullers Jonathan A et al: "Multiple genotypes of influenza B virus circulated between 1979 and 2003" Journal of Virology, vol. 78, No. 23, Dec. 2004, pp. 12817-12828.
McCullers Jonathan A et al: "Reassortment and insertion-deletion are strategies for the evolution of influenza B viruses in nature" Journal of Virology, vol. 73, No. 9, Sep. 1999, pp. 7343-7348.
Mena et al., 1994, "Synthesis of biologically active influenza virus core proteins using a vaccinia virus-T7 RNA polymerase expression system", J Gen Virol. 75 (Pt 8):2109-14.
Mena et al., 1996, "Rescue of a Synthetic Chloramphenicol Acetyltransferase RNA into Influenza Virus-Like Particles Obtained from Recombinant Plasmids", J. Virol. 70: 5015-S024.
Merten et al. "Production of influenza virus in Cell Cultures for Vaccine Preparation", Novel Strategies in Design and Production of Vaccines, pp. 141-151; (1996).
MMWR of Mar. 4, 2005, vol. 54, No. 8, 193-196, Update-Influenza Activity-United States 2004-2005 Season.
MMWR, Prevention and Control of Influenza Recommendations of the Advisory Committee on Immunization Practices (ACIP), 2004, Vol, 53, pp. 1-40.
Moyer et al., 1991, "Assembly and transcription of synthetic vesicular stomatitis virus nucleocapsids", J Virol. 65(5):2170-8.
Murphy & Coelingh, "Principles Underlying the Development and Use of Live Attenuated Cold-Adapted Influenza A and B Virus Vaccines", Viral Immunol. 15:295-323; (2002).
Muster et al., 1991, "An influenza A virus containing influenza B virus S' and 3' noncoding regions on the neuraminidase gene is attenuated in mice:". Proc Natl Acad Sci U S A. 88(12):5177-81.
Naito and Ishihama, 1976, "Function and Structure of RNA Polymerase from Vesicular Stomatitis Virus", J. Biol. Chem. 251 :4307-4314.
Nakajima et al., 2003. "Restriction of Amino Acid Change in Influenza A Virus H3HA: Comparison of Amino Acid Changes Observed . . . "; J, of Virology 77(18):10088-10098.
Nara et al., 1987. "Simple, Rapid, Quantitative, Syncytium-Forming Microassay for the Detection of Human Immunodeficiency Virus Neutralizing Antibody", AIDS Res. Hum. Retroviruses 3:283-302.
Nemeroff et al., 1998, "Influenza Virus NS1 Protein Interacts with the Cellular 30 kDa Subunit of CPSF and Inhibits 3' End Formation of Cellular Pre-mRNAs", Mol. Cell1 :991-1000.
Neumann et al., 1994, "RNA Polymerase I-Mediated Expression of Influenza Viral RNA Molecules", Virol, 202:477-479.
Neumann et al. "Generation of influenza A viruses entirely from cloned cDNAs", Proc. Natl. Acad. Sci.. Microbiology, Aug. 1999, vol. 96, pp. 9354-9350.
Neumann, et al., "Genetic Engineering of Influenza and Other Negative-Strand RNA Viruses Containing Segmented Genomes," Advances in Virus Research, 1999; 53: 265-300.
Newmann et al., "Reverse Genetics for the Control of Avian Influenza," Avian Diseases, 2003, vol. 47, pp. 882-887.
Nichol et al., "Effectiveness of live, attenuated Intranasal influenza virus vaccine in healthy, working adults: a randomized controlled trial", (1999) JAMA 282:137-144.
Palese et al., 1996, "Negative-Strand RNA Viruses: Genetic Engineering and Applications", Proc. Natl. Acad. Sci. USA 93,11354-11358.
Park et al., (1991) "Rescue of a Foreign Gene by Sendai Virus," PNAS USA 88:5537-5541.
Parkin et al.. "Temperature Sensitive Mutants of Influenza A Virus Generated by Reverse Genetics". Vir. Res. 46:31-44; (1996).
Parkin N. et al., "Genetically Engineered Live Attenuated Influenza A Virus Vaccine Candidates", J. Virol., pp. 2772-2778; (1997).
Pattnaik et al., 1991, Cells that express all flVe proteins of vesicular stomatitis virus from cloned cDNAs support replication, assembly, and budding of defective Interfering particles, Proc Nail Acad Sci USA. 88(4):1379-83.
Peeters et al., 1999, "Rescue of Newcastle Disease Virus from Cloned cDNA: Evidence that Cleavability of the Fusion Protein is a Major Determinant for Virulence", J. Virol. 73:5001-5009.
Pekosz et al., 1999, "Reverse genetics of negative-strand RNA viruses: closing the circle", Proc Natl Acad Sci USA. 96(16):8804-6.
Percy et al., 1994, "Expression of a foreign protein by influenza A virus", J Virol 68(7):4486-92.
Perez, Daniel R. et al., "The Matrix 1 Protein of Influenza A Virus Inhibits the TransciptaseActivity of a Model Influenza Reporter Genome in Vivo", Article No. VY989318, Virology, 1998. vol. 249. pp. 52-61.
Pleschka et al., 1996, "A Plasmid-Based Reverse Genetics System for Influenza A Virus", J. Virol. 70:4188-4192.
Qiu et. al.. 1994, "The influenza virus NS1 protein is a poly(A)-binding protein that inhibits nuclear export of mRNAs containing poly(A)", J Virol. 68(4):2425-32.
Qiu et.al., 1995. "The influenza virus NS1 protein binds to a specific region in human U6 snRNA and inhibits U6-U2 and U6-U4 snRNA", RNA 1:304-16.
Racaniello et al. 1981. "Cloned Poliovirus Complementary DNA is Infectious in Mammalian Cells", Science 214:916-919.
Radecke et al. 1995, "Rescue of measles viruses from cloned DNA". EMBO J. 14(23):5773-84.
Radecke et al.. "Reverse Genetics Meets the Nonsegmented Negative-Strand RNA Viruses", Medical Virology. vol. 7: 49-63 (1997).
Roberts and Rose. 1998. "Recovery of Negative-Strand RAN Viruses from Plasmid DNAs: a Positive Approach Revitalizes a Negative Field", Virol. 247:1-6.

(56) References Cited

OTHER PUBLICATIONS

Rose et al., 1996, "Positive Strands to the Rescue Again: . . . " PNAS USA 94:14998-15000.
Sasaki et al., Comparison of the Influenza Virus-Specific Effector and Memory B-Cell Responses to Immunization of Children and Adults with Live Attenuated or Inactivated Influenza Virus Vaccines, 2007, Journal of Virology, vol. 81, No. 1, pp. 215-228.
Schlesinger et al., 1995. "RNA viruses as vectors for the expression of heterologous proteins", Mol Biotechnol. 3(2):155-165.
Schlicki et al., Plasmid-only rescue of influenza A virus vaccine candidates, Philosophical Transactions of The Royal Society of London Series S, 2001, vol. 356, p. 1965-1973.
Schnell et al., 1994. "Infectious Rabies Viruses from Cloned cDNA", EMBO J. 13:4195-4203.
Scholtissek, et al., "The Nucleoprotein as a Possible Major Factor in Determining Host Specificity of Influenza H3N2 Viruses," Virology, 1985; 147:287-294.
Seong et al., 1992. A new method for reconstituting influenza polymerase and RNA in vitro: a study of the promoter elements for cRNA and vRNA synthesis in vitro and viral rescue in vivo. Virology. 166(1):247-260.
Sharma et al., "Comparative Sequence Analysis on Different Strains of Swine Influenza Virus Sub-type H1N1 for Neuraminidase and Hemagglutinin," Journal of Proteomics & Bioinformatics, vol. 3(2) : 055-060 (2010).
Shortridge et al., 1998, "Characterization of avian H5NI influenza viruses . . . ", Virology 252(2):331-42.
Sidhu et al., 1995, "Rescue of synthetic measles virus minireplicons: measles genomic termini direct efficient expression and propagation of a reporter gene". Virology, 208(2):600-607.
Snyder et al., "Four Viral Genes Independently Contribute to Attenuation of Live Influenza A/Ann Arbor/6/60 (H2N2) Cold-Adapted" J, Virol. 62:488-95; (1988).
Suarez et al., "Comparisons of Highly Virulent H5N1 Influenza A Viruses Isolated from Humans and Chickens from Hong Kong", Journal of Virology, vol. 72, No. 8 (1998).
Subbarao et al., "The Attenuation Phenotype Conferred by the M Gene of the Influenza A/Ann Arbor/6/60 Cold-Adapted Virus (H2N2) on the A/Korea/82 (H3N2) reassortant virus results from a gene constellation effect" Virus. Res., 25:37-50; (1992).
Subbarao et al., "Sequential Addition of Temperature-Sensitive Missense Mutations into the PB2 Gene of Influenza A Transfectant . . . ". J. of Vir., Am. Society of Microbiology. Oct. 1995. pp. 5969-5977.
Subbarao, K., et al., "Evaluation of Genetically Modified Reassortant H5N1 Influenza A Virus Vaccine Candidate Generated by Plasmid-Based Reverse Genetics." Virology (2003) 305: 192-200.
Suguitan et al., 2006, "Live, attenuated influenza A H5NI candidate vaccines . . . ", PLoS Med. Sep. 2006;3(9):e360.
Supplemental European Search Report dated: Aug. 27, 2012 in European Patent Application No. EP 04785947 filed on Jul. 9, 2009 based on International Application No. PCT/US2004/019372.
Supplemental European Search Report dated: Oct. 21, 2009 in European Patent Application No. EP 06736880.3 filed on Mar. 6, 2006 and published as EP1856271 on Sep. 21, 2006.
Szewczyk et al., 1988, Purification, Thioredoxin Renaturation, and Reconstituted Activity of the Three Subunits of the Influenza A Virus RNA Polymerase. Proc. Nat. Acad. Sci. USA 85:7907-7911.
Taylor et al., 1990, "Newcastle Disease Virus Fusion Protein Expressed in a Fowlpox Virus Recombinant Confers Protection in Chickens", J. Viral. 64:1441-1450.
UniProtKB Database <http://www.uniprot.org/uniprot/B2ZV32.txt> Database accession No. B2ZV32_91NFA, Jul. 1, 2008.
Wang et al., "Cloning of the canine RNA polymerase I promoter and establishment of reverse genetics for influenza A and B in MOCK cells", Virology Journal, Biomed Central, London, GB, vol. 4, No. 1, Oct. 23, 2007.
Ward et al., 1988, "Direct Measurement of the Poliovirus RNA Polymerase Error Frequency in Vitro", J. Virol. 62:558-562.

Wareing at al., 2001. "Immunogenic and Isotype-Specific Responses to Russian and US Cold-Adapted Influenza A Vaccine Donor Strains . . . " J of Medical Virology 65:171-177.
Webby et al., 2004, "Responsiveness to a pandemic alert: use of reverse genetics for rapid development of influenza vaccines", Lancet 363:1099-1103.
Whelan et al., 1995, "Efficient recovery of infectious vesicular stomatitis virus entirely from cDNA clones", Proc.Natl.Acad.Sci. USA 92: 8388-8392.
World Health Organization, Weekly epidemiological record 27, Feb. 2004, No. 9, pp. 85-92.
Written Opinion mailed on: Jul. 18, 2008 in International Application No. PCT/US2004/19372 filed on Jun. 16, 2004 and published as: WO 2005/018539 on Mar. 3, 2005.
Xu et al., 1995 #AAB06964 (abstract only),.
Xu et al., 1996, "Genetic Variation in Neuraminidase Genes of Influenza A (H3N2) Viruses", Virology 224:175-183.
Xu, Xiyan et al., "Genetic Characterization of the Pathogenic Influenza A/Goose/Guandong/1/96 (H5N1) Virus: Similarly of its Hemagglutinin Gene to Those of H5N1 Viruses form the 1997 Outbreaks in Hong Kong", Article 10 viro. 1999.9820, Virology, 1999, vol. 261, pp. 15-19.
Yamanaka et al.. "In vivo analysis of the promoter structure of the influenza virus RNA genome using a transfection system with an engineered RNA." Proc Nail Aced Sci USA 88: 5369-5373. 1991.
Yu et al., 1995, "Functional cDNA clones of the human respiratory syncytial (RS) virus N, P, and L proteins support replication RS virus genomic RNA analogs and define minimal trans-acting requirements for RNA replication", J Virol. 69(4):2412-9.
Yusoff et al.. 1987, "Nucleotide Sequence Analysis of the L Gene of Newcastle Disease Virus: Homologies with Sendi and Vesicular Stomatitis Viruses" Nucleic Acids Res. 15: 3961-3976.
Zaghouani el al., 1991, "Induction of antibodies to the envelope protein of the human immunodeficiency virus by Immunization with monoclonal anti-idiotypes", Proc. Natl. Acad. Sci. USA 88:5645-5649.
Zaghouani et al., 1992. "Cells Expressing an H Chain to Gene Carrying a Viral T Cell Epitope are Lysed by Specific Cytolytic T Cells", J. Immunol. 148:3604-3609.
Zhang and Air, 1994, "Expression of Functional Influenza Virus A Polymerase Proteins and Template from Cloned cDNAs in Recombinant Vaccinia Virus Infected Cells", Biochem. Biophys. Res. Commun. 200:95-101.
Zhang et al.. Persistence of four related human munodeficiency virus subtypes during the course of zidovudine therapy . . . J. Virol. 1994 66: 425-432.
Zhou et al., 1999, "Rapid evolution of H5Nl influenza viruses . . . ," J. Virol. 73(4):3366-74.
Zhou, Yan, et al., "Membrane-Anchored Incorporation of a Foreign Protein in Recombinant Influenza Virions", Article No. VY989169, Virology, 1998, vol. 246, pp. 83-94.
Zobel et al, 1993, "RNA polymerase I catalysed transcription of insert viral cDNA", Nucleic Acids Res. 21 (16):3607-14.
Office Action mailed on: Dec. 8, 2008 in U.S. Appl. No. 10/870,690, filed Jun. 16, 2004 and issued as 7,566,458 on Jul. 28, 2009.
Office Action mailed on: Mar. 18, 2008 in U.S. Appl. No. 10/870,690, filed Jun. 16, 2004 and issued as 7,566,458 on Jul. 28, 2009.
Office Action mailed on: Aug. 7, 2007 in U.S. Appl. No. 10/870,690, filed Jun. 16, 2004 and issued as 7,566,458 on Jul. 28, 2009.
Office Action mailed on: Aug. 1, 2008 in U.S. Appl. No. 11/368,246, filed Mar. 6, 2006 and issued as 7,459,162 on Dec. 2, 2008.
Office Action mailed on: Oct. 18, 2007 in U.S. Appl. No. 11/368,246, filed Mar. 6, 2006 and issued as 7,459,162 on Dec. 2, 2008.
Office Action mailed on: Feb. 18, 2010 in U.S. Appl. No. 12/262,215 and published as: 2009-0175898 on Jul. 9, 2009, now abandoned.
Office Action mailed on: Nov. 4, 2009 in U.S. Appl. No. 12/262,215 and published as: 2009-0175898 on Jul. 9, 2009, now abandoned.
Office Action mailed on: Mar. 8, 2010 in U.S. Appl. No. 12/399,077, filed Mar. 6, 2009 and published as 2009/0175908 on Jul. 9, 2009, now abandoned.
Office Action mailed on: Jun. 17, 2011, in U.S. Appl. No. 12/858,386, filed Aug. 17, 2010 and published as 2011/0070263 on Mar. 24, 2011.

(56) References Cited

OTHER PUBLICATIONS

Office Action mailed on: Jul. 22, 2013 in U.S. Appl. No. 13/003,559, filed Apr. 29, 2011 and published as 2011/0212117 on Sep. 1, 2011.
Office Action mailed on: Dec. 5, 2012 in U.S. Appl. No. 13/003,559, filed Apr. 29, 2011 and published as 2011/0212117 on Sep. 1, 2011.
Office Action mailed on: Jul. 21, 20121, in U.S. Appl. No. 12/877,000, filed Sep. 7, 2010 and issued as: 8,048,430 on: Nov. 1, 2011.
Office Action mailed on: Nov. 23, 2010, in U.S. Appl. No. 12/877,000, filed Sep. 7, 2010 and issued as: 8,048,430 on: Nov. 1, 2011.
Office Action mailed on: Feb. 2, 2012 in U.S. Appl. No. 13/247,903, filed Sep. 28, 2011 and published as 2012/0034265 on Feb. 9, 2012.
Office Action mailed on: Aug. 16, 2012 in U.S. Appl. No. 13/329,123, filed Dec. 16, 2011, issued as: 8,333,975 on Dec. 18, 2012.
Office Action mailed on: Apr. 25, 2012 in U.S. Appl. No. 13/329,123, filed Dec. 16, 2011, issued as: 8,333,975 on Dec. 18, 2012.
Office Action mailed on: Nov. 14, 2012 in U.S. Appl. No. 13/538,972, filed Jun. 29, 2012 and published as: 2012/0301503 on Nov. 12, 2012.
Office Action mailed on: Jun. 28, 2013 in U.S. Appl. No. 13/708,743, filed Dec. 7, 2012 and published as: 2013-0156810 on Jun. 20, 2013.
Office Action mailed on: Oct. 18, 2013 in U.S. Appl. No. 13/767,749, filed Feb. 14, 2013 and published as: 2013-0243816 on Sep. 19, 2013.
Office Action mailed on Nov. 20, 2013 in U.S. Appl. No. 14/037,222, filed Sep. 25, 2013 and published as US 2014-0023680 on Jan. 23, 2013.
GenBank Accession No. AFM 72356, Hemagglutinin [Influenza A virus (A/Wellington/01/2004 (H3N2))], 2012.
Zhao et al., "Surveillance of influenza and other respiratory viruses in the United Kingdom: Oct. 2004 to May 2005" CDR Supplement (2005), pp. 1-8.
Database UniProt, [online], May 20, 2008, accession No. B2BV76, [searched Jan. 7, 2014], internet <URL:http://www.uniprot.org/uniprot/B2BV76.txt?version=1> Influenza A virus (A/Wisconsin/67/2005 (H3N2)).
Database UniProt, [online], Apr. 8, 2008, accession No. A5A5V1, [searched Jan. 7, 2014], internet <URL:http://www.uniprot.org/uniprot/A5A5V1.txt?version=9> Influenza A virus (A/Wisconsin/67/2005 (H3N2)).
GenBank Accession No. ABW39974.1, neuraminidase [Influenza A virus (A/New York/UR06-0199/2007(H1N1))], Oct. 18, 2007.

* cited by examiner

Figure 1A

SEQ ID NO:1 ca A/Shandong/9/93

Nucleotide Sequence of ca_A_Shandong_9_93_HA Entire molecule length: 1745 bp

```
   1 caggggataa ttctattaac catgaagact atcattgctt tgagctacat
  51 tttatgtctg gttttcgctc aaaaacttcc cggaaatgac aacagcacag
 101 caacgctgtg cctgggacat catgcagtgc caaacggaac gctagtgaaa
 151 acaatcacga atgatcaaat tgaagtgact aatgctactg agttggttca
 201 gagttcctca acaggtagaa tatgcggcag tcctcaccga atccttgatg
 251 gaaaaaactg cacactgata gatgctctat tgggagaccc tcattgtgat
 301 ggcttccaaa ataaggaatg ggaccttttt gttgaacgca gcaaagctta
 351 cagcaactgt tacccttatg atgtgccgga ttatgcctcc cttaggtcac
 401 tagttgcctc atcaggcacc ctggagttta tcaatgaaga cttcaattgg
 451 actggagtcg ctcaggatgg gggaagctat gcttgcaaaa gaggatctgt
 501 taacagtttc tttagtagat tgaattggtt gcacaaatta gaatacaaat
 551 atccagcgct gaacgtgact atgccaaaca atggcaaatt tgacaaattg
 601 tacatttggg gggttcacca cccgagcacg gacagtgacc aaaccagcct
 651 atatgttcga gcatcaggga gagtcacagt ctctaccaaa agaagccaac
 701 aaactgtaac cccgaatatc gggtctagac cctgggtaag gggtcagtcc
 751 agtagaataa gcatctattg gacaatagta aaaccgggag acatactttt
 801 gattaatagc acagggaatc taattgctcc tcggggttac ttcaaaatac
 851 gaaatgggaa aagctcaata atgaggtcag atgcacccat tggcaactgc
 901 agttctgaat gcatcactcc aaatggaagc attcccaatg acaaaccttt
 951 tcaaaatgta aacagaatca catatggggc ctgcccccaga tatgttaagc
1001 aaaacactct gaaattggca acagggatgc ggaatgtacc agagaaacaa
1051 actagaggca tattcggcgc aatcgcaggt ttcatagaaa atggttggga
1101 gggaatggta gacggttggt acggtttcag gcatcaaaat tctgagggca
1151 caggacaagc agcagatctt aaaagcactc aagcagcaat cgaccaaatc
1201 aacgggaaac tgaataggtt aatcgagaaa acgaacgaga aattccatca
1251 aatcgaaaaa gaattctcag aagtagaagg gagaattcag gacctcgaga
1301 aatatgttga agacactaaa atagatctct ggtcttacaa cgcggagctt
1351 cttgttgccc tggagaacca acatacaatt gatctaactg actcagaaat
1401 gaacaaactg tttgaaaaaa caaggaagca actgagggaa aatgctgagg
1451 acatgggcaa tggttgcttc aaaatatacc acaaatgtga caatgcctgc
1501 atagggtcaa tcagaaatgg aacttatgac catgatgtat acagagacga
1551 agcattaaac aaccggttcc agatcaaagg tgttgagctg aagtcaggat
1601 acaaagattg gatcctatgg atttcctttg ccatatcatg ctttttgctt
1651 tgtgttgttt tgctggggtt catcatgtgg gcctgccaaa aaggcaacat
1701 taggtgcaac atttgcattt gagtgcatta attaaaaaca ccctg
```

SEQ ID NO:35

Amino Acid Sequence of ca_A_Shandong_9_93_HA Entire molecule length: 566 aa

```
   1 mktiialsyi lclvfaqklp gndnstatlc lghhavpngt lvktitndqi
  51 evtnatelvq ssstgricgs phrildgknc tlidallgdp hcdgfqnkew
 101 dlfverskay sncypydvpd yaslrslvas sgtlefined fnwtgvaqdg
 151 gsyackrgsv nsffsrlnwl hkleykypal nvtmpnngkf dklyiwgvhh
 201 pstdsdqtsl yvrasgrvtv stkrsqqtvt pnigsrpwvr gqssrisiyw
 251 tivkpgdill instgnliap rgyfkirngk ssimrsdapi gncssecitp
 301 ngsipndkpf qnvnrityga cpryvkqntl klatgmrnvp ekqtrgifga
 351 iagfiengwe gmvdgwygfr hqnsegtgqa adlkstqaai dqingklnrl
 401 iektnekfhq iekefseveg riqdlekyve dtkidlwsyn aellvalenq
 451 htidltdsem nklfektrkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1B

SEQ ID NO:2

Nucleotide Sequence of ca_A_Shandong_9_93_NA  Entire molecule length: 1429 bp

```
   1 aaagataata acaattggct ctgtttctct cactattgcc acaatatgct
  51 tccttatgca aattgccatc ctggtaacta ctgtaacatt gcacttcaag
 101 caatatgagt gcaactcccc cccaaacaac caagtaatgc tgtgtgaacc
 151 aacaataata gaaagaaaca taacagagat agtgtatctg accaacacca
 201 ccatagagaa agaaatatgc cccaaactag cagaatacag aaattggtca
 251 aagccgcaat gtaaaattac aggatttgca cctttttcta aggacaattc
 301 aattcggctt tcagctggtg gagacatttg ggtgacaaga gaaccttatg
 351 tgtcatgcga tcctggcaag tgttatcaat ttgcccttgg acagggaaca
 401 acactaaaca acaggcactc aaatgacaca gtacatgata ggacccctta
 451 tcgaacccta ttgatgaatg agttgggtgt tccatttcat ttgggaacca
 501 agcaagtgtg catagcatgg tccagctcaa gttgtcacga tggaaaagca
 551 tggctgcatg tttgtgtaac tgggcatgat gaaaatgcaa ctgctagctt
 601 catttacgat gggaggcttg tagatagtat tggttcatgg tccaaaaata
 651 tcctcaggac ccaggagtcg gaatgcgttt gtatcaatgg aacttgtaca
 701 gtagtaatga ctgatggaag tgcttcagaa agagctgata ctaaaatact
 751 attcattgaa gaggggaaaa tcgttcatat tagcccattg tcaggaagtg
 801 ctcagcatgt cgaggagtgc tcctgttatc ctcgatatcc tggtgtcaga
 851 tgtgtctgca gagacaactg gaaaggctcc aataggccca tcgtagatat
 901 aaatgtgaaa gattatagca ttgtttccag ttatgtgtgc tcaggacttg
 951 ttggagacac acccagaaaa acgacagct ccagcagtag ctattgccgg
1001 aatcctaaca atgagaaagg gagtcatgga gtgaaaggct gggcctttga
1051 tgatggaaat gacgtgtgga tgggaagaac gatcagcgag gagttacgct
1101 caggttatga aaccttcaaa gtcattggag gctggtccaa acctaactcc
1151 aaattgcaga taaataggca agtcatagtt gacagaggta ataggtccgg
1201 ttattctggt atttctctg ttgaaggcaa aagctgcatc aatcggtgct
1251 tttatgtgga gttgataagg ggaaggaaac aggaaactga agtctggtgg
1301 acctcaaaca gtattgttgt gttttgtggc acctcaggta catatggaac
1351 aggctcatgg ccctgatggg gcggacatca atctcatgcc tatataagct
1401 ttcgcaattt tagaaaaaaa ctccttgtt
```

SEQ ID NO:36

Amino Acid Sequence of ca_A_Shandong_9_93_NA Entire molecule length: 436 aa

```
   1 mqiailvttv tlhfkqyecn sppnnqvmlc eptiiernit eivyltntti
  51 ekeicpklae yrnwskpqck itgfapfskd nsirlsaggd iwvtrepyvs
 101 cdpgkcyqfa lgqgttlnnr hsndtvhdrt pyrtllmnel gvpfhlgtkq
 151 vciawssssc hdgkawlhvc vtghdenata sfiydgrlvd sigswsknil
 201 rtqesecvci ngtctvvmtd gsaseradtk ilfieegkiv hisplsgsaq
 251 hveecscypr ypgvrcvcrd nwkgsnrpiv dinvkdysiv ssyvcsglvg
 301 dtprkndsss ssycrnpnne kgshgvkgwa fddgndvwmg rtiseelrsg
 351 yetfkviggw skpnsklqin rqvivdrgnr sgysgifsve gkscinrcfy
 401 velirgrkqe tevwwtsnsi vvfcgtsgty gtgswp
```

Figure 1C

SEQ ID NO:3 ca A/Johannesburg/33/94-Like
Nucleotide Sequence of ca_A_Johannesburg_33_94_Like_HA Entire molecule length: 1755 bp

```
   1 agcaaaagca ggggataatt ctattaacca tgaagactat cattgctttg
  51 agctacattt tatgtctggt tttcgctcaa aaacttcccg gaaatgacaa
 101 cagcacagca acgctgtgcc tgggacacca tgcagtgcca aacggaacgc
 151 tagtgaaaac aatcacgaat gatcaaattg aagtgactaa tgctactgag
 201 ctggttcaga gttccccaac aggtagaata tgcgacagcc ctcaccgaat
 251 ccttgatgga aagaactgca cactgataga tgctctattg ggagaccctc
 301 attgtgatgg cttccaaaat aaggaatggg acctttttgt tgaacgcagc
 351 aaagcttaca gcaactgtta cccttatgat gtgccggatt atgcctccct
 401 taggtcacta gttgcctcat caggcaccct ggagtttatc aacgaaaact
 451 tcaattggac tggagtcgct caggatggga aaagctatgc ttgcaaaagg
 501 ggatctgtta acagtttctt tagtagattg aattggttgc acaaattaga
 551 atacaaatat ccagcgctga acgtgactat gccaaacaat ggcaaatttg
 601 acaaattgta catttggggg gttcaccacc cgagcacgga cagtgtccaa
 651 accagcctat atgtccgagc atcagggaga gtcacagtct ctaccaaaag
 701 aagccaacaa actgtaatcc cggatatcgg gtatagacca tgggtaaggg
 751 gtcagtccag tagaataagc atctattgga caatagtaaa accgggagac
 801 atacttttga ttaatagcac agggaatcta attgctcctc ggggttactt
 851 caaaatacga aatgggaaaa gctcaataat gaggtcagat gcacccattg
 901 gcaactgcag ttctgaatgc atcactccaa atggaagcat tcccaatgac
 951 aaaccttttc aaaatgtaaa caggatcaca tatggggcct gccccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagctg cagatcttaa aagcactcaa gcagcaatcg
1201 accaaatcaa cgggaaactg aataggttag tcgagaaaac gaacgagaaa
1251 ttccatcaaa tcgaaaaaga attctcagaa gtagaaggga gaattcagga
1301 cctcgagaaa tatgttgaag acactaaaat agatctctgg tcttacaatg
1351 cggaacttct tgttgctctg gagaaccaac atacaattga tctaactgac
1401 tcagaaatga acaaactgtt tgaaagaaca aggaagcaac tgagggaaaa
1451 tgctgaggac atgggcaatg gttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga ttctatggat ttcctttgcc atatcgtgct
1651 tttgctttg tgttgttttg cttgggttca tcatgtgggc ctgccaaaaa
1701 ggcaacatta ggtgcaacat ttgcatttga gtgcattaat taaaaacacc
1751 cttgt
```

SEQ ID NO:37

Amino Acid Sequence of ca_A_Johannesburg_33_94_Like_HA Entire molecule length: 566 aa

```
   1 mktiialsyi lclvfaqklp gndnstatlc lghhavpngt lvktitndqi
  51 evtnatelvq ssptgricds phrildgknc tlidallgdp hcdgfqnkew
 101 dlfverskay sncypydvpd yaslrslvas sgtlefinen fnwtgvaqdg
 151 ksyackrgsv nsffsrlnwl hkleykypal nvtmpnngkf dklyiwgvhh
 201 pstdsvqtsl yvrasgrvtv stkrsqqtvi pdigyrpwvr gqssrisiyw
 251 tivkpgdill instgnliap rgyfkirngk ssimrsdapi gncssecitp
 301 ngsipndkpf qnvnrityga cpryvkqntl klatgmrnvp ekqtrgifga
 351 iagfiengwe gmvdgwygfr hqnsegtgqa adlkstqaai dqingklnrl
 401 vektnekfhq iekefseveg riqdlekyve dtkidlwsyn aellvalenq
 451 htidltdsem nklfertrkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1D

SEQ ID NO:4

Nucleotide Sequence of ca_A_Johannesburg_33_94_Like_NA

Entire molecule length: 1354 bp

```
   1 gaaatgaat ccaaatcaaa agataataac aattggctct gtttctctca
  51 ctattgccac aatatgcttc cttatgcaaa ttgccatcct ggtaactact
 101 gtaacattgc atttcaagca atatgagtgc aactcccccc caaacaacca
 151 agtaatgctg tgtgaaccaa caataataga aagaaacata acagagatag
 201 tgtatctgac caacaccacc atagagaaag aaatatgccc caaactagca
 251 gaatacagaa attggtcaaa gccgcaatgt aaaattacag gatttgcacc
 301 ttttctaag gacaattcaa ttcggctttc cgctggtgga gacatttggg
 351 tgacaagaga accttatgtg tcatgcgatc ctggcaagtg ttatcaattt
 401 gccctcggac agggaacaac actaaacaac aggcattcaa atgacacagt
 451 acatgatagg acccttatc gaaccctatt gatgaatgag ttgggtgttc
 501 catttcattt gggaaccaag caagtgtgca tagcatggtc cagctcaagt
 551 tgtcacgatg gaaagcatg gctgcatgtt tgtgtaactg gcatgatga
 601 aaatgcaact gctagcttca tttacgatgg gaggcttgta gatagtattg
 651 gttcatggtc caaaaatatc ctcaggaccc aggagtcgga atgcgtttgt
 701 atcaatggaa cttgtacagt agtaatgact gatgaagtg cttcagaaag
 751 agctgatact aaaatactat tcattgaaga ggggaaaatc gttcatatta
 801 gcccattgtc aggaagtgct cagcatgtcg aggagtgctc ctgttatcct
 851 cgatatcctg gtgtcagatg tgtctgcaga gacaactgga aaggctccaa
 901 taggcccatc gtagatataa atgtgaaaga ttatagcatt gtttccagtt
 951 atgtgtgctc aggacttgtt ggagacacac ccagaaaaaa cgacagctcc
1001 agcagtagct attgctggaa tcctaacaat gagaaagggg gtcatggagt
1051 gaaaggctgg gcctttgatg atggaaatga cgtgtggatg gaagaacga
1101 tcagcgagga gttacgctca ggttatgaaa ccttcaaagt cattggaggc
1151 tggtccaaac ctaactccaa attgcagata aataggcaag tcatagttga
1201 cagaggtaat aggtccggtt attctggtat tttctctgtt gaaggcaaaa
1251 gctgcatcaa tcggtgcttt tatgtggagt tgataagggg aaggaaacag
1301 gaaactgaag tctggtggac ctcaaacagt attgttgtgt tttgtggcac
1351 ttca
```

SEQ ID NO:38

Amino Acid Sequence of ca_A_Johannesburg_33_94_Like_NA
Entire molecule length: 451 aa

```
   1 kmnpnqkiit igsvsltiat icflmqiail vttvtlhfkq yecnsppnnq
  51 vmlceptiie rniteivylt nttiekeicp klaeyrnwsk pqckitgfap
 101 fskdnsirls aggdiwvtre pyvscdpgkc yqfalgqgtt lnnrhsndtv
 151 hdrtpyrtll mnelgvpfhl gtkqvciaws ssschdgkaw lhvcvtghde
 201 natasfiydg rlvdsigsws knilrtqese cvcingtctv vmtdgsaser
 251 adtkilfiee gkivhispls gsaqhveecs cyprypgvrc vcrdnwkgsn
 301 rpivdinvkd ysivssyvcs glvgdtprkn dsssssycwn pnnekgghgv
 351 kgwafddgnd vwmgrtisee lrsgyetfkv iggwskpnsk lqinrqvivd
 401 rgnrsgysgi fsvegkscin rcfyvelirg rkqetevwwt snsivvfcgt
 451 s
```

Figure 1E

SEQ ID NO:5
ca A/Wuhan/395/95
Nucleotide Sequence of ca A/Wuhan/395/95 H3     Entire molecule length: 1762 bp

```
   1 agcaaaagca ggggataatt ctattaacca tgaagactat cattgctttg
  51 agctacattt tatgtctggt tttcgctcaa aaacttcccg gaaatgacaa
 101 cagcacggca acgctgtgcc tgggacacca tgcagtgcca aacggaacgc
 151 tagtgaaaac aatcacgaat gaccaaattg aagtgactaa tgctactgag
 201 ctggttcaga gttcctcaac aggtagaata tgcgacagtc ctcaccgaat
 251 ccttgatgga aaaaactgca cactgataga tgctctattg ggagaccctc
 301 attgtgatgg cttccaaaat aaggaatggg acctttttgt tgaacgcagc
 351 aaagcttaca gcaactgtta cccttatgat gtgccggatt atgcttccct
 401 taggtcacta gttgcctcat ccggcaccct ggagtttacc aatgaaggct
 451 tcaattggac tggagtcgct caggatggaa caagctatgc ttgcaaaagg
 501 ggatctgtta aaagtttctt tagtagattg aattggttgc acaaattaga
 551 atacaaatat ccagcactga acgtgactat gccaaacaat gacaaatttg
 601 acaaattgta catttggggg gttcaccacc cgagtacgga cagtgaccaa
 651 accagcatat atgttcaagc atcagggaga gtcacagtct ctaccaaaag
 701 aagccaacaa actgtaatcc cgaatatcgg gtctagaccc tgggtaaggg
 751 ggatctccag cagaataagc atctattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaactgcaa ttctgaatgc atcactccaa atggaagcat tcccaatgac
 951 aaaccttttc aaaatgtaaa caggatcaca tatggggcct gtcccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa tcgaaaaaga attctcagaa gtagaaggga gaattcagga
1301 cctcgagaaa tatgttgaag acactaaaat agatctctgg tcttacaacg
1351 cggagcttct tgttgccctg gagaaccaac atacaattga tctaactgac
1401 tcagaaatga acaaactgtt tgaaagaaca aggaagcaac tgagggaaaa
1451 tgctgaggac atgggcaatg gttgcttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgct
1651 tttgctttg tgttgttctg ctggggttca tcatgtgggc ctgccaaaaa
1701 ggcaacatta ggtgcaacat ttgcatttga gtgcattaat taaaaacacc
1751 cttgtttcta ct
```

SEQ ID NO:39

Amino Acid Sequence of ca A/Wuhan/395/95 H3 Entire molecule length: 566 aa

```
   1 mktiialsyi lclvfaqklp gndnstatlc lghhavpngt lvktitndqi
  51 evtnatelvq ssstgricds phrildgknc tlidallgdp hcdgfqnkew
 101 dlfverskay sncypydvpd yaslrslvas sgtleftneg fnwtgvaqdg
 151 tsyackrgsv ksffsrlnwl hkleykypal nvtmpnndkf dklyiwgvhh
 201 pstdsdqtsi yvqasgrvtv stkrsqqtvi pnigsrpwvr gissrisiyw
 251 tivkpgdill instgnliap rgyfkirsgk ssimrsdapi gncnsecitp
 301 ngsipndkpf qnvnrityga cpryvkqntl klatgmrnvp ekqtrgifga
 351 iagfiengwe gmvdgwygfr hqnsegtgqa adlkstqaai nqingklnrl
 401 iektnekfhq iekefseveg riqdlekyve dtkidlwsyn aellvalenq
 451 htidltdsem nklfertrkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1F

SEQ ID NO:6

Nucleotide Sequence of ca A/Wuhan/395/95 N2    Entire molecule length: 1451 bp

```
   1 agcaaaagca ggagtgaaaa tgaatccaaa tcaaaagata ataactattg
  51 gctctgtttc tctcactatt gccacaatat gcttccttat gcaaattgcc
 101 atcctggtaa ctactgtaac attacatttc aagcaatatg aatgcaactc
 151 ccccccaaac aaccaagtaa tgctgtgtga accaacaata atagaaagaa
 201 acataacaga gatagtgtat ctgaccaaca ccaccataga aaggaaata
 251 tgccccaaac tagcagaata cagaaattgg tcaaagccgc aatgtaaaat
 301 tacaggattt gcaccttttt ctaaggacaa ttcaattcgg ctttccgctg
 351 gtggggacat ttgggtgaca agagaacctt atgtgtcatg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgcatagca
 551 tggtccagct caagttgtca cgatggaaaa gcatggctgc atgtttgtgt
 601 aactgggcat gatgaaaatg caactgctag cttcatttac gatgggaggc
 651 ttgtagatag tattggttca tggtccaaaa aaatcctcag gacccaggag
 701 tcggaatgcg tttgtatcaa tggaacttgt acagtagtaa tgactgatgg
 751 aagtgcttca ggaagagctg atactaaaat actattcatt gaagagggga
 801 aaatcgttca tattagccca ttgtcaggaa gtgctcagca tgtcgaggag
 851 tgctcctgtt atcctcgata ttctggtgtc agatgtgtct gcagagacaa
 901 ctggaaaggc tccataggc ccatcgtaga tataaatgtg aaagattata
 951 gcattgtttc cagttatgtg tgctcaggac ttgttggaga cacacccaga
1001 aaaaacgaca gctccagcag tagccattgc ctgaatccta caatgaggaa
1051 aggggggtcat ggagtgaaag gctgggcctt tgatgatgga aatgacgtgt
1101 ggatgggaag aacgatcagc gagaagttac gctcaggtta tgaaaccttc
1151 aaagtcattg gaggctggtc caaacctaac tccaaattgc agataaatag
1201 acaagtcata gttgacagag gtaataggtc cggttattct ggtattttct
1251 ctgttgaagg caaaagctgc atcaatcggt gcttttatgt ggagttgata
1301 aggggaagga aacaggaaac tgaagtctgg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 a
```

SEQ ID NO:40

Amino Acid Sequence of ca A/Wuhan/395/95 N2    Entire molecule length: 469 aa

```
   1 mnpnqkiiti gsvsltiati cflmqiailv ttvtlhfkqy ecnsppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhisplsg saqhveecsc yprysqvrcv crdnwkgsnr
 301 pivdinvkdy sivssyvcsg lvgdtprknd sssshclnp nneegghgvk
 351 gwafddgndv wmgrtisekl rsgyetfkvi ggwskpnskl qinrqvivdr
 401 gnrsgysgif svegksccinr cfyvelirgr kqetevwwts nsivvfcgts
 451 gtygtgswpd gadinlmpi
```

Figure 1G

SEQ ID NO:7 ca A/Sydney/05/97

Nucleotide Sequence of ca A/Sydney/05/97 H3       Entire molecule length: 1762 bp

```
   1 agcaaaagca ggggataatt ctattaacca tgaagactat cattgctttg
  51 agctacattt tatgtctggt tttcgctcaa aaaattcccg gaaatgacaa
 101 cagcacggca acgctgtgcc tgggacacca tgcagtgcca aacggaacgc
 151 tagtgaaaac aatcacgaat gaccaaattg aagtgactaa tgctactgag
 201 ctggttcaga gttcctcaac aggtagaata tgcgacagtc ctcaccgaat
 251 ccttgatgga gaaaactgca cactgataga tgctctattg ggagaccctc
 301 attgtgatgg cttccaaaat aaggaatggg accttttttgt tgaacgcagc
 351 aaagcctaca gcaactgtta cccttatgat gtgccggatt atgcctccct
 401 taggtcacta gttgcctcat ccggcaccct ggagtttaac aatgaaagct
 451 tcaattggac tggagtcgct cagaatggaa caagctatgc ttgcaaaagg
 501 agttctatta aaagtttctt tagtagattg aattggttgc accaattaaa
 551 atacaaatat ccagcactga acgtgactat gccaaacaat gacaaatttg
 601 acaaattgta catttggggg gttcaccacc cgagtacgga cagtgaccaa
 651 accagcatat atgctcaagc atcagggaga gtcacagtct ccaccaaaag
 701 aagccaacaa actgtaatcc cgaatatcgg atctagaccc tgggtaaggg
 751 gtatctccag cagaataagc atccattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaaatgcaa ttctgaatgc atcactccaa atggaagcat tcccaatgac
 951 aaaccatttc aaaatgtaaa caggatcaca tatggggcct gtcccagata
1001 tgttaagcaa aacactctga aattggcaac agggatgcgg aatgtaccag
1051 agaaacaaac tagaggcata ttcggcgcaa tcgcaggttt catagaaaat
1101 ggttgggagg gaatggtaga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa ttgaaaaaga attctcagaa gtagaaggga gaattcagga
1301 cctcgagaaa tatgttgagg acactaaaat agatctctgg tcgtacaacg
1351 cggagcttct tgttgccctg gagaaccaac atacaattga tctaactgac
1401 tcagaaatga acaaactgtt tgaaagaaca aggaagcaac tgagggaaaa
1451 tgctgaggat atgggcaatg gttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgtt
1651 ttttgctttg tgttgttttg ctggggttca tcatgtgggc ctgccaaaaa
1701 ggcaacatta ggtgcaacat ttgcatttga gtgcattaat taaaaacacc
1751 cttgtttcta ct
```

SEQ ID NO:41

Amino Acid Sequence of ca A/Sydney/05/97 H3 Entire molecule length: 566 aa

```
  1 mktiialsyi lclvfaqkip gndnstatlc lghhavpngt lvktitndqi
 51 evtnatelvq ssstgricds phrildgenc tlidallgdp hcdgfqnkew
101 dlfverskay sncypydvpd yaslrslvas sgtlefnnes fnwtgvaqng
151 tsyackrssi ksffsrlnwl hqlkykypal nvtmpnndkf dklyiwgvhh
201 pstdsdqtsi yaqasgrvtv stkrsqqtvi pnigsrpwvr gissrisihw
251 tivkpgdill instgnliap rgyfkirsgk ssimrsdapi gkcnsecitp
301 ngsipndkpf qnvnrityga cpryvkqntl klatgmrnvp ekqtrgifga
351 iagfiengwe gmvdgwygfr hqnsegtgqa adlkstqaai nqingklnrl
401 iektnekfhq iekefseveg riqdlekyve dtkidlwsyn aellvalenq
451 htidltdsem nklfertrkq lrenaedmgn gcfkiyhkcd nacigsirng
501 tydhdvyrde alnnrfqikg velksgykdw ilwisfaisc fllcvvllgf
551 imwacqkgni rcnici
```

Figure 1H

SEQ ID NO:8

Nucleotide Sequence of ca A/Sydney/05/97 N2    Entire molecule length: 1467 bp

```
   1 agcaaaagca ggagtaaaga tgaatccaaa tcaaaagata ataacgattg
  51 gctctgtttc tctcactatt gccacaatat gcttccttat gcaaattgcc
 101 atcctggtaa ctactgtaac attgcatttc aagcaatatg aatgcagctc
 151 tccccccaaac aaccaagtaa tgctgtgtga accaacaata atagaaagaa
 201 acataacaga gatagtgtat ctgaccaaca ccaccataga gaaggaaata
 251 tgccccaaac tagcagaata cagaaattgg tcaaagccac aatgtaaaat
 301 tacaggattt gcacctttt ctaaggacaa ttcaattcgg cttttccgctg
 351 gtggggacat ttgggtgaca agggaacctt atgtgtcgtg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgcatagca
 551 tggtccagct caagttgtca cgatggaaaa gcatggctgc atgtttgtgt
 601 aactgggcat gatgaaaatg caactgctag cttcatttac gatgggaggc
 651 ttgtagatag tattggttca tggtccaaaa aaatcctcag gacccaggag
 701 tcggaatgcg tttgtatcaa tggaacttgt acagtagtaa tgactgatgg
 751 gagtgcttca ggaagagctg atactaaaat actattcatt gaggagggga
 801 aaatcgttca tatcagccca ctgtcaggaa gtgctcagca tgtcgaggag
 851 tgctcctgtt atcctcgata tcctggtgtc agatgtgtct gcagagacaa
 901 ctggaaaggc tccaataggc ccatcgtaga tataaatgta aaggattata
 951 gcattgtttc cagttatgtg tgctcaggac ttgttggaga cacacccaga
1001 aaaaacgaca gctccagcag tagtcattgc ctgaatccta caatgagga
1051 agggggtcat ggagtgaaag gctgggcctt tgatgatgga aatgacgtgt
1101 ggatgggaag aacgatcagc gagaagttcc gctcaggtta tgaaaccttc
1151 aaagtcattg aaggctggtc caaacctaac tccaaattgc agataaatag
1201 gcaagtcata gttgacagag gtaataggtc cggttattct ggtatttct
1251 ctgttgaagg caaaagctgc atcaatcggt gcttttatgt ggagttgata
1301 aggggaagga acaggaaac tgaagtctgg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 aactccttgt ttctact
```

SEQ ID NO:42

Amino Acid Sequence of ca A/Sydney/05/97 N2    Entire molecule length: 469 aa

```
   1 mnpnqkiiti gsvsltiati cflmqiailv ttvtlhfkqy ecssppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhisplsg saqhveecsc yprypgvrcv crdnwkgsnr
 301 pivdinvkdy sivssyvcsg lvgdtprknd ssssshclnp nneegghgvk
 351 gwafddgndv wmgrtisekf rsgyetfkvi egwskpnskl qinrqvivdr
 401 gnrsgysgif svegkscinr cfyvelirgr kqetevwwts nsivvfcgts
 451 gtygtgswpd gadinlmpi
```

Figure 1I

SEQ ID NO:9
ca A/Panama/2007/99
Nucleotide Sequence of ca A/Panama/2007/99 H3     Entire molecule length: 1762 bp

```
   1 agcaaaagca ggggataatt ctattaacca tgaagactat cattgctttg
  51 agctacattt tatgtctggt tttcgctcaa aaacttcccg gaaatgacaa
 101 cagcacggca acgctgtgcc tggggcacca tgcagtgtca acggaacgc
 151 tagtgaaaac aatcacgaat gaccaaattg aagtgactaa tgctactgag
 201 ctggttcaga gttcctcaac aggtagaata tgcgacagtc ctcaccaaat
 251 ccttgatgga gaaaactgca cactaataga tgctctattg ggagaccctc
 301 attgtgatgg cttccaaaat aaggaatggg accttttgt tgaacgcagc
 351 aaagcctaca gcaactgtta cccttatgat gtgccggatt atgcctccct
 401 taggtcacta gttgcctcat ccgcacact ggagtttaac aatgaaagct
 451 tcaattggac tggagtcgct cagaatggaa caagctctgc ttgcaaaagg
 501 ggatctaata aaagtttctt tagtagattg aattggttgc accaattaaa
 551 atacaaatat ccagcactga acgtgactat gccaaacaat gaaaaatttg
 601 acaaattgta catttggggg gttctccacc cgagtacgga cagtgaccaa
 651 atcagcctat atgctcaagc atcagggaga gtcacagtct ctaccaaaag
 701 aagccaacaa actgtaatcc cgaatatcgg atctagaccc tgggtaaggg
 751 gtgtctccag cagaataagc atcattgga caatagtaaa accgggagac
 801 atacttttga ttaacagcac agggaatcta attgctcctc ggggttactt
 851 caaaatacga agtgggaaaa gctcaataat gaggtcagat gcacccattg
 901 gcaaatgcaa ttctgaatgc atcactccaa atggaagcat tcccaatgac
 951 aaaccatttc aaaatgtaaa caggatcaca tatgggcct gtcccagata
1001 tgttaagcaa aacactctga aattggcaac agggatgcgg aatgtaccag
1051 agaaacaaac tagaggcata ttcggcgcaa tcgcgggttt catagaaaat
1101 ggttgggagg gaatggtgga cggttggtac ggtttcaggc atcaaaattc
1151 tgagggcaca ggacaagcag cagatcttaa aagcactcaa gcagcaatca
1201 accaaatcaa cgggaaactg aataggttaa tcgagaaaac gaacgagaaa
1251 ttccatcaaa ttgaaaaaga attctcagaa gtagaaggga gaattcagga
1301 cctcgagaaa tatgttgagg acactaaaat agatctctgg tcgtacaacg
1351 cggagcttct tgttgccctg gagaaccaac atacaattga tctaactgac
1401 tcagaaatga caaactgtt tgaaagaaca aagaagcaac tgagggaaaa
1451 tgctgaggat atgggcaatg ttgtttcaa aatataccac aaatgtgaca
1501 atgcctgcat agggtcaatc agaaatggaa cttatgacca tgatgtatac
1551 agagacgaag cattaaacaa ccggttccag atcaaaggtg ttgagctgaa
1601 gtcaggatac aaagattgga tcctatggat ttcctttgcc atatcatgct
1651 ttttgctttg tgttgttttg ctggggttca tcatgtgggc ctgccaaaaa
1701 ggcaacatta ggtgcaacat ttgcatttga gtgcattaat taaaaacacc
1751 cttgtttcta ct
```

SEQ ID NO:43
Amino Acid Sequence of ca A/Panama/2007/99 H3    Entire molecule length: 566 aa

```
   1 mktiialsyi lclvfaqklp gndnstatlc lghhavsngt lvktitndqi
  51 evtnatelvq ssstgricds phqildgenc tlidallgdp hcdgfqnkew
 101 dlfverskay sncypydvpd yaslrslvas sgtlefnnes fnwtgvaqng
 151 tssackrgsn ksffsrlnwl hqlkykypal nvtmpnnekf dklyiwgvlh
 201 pstdsdqisl yaqasgrvtv stkrsqqtvi pnigsrpwvr gvssrisiyw
 251 tivkpgdill instgnliap rgyfkirsgk ssimrsdapi gkcnsecitp
 301 ngsipndkpf qnvnrityga cpryvkqntl klatgmrnvp ekqtrgifga
 351 iagfiengwe gmvdgwygfr hqnsegtgqa adlkstqaai nqingklnrl
 401 iektnekfhq iekefseveg riqdlekyve dtkidlwsyn aellvalenq
 451 htidltdsem nklfertkkq lrenaedmgn gcfkiyhkcd nacigsirng
 501 tydhdvyrde alnnrfqikg velksgykdw ilwisfaisc fllcvvllgf
 551 imwacqkgni rcnici
```

Figure 1J

SEQ ID NO:10

Nucleotide Sequence of ca A/Panama/2007/99 N2   Entire molecule length: 1466 bp

```
   1 agcaaaagca ggagtaaaga tgaatccaaa tcaaaagata taacgattg
  51 gctctgtttc tctcactatt gccacaatat gcttccttat gcaaatagcc
 101 atcctggtaa ctactgtaac attgcatttc aagcaatatg aatgcaactc
 151 cccccaaac aaccaagtaa tgctgtgtga accaacaata atagaaagaa
 201 acataacaga gatagtgtat ctgaccaaca ccaccataga gaaggaaata
 251 tgccccaaac tagcagaata cagaaattgg tcaaagccgc aatgtaaaat
 301 tacaggattt gcaccttttt ctaaggataa ttcaattcgg ctttccgctg
 351 gtggggacat ttgggtgaca agagaacctt atgtgtcatg cgatcctgac
 401 aagtgttatc aatttgccct tggacaggga acaacactaa acaacaggca
 451 ttcaaatgac acagtacatg ataggacccc ttatcgaacc ctattgatga
 501 atgagttggg tgttccattt catttgggaa ccaagcaagt gtgtatagca
 551 tggtccagct caagttgtca cgatggaaaa gcatggctgc atgtttgtgt
 601 aactgggcat gatgaaaatg caactgctag cttcatttac gatgggagac
 651 ttgtagatag tattggttca tggtccaaaa aaatcctcag gacccaggag
 701 tcggaatgcg tttgtatcaa tggaacttgt acagtagtaa tgactgatgg
 751 gagtgcttca ggaagagctg atactaaaat acttttcatt gaggagggga
 801 aaatcgttca tactagcaaa ttgtcaggaa gtgctcagca tgtcgaggag
 851 tgctcctgtt atcctcgata tcctggtgtc agatgtgtct gcagagacaa
 901 ctggaaggc tccaataggc catcgtaga tataaatgta aaggattata
 951 gcattgtttc cagttatgtg tgctcaggac ttgttggaga cacacccaga
1001 aaaaacgaca gctccagcag tagccattgc ctggatccta acaatgaaga
1051 aggggtcat ggagtgaaag ctgggccctt tgatgatgga aatgacgtgt
1101 ggatgggaag aacgatcagc gagaagtcac gctcaggtta tgaaaccttc
1151 aaggtcattg aaggctggtc caaacctaac tccaaattgc agataaatag
1201 gcaagtcata gttgaaagag gtaatatgtc cggttattct ggtattttct
1251 ctgttgaagg caaaagctgc atcaatcggt gcttttatgt ggagttgata
1301 aggggaagga aacaggaaac tgaagtctgg tggacctcaa acagtattgt
1351 tgtgttttgt ggcaccctcag gtacatatgg aacaggctca tggcctgatg
1401 gggcggacat caatctcatg cctatataag ctttcgcaat tttagaaaaa
1451 actccttgtt tctact
```

SEQ ID NO:44

Amino Acid Sequence of ca A/Panama/2007/99 N2   Entire molecule length: 469 aa

```
   1 mnpnqkiiti gsvsltiati cflmqiailv ttvtlhfkqy ecnsppnnqv
  51 mlceptiier niteivyltn ttiekeicpk laeyrnwskp qckitgfapf
 101 skdnsirlsa ggdiwvtrep yvscdpdkcy qfalgqgttl nnrhsndtvh
 151 drtpyrtllm nelgvpfhlg tkqvciawss sschdgkawl hvcvtghden
 201 atasfiydgr lvdsigswsk kilrtqesec vcingtctvv mtdgsasgra
 251 dtkilfieeg kivhtsklsg saqhveecsc yprypgvrcv crdnwkgsnr
 301 pivdinvkdy sivssyvcsg lvgdtprknd ssssshcldp nneegghgvk
 351 gwafddgndv wmgrtiseks rsqyetfkvi egwskpnskl qinrqviver
 401 gnmsgysgif svegkscinr cfyvelirgr kqetevwwts nsivvfcgts
 451 gtygtgswpd gadinlmpi
```

Figure 1K

SEQ ID NO:11 ca A/Wyoming/03/2003

Nucleotide Sequence of ca A/Wyoming/03/2003 H3  Entire molecule length: 1762 bp

```
   1 agcaaaagca ggggataatt ctattaacca tgaagactat cattgcttta
  51 agctacattc tatgtctggt tttctctcaa aagcttcccg gaaatgacaa
 101 cagcacggca acgctgtgcc ttgggcacca tgcagtacca aacggaacga
 151 tagtgaaaac aatcacgaat gaccaaattg aagttactaa tgctactgag
 201 ctggttcaga gttcctcaac aggtggaata tgcgacagtc ctcatcagat
 251 ccttgatgga gaaaactgca cactaataga tgctctattg ggagaccctc
 301 agtgtgatgg cttccaaaat aagaatggg acctttttgt tgaacgcagc
 351 aaagcctaca gcaactgtta cccttatgat gtgccggatt atgcctcct
 401 taggtcacta gttgcctcat ccggcacact ggagtttaac aatgaaagct
 451 tcaattgggc tggagtcact cagaatggaa caagctctgc ttgcaaaagg
 501 agatctaata aaagtttctt tagtagattg aattggttga cccacttaaa
 551 atacaaatac ccagcattga acgtgactat gccaaacaat gaaaaatttg
 601 acaaattgta catttggggg gttcaccacc cggttacgga cagtgaccaa
 651 atcagcctat atgctcaagc atcaggaaga atcacagtct ctaccaaaag
 701 aagccaacaa actgtaatcc cgaatatcgg atatagaccc agggtaaggg
 751 atatctccag cagaataagc atctattgga caatagtaaa accgggagac
 801 atactttga ttaacagcac aggaaatcta attgctcctc ggggttactt
 851 caaaatacga agtgggaaaa gctcaataat gagatcagat gcacccattg
 901 gcaaatgcaa ttctgaatgc atcactccaa atggaagcat tcccaatgac
 951 aaaccatttc aaaatgtaaa caggatcaca tatgggcct gtcccagata
1001 tgttaagcaa acactctga aattggcaac agggatgcga aatgtaccag
1051 agaaacaaac tagaggcata tttgcgcaa tcgcgggttt catagaaaat
1101 ggttgggagg aatggtgga cggttggtac ggtttcaggc atcaaaattc
1151 tgagggcaca ggacaagcag cagatctcaa aagcactcaa gcagcaatca
1201 accaaatcaa tgggaaactg aataggttaa tcgggaaaac aaacgagaaa
1251 ttccatcaga ttgaaaaaga attctcagaa gtagaaggga gaattcagga
1301 cctcgagaaa tatgttgagg acactaaaat agatctctgg tcatacaacg
1351 cggagcttct tgttgccctg gaaaaccaac atacaattga tctaactgac
1401 tcagaaatga caaaactgtt tgaaagaaca aagaagcaac tgagggaaaa
1451 tgctgaggat atgggcaatg gttgtttcaa aatataccac aaatgtgaca
1501 atgcctgcat agagtcaatc agaaatggaa cttatgacca tgatgtatac
1551 agagatgaag cattaaacaa ccggttccag atcaaaggtg ttgagctgaa
1601 gtcaggatac aaagattgga tcctatggat ttcctttgcc atatcatgtt
1651 ttttgctttg tgttgctttg ttggggttca tcatgtgggc ctgccaaaaa
1701 ggcaacatta ggtgcaacat ttgcatttga gtgcattaat taaaaacacc
1751 cttgtttcta ct
```

SEQ ID NO:45

Amino Acid Sequence of ca A/Wyoming/03/2003 H3 Entire molecule length: 566 aa

```
   1 mktiialsyi lclvfsqklp gndnstatlc lghhavpngt ivktitndqi
  51 evtnatelvq ssstggicds phqildgenc tlidallgdp qcdgfqnkkw
 101 dlfverskay sncypydvpd yaslrslvas sgtlefnnes fnwagvtqng
 151 tssackrrsn ksffsrlnwl thlkykypal nvtmpnnekf dklyiwgvhh
 201 pvtdsdqisl yaqasgritv stkrsqqtvi pnigyrprvr dissrisiyw
 251 tivkpgdill instgnliap rgyfkirsgk ssimrsdapi gkcnsecitp
 301 ngsipndkpf qnvnrityga cpryvkqntl klatgmrnvp ekqtrgifga
 351 iagfiengwe gmvdgwygfr hqnsegtgqa adlkstqaai nqingklnrl
 401 igktnekfhq iekefseveg riqdlekyve dtkidlwsyn aellvalenq
 451 htidltdsem nklfertkkq lrenaedmgn gcfkiyhkcd naciesirng
 501 tydhdvyrde alnnrfqikg velksgykdw ilwisfaisc fllcvallgf
 551 imwacqkgni rcnici
```

Figure 1L

SEQ ID NO:12

Nucleotide Sequence of ca A/Wyoming/03/2003 N2   Entire molecule length: 1467 bp

```
   1 agcaaaagca ggagtaaaga tgaatccaaa tcaaaagata ataacgattg
  51 gctctgtttc cctcaccatt tccacaatat gcttcttcat gcaaattgcc
 101 atcctgataa ctactgtaac attgcatttc aagcaatatg aattcaactc
 151 cccccccaaac aaccaagtga tgctgtgtga accaacaata atagaaagaa
 201 acataacaga gatagtgtat ctgaccaaca ccaccataga gaaggaaata
 251 tgccccaaac tagcagaata cagaaattgg tcaaagccgc aatgtaacat
 301 tacaggattt gcaccttttt ctaaggacaa ttcgattcgg ctttccgctg
 351 gtggggacat ctggtgaca agagaacctt atgtgtcatg cgatcctgac
 401 aagtgttatc aatttgccct tggacaggga acaacactaa caacgtgca
 451 ttcaaatgac acagtacatg ataggacccc ttatcggacc ctattgatga
 501 atgagttggg tgttccattt catctgggga ccaagcaagt gtgcatagca
 551 tggtccagct caagttgtca cgatggaaaa gcatggctgc atgtttgtgt
 601 aacgggggat gatgaaaatg caactgctag cttcatttac aatgggaggc
 651 ttgtagatag tattgtttca tggtccaaaa aaatcctcag gacccaggag
 701 tcagaatgcg tttgtatcaa tggaacttgt acagtagtaa tgactgatgg
 751 gagtgcttca ggaaaagctg atactaaaat actattcatt gaggagggga
 801 aaattgttca tactagcaca ttatcaggaa gtgctcagca tgtcgaggag
 851 tgctcctgtt atcctcgata tcctggtgtc agatgtgtct gcagagacaa
 901 ctggaaaggc tccaataggc ccatcgtaga tataaacata aaggattata
 951 gcattgtttc cagttatgtg tgctcaggac ttgttggaga cacacccaga
1001 aaaacgaca gctccagcag tagccattgc ttggatccaa acaatgagga
1051 aggtggtcat ggagtgaaag gctgggcatt tgatgatgga aatgacgtgt
1101 ggatgggaag aacgatcagc gagaagttac gctcaggata tgaaaccttc
1151 aaagtcattg aaggctggtc aacccctaac tccaaattgc agataaatag
1201 gcaagtcata gttgacagag taacaggtc cggttattct ggtattttct
1251 ctgttgaagg caaaagctgc atcaatcggt gcttttatgt ggagttgata
1301 aggggaagaa aacaggaaac tgaagtcttg tggacctcaa acagtattgt
1351 tgtgttttgt ggcacctcag gtacatatgg aacaggctca tggcctgatg
1401 gggcggacat caatctcatg cctatataag ctttcgcaat tttagaaaaa
1451 aactccttgt ttctact
```

SEQ ID NO:46

Amino Acid Sequence of ca A/Wyoming/03/2003 N2Entire molecule length: 469 aa

```
   1 mnpnqkiiti gsvsltisti cffmqiaili ttvtlhfkqy efnsppnnqv
  51 mlceptiier niteivyltn ttiekeicpk laeyrnwskp qcnitgfapf
 101 skdnsirlsa ggdiwvtrep yvscdpdkcy qfalgqgttl nnvhsndtvh
 151 drtpyrtllm nelgvpfhlg tkqvciawss sschdgkawl hvcvtgdden
 201 atasfiyngr lvdsivswsk kilrtqesec vcingtctvv mtdgsasgka
 251 dtkilfieeg kivhtstlsg saqhveecsc yprypgvrcv crdnwkgsnr
 301 pivdinikdy sivssyvcsg lvgdtprknd sssshcldp nneegghgvk
 351 gwafddgndv wmgrtisekl rsgyetfkvi egwsnpnskl qinrqvivdr
 401 gnrsgysgif svegkscinr cfyvelirgr kqetevlwts nsivvfcgts
 451 gtygtgswpd gadinlmpi
```

Figure 1M

SEQ ID NO:13
ca A/Texas/36/91
Nucleotide Sequence of ca A/Texas/36/91 H1 Entire molecule length: 1778 bp

```
   1 agcaaaagca ggggaaaata aaaacaacca aaatgaaagc aaaactacta
  51 gtcctgttat gtgcatttac agctacatat gcagacacaa tatgtatagg
 101 ctaccatgcg aacaactcaa ccgacactgt tgacacagta cttgagaaga
 151 acgtgacagt gacacactct gtcaacctac ttgaggacag tcacaacgga
 201 aaactatgtc gactaaaggg aatagcccca ctacaattgg gtaattgcag
 251 cgttgccgga tggatcttag gaaacccaaa atgcgaatca ctgttttcta
 301 aggaatcatg gtcctacatt gcagaaacac caaaccctga gaatggaaca
 351 tgttacccag ggtatttcgc cgactatgag gaactgaggg agcaattgag
 401 ttcagtatca tcattcgaga gattcgaaat attccccaaa gaaagctcat
 451 ggcccaacca caccgtaacc aaaggagtaa cgacatcatg ctcccataat
 501 gggaaaagca gtttttacag aaatttgcta tggctgacga agaagaatgg
 551 cttgtaccca aatgtgagca agtcctatgt aaacaacaaa gagaaagaag
 601 tccttgtact atggggtgtt catcacccgt ctaacatagg ggaccaaagg
 651 gccatctatc atacagaaaa tgcttatgtc tctgtagtgt cttcacatta
 701 tagcagaaga ttcaccccag aaatagcaaa aagacccaaa gtaagagatc
 751 aagaaggaag aattaactac tactggactc tgctggaacc cggggacaca
 801 ataatatttg aggcaaatgg aaatctaata gcgccatggt atgctttcgc
 851 actgagtaga ggctttgggt caggaatcat cacctcaaac gcatcaatgg
 901 atgaatgtga cgcgaagtgt caaacacccc agggagctat aaacagtagt
 951 cttcctttcc agaatgtaca cccagtcaca ataggagagt gtccaaagta
1001 tgtcaggagt acaaaattaa ggatggttac aggactaagg aacatcccat
1051 ccattcaatc cagaggtttg tttggagcca ttgccggttt cattgaaggg
1101 gggtggactg gaatgataga tggatggtat ggttatcatc atcagaatga
1151 acaaggatct ggctatgctg cggaccaaaa aagcacacaa aatgccatta
1201 acgggattac aaacaaggtg aattctgtaa tcgagaaaat gaacactcaa
1251 ttcacagctg tgggcaaaga attcaacaaa ttagaaagaa ggatggaaaa
1301 cttaaataaa aaagttgatg atggatttct ggacatttgg acatataatg
1351 cagaattgtt ggttctactg gaaaatggaa ggactttgga ttttcatgac
1401 tcaaatgtga agaatctgta tgagaaagta aaaagccaat tgaagaataa
1451 tgccaaagaa atagggaacg ggtgttttga attctatcac aagtgtaaca
1501 atgaatgcat ggaaagtgtg aaaaatggaa cttatgacta tccaaaatat
1551 tccgaagaat caaagttaaa caggggaaaa attgatggag tgaaattgga
1601 atcaatggga gtctatcaga ttctggcgat ctactcaact gtcgccagtt
1651 cactggtgct tttggtctcc ctgggggcaa tcagcttctg gatgtgttct
1701 aatgggtctt tgcagtgtag aatatgcatc tgagaccaga atttcagaaa
1751 tataagaaaa aacacccttg tttctact
```

SEQ ID NO:47

Amino Acid Sequence of ca A/Texas/36/91 H1 Entire molecule length: 566 aa

```
   1 mkakllvllc aftatyadti cigyhannst dtvdtvlekn vtvthsvnll
  51 edshngklcr lkgiaplqlg ncsvagwilg npkceslfsk eswsyiaetp
 101 npengtcypg yfadyeelre qlssvssfer feifpkessw pnhtvtkgvt
 151 tscshngkss fyrnllwltk knglypnvsk syvnnkekev lvlwgvhhps
 201 nigdqraiyh tenayvsvvs shysrrftpe iakrpkvrdq egrinyywtl
 251 lepgdtiife angnliapwy afalsrgfgs giitsnasmd ecdakcqtpq
 301 gainsslpfq nvhpvtigec pkyvrstklr mvtglrnips iqsrglfgai
 351 agfieggwtg midgwygyhh qneqgsgyaa dqkstqnain gitnkvnsvi
 401 ekmntqftav gkefnklerr menlnkkvdd gfldiwtyna ellvllengr
 451 tldfhdsnvk nlyekvksql knnakeigng cfefyhkcnn ecmesvkngt
 501 ydypkysees klnrgkidgv klesmgvyqi laiystvass lvllvslgai
 551 sfwmcsngsl qcrici
```

Figure 1N

SEQ ID NO:14

Nucleotide Sequence of ca A/Texas/36/91 N1        Entire molecule length: 1463 bp

```
   1 agcaaaagca ggagtttaaa atgaatccaa atcaaaaaat aataatcata
  51 ggatcaatca gtatggcaat cggaataatt agtctaatat tgcaaatagg
 101 aaatattatt tcaatatggg ctagccactc aatccaaact ggaagtcaaa
 151 accacactgg aatatgcaac caaagaatca ttacatatga aaatagcacc
 201 tgggtgaatc aaacatatgt taatattaac aacactaatg ttgttgctgg
 251 aaaggacaaa acttcagtga cattggccgg caattcatct ctttgcccta
 301 tccgtgggtg ggctatatac acaaaagaca acagcataag aattggttcc
 351 aaaggagatg tttttgtcat aagagagcct tttatatcat gttctcactt
 401 ggaatgcaga acctttttc tgacccaagg tgctctatta aatgacaagc
 451 attcaaatgg gaccgttaag gacagaagcc cttatagggc cttaatgagc
 501 tgtcctctag gtgaagctcc gtctccatac aattcaagat ttgaatcagt
 551 tgcttggtca gcaagcgcat gccatgatgg catgggctgg ctaacaatcg
 601 gaatttctgg tccagataat ggagcagtgg ctgtactaaa atacaacggc
 651 ataataactg aaaccataaa aagttggaag aagcgaatat taagaacaca
 701 agagtctgaa tgtgtctgtg tgaacggttc atgttttacc ataatgaccg
 751 atggcccgag taatggggcc gcctcgtaca gaatcttcaa aatcgagaag
 801 gggaaggtta ctaaatcaat agagttggat gcacccaatt atcattacga
 851 ggaatgttcc tgttacccag acaccggcac agtgatgtgt gtgtgcaggg
 901 acaattggca cggttcaaat cgaccttggg tgtcttttaa tcaaaacctg
 951 gattatcaaa taggatacat ctgcagtggg gtgttcggtg acaatccgcg
1001 tcccaaagat ggagaaggca gctgtaatcc agtgactgtt gatggagcag
1051 acggagtaaa ggggttttca tacagatatg gtaatggtgt ttggatagga
1101 aggactaaaa gtaacagact cagaaaggga tttgagatga tttgggatcc
1151 taatggatgg acagataccg acagtgattt ctctgtgaaa caggatgtcg
1201 tggcaatgac tgattggtca gggtacagcg gaagtttcgt tcaacatcct
1251 gagctaacag gattggactg tatgagacct gcttctgggg ttgaattaat
1301 cagagggcga cctagagaaa atacaacaat ctggactagt gggagcagca
1351 tttctttttg tggcgtaaat agcgatactg caaactggtc ttggccagac
1401 ggtgccgagt tgccattcac cattgacaag tagtccgttg aaaaaaaact
1451 ccttgtttct act
```

SEQ ID NO:48

Amino Acid Sequence of ca A/Texas/36/91 N1        Entire molecule length: 470 aa

```
   1 mnpnqkiiii gsismaigii slilqignii siwashsiqt gsqnhtgicn
  51 qriityenst wvnqtyvnin ntnvvagkdk tsvtlagnss lcpirgwaiy
 101 tkdnsirigs kgdvfvirep fiscshlecr tffltqgall ndkhsngtvk
 151 drspyralms cplgeapspy nsrfesvaws asachdgmgw ltigisgpdn
 201 gavavlkyng iitetikswk krilrtqese cvcvngscft imtdgpsnga
 251 asyrifkiek gkvtksield apnyhyeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsvk qdvvamtdws
 401 gysgsfvqhp eltgldcmrp cfwvelirgr prenttiwts gssisfcgvn
 451 sdtanwswpd gaelpftidk
```

Figure 1O

SEQ ID NO:15
ca A/Shenzhen/227/95
Nucleotide Sequence of ca A/Shenzhen/227/95 H1      Entire molecule length: 1689 bp

```
   1 aaatgaaagc aaaactacta gtcctgttgt gtgcatttac agctacatat
  51 gcagacacaa tatgtatagg ctaccatgcg aacaactcaa ccgacactgt
 101 tgacacagta cttgagaaga acgtgacagt gacacactct gtcaacctac
 151 ttgaggacag tcaacggaaa actatgcc gactaaaagg aacagcccca
 201 ctacaattgg gtaattgcag cgttgccgga tggatcttag gaaacccaga
 251 atgcgaatca ctgttttcta aggaatcatg gtcctacatt gcagaaacac
 301 caaaccctga gaatggaaca tgttacccag ggtatttcgc cgactatgag
 351 gaactgaggg agcaattgag ctcagtatca tcattcgaga gattcgaaat
 401 attccccaag gaaagctcat ggcccaaaca caccgtaacc aaaggagtga
 451 cggcatcatg ctcccataat gggaaaagca gttttacaa aaatttgcta
 501 tggctgacgg aaaagaatgg cttgtaccca atctgagca agtcctatgt
 551 aaacaacaag gagaaagaag tccttgtact atggggtgtt catcacccgt
 601 ctaacatagg ggaccaaagg gccatctatc atacagaaaa tgcttatgtc
 651 tctgtagtgt cttcacatta tagcagaaga ttcaccccag aaatagcaaa
 701 aagacccaaa gtaagaggtc aagaagggag aattaactac tactggactc
 751 tgctggaacc cggggacaca ataatatttg aggcaaatgg aaatctaata
 801 gcgccatggt acgctttcgc actgagtaga ggctttgggt caggaatcat
 851 cacctcaacc gcatcaatgg gtgaatgtga cgctaagtgt caaacacccc
 901 aaggagctat aaacagtagt cttccttttcc agaatgtaca cccagtcaca
 951 ataggagagt gtcccaagta tgtcaggagt acaaaattaa ggatggttac
1001 aggactaaga aacatccat ccattcaatc tagaggtttg tttggagcca
1051 ttgccggttt cattgaaggg gggtggactg gaatgataga tggatggtat
1101 ggttatcatc atcagaatga acaaggatct ggctatgctg cagaccaaaa
1151 aagcacacaa aatgccattg atgggattac aaacaaggtg aattctgtaa
1201 tcgagaaaat gaacactcaa ttcacagctg taggcaaaga attcaacaaa
1251 ttagagagaa ggatgaaaa cttaaataag aaagttgatg atggatttct
1301 ggacatttgg acatataatg cagagttgtt ggttctcctg gaaaatggaa
1351 ggactttggg ttttcatgac tcaaatgtga agaatctgta tgagaaagta
1401 aaaaaccaat tgaagaataa tgccaaagaa atcgggaacg ggtgttttga
1451 attctatcac aagtgtaaca atgaatgcat ggaaagtgtg aaaaatggaa
1501 cttatgacta tccaaaatat tccgaagaat caaagttaaa cagggaaaaa
1551 attgatggag tgaaattgga atcaatggga gtctatcaga ttctggcgat
1601 ctactcaact gtcgccagtt cactggtgct tttggtctcc ctgggggcaa
1651 tcagtttctg gatgtgttct aatgggtctt tgcagtgta
```

SEQ ID NO:49
Amino Acid Sequence of ca A/Shenzhen/227/95 H1   Entire molecule length: 562 aa

```
   1 mkakllvllc aftatyadti cigyhannst dtvdtvlekn vtvthsvnll
  51 edshngklcr lkgtaplqlg ncsvagwilg npeceslfsk eswsyiaetp
 101 npengtcypg yfadyeelre qlssvssfer feifpkessw pkhtvtkgvt
 151 ascshngkss fyknllwlte knglypnlsk syvnnkekev lvlwgvhhps
 201 nigdqraiyh tenayvsvvs shysrrftpe iakrpkvrgq egrinyywtl
 251 lepgdtiife angnliapwy afalsrgfgs giitstasmg ecdakcqtpq
 301 gainsslpfq nvhpvtigec pkyvrstklr mvtglrnips iqsrglfgai
 351 agfieggwtg midgwygyhh qneqgsgyaa dqkstqnaid gitnkvnsvi
 401 ekmntqftav gkefnklerr menlnkkvdd gfldiwtyna ellvllengr
 451 tlgfhdsnvk nlyekvknql knnakeigng cfefyhkcnn ecmesvkngt
 501 ydypkysees klnrekidgv klesmgvyqi laiystvass lvllvslgai
 551 sfwmcsngsl qc
```

Figure 1P

SEQ ID NO:16
Nucleotide Sequence of ca A/Shenzhen/227/95 N1    Entire molecule length: 1447 bp

```
   1 agcaaaagca ggagtttaaa atgaatccaa atcaaaaat aataaccatt
  51 ggatcaatca gtattgcaat tggaataatt agtctgatat tgcaaatagg
 101 aaatattatt tcaatatggg ctagccactc aatccaaact ggaagtcaaa
 151 accacactgg aatatgcaac caaagaatca ttacatatga aaatagcacc
 201 tgggtaaatc aaacatatgt taatattaac aacactaatg ttgttgctgg
 251 aaaggacaaa acctcaatga cattggccgg caattcatct ctttgcccta
 301 tccgtggatg ggctatatac acaaaagaca acagcataag aattggttcc
 351 aaggagatg ttttgtcat aagagagcct tttatatcat gttctcactt
 401 ggaatgcaga accttttttc tgacccaagg tgctctatta aatgacaagc
 451 attcaaatgg gaccgttaag gacagaagcc cttataggc cttaatgagc
 501 tgtcctctag gtgaagctcc gtctccatac aattcaagat ttgaatcagt
 551 tgcttggtca gcaagcgcat gccatgatgg cttgggctgg ctaacaatcg
 601 gaatttctgg tccagataat ggggcagtgg ctgtactaaa atacaacggc
 651 ataataactg aaaccattaa aagttggaag aagcgaatat taagaacaca
 701 agagtctgaa tgtgtctgta tgaacggttc atgttttacc ataatgaccg
 751 atggcccgag taatgggcc gcatcgtaca gaatcttcaa aatcgagaag
 801 gggagagtta ctaaatcaat agagttggat gcacccaatt atcattacga
 851 ggaatgttca tgttacccag acaccggcac agtgatgtgt gtgtgcaggg
 901 acaattggca cggttcaaat cgaccttggg tgtcttttaa tcaaaacctg
 951 gattatcaaa taggatacat ctgcagtggg gtgttcggtg acaatccgcg
1001 tcccaaagat ggagaaggca gctgtaatcc agtgactgtt gatggagcag
1051 acggagtaaa ggggttttca tacagatatg gtaatggtgt ttggatagga
1101 aggactaaaa gtaacagact cagaaaggga tttgagatga tttgggatcc
1151 taatggatgg acagataccg acagtgattt ctcaatgaaa caggatatcg
1201 tggcaatgac tgattggtca gggtacagcg gaagttttgt tcaacatcct
1251 gagctaacag gattggactg tatgagacct tgcttttggg ttgaattagt
1301 cagagggcta cctagagaaa atacaacaat ctggactagt gggagcagca
1351 tttcttttgt ggcgtaaat agcgatactg caaactggtc ttggccagac
1401 ggtgccgagt tgccattcac cattgacaag tagtccgttg aaaaaaa
```

SEQ ID NO:50
Amino Acid Sequence of ca A/Shenzhen/227/95 N1    Entire molecule length: 470 aa

```
   1 mnpnqkiiti gsisiaigii slilqignii siwashsiqt gsqnhtgicn
  51 qriityenst wvnqtyvnin ntnvvagkdk tsmtlagnss lcpirgwaiy
 101 tkdnsirigs kgdvfvirep fiscshlecr tffltqgall ndkhsngtvk
 151 drspyralms cplgeapspy nsrfesvaws asachdglgw ltigisgpdn
 201 gavavlkyng iitetikswk krilrtqese cvcmngscft imtdgpsnga
 251 asyrifkiek grvtksield apnyheeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsmk qdivamtdws
 401 gysgsfvqhp eltgldcmrp cfwvelvrgl prenttiwts gssisfcgvn
 451 sdtanwswpd gaelpftidk
```

Figure 1Q

SEQ ID NO:17
ca A/Beijing/262/95
Nucleotide Sequence of ca A/Beijing/262/95 H1     Entire molecule length: 1775 bp

```
   1 agcaaaagca ggggaaaata aaaacaacca aaatgaaagc aaaactacta
  51 gtcctgttat gtacatttac agctacatat gcagacacaa tatgtatagg
 101 ctaccatgcc aacaactcaa ccgacactgt tgacacagta cttgagaaga
 151 atgtgacagt gacacactct gtcaacctac ttgaggacag tcacaatgga
 201 aaactatgtc tactaaaagg aatagcccca ctacaattgg gtaattgcag
 251 cgttgccgga tggatcttag gaaacccaga atgcgaatca ctgatttcta
 301 aggaatcatg gtcctacatt gtagagacac caaaccctga gaatggaaca
 351 tgttacccag ggtatttcgc cgactatgag gaactgaggg agcaattgag
 401 ttcagtatca tcatttgaga gattcgaaat attccccaaa gaaagctcat
 451 ggcccaaaca caccgtaaca ggagtaacgg catcatgctc ccataatggg
 501 aaaagcagtt tttacagaaa tttgctatgg ctgacggaga agaatggctt
 551 gtacccaaat ctgagcaatt cctatgtgaa caacaaagag aaagaagtcc
 601 ttgtactatg ggtgttcat cacccatcta acatagggga ccaaagggcc
 651 atctatcata cagaaaacgc ttatgtctct gtagtgtctt cacattatag
 701 cagaagattc accccagaaa tagcaaaaag acccaaagta agaggtcagg
 751 aaggaagaat caactactac tggactctgc tggaacccgg ggacacaata
 801 atatttgagg caaatggaaa tctaatagcg ccatggtatg ctttcgcact
 851 gagtagaggc tttgggtcag gaatcatcac ctcaaatgca ccaatgaatg
 901 aatgtgatgc gaagtgtcaa acacctcagg gagctataaa cagtagtctt
 951 cctttccaga atgtacaccc agtcacaata ggagagtgtc caaagtatgt
1001 caggagtaca aaattaagga tggttacagg actaaggaat atcccatcca
1051 ttcaatccag aggtttgttt ggagccattg ccggtttcat tgaagggggg
1101 tggactggaa tgatggatgg gtggtatggt tatcatcatc agaatgagca
1151 aggatctggc tatgctgcag atcaaaaaag cacacaaaat gccattaacg
1201 ggattacaaa taaggtgaat tctgtaattg agaaaatgaa cactcaattc
1251 acagctgtgg gcaaagaatt caacaaatta gaaagaagga tggaaaactt
1301 aaataaaaaa gttgatgatg gatttctaga catttggaca tataatgcag
1351 aattgttggt tctactggaa aatgaaagga ctttggattt ccatgactca
1401 aatgtgaaga atctgtatga gaaagtgaaa agccaattaa agaataatgc
1451 caaagaaata gggaacgggt gttttgaatt ctatcacaag tgtaacaatg
1501 aatgcatgga aagtgtgaaa aatggaactt atgactatcc aaaatattcc
1551 gaagaatcaa agttaaacag ggagaaaatt gatggagtga aattggaatc
1601 aatgggagtc tatcagattc tggcgatcta ctcaactgtc gccagttcac
1651 tggttctttt ggtctccctg gggggcaatca gcttctggat gtgttccaat
1701 gggtctttgc agtgtagaat atgcatctga gaccagaatt tcagaaatat
1751 aagaaaaaac acccttgttt ctact
```

SEQ ID NO:51

Amino Acid Sequence of ca A/Beijing/262/95 H1 Entire molecule length: 565 aa

```
   1 mkakllvllc tftatyadti cigyhannst dtvdtvlekn vtvthsvnll
  51 edshngklcl lkgiaplqlg ncsvagwilg npeceslisk eswsyivetp
 101 npengtcypg yfadyeelre qlssvssfer feifpkessw pkhtvtgvta
 151 scshngkssf yrnllwltek nglypnlsns yvnnkekevl vlwgvhhpsn
 201 igdqraiyht enayvsvvss hysrrftpei akrpkvrgqe grinyywtll
 251 epgdtiifea ngnliapwya falsrgfgsg iitsnapmne cdakcqtpqg
 301 ainsslpfqn vhpvtigecp kyvrstklrm vtglrnipsi qsrglfgaia
 351 gfieggwtgm mdgwygyhhq neqgsgyaad qkstqnaing itnkvnsvie
 401 kmntqftavg kefnklerrm enlnkkvddg fldiwtynae llvllenert
 451 ldfhdsnvkn lyekvksqlk nnakeigngc fefyhkcnne cmesvkngty
 501 dypkyseesk lnrekidgvk lesmgvyqil aiystvassl vllvslgais
 551 fwmcsngslq crici
```

Figure 1R

SEQ ID NO:18

Nucleotide Sequence of ca A/Beijing/262/95 N1 Entire molecule length: 1463 bp

```
   1 agcaaaagca ggagtttaaa atgaatccaa atcaaaaaat aataaccatt
  51 ggatcaatca gtatagtaat cgggataatt agtctaatgt tgcaaatagg
 101 aaatattatt tcaatatggg ctagtcactc aatccaaact ggaagtcaaa
 151 accacactgg aatatgcaac caaagaatca tcacatatga aaatagcacc
 201 tgggtgaatc acacatatgt taatattaac aacactaatg ttgttgctgg
 251 aaaggacaaa acttcagtga cattggccgg caattcatca ctttgttcta
 301 tcagtggatg ggctatatac acaaaagaca acagcataag aattggttcc
 351 aaaggagatg tttttgtcat aagagagcct tttatatcat gttctcactt
 401 ggaatgcaga accttttttc tgacccaagg tgctctatta aatgacaaac
 451 attcaaatgg gaccgttaag gacagaagtc cttatagggc cttaatgagc
 501 tgtcctctag gcgaagctcc gtctccatat aattcaaagt ttgaatcagt
 551 tgcttggtca gcaagcgcat gtcatgatgg catgggctgg ttaacaatcg
 601 gaatttctgg tccagataat ggagcagtgg ctgtactaaa atacaacggc
 651 ataataactg aaaccataaa aagttggaaa aagcgaatat taagaacaca
 701 agagtctgaa tgtgtctgtg tgaacgggtc atgttttacc ataatgaccg
 751 atggcccgag taatggggcc gcctcgtaca aaatcttcaa gattgagaag
 801 gggaaggtta ctaaatcaat agagttgaat gcacccaatt ctcattatga
 851 ggaatgttcc tgttacccag acactggcac agtgatgtgt gtatgcaggg
 901 acaattggca cggttcaaat cgacccttggg tgtcttttaa tcaaaacctg
 951 gattatcaaa taggatacat ctgcagtggg gtgttcggtg acaatccgcg
1001 tcccaaagat ggagagggca gctgtaatcc agtgactgtt gatggagcag
1051 acggagtaaa ggggttttca tacagatatg gtaatggtgt ttggatagga
1101 aggactaaaa gtaacagact cagaaaggga tttgagatga tttgggatcc
1151 taatggatgg acagataccg acagtgattt ctcagtgaaa caggatgttg
1201 tggcaatgac tgattggtca gggtacagcg gaagtttcgt tcaacatcct
1251 gagctaacag gattggactg tataagacct tgcttctggg ttgaattagt
1301 cagaggacgg cctagagaaa atacaacaat ctggactagt gggagcagca
1351 tttctttttg tggcgtaaat agtgatactg caaactggtc ttggccagac
1401 ggtgctgagt tgccattcac cattgacaag tagtccgttg aaaaaaaact
1451 ccttgtttct act
```

SEQ ID NO:52

Amino Acid Sequence of ca A/Beijing/262/95 N1 Entire molecule length: 470 aa

```
   1 mnpnqkiiti gsisivigii slmlqignii siwashsiqt gsqnhtgicn
  51 qriityenst wvnhtyvnin ntnvvagkdk tsvtlagnss lcsisgwaiy
 101 tkdnsirigs kgdvfvirep fiscshlecr tffltqgall ndkhsngtvk
 151 drspyralms cplgeapspy nskfesvaws asachdgmgw ltigisgpdn
 201 gavavlkyng iitetikswk krilrtqese cvcvngscft imtdgpsnga
 251 asykifkiek gkvtksieln apnshyeecs cypdtgtvmc vcrdnwhgsn
 301 rpwvsfnqnl dyqigyicsg vfgdnprpkd gegscnpvtv dgadgvkgfs
 351 yrygngvwig rtksnrlrkg femiwdpngw tdtdsdfsvk qdvvamtdws
 401 gysgsfvqhp eltgldcirp cfwvelvrgr prenttiwts gssisfcgvn
 451 sdtanwswpd gaelpftidk
```

Figure 1S

SEQ ID NO:19
ca A/New Caledonia/20/99
Nucleotide Sequence of ca A/New Caledonia/20/99 H1   Entire molecule length: 1775 bp

```
   1 agcaaaagca ggggaaaata aaacaacca aaatgaaagc aaaactactg
  51 gtcctgttat gtacatttac agctacatat gcagacacaa tatgtatagg
 101 ctaccatgcc aacaactcaa ccgacactgt tgacacagta cttgagaaga
 151 atgtgacagt gacacactct gtcaacctac ttgaggacag tcacaatgga
 201 aaactatgtc tactaaaagg aatagcccca ctacaattgg gtaattgcag
 251 cgttgccgga tggatcttag gaaacccaga atgcgaatta ctgatttcca
 301 aggaatcatg gtcctacatt gtagaaacac caaatcctga gaatggaaca
 351 tgttacccag ggtatttcgc cgactatgag gaactgaggg agcaattgag
 401 ttcagtatct tcatttgaga gattcgaaat attccccaaa gaaagctcat
 451 ggcccaaaca caccgtaacc ggagtatcag catcatgctc ccataatggg
 501 aaaaacagtt tttacagaaa tttgctatgg ctgacgggga agaatggttt
 551 gtacccaaac ctgagcaagt cctatgtaaa caacaaagag aaagaagtcc
 601 ttgtactatg gggtgttcat cacccgccta acataggga ccaagggcc
 651 ctctatcata cagaaaatgc ttatgtctct gtagtgtctt cacattatag
 701 cagaagattc accccagaaa tagccaaaag acccaaagta agagatcagg
 751 aaggaagaat caactactac tggactctgc tggaacctgg ggatacaata
 801 atatttgagg caaatggaaa tctaatagcg ccatggtatg cttttgcact
 851 gagtagaggc tttggatcag gaatcatcac ctcaaatgca ccaatggatg
 901 aatgtgatgc gaagtgtcaa acacctcagg gagctataaa cagcagtctt
 951 cctttccaga atgtacaccc agtcacaata ggagagtgtc caagtatgt
1001 caggagtgca aaattgagga tggttacagg actaaggaac atcccatcca
1051 ttcaatccag aggtttgttt ggagccattg ccggtttcat tgaaggggg
1101 tggactgaa tggtagatgg gtggtatggt tatcatcatc agaatgagca
1151 aggatctggc tatgctgcag atcaaaaaag tacacaaaat gccattaacg
1201 ggattacaaa caaggtgaat ctgtaattg agaaaatgaa cactcaattc
1251 acagctgtgg gcaaagaatt caacaaattg gaaagaagga tggaaaactt
1301 aaataaaaaa gttgatgatg ggtttctaga catttggaca tataatgcag
1351 aattgttggt tctactggaa aatgaaagga ctttggattt ccatgactcc
1401 aatgtgaaga atctgtatga gaaagtaaaa agccaattaa agaataatgc
1451 caaagaaata ggaaacgggt gttttgaatt ctatcacaag tgtaacaatg
1501 aatgcatgga gagtgtgaaa atggaactt atgactatcc aaaatattcc
1551 gaagaatcaa agttaaacag ggagaaaatt gatggagtga aattggaatc
1601 aatgggagtc tatcagattc tggcgatcta ctcaactgtc gccagttccc
1651 tggttctttt ggtctccctg ggggcaatca gcttctggat gtgttccaat
1701 gggtctttgc agtgtagaat atgcatctga gaccagaatt tcagaagtat
1751 aagaaaaaac acccttgttt ctact
```

SEQ ID NO:53
Amino Acid Sequence of ca A/ New Caledonia /20/99 H1   Entire molecule length: 565 aa

```
   1 mkakllvllc tftatyadti cigyhannst dtvdtvlekn vtvthsvnll
  51 edshngklcl lkgiaplqlg ncsvagwilg npecellisk eswsyivetp
 101 npengtcypg yfadyeelre qlssvssfer feifpkessw pkhtvtgvsa
 151 scshngknsf yrnllwltgk nglypnlsks yvnnkekevl vlwgvhhppn
 201 igdqralyht enayvsvvss hysrrftpei akrpkvrdqe grinyywtll
 251 epgdtiifea ngnliapwya falsrgfgsg iitsnapmde cdakcqtpqg
 301 ainsslpfqn vhpvtigecp kyvrsaklrm vtglrnipsi qsrglfgaia
 351 gfieggwtgm vdgwygyhhq neqgsgyaad qkstqnaing itnkvnsvie
 401 kmntqftavg kefnklerrm enlnkkvddg fldiwtynae llvllenert
 451 ldfhdsnvkn lyekvksqlk nnakeigngc fefyhcnne cmesvkngty
 501 dypkyseesk lnrekidgvk lesmgvyqil aiystvassl vllvslgais
 551 fwmcsngslq crici
```

Figure 1T

SEQ ID NO:20
Nucleotide Sequence of ca A/New Caledonia/20/99 N1      Entire molecule length: 1463 bp

```
   1 agcaaaagca ggagtttaaa atgaatccaa atcaaaaat aataaccatt
  51 ggatcaatca gtatagcaat cggaataatt agtctaatgt tgcaaatagg
 101 aaatattatt tcaatatggg ctagtcactc aatccaaact ggaagtcaaa
 151 accacactgg agtatgcaac caaagaatca tcacatatga aaacagcacc
 201 tgggtgaatc acacatatgt taatattaac aacactaatg ttgttgctgg
 251 aaaggacaaa acttcagtga cattggccgg caattcatct ctttgttcta
 301 tcagtggatg ggctatatac acaaaagaca acagcataag aattggctcc
 351 aaaggagatg tttttgtcat aagagaacct ttcatatcat gttctcactt
 401 ggaatgcaga accttttttc tgacccaagg tgctctatta aatgacaaac
 451 attcaaatgg gaccgttaag gacagaagtc cttatagggc cttaatgagc
 501 tgtcctctag gtgaagctcc gtccccatac aattcaaagt ttaatcagt
 551 tgcatggtca gcaagcgcat gccatgatgg catgggctgg ttaacaatcg
 601 gaatttctgg tccagacaat ggagctgtgg ctgtactaaa atacaacggc
 651 ataataactg aaaccataaa aagttggaaa aagcgaatat taagaacaca
 701 agagtctgaa tgtgtctgtg tgaacgggtc atgtttcacc ataatgaccg
 751 atggcccgag taatgggcc gcctcgtaca aaatcttcaa gatcgaaaag
 801 gggaaggtta ctaaatcaat agagttgaat gcacccaatt ttcattatga
 851 ggaatgttcc tgttacccag acactggcac agtgatgtgt gtatgcaggg
 901 acaactggca tggttcaaat cgaccttggg tgtcttttaa tcaaaacctg
 951 gattatcaaa taggatacat ctgcagtggg gtgttcggtg acaatccgcg
1001 tcccaaagat ggagagggca gctgtaatcc agtgactgtt gatggagcag
1051 acggagtaaa ggggttttca tacaaatatg gtaatggtgt ttggatagga
1101 aggactaaaa gtaacagact tagaaagggg tttgagatga tttgggatcc
1151 taatggatgg acagataccg acagtgattt ctcagtgaaa caggatgttg
1201 tggcaataac tgattggtca gggtacagcg gaagtttcgt tcaacatcct
1251 gagttaacag gattggactg tataagacct tgcttctggg ttgagttagt
1301 cagaggactg cctagagaaa atacaacaat ctggactagt gggagcagca
1351 tttctttttg tggcgtaaat agtgatactg caaactggtc ttggccagac
1401 ggtgctgagt tgccgttcac cattgacaag tagttcgttg aaaaaaaact
1451 ccttgtttct act
```

SEQ ID NO:54
Amino Acid Sequence of ca A/New Caledonia/20/99 N1      Entire molecule length: 470 aa

```
   1 mnpnqkiiti gsisiaigii slmlqignii siwashsiqt gsqnhtgvcn
  51 qriityenst wvnhtyvnin ntnvvagkdk tsvtlagnss lcsisgwaiy
 101 tkdnsirigs kgdvfvirep fiscshlecr tffltqgall ndkhsngtvk
 151 drspyralms cplgeapspy nskfesvaws asachdgmgw ltigisgpdn
 201 gavavlkyng iitetikswk krilrtqese cvcvngscft imtdgpsnga
 251 asykifkiek gkvtksieln apnfhyeecs cypdtgtvmc vcrdnwhgsn
 301 rpwvsfnqnl dyqigyicsg vfgdnprpkd gegscnpvtv dgadvkgfs
 351 ykygngvwig rtksnrlrkg femiwdpngw tdtdsdfsvk qdvvaitdws
 401 gysgsfvqhp eltgldcirp cfwvelvrgl prenttiwts gssisfcgvn
 451 sdtanwswpd gaelpftidk
```

Figure 1U

SEQ ID NO:21
ca B/Ann Arbor/1/94
Nucleotide Sequence of ca B/Ann Arbor/1/94 HA    Entire molecule length: 1879 bp

```
   1 agcagaagca gagcattttc taatatccac aaaatgaagg caataattgt
  51 actactcatg gtagtaacat ccaacgcaga tcgaatctgc actgggataa
 101 catcttcaaa ctcacctcat gtggtcaaaa cagctactca agggggaagtc
 151 aatgtgactg gtgtgatacc actgacaaca acaccaacaa aatctcattt
 201 tgcaaatctc aaaggaacaa agaccagagg gaaactatgc ccaaactgtc
 251 tcaactgcac agatctggat gtggccttgg gcagaccaat gtgtataggg
 301 atcacacctt cggcaaaagc ttcaatactc cacgaagtca gacctgttac
 351 atccggggtgc tttcctataa tgcacgacag aacaaaaatc agacagctac
 401 ccaatcttct cagaggatat gaacatatca gattatcaac ccataacgtt
 451 atcaacgcag aaagggcacc aggaggaccc tacagacttg gaacctcagg
 501 atcttgccct aacgttacca gtagaagcgg attcttcgca acaatggctt
 551 gggctgtccc aagggacaac aaaacagcaa cgaacccact aacagtagaa
 601 gtaccataca tttgtacaaa aggagaagac caaattactg tttggggggtt
 651 ccattctgat aacaaaatcc aaatgaaaaa cctctatgga gactcaaatc
 701 ctcaaaagtt cacctcatct gccaatggaa taaccacaca ttatgtttct
 751 cagattggtg gcttcccaaa tcaaacagaa gacggagggc taccacaaag
 801 cggcagaatt gttgttgatt acatggtgca aaaacctggg aaaacaggaa
 851 caattgtcta tcaaagaggt gttttgttgc ctcaaaaggt gtggtgtgca
 901 agtggcagga gcaaggtaat aaaagggtcc ttgcctttaa ttggtgaagc
 951 agattgcctt cacgaaaaat acgtggatt aaacaaaagc aagccttact
1001 acacaggaga acatgcaaaa gccataggaa attgcccaat atgggtgaaa
1051 acacctttaa agcttgccaa tggaaccaaa tatagacctc ccgcaaaact
1101 attaaaggaa aagggtttct tcggagctat tgctggtttc ttagaaggag
1151 gatgggaagg aatgattgca ggttggcacg gatacacatc tcatggagca
1201 catggggtgg cagtggcagc agaccttaag agtacgcaag aagccataaa
1251 caagataaca aaaaatctca attctttgag tgagctagaa gtaaagaatc
1301 ttcaaagact aagtggtgcc atggatgaac tccacaacga aatactcgag
1351 ctggatgaga aagtggatga tctcagagct gacacaataa gctcgcaaat
1401 agagcttgca gtcttgcttt ccaatgaagg aataataaac agtgaagatg
1451 agcatctatt ggcacttgag agaaaactaa agaaaatgct gggtccctct
1501 gctgtagaca tagggaatgg atgcttcgaa accaaacaca gtgcaacca
1551 gacctgctta gacaggatag ctgctggcac ctttaatgca ggagaatttt
1601 ctcttcccac ttttgattca ctgaatatta ctgctgcatc tttaaatgat
1651 gatgattgg ataatcatac tatactgctc tactactcaa ctgcggcttc
1701 tagtttggct gtaacattga tgatagctat ttttattgtt tatatggtct
1751 ccagagacaa tgtttcttgc tccatctgtc tataggaaaa attgagccct
1801 gtattttcct ttattgtggt gcttgtttgc ttgttgccat tacagagaaa
1851 cgttattgaa aaatgctctt gttactact
```

SEQ ID NO:55
Amino Acid Sequence of ca B/Ann Arbor/1/94 HA    Entire molecule length: 583 aa

```
   1 mkaiivllmv vtsnadrict gitssnsphv vktatqgevn vtgvipltt
  51 ptkshfanlk gtktrgklcp nclnctdldv algrpmcigi tpsakasilh
 101 evrpvtsgcf pimhdrtkir qlpnllrgye hirlsthnvi naerapgqpy
 151 rlgtsgscpn vtsrsgffat mawavprdnk tatnpltvev pyictkgedq
 201 itvwgfhsdn kiqmknlygd snpqkftssa ngitthyvsq iggfpnqted
 251 gglpqsgriv vdymvqkpgk tgtivyqrgv llpqkvwcas grskvikgsl
 301 pligeadclh ekygglnksk pyytgehaka igncpiwvkt plklangtky
 351 rppakllkek gffgaiagfl eggwegmiag whgytshgah gvavaadlks
 401 tqeainkitk nlnslselev knlqrlsgam delhneilel dekvddlrad
 451 tissqielav llsnegiins edehllaler klkkmlgpsa vdigngcfet
 501 khkcnqtcld riaagtfnag efslptfdsl nitaaslndd gldnhtilly
 551 ystaasslav tlmiaifivy mvsrdnvscs icl
```

Figure 1V

SEQ ID NO:22

Nucleotide Sequence of ca B/Ann Arbor/1/94 NA Entire molecule length: 1554 bp

```
   1 agcagaagca gagcatcttc tcaaaactga agtaaagagg ccaaaaatga
  51 acaatgctac cttcaactat acaaacgtta accctatttc tcacatcagg
 101 gggagtgtta ttatcactat atgtgtcagc cttactgtca tacttattgt
 151 attcggatat attgctaaaa ttttcaccaa aaataattgc accaacaacg
 201 tcgttggact gcgcgaacgc atcaaatgtt caggctgtga accattctgc
 251 aacaaaagag atgaaattcc ttcccccaga accggagtgg acatacccc
 301 gtttatcttg ccagggttca accttccaga aagcactctt aattagccct
 351 catagatttg gagaagccaa aggaaactca gctcccttga taataaggga
 401 accttttatt gcttgtggac caaaggagtg caaacacttt gctctaaccc
 451 attatgcagc tcaaccaggg ggatactaca atggaacaag agaggacaga
 501 aacaagctga ggcatctgat ttcagtcaac ttaggcaaaa tcccaactgt
 551 agaaaactcc attttccata tggcagcttg gagtggatcc gcatgccatg
 601 atggtagaga atggacatat atcggagttg atggtcctga cagtaatgca
 651 ttgatcaaaa taaaatatgg agaagcatac actgacacat accattccta
 701 tgcaaacaac atcctaagaa cacaagaaag tgcctgcaat tgcatcgggg
 751 gagattgtta tcttatgata actgatggct cagcttcagg aattagtaaa
 801 tgcagattcc ttaagatccg agagggtcga ataataaaag aaatatttcc
 851 aacaggaagg gtagagcaca ctgaagaatg cacatgcgga tttgccagca
 901 acaaaaccat agaatgtgcc tgtagagata acagttacac agcaaaaaga
 951 ccctttgtca aattaaatgt ggagactgat acagctgaaa taagattgat
1001 gtgcacagag acttatttgg acacccccag accagatgat ggaagcataa
1051 cagggccttg cgaatctaat ggggacaaag ggagtggagg tgtcaaggga
1101 ggatttgttc atcaaagaat ggcatccaag attggaagat ggtactcccg
1151 aacgatgtct aaaactaaaa gaatggggat ggaactgtat gtcaagtatg
1201 atggagaccc atggactgac agtgacgccc ttgctcctag tggagtaatg
1251 gtctcaatgg aagaacctgg ttggtactct ttcggcttcg aaataaaaga
1301 taagaaatgt gatgtcccct gtattgggat agagatggta catgatggtg
1351 gaaaaaggac ttggcactca gcagcaacag ccatttactg tttaatgggc
1401 tcaggacagt tgctatggga cactgtcaca ggtgttaata tggctctgta
1451 atggaggaat ggttgaatct gttctaaacc ctttgttcct attttatttg
1501 aacaattgtc cttactggac ttaattgttt ctgaaaaatg ctcttgttac
1551 tact
```

SEQ ID NO:56

Amino Acid Sequence of ca B/Ann Arbor/1/94 NA Entire molecule length: 465 aa

```
   1 mlpstiqtlt lfltsggvll slyvsallsy llysdillkf spkiiaptts
  51 ldcanasnvq avnhsatkem kflppepewt yprlscqgst fqkallisph
 101 rfgeakgnsa pliirepfia cgpkeckhfa lthyaaqpgg yyngtredrn
 151 klrhlisvnl gkiptvensi fhmaawsgsa chdgrewtyi gvdgpdsnal
 201 ikikygeayt dtyhsyanni lrtqesacnc iggdcylmit dgsasgiskc
 251 rflkiregri ikeifptgrv ehteectcgf asnktiecac rdnsytakrp
 301 fvklnvetdt aeirlmctet yldtprpddg sitgpcesng dkgsggvkgg
 351 fvhqrmaski grwysrtmsk tkrmgmelyv kydgdpwtds dalapsgvmv
 401 smeepgwysf gfeikdkkcd vpcigiemvh dggkrtwhsa ataiyclmgs
 451 gqllwdtvtg vnmal
```

Figure 1W

SEQ ID NO:23
ca B/Yamanashi/166/98
Nucleotide Sequence of ca B/Yamanashi/166/98 HA          Entire molecule length: 1881 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcacctcat gtggtcaaaa cagctactca agggaggtc
 151 aatgtgactg gtgtgatacc actgacaaca acaccaacaa atctcatttt
 201 tgcaaatctc aaaggaacaa agaccagagg gaaactatgc ccaacctgtc
 251 tcaactgcac agatctggat gtggccttag gcagaccaat gtgtgtgggg
 301 gtcacacctt cggcaaaagc ttcaatactc cacgaagtca ggcctgttac
 351 atccggatgc tttcctataa tgcacgacag aacaaaaatc agacagctac
 401 ccaatcttct cagaggatat gaaaaaatca gattatcaac ccaaatcgtt
 451 atcaacgcag aaaaggcacc aggaggaccc tacagacttg gaacctcagg
 501 atcttgccct aacgctacca gtagaagcgg attttctgca acaatggctt
 551 gggctgtccc aaaggacaac aacaaaacag caacgaatcc actaacagta
 601 gaagtaccac acatctgtac aaaagaagaa gaccaaatta ctgtttgggg
 651 gttccattct gatgacaaaa cccaaatgaa aaacctctat ggagactcaa
 701 atcctcaaaa gttcacctca tctgctaatg gagtaaccac acattatgtt
 751 tctcagattg gcggcttccc ggatcaaaca gaagacggag ggctaccaca
 801 aagcggcaga attgttgttg attacatggt gcaaaaacct gggaaaacag
 851 gaacaattgt ctatcaaaga ggtattttgt tgcctcaaaa ggtgtggtgc
 901 gcgagtggca ggagcaaagt aataaaaggg tccttgcctt taattggtga
 951 agcagattgc cttcacgaaa aatacggtgg attaaacaaa agcaagcctt
1001 actacacagg agaacatgca aaagccatag aaattgccc aatatgggtg
1051 aaaacacctt tgaagcttgc caatggaacc aaatatagac tcctgcaaa
1101 actattaaag gaaaggggtt tcttcggagc tattgctggt ttcttagaag
1151 gaggatggga aggaatgatt gcaggttggc acggatacac atctcacgga
1201 gcacatggag tggcagtggc agcagacctt aagagtacgc aagaagccat
1251 aaacaagata acaaaaaatc tcaattcttt gagtgagcta gaagtaaaga
1301 atcttcaaag actaagtggt gccatggatg aactccacaa cgaaatactc
1351 gagctggatg agaaagtgga tgatctcaga gctgacacaa taagctcaca
1401 aatagaactt gcagtcttgc tttccaacga aggaataata aacagtgaag
1451 atgagcatct attggcactt gagagaaaac taaagaaaat gctgggtccc
1501 tctgctgtag acatagggaa tggatgcttc gaaccaaac acaagtgcaa
1551 ccagacctgc ttagacagga tagctgctgg cacctttaat gcaggagaat
1601 tttctcttcc cactttgat tcactgaata ttactgctgc atctttaaat
1651 gatgatggat tggataacca tactatactg ctctactact caactgctgc
1701 ttctagtttg gctgtaacat tgatgatagc tatttttatt gtttatatga
1751 tctccagaga caatgtttct tgctccatct gtctataggg aaattaagcc
1801 ctgtattttc ctttattgta gtgcttgttt gcttgttatc attacaaaga
1851 aacgttattg aaaaatgctc ttgttactac t
```

SEQ ID NO:57
Amino Acid Sequence of ca B/Yamanashi/166/98 HA          Entire molecule length: 584 aa

```
  1 mkaiivllmv vtsnadrict gitssnsphv vktatqgevn vtgvipltt
 51 ptkshfanlk gtktrgklcp tclnctdldv algrpmcvgv tpsakasilh
101 evrpvtsgcf pimhdrtkir qlpnllrgye kirlstqivi naekapgpy
151 rlgtsgscpn atsrsgffat mawavpkdnn ktatnpltve vphictkeed
201 qitvwgfhsd dktqmknlyg dsnpqkftss angvtthyvs qiggfpdqte
251 dgglpqsgri vvdymvqkpg ktgtivyqrg illpqkvwca sgrskvikgs
301 lpligeadcl hekygglnks kpyytgehak aigncpiwvk tplklangtk
351 yrppakllke rgffgaiagf leggwegmia gwhgytshga hgvavaadlk
401 stqeainkit knlnslsele vknlqrlsga mdelhneile ldekvddlra
451 dtissqiela vllsnegiin sedehllale rklkkmlgps avdigngcfe
501 tkhkcnqtcl driaagtfna gefslptfds lnitaaslnd dgldnhtill
551 yystaassla vtlmiaifiv ymisrdnvsc sicl
```

Figure 1X

SEQ ID NO:24
Nucleotide Sequence of ca B/Yamanashi/166/98 NA  Entire molecule length: 1557 bp

```
   1 agcagaagca gagcatcttc tcaaaactga ggcaaatagg ccaaaaatga
  51 acaatgctac cttcaactat acaaacgtta accctatttc tcacatcagg
 101 gggagtgtta ttatcactat atgtgtcagc ttcactgtca tacttactat
 151 attcggatat attgctaaaa ttttcaccaa cagaaataac tgcaccaaca
 201 atgccattga attgtgcaaa cgcatcaaat gttcaggctg tgaaccgttc
 251 tgcaacaaaa ggggtgacac ttcctctccc agaaccggag tggacatacc
 301 ctcgtttatc ttgcccgggc tcaaccttte agaaagcact cctaattagc
 351 cctcatagat cggagaaac caaggaaac tcagctccct tgataataag
 401 ggaaccttt attgcttgtg gaccaaagga atgcagacac tttgctctaa
 451 cccattatgc agcccaacca ggggatact acaatggaac aagagaagac
 501 agaaacaagc tgaggcatct aatttcagtc aaattgggca aatcccaac
 551 agtagaaaac tccattttcc acatggcagc ttggagcggg tccgcatgcc
 601 atgatggtag agaatggaca tatatcggag ttgatggccc tgacagtaat
 651 gcattgctca aaataaaata tggagaagca tatactgaca cataccattc
 701 ctatgcaaac aacatcctaa gaacacaaga aagtgcctgc aattgcatcg
 751 ggggagattg ttatcttatg ataactgatg gctcagcttc agggattagt
 801 gaatgcagat tcttaagat cgagagggc cgaataataa aagaaatatt
 851 tccaacagga agagtagaac atactgaaga atgcacatgc ggatttgcca
 901 gcaataaaac catagaatgt gcctgtagag ataacagtta cacagcaaaa
 951 agaccctttg tcaaattaaa tgtggagact gatacagcag aaataagatt
1001 gatgtgcaca gagacttact tggacacccc cagaccagat gatggaagca
1051 taacagggcc ttgtgaatct aatggggata agggagtgg aggcatcaag
1101 ggaggatttg ttcatcaaag aatggcatcc aagattggaa ggtggtactc
1151 tcgaacgatg tctaaaacta aaaggatggg gatgggactg tatgtcaagt
1201 atgatggaga cccatggatt gacagtgatg cccttactct agcggagta
1251 atggtttcaa tggaagaacc tggttggtat ccttttggct cgaaataaa
1301 agataagaaa tgtgatgtcc cctgtattgg gatagagatg gtacatgatg
1351 gtggaaagaa gacttggcac tcagcagcaa cagccattta ctgtttaatg
1401 ggctcaggac aactgctatg ggacactgtc acaggcgttg atatggctct
1451 gtaatggagg aatggttgag tctgttctaa accctttgtt cctattttgt
1501 ttgaacaatt gtccttactg aacttaattg tttctgaaaa atgctcttgt
1551 tactact
```

SEQ ID NO:58
Amino Acid Sequence of ca B/Yamanashi/166/98 NA    Entire molecule length: 466 aa

```
   1 mlpstiqtlt lfltsggvll slyvsaslsy llysdillkf spteitaptm
  51 plncanasnv qavnrsatkg vtlplpepew typrlscpgs tfqkallisp
 101 hrfgetkgns apliirepfi acgpkecrhf althyaaqpg gyyngtredr
 151 nklrhlisvk lgkiptvens ifhmaawsgs achdgrewty igvdgpdsna
 201 llkikygeay tdtyhsyann ilrtqesacn ciggdcylmi tdgsasgise
 251 crflkiregr iikeifptgr vehteectcg fasnktieca crdnsytakr
 301 pfvklnvetd taeirlmcte tyldtprpdd gsitgpcesn gdkgsggikg
 351 gfvhqrmask igrwysrtms ktkrmgmgly vkydgdpwid sdaltlsgvm
 401 vsmeepgwys fgfeikdkkc dvpcigiemv hdggkktwhs aataiyclmg
 451 sgqllwdtvt gvdmal
```

Figure 1Y

SEQ ID NO:25
ca B/Johannesburg/5/99
Nucleotide Sequence of ca_B_Johannesburg_5_99_HA       Entire molecule length: 1882 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcacctcat gtggtcaaaa cagctactca aggggaggtc
 151 aatgtgactg gtgcgatacc attgacaaca acaccaacaa aatctcattt
 201 tgcaaatctc aaaggaacaa agaccagagg gaaactatgc ccaacctgtc
 251 tcaactgcac agatctggat gtggccttgg cagaccaat gtgtgtgggg
 301 atcacacctt cggcaaaagc ttcaatactc cacgaagtca gacctgttac
 351 atccggatgc tttcctataa tgcacgacag aacaaaaatc agacagctac
 401 ccaatcttct cagaggatat gaaaaaatca gattatcaac ccaaaacgtt
 451 atcaacgcag aaaaggcacc aggaggaccc tacagacttg aacttcagg
 501 atcttgccct aacgctacca gtaaaagcgg attttcgca acaatggctt
 551 gggctgtccc aagggacaac aacaaaacag caacgaatcc actaacagta
 601 gaagtaccac acatctgtac aaaagaagaa gaccaaatta ctgtttgggg
 651 gttccattct gatgacaaaa cccaaatgaa aaacctctat ggagactcaa
 701 atcctcaaaa gttcacctca tctgctaatg gaataaccac acattatgtt
 751 tctcagattg gcggcttccc ggaccaaaca gaagacggag ggctaccaca
 801 aagcggcaga attgttgttg attacatggt gcaaaaacct gggaaaacag
 851 gaacaattgt ctatcaaaga gggatcttgt gcctcaaaa ggtgtggtgc
 901 gcgagtggca ggagcaaagt aataaaaggg tccttgcctt taattggtga
 951 agcagattgc cttcacgaaa atacggtgg attaaacaaa agcaagcctt
1001 actacacagg agaacatgca aaagccatag gaattgccc aatatgggtg
1051 aaaacacctt tgaagcttgc caatggaacc aagtatagac ctcctgcaaa
1101 actattaaag gaaaggggtt tcttcggagc tattgctggt ttcttagaag
1151 gaggatggga aggaatgatt gcaggttggc acggatacac atctcacgga
1201 gcacacggag tggcagtggc agcagacctt aagagtacgc aagaagccat
1251 aaacaagata acaaaaaatc tcaattcttt gagtgagtta gaagtaaaga
1301 accttcaaag actaagtggt gccatggatg aactccataa cgaaatactc
1351 gagctgaatg agaaagtgga tgatctcaga gctgacacaa taagctcaca
1401 aatagaactt gcagtcttgc tttccaacga aggaataata aacagtgaag
1451 atgagcatct attggcactt gagagaaaac taaagaagat gctgggtccc
1501 tctgctatag acataggaa tggatgcttc gaaaccaaac acaagtgcaa
1551 ccagacctgc ttagacagga tagctgctgg caccttaat gcaggagaat
1601 tttctcttcc cacttttgat tcactgaaca ttactgctgc atctttaaat
1651 gatgatggat tggataacca tactatactg ctctactact caactgctgc
1701 ttctagtttg gctgtaacat tgatgatagc tatttttatt gtttatatga
1751 tctccagaga caatgtttct tgctccatct gtctataagg aaaattaagc
1801 cctgtatttt cctttattgt agtgcttgtt tgcttgttat cattacaaag
1851 aaacgttatt gaaaaatgct cttgttacta ct
```

SEQ ID NO:59
Amino Acid Sequence of ca_B_Johannesburg_5_99_HA       Entire molecule length: 584 aa

```
   1 mkaiivllmv vtsnadrict gitssnsphv vktatqgevn vtgaiplttt
  51 ptkshfanlk gtktrgklcp tclnctdldv algrpmcvgi tpsakasilh
 101 evrpvtsgcf pimhdrtkir qlpnllrgye kirlstqnvi naekapgpy
 151 rlgtsgscpn atsksgffat mawavprdnn ktatnpltve vphictkeed
 201 qitvwgfhsd dktqmknlyg dsnpqkftss angitthyvs qiggfpdqte
 251 dgglpqsgri vvdymvqkpg ktgtivyqrg illpqkvwca sgrskvikgs
 301 lpligeadcl hekygglnks kpyytgehak aigncpiwvk tplklangtk
 351 yrppakllke rgffgaiagf leggwegmia gwhgytshga hgvavaadlk
 401 stqeainkit knlnslsele vknlqrlsga mdelhneile ldekvddlra
 451 dtissqiela vllsnegiin sedehllale rklkkmlgps aidigngcfe
 501 tkhkcnqtcl driaagtfna gefslptfds lnitaaslnd dgldnhtill
 551 yystaassla vtlmiaifiv ymisrdnvsc sicl
```

Figure 1Z

SEQ ID NO:26

Nucleotide Sequence of ca B_Johannesburg_5_99_NA          Entire molecule length: 1557 bp

```
   1 agcagaagca gagcatcttc tcaaaactga ggcaaatagg ccaaaaatga
  51 acaatgctac cctcaactat acaaacgtta accctattcc tcacatcagg
 101 gggagtgtta ttatcactat atgtgtcagc ttcactgtca tacttactat
 151 attcggatat attgctaaaa ttttcaccaa cagaaataac tgcaccagca
 201 atgcccttgg attgtgcaaa cgcatcaaat gttcaggctg tgaaccgttc
 251 tgcaacaaaa ggggtgacac ttcttctccc agaaccggag tggacatacc
 301 cgcgtttatc ttgcccgggc tcaacctttc agaaagcact cctaattagc
 351 cctcatagat tcggagaaac caaaggaaac tcagctccct tgataataag
 401 ggaacctttt attgcttgtg gaccaaagga atgcaaacac tttgctctaa
 451 cccattatgc agcccaacca ggggatact acaatggaac aagagaagac
 501 agaaacaagc taaggcatct aatttcagtc aaatttggta aatcccaac
 551 agtagaaaac tccattttcc acatggcagc atggagcggg tccgcatgcc
 601 atgatggtaa agaatggaca tatatcggag ttgatggccc tgacagtaat
 651 gcattgctca aaataaaata tggagaagca tatactgaca cataccattc
 701 ctatgcaaac aacatcctaa gaacacaaga aagtgcctgc aattgcatcg
 751 ggggaaattg ttatcttatg ataactgatg gctcagcttc aggtattagt
 801 gagtgcagat ttcttaagat tcgagagggc cgaataataa agaaatatt
 851 tccaacagga agagtaaaac atactgaaga atgcacatgc ggatttgcca
 901 gcaataaaac catagaatgt gcctgtagag ataacagtta cacagcaaaa
 951 agaccctttg tcaaattaaa tgtggagact gatacagcag aaataagatt
1001 gatgtgcaca gagacttatt ggacaccccc cagaccagat gatggaagca
1051 taacagggcc ttgtgaatct aatggggata aagggagtgg aggcatcaag
1101 ggaggatttg ttcatcaaag aatggcatcc aagattggaa ggtggtactc
1151 tcgaacaatg tctaaaacta aaaggatggg gatgggactg tatgtcaagt
1201 atgatggaga cccatggact gacagtgatg cccttgctct tagtggagta
1251 atggtttcaa tggaagaacc tggttggtac tcctttggct tcgaaataaa
1301 agataagaaa tgtgatgtcc cctgtattgg gatagagatg gtacatgatg
1351 gtggaaagga gacttggcac tcagcagcaa cagccattta ctgtttaatg
1401 ggctcaggac aactgctatg gacactgtc acaggtgttg atatggctct
1451 gtaatggagg aatggttgag tctgttctaa acccttgtt cctattttgt
1501 ttgaacaatt gtccttactg aacttaattg tttctgaaaa atgctcttgt
1551 tactact
```

SEQ ID NO:60

Amino Acid Sequence of ca B_Johannesburg_5_99_NA          Entire molecule length: 466 aa

```
   1 mlpstiqtlt lfltsggvll slyvsaslsy llysdillkf spteitapam
  51 pldcanasnv qavnrsatkg vtlllpepew typrlscpgs tfqkallisp
 101 hrfgetkgns apliirepfi acgpkeckhf althyaaqpg gyyngtredr
 151 nklrhlisvk fgkiptvens ifhmaawsgs achdgkewty igvdgpdsna
 201 llkikygeay tdtyhsyann ilrtqesacn ciggncylmi tdgsasgise
 251 crflkiregr iikeifptgr vkhteectcg fasnktieca crdnsytakr
 301 pfvklnvetd taeirlmcte tyldtprpdd gsitgpcesn gdkgsggikg
 351 gfvhqrmask igrwysrtms ktkrmgmgly vkydgdpwtd sdalalsgvm
 401 vsmeepgwys fgfeikdkkc dvpcigiemv hdggketwhs aataiyclmg
 451 sgqllwdtvt gvdmal
```

Figure 1AA
SEQ ID NO:27
ca B/Victoria/504/2000
Nucleotide Sequence of ca B/Victoria/504/2000 HA Entire molecule length: 1879 bp

```
   1 agcagaagca gagcattttc taatatccac aaaatgaagg caataattgt
  51 actactcatg gtagtaacat ccaacgcaga tcgaatctgc actgggataa
 101 catcttcaaa ctcacctcat gtggtcaaaa cagctactca aggggaagtc
 151 aatgtgactg gtgtgatacc actgacaaca acaccaacaa aatctcattt
 201 tgcaaatctc aaaggaacaa agaccagagg gaaactatgc ccaaactgtc
 251 tcaactgcac agatctggat gtggccttgg gcagaccaat gtgtataggg
 301 atcacacctt cggcaaaagc ttcaatactc cacgaagtca gacctgttac
 351 atccgggtgc tttcctataa tgcacgacag aacaaaaatc agacagctac
 401 ccaatcttct cagaggatat gaacatatca gattatcaac ccataacgtt
 451 atcaacgcag aaagggcacc aggaggaccc tacagacttg gaacctcagg
 501 atcttgccct aacgttacca gtagaagcgg attcttcgca acaatggctt
 551 gggctgtccc aagggacaac aaaacagcaa cgaacccact aacagtagaa
 601 gtaccataca tttgtacaaa aggagaagac caaattactg tttggggttt
 651 ccattctgat aacaaaatcc aaatgaaaaa cctctatgga gactcaaatc
 701 ctcaaaagtt cacctcatct gccaatggaa taaccacaca ttatgtttct
 751 cagattggtg gcttcccaaa tcaaacagaa gacggagggc taccacaaag
 801 cggcagaatt gttgttgatt acatggtgca aaaacctggg aaaacaggaa
 851 caattgtcta tcaaagaggt gttttgttgc ctcaaaaggt gtggtgtgca
 901 agtggcagga gcaaggtaat aaaagggtcc ttgcctttaa ttggtgaagc
 951 agattgcctt cacgaaaaat acggtggatt aaacaaaagc aagccttact
1001 acacaggaga acatgcaaaa gccataggaa attgcccaat atgggtgaaa
1051 acacctttaa agcttgccaa tggaaccaaa tatagacctc ccgcaaaact
1101 attaaaggaa aagggtttct tcggagctat tgctggtttc ttagaaggag
1151 gatgggaagg aatgattgca ggttggcacg gatacacatc tcatggagca
1201 catggggtgg cagtggcagc agaccttaag agtacgcaag aagccataaa
1251 caagataaca aaaaatctca attctttgag tgagctagaa gtaaagaatc
1301 ttcaaagact aagtggtgcc atggatgaac tccacaacga aatactcgag
1351 ctggatgaga aagtggatga tctcagagct gacacaataa gctcgcaaat
1401 agagcttgca gtcttgcttt ccaatgaagg aataataaac agtgaagatg
1451 agcatctatt ggcacttgag agaaaactaa agaaaatgct gggtccctct
1501 gctgtagaca tagggaatgg atgcttcgaa accaaacaca agtgcaacca
1551 gacctgctta gacaggatag ctgctggcac ctttaatgca ggagaatttt
1601 ctcttcccac ttttgattca ctgaatatta ctgctgcatc tttaaatgat
1651 gatggattgg ataatcatac tatactgctc tactactcaa ctgcggcttc
1701 tagtttggct gtaacattga tgatagctat ttttattgtt tatatggtct
1751 ccagagacaa tgtttcttgc tccatctgtc tatagggaaa attgagccct
1801 gtattttcct ttattgtggt gcttgtttgc ttgttgccat tacagagaaa
1851 cgttattgaa aaatgctctt gttactact
```

SEQ ID NO:61

Amino Acid Sequence of ca B/Victoria/504/2000 HA Entire molecule length: 583 aa

```
   1 mkaiivllmv vtsnadrict gitssnsphv vktatqgevn vtgviplttt
  51 ptkshfanlk gtktrgklcp nclnctdldv algrpmcigi tpsakasilh
 101 evrpvtsgcf pimhdrtkir qlpnllrgye hirlsthnvi naerapggpy
 151 rlgtsgscpn vtsrsgffat mawavprdnk tatnpltvev pyictkgedq
 201 itvwgfhsdn kiqmknlygd snpqkftssa ngitthyvsq iggfpnqted
 251 gglpqsgriv vdymvqkpgk tgtivyqrgv llpqkvwcas grskvikgsl
 301 pligeadclh ekygglnksk pyytgehaka igncpiwvkt plklangtky
 351 rppakllkek gffgaiagfl eggwegmiag whgytshgah gvavaadlks
 401 tqeainkitk nlnslselev knlqrlsgam delhneilel dekvddlrad
 451 tissqielav llsnegiins edehllaler klkkmlgpsa vdigngcfet
 501 khkcnqtcld riaagtfnag efslptfdsl nitaaslndd gldnhtilly
 551 ystaasslav tlmiaifivy mvsrdnvscs icl
```

Figure 1BB

SEQ ID NO:28

Nucleotide Sequence of ca B/Victoria/504/2000 NA     Entire molecule length: 1554 bp

```
   1 agcagaagca gagcatcttc tcaaaactga agtaaagagg ccaaaaatga
  51 acaatgctac cttcaactat acaaacgtta accctatttc tcacatcagg
 101 gggagtgtta ttatcactat atgtgtcagc cttactgtca tacttattgt
 151 attcggatat attgctaaaa ttttcaccaa aataattgc accaacaacg
 201 tcgttggact gcgcgaacgc atcaaatgtt caggctgtga accattctgc
 251 aacaaaagag atgaaattcc ttcccccaga accggagtgg acatacccc
 301 gtttatcttg ccagggttca accttccaga aagcactctt aattagccct
 351 catagatttg gagaagccaa aggaaactca gctcccttga taataaggga
 401 acctttatt gcttgtggac caaaggagtg caaacactt gctctaaccc
 451 attatgcagc tcaaccaggg ggatactaca atggaacaag agaggacaga
 501 aacaagctga ggcatctgat ttcagtcaac ttaggcaaaa tcccaactgt
 551 agaaaactcc attttccata tggcagcttg gagtggatcc gcatgccatg
 601 atggtagaga atggacatat atcggagttg atggtcctga cagtaatgca
 651 ttgatcaaaa taaatatgg agaagcatac actgacacat accattccta
 701 tgcaaacaac atcctaagaa cacaagaaag tgcctgcaat tgcatcgggg
 751 gagattgtta tcttatgata actgatggct cagcttcagg aattagtaaa
 801 tgcagattcc ttaagatccg agagggtcga ataataaaag aaatatttcc
 851 aacaggaagg gtagagcaca ctgaagaatg cacatgcgga tttgccagca
 901 acaaaaccat agaatgtgcc tgtagagata cagttacac agcaaaaaga
 951 ccctttgtca aattaaatgt ggagactgat acagctgaaa taagattgat
1001 gtgcacagag acttatttgg acacccccag accagatgat ggaagcataa
1051 cagggcctg cgaatctaat ggggacaaag ggagtggagg tgtcaaggga
1101 ggatttgttc atcaaagaat ggcatccaag attggaagat ggtactcccg
1151 aacgatgtct aaaactaaaa gaatggggat ggaactgtat gtcaagtatg
1201 atggagaccc atggactgac agtgacgccc ttgctcctag tggagtaatg
1251 gtctcaatgg aagaacctgg ttggtactct ttcggcttcg aaataaaaga
1301 taagaaatgt gatgtcccct gtattgggat agagatggta catgatggtg
1351 gaaaaaggac ttggcactca gcagcaacag ccatttactg tttaatgggc
1401 tcaggacagt tgctatggga cactgtcaca ggtgttaata tggctctgta
1451 atggaggaat ggttgaatct gttctaaacc ctttgttcct attttatttg
1501 aacaattgtc cttactggac ttaattgttt ctgaaaaatg ctcttgttac
1551 tact
```

SEQ ID NO:62

Amino Acid Sequence of ca B/Victoria/504/2000 NA     Entire molecule length: 465 aa

```
   1 mlpstiqtlt lfltsggvll slyvsallsy llysdillkf spkiiaptts
  51 ldcanasnvq avnhsatkem kflppepewt yprlscqgst fqkallisph
 101 rfgeakgnsa pliirepfia cgpkeckhfa lthyaaqpgg yyngtredrn
 151 klrhlisvnl gkiptvensi fhmaawsgsa chdgrewtyi gvdgpdsnal
 201 ikikygeayt dtyhsyanni lrtqesacnc iggdcylmit dgsasgiskc
 251 rflkiregri ikeifptgrv ehteectcgf asnktiecac rdnsytakrp
 301 fvklnvetdt aeirlmctet yldtprpddg sitgpcesng dkgsggvkgg
 351 fvhqrmaski grwysrtmsk tkrmgmelyv kydgdpwtds dalapsgvmv
 401 smeepgwysf gfeikdkkcd vpcigiemvh dggkrtwhsa ataiyclmgs
 451 gqllwdtvtg vnmal
```

Figure 1CC

SEQ ID NO:29
ca B/Hong Kong/330/01
Nucleotide Sequence of ca B/Hong Kong/330/01 HA Entire molecule length: 1885 bp

```
   1 agcagaagca gagcattttc taatatccac aaaatgaagg caataattgt
  51 actactcatg gtagtaacat ccaatgcaga tcgaatctgc actggaataa
 101 catcgtcaaa ctcaccccat gtggtcaaaa ctgctactca aggggaagtc
 151 aatgtgactg gtgtgatacc actgacaaca acacccacca aatctcattt
 201 tgcaaatctc aaaggaacaa aaaccagagg gaaactatgc ccaaaatgtc
 251 tcaactgcac agatctggac gtggccttgg gcagaccaaa atgcacgggg
 301 aacatacctt cggcaaaagt ttcaatactc catgaagtaa gacctgttac
 351 atctgggtgc tttcctataa tgcacgacag aacaaaaatt agacagctgc
 401 ccaatcttct cagaggatac gaacgtatca ggttatcaaa ccataacgtt
 451 atcaatgcag aaaaagcacc aggaggaccc tacaaaattg gaacctcagg
 501 gtcttgccct aacgttacca atggaaacgg attcttcgca acaatggctt
 551 gggctgtccc aaaaaacgaa aacaacaaaa cagcaacaaa ttcattaaca
 601 atagaagtac catacatttg tacagaagga gaagaccaaa ttaccgtttg
 651 ggggttccac tctgatagcg aaacccaaat ggcaaaactc tatggagact
 701 caaagcctca gaagttcact tcatctgcta acggagtgac cacacattac
 751 gtttcacaga ttggtggctt cccaaatcaa acagaagacg gaggactacc
 801 acaaagtggt agaattgttg ttgattacat ggtgcaaaaa tctggaaaaa
 851 caggaacaat tacctatcaa agaggtattt tattgcctca aaaagtgtgg
 901 tgcgcaagtg gcaggagcaa ggtaataaaa ggatccttgc ctttaattgg
 951 agaagcagat tgcctccacg aaaaatacgg tggattaaac aaaagcaagc
1001 cttactatac aggggaacat gcaaaagcca taggaaattg cccaatatgg
1051 gtgaaaacac ccttgaagct ggccaatgga accaaatata gacctcctgc
1101 aaaactatta aaggaaaggg gtttcttcgg agctattgct ggtttcttag
1151 aaggaggatg ggaaggaatg attgcaggtt ggcacggata cacatcccat
1201 ggagcacatg gagtagcagt ggcagcagac cttaagagta ctcaagaagc
1251 cataaacaag atcacaaaaa atctcaactc tttgagtgag ctggaagtaa
1301 agaatcttca aagactaagc ggagccatgg atgaactcca caacgaaata
1351 ctagaactag atgagaaagt ggatgatctc agagctgata caataagctc
1401 gcaaatagaa ctcgcagtct tgctttccaa tgaaggaata ataaacagtg
1451 aagatgagca tctcttggcg cttgaaagaa aactgaagaa aatgctgggc
1501 ccctctgctg tagagatagg gaatggatgc ttcgaaacca aacacaagtg
1551 caaccagacc tgcctcgata gaatagctgc tggcaccttt aatgcaggag
1601 aattttctct ccccaccttt gattcactaa atattactgc tgcatcttta
1651 aatgacgatg gattggataa tcatactata ctgctttact actcaactgc
1701 tgcttccagt ttggctgtaa cattgatgat agctatcttt gttgtttata
1751 tggtctccag agacaatgtt tcttgttcca tctgtctata aggaaagtta
1801 agccccgtat tttcctttat tgtagtactt gtttgcttgt tatcattaca
1851 aaaaaacgtt attgaaaaat gctcttgtta ctact
```

SEQ ID NO:63

Amino Acid Sequence of ca B/Hong Kong/330/01 HA Entire molecule length: 585 aa

```
   1 mkaiivllmv vtsnadrict gitssnsphv vktatqgevn vtgviplttt
  51 ptkshfanlk gtktrgklcp kclnctdldv algrpkctgn ipsakvsilh
 101 evrpvtsgcf pimhdrtkir qlpnllrgye rirlsnhnvi naekapggpy
 151 kigtsgscpn vtngngffat mawavpknen nktatnslti evpyictege
 201 dqitvwgfhs dsetqmakly gdskpqkfts sangvtthyv sqiggfpnqt
 251 edgglpqsgr ivvdymvqks gktgtityqr gillpqkvwc asgrskvikg
 301 slpligeadc lhekygglnk skpyytgeha kaigncpiwv ktplklangt
 351 kyrppakllk ergffgaiag fleggwegmi agwhgytshg ahgvavaadl
 401 kstqeainki tknlnslsel evknlqrlsg amdelhneil eldekvddlr
 451 adtissqiel avllsnegii nsedehllal erklkkmlgp saveigngcf
 501 etkhkcnqtc ldriaagtfn agefslptfd slnitaasln ddgldnhtil
 551 lyystaassl avtlmiaifv vymvsrdnvs csicl
```

Figure 1DD

SEQ ID NO:30
Nucleotide Sequence of ca B/Hong Kong/330/01 NA Entire molecule length: 1544 bp

```
   1 agcagagcat cttctcaaaa ctgaagcaaa taggccaaaa tgaacaatgc
  51 taccctcaac tatacaaaca ttaaccctat ttctcacatc aggggagtg
 101 ttattatcac tatatgtgtc agccttactg tcatacttac tgtattcgga
 151 tatattgcta aaattttcac caacaaaat aattgcacca caacgtcgt
 201 tggactccgc gaacgcatca aatttcagg ccgtgaacca ttctgcaaca
 251 aaagagatga catttcttct cccagaaccg gagtggacat accctcgttt
 301 atcttgccag ggttcaacct ttcaaaaagc actcctaatt agccctcata
 351 gattcggaga agccaaagga aactcagctc ccttgataat aagggaacct
 401 tttattgctt gtggaccaaa ggagtgtaaa cactttgctc taacccatta
 451 tgcagctcaa ccaggggat actacaatgg aacaagagag gacagaaaca
 501 agctgaggca tctgatttca gtcaacttag gcaaaatacc aactgtagaa
 551 aactccattt tccacatggc agcttggagt gggtccgcat gccatgatgg
 601 tagagagtgg acttatatcg gagttgatgg ccctgacagt aatgcattga
 651 tcaaaataaa atatggagaa gcatacactg acacatacca ttcctatgca
 701 aacaacatcc taagaacaca gaaagtgcc tgcaactgca tcggggagga
 751 ttgttatctt atgataactg atggctcagc ttcaggaatt agtaaatgca
 801 gattccttaa gattcgagag ggtcgaatag taaagaaat atttccaaca
 851 ggaagagtag agcatactga agaatgcaca tgcggatttg ccagcaataa
 901 aaccatagaa tgtgcctgta gagataacag ttacacagca aaaagaccct
 951 ttgtcaaatt aaatgtggaa actgatacag cagaaataag attgatgtgc
1001 acagagactt atttggacac ccccagacca gatgatggaa gcataacagg
1051 gccttgcgaa tctaatgggg acaaaggag tggaggtatc aagggaggat
1101 ttgtccatca agaatggca tccaagattg gaagatggta ctctcgaacg
1151 atgtctaaaa ctaaagaat ggggatggaa ctgtatgtca agtatgatgg
1201 agacccatgg actgacagtg atgcccttgc tcctagtgga gtaatggtct
1251 caatagaaga acctggttgg tattctttcg gcttcgaaat aaaagataag
1301 aaatgcgatg tcccctgtat tgggatagag atggtacacg atggtggaaa
1351 aacaacttgg cactcagcag caacagccat ttactgttta atgggctcag
1401 gacagttgct atgggacact atcacaggtg ttgatatggc tctgtaatgg
1451 aggaatggtt gaatctgttc taaacccttt gttcctattt tgtttgaaca
1501 attgtcctta ctggacttaa ttgtttctga aaatgctct tgtt
```

SEQ ID NO:64
Amino Acid Sequence of ca B/Hong Kong/330/01 NA    Entire molecule length: 466 aa

```
   1 mlpstiqtlt lfltsggvll slyvsallsy llysdillkf sptkiiaptt
  51 sldsanasnf qavnhsatke mtfllpepew typrlscqgs tfqkallisp
 101 hrfgeakgns apliirepfi acgpkeckhf althyaaqpg gyyngtredr
 151 nklrhlisvn lgkiptvens ifhmaawsgs achdgrewty igvdgpdsna
 201 likikygeay tdtyhsyann ilrtqesacn ciggdcylmi tdgsasgisk
 251 crflkiregr ivkeifptgr vehteectcg fasnktieca crdnsytakr
 301 pfvklnvetd taeirlmcte tyldtprpdd gsitgpcesn gdkgsggikg
 351 gfvhqrmask igrwysrtms ktkrmgmely vkydgdpwtd sdalapsgvm
 401 vsieepgwys fgfeikdkkc dvpcigiemv hdggkttwhs aataiyclmg
 451 sgqllwdtit gvdmal
```

Figure 1EE

SEQ ID NO:31
ca B/Brisbane/32/2002
Nucleotide Sequence of ca B_Brisbane_32_2002_HA    Entire molecule length: 1885 bp

```
   1 agcagaagca gagcattttc taatatccac aaaatgaagg caataattgt
  51 actactcatg gtagtaacat ccaatgcaga tcgaatctgc actgggataa
 101 catcgtcaaa ctcaccccat gtggtcaaaa ctgctactca agggaggtc
 151 aatgtgactg tgtgatacc actgacaaca cacccacca aatctcattt
 201 tgcaaatctc aaaggaacaa aaaccagagg gaaactatgc ccaaaatgcc
 251 tcaactgcac agatctggac gtggccttgg cagaccaaa atgcacgggg
 301 aacataccct cggcaaaagt ttcaatactc catgaagtca gacctgttac
 351 atctgggtgc tttcctataa tgcacgacag aacaaaaatt agacagctgc
 401 ccaatcttct cagaggatac gaacatatca ggttatcaac tcataacgtt
 451 atcaatgcag aaaaggcacc aggaggaccc tacaaaattg gaacctcagg
 501 gtcttgccct aacgttacca atggaaacgg atttttcgca acaatggctt
 551 gggccgtccc aaaaaacgac aacaacaaaa cagcaacaaa ttcattaaca
 601 atagaagtac catacatttg tacagaagga gaagaccaaa ttaccgtttg
 651 ggggttccac tctgataacg aagcccaaat ggcaaaactc tatggggact
 701 caaagcccca gaagttcacc tcatctgcca acggagtgac cacacattac
 751 gtttcacaga ttggtggctt cccaaatcaa acagaagacg gaggactacc
 801 acaaagtggt agaattgttg ttgattacat ggtgcaaaaa tctgggaaaa
 851 caggaacaat tacctatcaa agaggtattt tattgcctca aaaagtgtgg
 901 tgcgcaagtg gcaggagcaa ggtaataaaa ggatccttgc ctttaattgg
 951 agaagcagat tgcctccacg aaaaatacgg tggattaaac aaaagcaagc
1001 cttactacac aggggaacat gcaaaggcca taggaaattg cccaatatgg
1051 gtgaaaacac ccttgaagct ggccaatgga accaaatata gacctcctgc
1101 aaaactatta aaggaaagag gtttcttcgg agctattgct ggtttcttag
1151 aaggaggatg ggaaggaatg attgcaggtt ggcacggata cacatcccat
1201 ggggcacatg gagtagcagt ggcagcagac cttaagagta ctcaagaagc
1251 cataaacaag ataacaaaaa atctcaactc tttgagtgag ctggaagtaa
1301 agaatcttca aagactaagc ggtgccatgg atgaactcca caacgaaata
1351 ctagaactag acgagaaagt ggatgatctc agagctgata caataagctc
1401 acaaatagaa ctcgcagtct gcttccaa tgaaggaata ataaacagtg
1451 aagatgagca tctcttggcg cttgaaagaa agctgaagaa aatgctgggc
1501 ccctctgctg tagagatagg aatggatgc ttcgaaacca acacaagtg
1551 caaccagacc tgtctcgaca gaatagctgc tggtacctt gatgcaggag
1601 aattttctct ccccacttt gattcactga atattactgc tgcatcttta
1651 aatgacgatg gattggataa tcatactata ctgctttact actcaactgc
1701 tgcctccagt ttggctgtaa cattgatgat agctatcttt gttgtttata
1751 tggtctccag agacaatgtt tcttgctcca tctgtctata aggaaagtta
1801 agccctgtat tttcctttat tgtagtgctt gtttgcttgt taccattaca
1851 aaaaaacgtt attgaaaaat gctcttgtta ctact
```

SEQ ID NO:65
Amino Acid Sequence of ca B_Brisbane_32_2002_HA    Entire molecule length: 585 aa

```
   1 mkaiivllmv vtsnadrict gitssnsphv vktatqgevn vtgviplttt
  51 ptkshfanlk gtktrgklcp kclnctdldv algrpkctgn ipsakvsilh
 101 evrpvtsgcf pimhdrtkir qlpnllrgye hirlsthnvi naekapggpy
 151 kigtsgscpn vtngngffat mawavpkndn nktatnslti evpyictege
 201 dqitvwgfhs dneaqmakly gdskpqkfts sangvtthyv sqiggfpnqt
 251 edgglpqsgr ivvdymvqks gktgtityqr gillpqkvwc asgrskvikg
 301 slpligeadc lhekygglnk skpyytgeha kaigncpiwv ktplklangt
 351 kyrppakllk ergffgaiag fleggwegmi agwhgytshg ahgvavaadl
 401 kstqeainki tknlnslsel evknlqrlsg amdelhneil eldekvddlr
 451 adtissqiel avllsnegii nsedehllal erklkkmlgp saveigngcf
 501 etkhkcnqtc ldriaagtfd agefslptfd slnitaasln ddgldnhtil
 551 lyystaassl avtlmiaifv vymvsrdnvs csicl
```

Figure 1FF

SEQ ID NO:32

Nucleotide Sequence of ca B_Brisbane_32_2002_NA     Entire molecule length: 1557 bp

```
   1 agcagaagca gagcatcttc tcaaaactga ggcaaatagg ccaaaaatga
  51 acaatgctac cttcaactat acaaacgtta accctatttc tcacatcagg
 101 gggagtatta ttatcactat atgtgtcagc ttcattgtca tacttactat
 151 attcggatat attgctaaaa ttctcaccaa cagaaataac tgcaccaaca
 201 atgccattgg attgtgcaaa cgcatcaaat gttcaggctg tgaaccgttc
 251 tgcaacaaaa ggggtgacac ttcttctccc agaaccagag tggacatacc
 301 cgcgtttatc ttgcccgggc tcaaccttto agaaagcact cctaattagc
 351 cctcatagat tcggagaaac caaggaaac tcagctccct tgataataag
 401 ggaaccttt attgcttgtg gaccaaagga atgcaaacac tttgctctaa
 451 cccattatgc agcccaacca ggggatact acaatggaac aagaggagac
 501 agaaacaagc tgaggcatct aatttcagtc aaattgggca aatcccaac
 551 agtagaaaac tccatttcc acatggcagc atggagcggg tccgcatgcc
 601 atgatggtaa agaatggaca tatatcggag ttgatggccc tgacaataat
 651 gcattgctca aaataaaata tggagaagca tatactgaca cataccattc
 701 ctatgcaaac aacatcctaa gaacacaaga agtgcctgc aattgcatcg
 751 gggaaattg ttatcttatg ataactgatg gctcagcttc aggtattagt
 801 gaatgcagat tcttaaaat tcgagagggc cgaataataa agaaatatt
 851 tccaacagga agagtaaaac atactgaaga atgcacatgc ggatttgcca
 901 gcaataagac catagaatgt gcctgtagag ataacagtta cacagcaaaa
 951 agacccttg tcaaattaaa cgtggagact gatacagcag aaataagatt
1001 gatgtgcaca gagacttatt tggacacccc cagaccagat gatggaagca
1051 taacagggcc ttgtgaatct aatggggaca aagggagtgg aggcatcaag
1101 ggaggatttg ttcatcaaag aatggcatcc aagattggaa ggtggtactc
1151 tcgaacgatg tctaaaacta aaggatggg gatgggactg tatgtcaagt
1201 atgatggaga cccatggct gacagtgatg cccttgctct tagtggagta
1251 atggtttcaa tggaagaacc tggttggtac tcctttggct tcgaaataaa
1301 agataagaaa tgtgatgtcc cctgtattgg aatagagatg gtacatgatg
1351 gtggaaaaga gacttggcac tcagcagcaa cagccattta ctgtttaatg
1401 ggctcaggac agctgctgtg gacactgtc acaggtgttg atatggctct
1451 gtaatggagg aatggttgag tctgttctaa accctttgtt cctattttgt
1501 ttgaacaatt gtccttactg aacttaattg tttctgaaaa atgctcttgt
1551 tactact
```

SEQ ID NO:66

Amino Acid Sequence of ca B_Brisbane_32_2002_NA     Entire molecule length: 466 aa

```
  1 mlpstiqtlt lfltsggvll slyvsaslsy llysdillkf spteitaptm
 51 pldcanasnv qavnrsatkg vtlllpepew typrlscpgs tfqkallisp
101 hrfgetkgns apliirepfi acgpkeckhf althyaaqpg gyyngtrgdr
151 nklrhlisvk lgkiptvens ifhmaawsgs achdgkewty igvdgpdnna
201 llkikygeay tdtyhsyann ilrtqesacn ciggncylmi tdgsasgise
251 crflkiregr iikeifptgr vkhteectcg fasnktieca crdnsytakr
301 pfvklnvetd taeirlmcte tyldtprpdd gsitgpcesn gdkgsggikg
351 gfvhqrmask igrwysrtms ktkrmgmgly vkydgdpwad sdalalsgvm
401 vsmeepgwys fgfeikdkkc dvpcigiemv hdggketwhs aataiyclmg
451 sgqllwdtvt gvdmal
```

Figure 1GG

SEQ ID NO:33
ca B/Jilin/20/2003
Nucleotide Sequence of ca B/Jilin/20/03 HA Entire molecule length: 1853 bp

```
   1 tctaatatcc acaaaatgaa ggcaataatt gtactactca tggtagtaac
  51 atccaatgca gatcgaatct gcactgggat aacatcttca aactcacctc
 101 atgtggtcaa aacagctact caaggggagg tcaatgtgac tggtgtaata
 151 ccactgacaa caacaccaac aaaatcttat tttgcaaatc tcaaaggaac
 201 aaggaccaga gggaaactat gtccagactg tctcaactgt acagatctgg
 251 atgtggcctt gggcagacca atgtgtgtgg ggaccacacc ttcggcaaaa
 301 gcttcaatac tccacgaagt cagacctgtt acatccgggt gctttcctat
 351 aatgcacgac agaacaaaaa tcagacaact acccaatctt ctcagaggat
 401 atgaaaatat cagattatca acccaaaacg ttatcgatgc agaaaatgca
 451 ccaggaggac cctacagact ggaacctca ggatcttgcc ctaacgctac
 501 cagtaaaagc ggattttttcg caacaatggc ttgggctgtc caaaggaca
 551 acaacaaaaa tgcaacgaac ccactaacag tagaagtacc atacgtttgt
 601 acagaagggg aagaccaaat tactgtttgg gggttccatt cagataacaa
 651 aaccccaatg aagaacctct atggagactc aaatcctcaa aagttcacct
 701 catctgctaa tggagtaacc acacattatg tttctcagat tggcggcttc
 751 ccagctcaaa cagaagacga aggactacca caagcggca gaattgttgt
 801 tgattacatg gtgcaaaaac ctaggaaaac aggaacaatt gtctatcaaa
 851 gaggtgtttt gttgcctcaa aaggtgtggt gcgcgagtgg caggagcaaa
 901 gtaataaaag ggtccttgcc tttaattggt gaagcagatt gccttcatga
 951 aaaatacggt ggattaaaca aaagccaagcc ttactacaca ggagaacatg
1001 caaaagccat aggaaattgc ccaatatggg tgaaaacacc tttgaagctt
1051 gccaatggaa ccaaatatag acctcctgca aaactattaa aggaaagggg
1101 tttcttcgga gctattgctg gtttcctaga aggaggatgg gaaggaatga
1151 ttgcaggttg gcacggatac acatctcacg gagcacatgg agtggcagtg
1201 gcggcagacc ttaagagtac gcaagaagct ataaacaaga taacaaaaaa
1251 tctcaattct ttgagtgagc tagaagtaaa gaatcttcaa agactaagtg
1301 gtgccatgga tgaactccac aacgaaatac tcgagctgga tgagaaagtg
1351 gatgatctca gagctgacac tataagctcg caaatagaac ttgcagtctt
1401 gctttccaat gaaggaataa taaacagtga agatgagcat ctattggcac
1451 ttgagagaaa actaaagaaa atgctgggtc cctctgctgt agacatagga
1501 aatggatgct cgaaaccaa acacaagtgc aaccagacct gcttagacag
1551 gatagctgct ggcacctta atgcaggaga ttttctctc cccacttttg
1601 attcactgaa cattactgct gcatctttaa atgatgatgg attggataac
1651 catactatac tgctctatta ctcaactgct gcttctagtt tggctgtaac
1701 attgatgcta gctatttta ttgtttatat ggtctccaga gacaacgttt
1751 catgctccat ctgtctataa ggaagattaa gccttgtatt ttcctttatt
1801 gtagtgcttg tttgcttgtc atcattacaa agaaacgtta ttgaaaaatg
1851 ctc
```

SEQ ID NO:67
Amino Acid Sequence of ca B/Jilin/20/03 HA        Entire molecule length: 584 aa

```
   1 mkaiivllmv vtsnadrict gitssnsphv vktatqgevn vtgviplttt
  51 ptksyfanlk gtrtrgklcp dclnctdldv algrpmcvgt tpsakasilh
 101 evrpvtsgcf pimhdrtkir qlpnllrgye nirlstqnvi daenapggpy
 151 rlgtsgscpn atsksgffat mawavpkdnn knatnpltve vpyvcteged
 201 qitvwgfhsd nktpmknlyg dsnpqkftss angvtthyvs qiggfpaqte
 251 deglpqsgri vvdymvqkpr ktgtivyqrg vllpqkvwca sgrskvikgs
 301 lpligeadcl hekygglnks kpyytgehak aigncpiwvk tplklangtk
 351 yrppakllke rgffgaiagf leggwegmia gwhgytshga hgvavaadlk
 401 stqeainkit knlnslsele vknlqrlsga mdelhneile ldekvddlra
 451 dtissqiela vllsnegiin sedehllale rklkkmlgps avdigngcfe
 501 tkhkcnqtcl driaagtfna gefslptfds lnitaaslnd dgldnhtill
 551 yystaassla vtlmlaifiv ymvsrdnvsc sicl
```

Figure 1HH

SEQ ID NO:34
Nucleotide Sequence of ca B/Jilin/20/03 NA Entire molecule length: 1529 bp

```
   1 tctcaaaact gaggcaaata ggccaaaaat gaacaatgct accctcaact
  51 atacaaacgt taaccctatt cctcacatca gggggagtgt tattatcact
 101 atatgtgtca gcttcactgt catacttact atattcggat atattgctaa
 151 aattttcaac aacagaaata actgcaccaa caatgccatt ggattgtgca
 201 aacgcatcaa atgttcaggc tgtgaaccgt tctgcaacaa aagggggtgac
 251 acttcttctc ccagaaccgg agtggacata cccgcgttta tcttgcccgg
 301 gctcaacctt tcagaaagca ctcctaatta gccctcatag attcggagaa
 351 accaaaggaa actcagctcc cttgataata agggaacctt ttattgcttg
 401 tggaccaaag gaatgcaaac actttgctct aacccattat gcagcccaac
 451 caggggata ctacaatgga acaaaagaag acagaaacaa gctgaggcat
 501 ctaatttcag tcaaattggg caaaatccca acagtagaaa actccatttt
 551 ccacatggca gcatggagcg ggtccgcatg ccatgatggt aaagaatgga
 601 catatatcgg agttgatggc cctgacagta atgcattgct caaaataaaa
 651 tatggagaag catatactga cacataccat tcctatgcaa acaacatcct
 701 aagaacacaa gaaagtgcct gcaattgcat cgggggaaat tgttatctta
 751 tgataactga tggctcagct tcaggtatta gtgagtgcag atttcttaag
 801 attcgagagg gccgaataat aaaagaaata tttccaacag gaagagtaaa
 851 acatactgaa gaatgcacat gcggatttgc cagcaataaa accatagaat
 901 gtgcctgtag agataacagt tacacagcaa aagacccctt tgtcaaatta
 951 aatgtggaga ctgatacagc agaaataaga ttgatgtgca cagagactta
1001 tttggacacc cccagaccag atgatggaag cataacaggg ccttgtgaat
1051 ctaatgggaa taaagggagt ggaggcatca agggaggatt tgttcatcaa
1101 agaatggcat ccaaaattgg aaggtggtac tctcgaacaa tgtctaaaac
1151 caaaaggatg ggaatgggac tgtatgtcaa gtatgatgga gacccatgga
1201 ctgacagtga tgcccttgct cttagtggag taatggtttc aatggaagaa
1251 cctggttggt actcatttgg cttcgaaata aagataaga aatgtgatgt
1301 cccctgtatt gggatagaga tggtacatga tggtggaaag gagacttggc
1351 actcagcagc aacagccatt tactgtttaa tgggctcagg acaactgttg
1401 tgggacactg tcacaggtgt tgatatggct ctgtaatggg ggaatggttg
1451 agtctgttct aaacccttg ttcctatttt gtttgaacaa ttgtccttgc
1501 tgaacttaat tgtttctgaa aaatgctct
```

SEQ ID NO:68
Amino Acid Sequence of ca B/Jilin/20/03 NA    Entire molecule length: 466 aa

```
   1 mlpstiqtlt lfltsggvll slyvsaslsy llysdillkf stteitaptm
  51 pldcanasnv qavnrsatkg vtlllpepew typrlscpgs tfqkallisp
 101 hrfgetkgns apliirepfi acgpkeckhf althyaaqpg gyyngtkedr
 151 nklrhlisvk lgkiptvens ifhmaawsgs achdgkewty igvdgpdsna
 201 llkikygeay tdtyhsyann ilrtqesacn ciggncylmi tdgsasgise
 251 crflkiregr iikeifptgr vkhteectcg fasnktieca crdnsytakr
 301 pfvklnvetd taeirlmcte tyldtprpdd gsitgpcesn gnkgsggikg
 351 gfvhqrmask igrwysrtms ktkrmgmgly vkydgdpwtd sdalalsgvm
 401 vsmeepgwys fgfeikdkkc dvpcigiemv hdggketwhs aataiyclmg
 451 sgqllwdtvt gvdmal
```

Figure 2

| SEQ ID NO | HA or NA | Strain Name |
|---|---|---|
| SEQ ID NO:1 | HA | ca A/Shandong/9/93 |
| SEQ ID NO:2 | NA | ca A/Shandong/9/93 |
| SEQ ID NO:3 | HA | ca A/Johannesburg/33/94-Like |
| SEQ ID NO:4 | NA | ca A/Johannesburg/33/94-Like |
| SEQ ID NO:5 | HA (H3) | ca A/Wuhan/395/95 |
| SEQ ID NO:6 | NA (N2) | ca A/Wuhan/395/95 |
| SEQ ID NO:7 | HA (H3) | ca A/Sydney/05/97 |
| SEQ ID NO:8 | NA (N2) | ca A/Sydney/05/97 |
| SEQ ID NO:9 | HA (H3) | ca A/Panama/2007/99 |
| SEQ ID NO:10 | NA (N2) | ca A/Panama/2007/99 |
| SEQ ID NO:11 | HA (H3) | ca A/Wyoming/03/2003 |
| SEQ ID NO:12 | NA (N2) | ca A/Wyoming/03/2003 |
| SEQ ID NO:13 | HA (H1) | ca A/Texas/36/91 |
| SEQ ID NO:14 | NA (N1) | ca A/Texas/36/91 |
| SEQ ID NO:15 | HA (H1) | ca A/Shenzhen/227/95 |
| SEQ ID NO:16 | NA (N1) | ca A/Shenzhen/227/95 |
| SEQ ID NO:17 | HA (H1) | ca A/Beijing/262/95 |
| SEQ ID NO:18 | NA (N1) | ca A/Beijing/262/95 |
| SEQ ID NO:19 | HA (H1) | ca A/New Caledonia/20/99 |
| SEQ ID NO:20 | NA (N1) | ca A/New Caledonia/20/99 |
| SEQ ID NO:21 | HA | ca B/Ann Arbor/1/94 |
| SEQ ID NO:22 | NA | ca B/Ann Arbor/1/94 |
| SEQ ID NO:23 | HA | ca B/Yamanashi/166/98 |
| SEQ ID NO:24 | NA | ca B/Yamanashi/166/98 |
| SEQ ID NO:25 | HA | ca B/Johannesburg/5/99 |
| SEQ ID NO:26 | NA | ca B/Johannesburg/5/99 |
| SEQ ID NO:27 | HA | ca B/Victoria/504/2000 |
| SEQ ID NO:28 | NA | ca B/Victoria/504/2000 |
| SEQ ID NO:29 | HA | ca B/Hong Kong/330/01 |
| SEQ ID NO:30 | NA | ca B/Hong Kong/330/01 |
| SEQ ID NO:31 | HA | ca B/Brisbane/32/2002 |
| SEQ ID NO:32 | NA | ca B/Brisbane/32/2002 |
| SEQ ID NO:33 | HA | ca B/Jilin/20/2003 |
| SEQ ID NO:34 | NA | ca B/Jilin/20/2003 |

SEQUENCE LISTING

<160> NUMBER OF SEQ ID NOS: 68

<210> SEQ ID NO 1
<211> LENGTH: 1745

```
<212> TYPE: DNA
<213> ORGANISM: Influenza A virus

<400> SEQUENCE: 1
caggggataa ttctattaac catgaagact atcattgctt tgagctacat tttatgtctg    60
gttttcgctc aaaaacttcc cggaaatgac aacagcacag caacgctgtg cctgggacat   120
catgcagtgc aaacggaac gctagtgaaa acaatcacga atgatcaaat tgaagtgact   180
aatgctactg agttggttca gagttcctca acaggtagaa tatgcggcag tcctcaccga   240
atccttgatg gaaaaaactg cacactgata gatgctctat gggagacccc tcattgtgat   300
ggcttccaaa ataaggaatg ggaccttttt gttgaacgca gcaaagctta cagcaactgt   360
tacccttatg atgtgccgga ttatgcctcc cttaggtcac tagttgcctc atcaggcacc   420
ctggagtttt caatgaaga cttcaattgg actggagtcg ctcaggatgg gggaagctat   480
gcttgcaaaa gaggatctgt taacagtttc tttagtagat tgaattggtt gcacaaatta   540
gaatacaaat atccagcgct gaacgtgact atgccaaaca atggcaaatt tgacaaattg   600
tacatttggg gggttcacca cccgagcacg gacagtgacc aaaccagcct atatgttcga   660
gcatcaggga gagtcacagt tctctaccaaa agaagccaac aaactgtaac ccgaatatc   720
gggtctagac cctgggtaag gggtcagtcc agtagaataa gcatctattg gacaatagta   780
aaaccgggag acatactttt gattaatagc acagggaatc taattgctcc tcggggttac   840
ttcaaaatac gaaatgggaa aagctcaata atgaggtcag atgcacccat tggcaactgc   900
agttctgaat gcatcactcc aaatggaagc attcccaatg acaaaccttt tcaaaatgta   960
aacagaatca catatgggg ctgccccaga tatgttaagc aaaacactct gaaattggca  1020
acagggatgc ggaatgtacc agagaaacaa actagaggca tattcggcgc aatcgcaggt  1080
ttcatagaaa atggttggga gggaatggta gacggttggt acggtttcag gcatcaaaat  1140
tctgagggca caggacaagc agcagatctt aaaagcactc aagcagcaat cgaccaaatc  1200
aacgggaaac tgaataggtt aatcgagaaa acgaacgaga attccatca atcgaaaaaa  1260
gaattctcag aagtagaagg gagaattcag gacctcgaga aatatgttga agacactaaa  1320
atagatctct ggtcttacaa cgcggagctt cttgttgccc tggagaacca acatacaatt  1380
gatctaactg actcagaaat gaacaaactg tttgaaaaaa caaggaagca actgagggaa  1440
aatgctgagg catgggcaa tggttgcttc aaaaatatacc acaaatgtga caatgcctgc  1500
ataggtcaa tcagaaatgg aacttatgac catgatgtat acagagacga agcattaaac  1560
aaccggttcc agatcaaagg tgttgagctg aagtcaggat acaaagattg gatcctatgg  1620
atttccttg ccatatcatg ctttttgctt tgtgttgttt gctggggtt catcatgtgg  1680
gcctgccaaa aaggcaacat taggtgcaac atttgcattt gagtgcatta attaaaaaca  1740
ccctg                                                              1745

<210> SEQ ID NO 2
<211> LENGTH: 1429
<212> TYPE: DNA
<213> ORGANISM: Influenza A virus

<400> SEQUENCE: 2
aaagataata acaattggct ctgtttctct cactattgcc acaatatgct tccttatgca     60
aattgccatc ctggtaacta ctgtaacatt gcacttcaag caatatgagt gcaactcccc    120
cccaaacaac caagtaatgc tgtgtgaacc aacaataata gaaagaaaca tacagagat    180
```

-continued

```
agtgtatctg accaacacca ccatagagaa agaaatatgc cccaaactag cagaatacag    240
aaattggtca aagccgcaat gtaaaattac aggatttgca cctttttcta aggacaattc    300
aattcggctt tcagctggtg gagacatttg ggtgacaaga gaaccttatg tgtcatgcga    360
tcctggcaag tgttatcaat ttgcccttgg acagggaaca cactaaaaca caggcactc    420
aaatgacaca gtacatgata ggaccccta tcgaaccta ttgatgaatg agttgggtgt    480
tccatttcat ttgggaacca agcaagtgtg catagcatgg tccagctcaa gttgtcacga    540
tggaaaagca tggctgcatg tttgtgtaac tgggcatgat gaaaatgcaa ctgctagctt    600
catttacgat gggaggcttg tagatagtat tggttcatgg tccaaaaata tcctcaggac    660
ccaggagtcg gaatgcgttt gtatcaatgg aacttgtaca gtagtaatga ctgatggaag    720
tgcttcagaa agagctgata ctaaaatact attcattgaa gaggggaaaa tcgttcatat    780
tagcccattg tcaggaagtg ctcagcatgt cgaggagtgc tcctgttatc ctcgatatcc    840
tggtgtcaga tgtgtctgca gagacaactg gaaaggctcc aataggccca tcgtagatat    900
aaaatgtgaaa gattatagca ttgttttccag ttatgtgtgc tcaggacttg tttggagacac    960
acccagaaaa aacgacagct ccagcagtag ctattgccgg aatcctaaca atgagaaagg    1020
gagtcatgga gtgaaaggct gggcctttga tgatggaaat gacgtgtgga tgggaagaac    1080
gatcagcgag gagttacgct caggttatga aaccttcaaa gtcattggag ctggtccaa    1140
acctaactcc aaaattgcaga taaataggca agtcatagtt gacagaggta ataggtccgg    1200
ttattctggt attttctctg ttgaaggcaa aagctgcatc aatcggtgct tttatgtgga    1260
gttgataagg ggaaggaaac aggaaactga agtctggtgg acctcaaaca gtattgttgt    1320
gttttgtggc acctcaggta catatggaac aggctcatgg ccctgatggg cggacatca    1380
atctcatgcc tatataagct ttcgcaattt tagaaaaaaa ctccttgtt                1429
```

<210> SEQ ID NO 3
<211> LENGTH: 1755
<212> TYPE: DNA
<213> ORGANISM: Influenza A virus

<400> SEQUENCE: 3

```
agcaaaagca ggggataatt ctattaacca tgaagactat cattgctttg agctacattt     60
tatgtctggt tttcgctcaa aaacttcccg gaaatgacaa cagcacagca acgctgtgcc    120
tgggacacca tgcagtgcca acggaacgc tagtgaaaac aatcacgaat gatcaaattg    180
aagtgactaa tgctactgag ctggttcaga gttccccaac aggtagaata tgcgacagcc    240
ctcaccgaat ccttgatgga agaactgca cactgataga tgctctattg ggagaccctc    300
attgtgatgg cttccaaaat aaggaatggg acctttttgt tgaacgcagc aaagcttaca    360
gcaactgtta cccttatgat gtgccggatt atgcctccct taggtcacta gttgcctcat    420
caggcaccct ggagtttatc aacgaaaact tcaattggac tggagtcgct caggatggga    480
aaagctatgc ttgcaaaagg ggatctgtta acagttctt tagtagattg aattggttgc    540
acaaattaga atacaaatat ccagcgctga acgtgactat gccaaacaat ggcaaatttg    600
acaaattgta catttgggg gttcaccacc cgagcacgga cagtgtccaa accagcctat    660
atgtccgagc atcagggaga gtcacagtct ctaccaaaag aagccaacaa actgtaatcc    720
cggatatcgg gtatagacca tgggtaaggg gtcagtccag tagaataagc atctattgga    780
caatagtaaa accgggagac atactttga ttaatgcac agggaatcta attgctcctc    840
ggggttactt caaaatacga aatgggaaaa gctcaataat gaggtcagat gcacccattg    900
```

| | |
|---|---|
| gcaactgcag ttctgaatgc atcactccaa atggaagcat tcccaatgac aaacctttc | 960 |
| aaaatgtaaa caggatcaca tatggggcct gccccagata tgttaagcaa acactctga | 1020 |
| aattggcaac agggatgcgg aatgtaccag agaaacaaac tagaggcata ttcggcgcaa | 1080 |
| tcgcaggttt catagaaaat ggttgggagg gaatggtaga cggttggtac ggtttcaggc | 1140 |
| atcaaaattc tgagggcaca ggacaagctg cagatcttaa aagcactcaa gcagcaatcg | 1200 |
| accaaatcaa cgggaaactg aataggttag tcgagaaaac gaacgagaaa ttccatcaaa | 1260 |
| tcgaaaaaga attctcagaa gtagaaggga gaattcagga cctcgagaaa tatgttgaag | 1320 |
| acactaaaat agatctctgg tcttacaatg cggaacttct tgttgctctg agaaccaac | 1380 |
| atacaattga tctaactgac tcagaaatga caaactgtt tgaagaaca aggaagcaac | 1440 |
| tgagggaaaa tgctgaggac atgggcaatg gttgtttcaa aatataccac aaatgtgaca | 1500 |
| atgcctgcat agggtcaatc agaaatggaa cttatgacca tgatgtatac agagacgaag | 1560 |
| cattaaacaa ccggttccag atcaaggtg ttgagctgaa gtcaggatac aaagattgga | 1620 |
| ttctatggat ttcctttgcc atatcgtgct ttttgctttg tgttgttttg cttgggttca | 1680 |
| tcatgtgggc ctgccaaaaa ggcaacatta ggtgcaacat ttgcatttga gtgcattaat | 1740 |
| taaaaacacc cttgt | 1755 |

<210> SEQ ID NO 4
<211> LENGTH: 1354
<212> TYPE: DNA
<213> ORGANISM: Influenza A virus

<400> SEQUENCE: 4

| | |
|---|---|
| gaaaatgaat ccaaatcaaa agataataac aattggctct gtttctctca ctattgccac | 60 |
| aatatgcttc cttatgcaaa ttgccatcct ggtaactact gtaacattgc atttcaagca | 120 |
| atatgagtgc aactcccccc caaacaacca gtaatgctg tgtgaaccaa caataataga | 180 |
| aagaaacata acagagatag tgtatctgac caacaccacc atagagaaag aaatatgccc | 240 |
| caaactagca gaatacagaa attggtcaaa gccgcaatgt aaaattacag gatttgcacc | 300 |
| tttttctaag gacaattcaa ttcggctttc cgctggtgga acatttggg tgacaagaga | 360 |
| acctttatgtg tcatgcgatc ctggcaagtg ttatcaattt gccctcggac agggaacaac | 420 |
| actaaacaac aggcattcaa atgacacagt acatgatagg ccccttatc gaaccctatt | 480 |
| gatgaatgag ttgggtgttc catttcattt gggaaccaag caagtgtgca tagcatggtc | 540 |
| cagctcaagt tgtcacgatg aaaaagcatg gctgcatgtt tgtgtaactg gcatgatga | 600 |
| aaatgcaact gctagcttca tttacgatgg gaggcttgta gatagtattg gttcatggtc | 660 |
| caaaaatatc tcaggaccc aggagtcgga atgcgtttgt atcaatggaa cttgtacagt | 720 |
| agtaatgact gatggaagtg cttcagaaag agctgatact aaaatactat tcattgaaga | 780 |
| ggggaaaatc gttcatatta gcccattgtc aggaagtgct cagcatgtcg aggagtgctc | 840 |
| ctgttatcct cgatatcctg gtgtcagatg tgtctgcaga gacaactgga aaggctccaa | 900 |
| taggcccatc gtagatataa atgtgaaaga ttatagcatt gttccagtt atgtgtgctc | 960 |
| aggacttgtt ggagacacac ccagaaaaaa cgacagctcc agcagtagct attgctggaa | 1020 |
| tcctaacaat gagaaagggg gtcatggagt gaaaggctgg gcctttgatg atggaaatga | 1080 |
| cgtgtggatg ggaagaacga tcagcgagga gttacgctca ggttatgaaa ccttcaaagt | 1140 |
| cattggaggc tggtccaaac ctaactccaa attgcagata ataggcaag tcatagttga | 1200 |

```
cagaggtaat aggtccggtt attctggtat tttctctgtt gaaggcaaaa gctgcatcaa      1260
tcggtgcttt tatgtggagt tgataagggg aaggaaacag gaaactgaag tctggtggac      1320
ctcaaacagt attgttgtgt tttgtggcac ttca                                  1354

<210> SEQ ID NO 5
<211> LENGTH: 1762
<212> TYPE: DNA
<213> ORGANISM: Influenza A virus

<400> SEQUENCE: 5
agcaaaagca gggataatt ctattaacca tgaagactat cattgctttg agctacattt        60
tatgtctggt tttcgctcaa aaacttcccg gaaatgacaa cagcacggca acgctgtgcc      120
tgggacacca tgcagtgcca aacggaacgc tagtgaaaac aatcacgaat gaccaaattg      180
aagtgactaa tgctactgag ctggttcaga gttcctcaac aggtagaata tgcgacagtc      240
ctcaccgaat ccttgatgga aaaaactgca cactgataga tgctctattg ggagaccctc      300
attgtgatgg cttccaaaat aaggaatggg accttttttgt tgaacgcagc aaagcttaca      360
gcaactgtta cccttatgat gtgccggatt atgcttccct taggtcacta gttgcctcat      420
ccggcaccct ggagtttacc aatgaaggct tcaattggac tggagtcgct caggatggaa      480
caagctatgc ttgcaaaagg ggatctgtta aagtttctt tagtagattg aattggttgc      540
acaaattaga atacaaatat ccagcactga acgtgactat gccaaacaat gacaaatttg      600
acaaattgta catttggggg gttcaccacc cgagtacgga cagtgaccaa accagcatat      660
atgttcaagc atcagggaga gtcacagtct ctaccaaaag aagccaacaa actgtaatcc      720
cgaatatcgg gtctagaccc tgggtaaggg ggatctccag cagaataagc atctattgga      780
caatagtaaa accgggagac atactttga ttaacagcac agggaatcta attgctcctc      840
ggggttactt caaaatacga agtgggaaaa gctcaataat gaggtcagat gcacccattg      900
gcaactgcaa ttctgaatgc atcactccaa atggaagcat tcccaatgac aaaccttttc      960
aaaatgtaaa caggatcaca tatggggcct gtcccagata tgttaagcaa aacactctga     1020
aattggcaac agggatgcgg aatgtaccag agaaacaaac tagaggcata ttcggcgcaa     1080
tcgcaggttt catagaaaat ggttgggagg gaatggtaga cggttggtac ggtttcaggc     1140
atcaaaattc tgagggcaca ggacaagcag cagatcttaa aagcactcaa gcagcaatca     1200
accaaatcaa cgggaaactg aataggttaa tcgagaaaac gaacgagaaa ttccatcaaa     1260
tcgaaaaaga attctcagaa gtagaaggga aattcagga cctcgagaaa tatgttgaag     1320
acactaaaat agatctctgg tcttacaacg cggagcttct tgttgccctg gagaaccaac     1380
atacaattga tctaactgac tcagaaatga acaaactgtt tgaaagaaca aggaagcaac     1440
tgagggaaaa tgctgaggac atgggcaatg gttgcttcaa aatataccac aaatgtgaca     1500
atgcctgcat agggtcaatc agaaatgaa cttatgacca tgatgtatac agagacgaag     1560
cattaaacaa ccggttccag atcaaggtg ttgagctgaa gtcaggatac aaagattgga     1620
tcctatggat ttcctttgcc atatcatgct ttttgctttg tgttgttctg ctggggttca     1680
tcatgtgggc ctgccaaaaa ggcaacatta ggtgcaacat ttgcatttga gtgcattaat     1740
taaaaacacc cttgtttcta ct                                              1762

<210> SEQ ID NO 6
<211> LENGTH: 1451
<212> TYPE: DNA
<213> ORGANISM: Influenza A virus
```

<400> SEQUENCE: 6

```
agcaaaagca ggagtgaaaa tgaatccaaa tcaaaagata taactattg gctctgtttc      60
tctcactatt gccacaatat gcttccttat gcaaattgcc atcctggtaa ctactgtaac    120
attcatttc aagcaatatg aatgcaactc ccccccaaac aaccaagtaa tgctgtgtga     180
accaacaata atagaaagaa acataacaga gatagtgtat ctgaccaaca ccaccataga    240
gaaggaaata tgccccaaac tagcagaata cagaaattgg tcaaagccgc aatgtaaaat    300
tacaggattt gcaccttttt ctaaggacaa ttcaattcgg ctttccgctg gtggggacat    360
ttgggtgaca agagaacctt atgtgtcatg cgatcctgac aagtgttatc aatttgccct    420
tggacaggga acaacactaa acaacaggca ttcaaatgac acagtacatg ataggacccc    480
ttatcgaacc ctattgatga atgagttggg tgttccattt catttgggaa ccaagcaagt    540
gtgcatagca tggtccagct caagttgtca cgatggaaaa gcatggctgc atgtttgtgt    600
aactgggcat gatgaaaatg caactgctag cttcatttac gatgggaggc ttgtagatag    660
tattggttca tggtccaaaa aaatcctcag gacccaggag tcggaatgcg tttgtatcaa    720
tggaacttgt acagtagtaa tgactgatgg aagtgcttca ggaagagctg atactaaaat    780
actattcatt gaagagggga aaatcgttca tattagccca ttgtcaggaa gtgctcagca    840
tgtcgaggag tgctcctgtt atcctcgata ttctggtgtc agatgtgtct gcagagacaa    900
ctggaaggc tccaataggc ccatcgtaga tataaatgtg aaagattata gcattgtttc    960
cagttatgtg tgctcaggac ttgttggaga cacacccaga aaaacgaca gctccagcag   1020
tagccattgc ctgaatccta caatgagga agggggtcat ggagtgaaag ctgggcctt   1080
tgatgatgga aatgacgtgt ggatgggaag aacgatcagc gagaagttac gctcaggtta   1140
tgaaaccttc aaagtcattg gaggctggtc caaacctaac tccaaattgc agataaatag   1200
acaagtcata gttgacagag gtaataggtc cggttattct ggtattttct ctgttgaagg   1260
caaaagctgc atcaatcggt gctttttatgt ggagttgata aggggaagga acaggaaac   1320
tgaagtctgg tggaccctca acagtattgt tgtgtttgt ggcacctcag gtacatatgg   1380
aacaggctca tggcctgatg gggcggacat caatctcatg cctatataag ctttcgcaat   1440
tttagaaaaa a                                                        1451
```

<210> SEQ ID NO 7
<211> LENGTH: 1762
<212> TYPE: DNA
<213> ORGANISM: Influenza A virus

<400> SEQUENCE: 7

```
agcaaaagca gggataatt ctattaacca tgaagactat cattgctttg agctacattt      60
tatgtctggt tttcgctcaa aaaattcccg gaaatgacaa cagcacggca acgctgtgcc    120
tgggacacca tgcagtgcca acggaacgc tagtgaaaac aatcacgaat gaccaaattg    180
aagtgactaa tgctactgag ctggttcaga gttcctcaac aggtagaata tgcgacagtc    240
ctcaccgaat ccttgatgga gaaaactgca cactgataga tgctctattg ggagaccctc    300
attgtgatgg cttccaaaat aaggaatggg accttttttgt tgaacgcagc aaagcctaca    360
gcaactgtta cccttatgat gtgccggatt atgcctccct aggtcacta gttgcctcat    420
ccggcaccct ggagtttaac aatgaaagct tcaattggac tggagtcgct cagaatggaa    480
caagctatgc ttgcaaaagg agttctatta aaagtttctt tagtagattg aattggttgc    540
```

```
accaattaaa atacaaatat ccagcactga acgtgactat gccaaacaat gacaaatttg    600
acaaattgta catttggggg gttcaccacc cgagtacgga cagtgaccaa accagcatat    660
atgctcaagc atcagggaga gtcacagtct ccaccaaaag aagccaacaa actgtaatcc    720
cgaatatcgg atctagaccc tgggtaaggg gtatctccag cagaataagc atccattgga    780
caatagtaaa accgggagac atacttttga ttaacagcac agggaatcta attgctcctc    840
ggggttactt caaaatacga agtgggaaaa gctcaataat gaggtcagat gcacccattg    900
gcaaatgcaa ttctgaatgc atcactccaa atggaagcat tcccaatgac aaaccatttc    960
aaaatgtaaa caggatcaca tatggggcct gtcccagata tgttaagcaa acactctga   1020 aattggcaac agggatgcgg aatgtaccag agaaacaaac tagaggcata ttcggcgcaa   1080
tcgcaggttt catagaaaat ggttgggagg gaatggtaga cggttggtac ggtttcaggc   1140
atcaaaattc tgagggcaca ggacaagcag cagatcttaa aagcactcaa gcagcaatca   1200
accaaatcaa cggaaaactg aataggttaa tcgagaaaac gaacgagaaa ttccatcaaa   1260
ttgaaaaaga attctcagaa gtagaaggga gaattcagga cctcgagaaa tatgttgagg   1320
acactaaaat agatctctgg tcgtacaacg cggagcttct tgttgccctg gagaaccaac   1380
atacaattga tctaactgac tcagaaatga acaaactgtt tgaaagaaca aggaagcaac   1440
tgagggaaaa tgctgaggat atgggcaatg gttgtttcaa atataccac aaatgtgaca   1500 atgcctgcat agggtcaatc agaaatggaa cttatgacca tgatgtatac agagacgaag   1560
cattaaacaa ccggttccag atcaaggtg ttgagctgaa gtcaggatac aaagattgga   1620
tcctatggat ttccttttgcc atatcatgtt ttttgctttg tgttgttttg ctggggttca   1680
tcatgtgggc ctgccaaaaa ggcaacatta ggtgcaacat ttgcatttga gtgcattaat   1740
taaaaacacc cttgtttcta ct                                          1762

<210> SEQ ID NO 8
<211> LENGTH: 1467
<212> TYPE: DNA
<213> ORGANISM: Influenza A virus

<400> SEQUENCE: 8
agcaaaagca ggagtaaaga tgaatccaaa tcaaaagata ataacgattg gctctgtttc    60
tctcactatt gccacaatat gcttccttat gcaaattgcc atcctggtaa ctactgtaac   120
attgcatttc aagcaatatg aatgcagctc tccccaaac aaccaagtaa tgctgtgtga   180
accaacaata atagaaagaa cataacaga atagtgtat ctgaccaaca ccaccataga   240
gaaggaaata tgccccaaac tagcagaata cagaaattgg tcaaagccac aatgtaaaat   300
tacaggattt gcaccttttt ctaaggacaa ttcaattcgg ctttccgctg gtggggacat   360
ttgggtgaca agggaacctt atgtgtcgtg cgatcctgac aagtgttatc aatttgccct   420
tggacaggga acaacactaa acaacaggca ttcaaatgac acagtacatg ataggacccc   480
ttatcgaacc ctattgatga atgagttggg tgttccattt catttgggaa ccaagcaagt   540
gtgcatagca tggtccagct caagttgtca cgatggaaaa gcatggctgc atgtttgtgt   600
aactgggcat gatgaaaatg caactgctag cttcatttac gatgggaggc ttgtagatag   660
tattggttca tggtccaaaa aaatcctcag acccaggag tcggaatgcg tttgtatcaa   720
tggaacttgt acagtagtaa tgactgatgg gagtgcttca ggaagagctg atactaaat   780 actattcatt gaggagggga aaatcgttca tatcagccca ctgtcaggaa gtgctcagca   840
tgtcgaggag tgctcctgtt atcctcgata tcctggtgtc agatgtgtct gcagagacaa   900
```

-continued

```
ctggaaaggc tccaataggc ccatcgtaga tataaatgta aaggattata gcattgtttc    960
cagttatgtg tgctcaggac ttgttggaga cacacccaga aaaacgaca gctccagcag    1020
tagtcattgc ctgaatccta acaatgagga agggggtcat ggagtgaaag gctgggcctt   1080
tgatgatgga aatgacgtgt ggatgggaag aacgatcagc gagaagttcc gctcaggtta   1140
tgaaaccttc aaagtcattg aaggctggtc caaacctaac tccaaattgc agataaatag   1200
gcaagtcata gttgacagag gtaataggtc cggttattct ggtatttct ctgttgaagg    1260
caaaagctgc atcaatcggt gcttttatgt ggagttgata aggggaagga acaggaaac    1320
tgaagtctgg tggaccctcaa acagtattgt tgtgttttgt ggcacctcag gtacatatgg  1380
aacaggctca tggcctgatg gggcggacat caatctcatg cctatataag ctttcgcaat   1440
tttagaaaaa aactccttgt ttctact                                        1467

<210> SEQ ID NO 9
<211> LENGTH: 1762
<212> TYPE: DNA
<213> ORGANISM: Influenza A virus

<400> SEQUENCE: 9
agcaaaagca ggggataatt ctattaacca tgaagactat cattgctttg agctacattt    60
tatgtctggt tttcgctcaa aaacttcccg gaaatgacaa cagcacggca acgtgtgcc    120
tggggcacca tgcagtgtca acggaacgc tagtgaaaac aatcacgaat gaccaaattg    180
aagtgactaa tgctactgag ctggttcaga gttcctcaac aggtagaata tgcgacagtc    240
ctcaccaaat ccttgatgga gaaaactgca cactaataga tgctctattg ggagaccctc    300
attgtgatgg cttccaaaat aaggaatggg acctttttgt tgaacgcagc aaagcctaca    360
gcaactgtta cccttatgat gtgccggatt atgcctccct taggtcacta gttgcctcat    420
ccggcacact ggagtttaac aatgaaagct tcaattggac tggagtcgct cagaatggaa    480
caagctctgc ttgcaaaagg ggatctaata aaagtttctt tagtagattg aattggttgc    540
accaattaaa atacaaatat ccagcactga acgtgactat gccaaacaat gaaaaatttg    600
acaaattgta catttggggg gttctccacc cgagtacgga cagtgaccaa atcagcctat    660
atgctcaagc atcagggaga gtcacagtct ctaccaaaag aagccaacaa actgtaatcc    720
cgaatatcgg atctagaccc tgggtaaggg gtgtctccag cagaataagc atctattgga    780
caatagtaaa accggggagac atactttga ttaacagcac agggaatcta attgctcctc    840
ggggttactt caaaatacga agtgggaaaa gctcaataat gaggtcagat gcacccattg    900
gcaaatgcaa ttctgaatgc atcactccaa atggaagcat tcccaatgac aaaccatttc    960
aaaatgtaaa caggatcaca tatggggcct gtcccagata tgttaagcaa aacactctga    1020
aattggcaac agggatgcgg aatgtaccag agaaacaaac tagaggcata ttcggcgcaa   1080
tcgcgggttt catagaaaat ggttgggagg gaatggtgga cggttggtac ggtttcaggc   1140
atcaaaattc tgagggcaca ggacaagcag cagatcttaa aagcactcaa gcagcaatca    1200
accaaatcaa cggggaaactg aataggttaa tcgagaaaac gaacgagaaa ttccatcaaa    1260
ttgaaaaaga attctcagaa gtagaaggga gaattcagga cctcgagaaa tatgttgagg    1320
acactaaaat agatctctgg tcgtacaacg cggagcttct tgttgccctg gagaaccaac    1380
atacaattga tctaactgac tcagaaatga acaaactgtt tgaaagaaca agaagcaac    1440
tgagggaaaa tgctgaggat atgggcaatg gttgtttcaa aatataccac aaaatgtgaca    1500
```

-continued

| | |
|---|---|
| atgcctgcat agggtcaatc agaaatggaa cttatgacca tgatgtatac agagacgaag | 1560 |
| cattaaacaa ccggttccag atcaaaggtg ttgagctgaa gtcaggatac aaagattgga | 1620 |
| tcctatggat ttcctttgcc atatcatgct ttttgctttg tgttgttttg ctggggttca | 1680 |
| tcatgtgggc ctgccaaaaa ggcaacatta ggtgcaacat ttgcatttga gtgcattaat | 1740 |
| taaaaacacc cttgtttcta ct | 1762 |

<210> SEQ ID NO 10
<211> LENGTH: 1466
<212> TYPE: DNA
<213> ORGANISM: Influenza A virus

<400> SEQUENCE: 10

| | |
|---|---|
| agcaaaagca ggagtaaaga tgaatccaaa tcaaaagata ataacgattg gctctgtttc | 60 |
| tctcactatt gccacaatat gcttccttat gcaaatagcc atcctggtaa ctactgtaac | 120 |
| attgcatttc aagcaatatg aatgcaactc cccccccaaac aaccaagtaa tgctgtgtga | 180 |
| accaacaata atagaaagaa acataacaga gatagtgtat ctgaccaaca ccaccataga | 240 |
| gaaggaaata tgccccaaac tagcagaata cagaaattgg tcaaagccgc aatgtaaaat | 300 |
| tacaggattt gcacctttt ctaaggataa ttcaattcgg cttccgctg gtggggacat | 360 |
| ttgggtgaca agagaacctt atgtgtcatg cgatcctgac aagtgttatc aatttgccct | 420 |
| tggacaggga acaacactaa acaacaggca ttcaaatgac acagtacatg ataggacccc | 480 |
| ttatcgaacc ctattgatga atgagttggg tgttccattt catttgggaa ccaagcaagt | 540 |
| gtgtatagca tggtccagct caagttgtca cgatggaaaa gcatggctgc atgtttgtgt | 600 |
| aactgggcat gatgaaaatg caactgctag cttcatttac gatgggagac ttgtagatag | 660 |
| tattggttca tggtccaaaa aaatcctcag gacccaggag tcggaatgcg tttgtatcaa | 720 |
| tggaacttgt acagtagtaa tgactgatgg gagtgcttca ggaagagctg atactaaaat | 780 |
| acttttcatt gaggagggga aaatcgttca tactagcaaa ttgtcaggaa gtgctcagca | 840 |
| tgtcgaggag tgctcctgtt atcctcgata tcctggtgtc agatgtgtct gcagagacaa | 900 |
| ctggaaaggc tccaataggc ccatcgtaga tataaatgta aaggattata gcattgtttc | 960 |
| cagttatgtg tgctcaggac ttgttggaga cacacccaga aaaaacgaca gctccagcag | 1020 |
| tagccattgc ctggatccta acaatgaaga agggggtcat ggagtgaaag ctgggcctt | 1080 |
| tgatgatgga aatgacgtgt ggatgggaag aacgatcagc gagaagtcac gctcaggtta | 1140 |
| tgaaaccttc aaggtcattg aaggctggtc caaacctaac tccaaattgc agataaatag | 1200 |
| gcaagtcata gttgaaagag gtaatatgtc cggttattct ggtattttct ctgttgaagg | 1260 |
| caaaagctgc atcaatcggt gcttttatgt ggagttgata aggggaagga acaggaaac | 1320 |
| tgaagtctgg tggacctcaa acagtattgt tgtgttttgt ggcacctcag gtacatatgg | 1380 |
| aacaggctca tggcctgatg gggcggacat caatctcatg cctatataag ctttcgcaat | 1440 |
| tttagaaaaa actccttgtt tctact | 1466 |

<210> SEQ ID NO 11
<211> LENGTH: 1762
<212> TYPE: DNA
<213> ORGANISM: Influenza A virus

<400> SEQUENCE: 11

| | |
|---|---|
| agcaaaagca gggataatt ctattaacca tgaagactat cattgcttta agctacattc | 60 |
| tatgtctggt tttctctcaa aagcttcccg gaaatgacaa cagcacggca acgctgtgcc | 120 |

```
ttgggcacca tgcagtacca aacggaacga tagtgaaaac aatcacgaat gaccaaattg      180
aagttactaa tgctactgag ctggttcaga gttcctcaac aggtggaata tgcgacagtc      240
ctcatcagat ccttgatgga gaaaactgca cactaataga tgctctattg ggagaccctc      300
agtgtgatgg cttccaaaat aagaaatggg acctttttgt tgaacgcagc aaagcctaca      360
gcaactgtta cccttatgat gtgccggatt atgcctccct taggtcacta gttgcctcat      420
ccggcacact ggagtttaac aatgaaagct tcaattgggc tggagtcact cagaatggaa      480
caagctctgc ttgcaaaagg agatctaata aaagtttctt tagtagattg aattggttga      540
cccacttaaa atacaaatac ccagcattga acgtgactat gccaaacaat gaaaaatttg      600
acaaattgta catttggggg gttcaccacc cggttacgga cagtgaccaa atcagcctat      660
atgctcaagc atcaggaaga atcacagtct ctaccaaaag aagccaacaa actgtaatcc      720
cgaatatcgg atatagaccc agggtaaggg atatctccag cagaataagc atctattgga      780
caatagtaaa accgggagac atactttga ttaacagcac aggaaatcta attgctcctc       840
ggggttactt caaaatacga agtgggaaaa gctcaataat gagatcagat gcacccattg      900
gcaaatgcaa ttctgaatgc atcactccaa atggaagcat tcccaatgac aaaccatttc      960
aaaatgtaaa caggatcaca tatgggggcct gtcccagata tgttaagcaa acactctga     1020 aattggcaac agggatgcga atgtaccag agaaacaaac tagaggcata tttgcgcaa      1080 tcgcgggttt catagaaaat ggttgggagg gaatggtgga cggttggtac ggtttcaggc     1140
atcaaaattc tgagggcaca ggacaagcag cagatctcaa aagcactcaa gcagcaatca     1200
accaaatcaa tgggaaactg aataggttaa tcgggaaaac aaacgagaaa ttccatcaga     1260
ttgaaaaaga attctcagaa gtagaaggga gaattcagga cctcgagaaa tatgttgagg     1320
acactaaaat agatctctgg tcatacaacg cggagcttct tgttgccctg gaaaaccaac     1380
atacaattga tctaactgac tcagaaatga acaaactgtt tgaaagaaca agaagcaac      1440 tgagggaaaa tgctgaggat atgggcaatg gttgtttcaa atataccac aaatgtgaca     1500 atgcctgcat agagtcaatc agaaatggaa cttatgacca tgatgtatac agagatgaag     1560
cattaaacaa ccggttccag atcaaggtg ttgagctgaa gtcaggatac aaagattgga     1620
tcctatggat ttcctttgcc atatcatgtt ttttgctttg tgttgctttg ttggggttca     1680
tcatgtgggc ctgccaaaaa ggcaacatta ggtgcaacat tgcatttga gtgcattaat     1740 taaaaacacc cttgtttcta ct                                              1762

<210> SEQ ID NO 12
<211> LENGTH: 1467
<212> TYPE: DNA
<213> ORGANISM: Influenza A virus

<400> SEQUENCE: 12
agcaaaagca ggagtaaaga tgaatccaaa tcaaaagata ataacgattg gctctgtttc       60
cctcaccatt tccacaatat gcttcttcat gcaaattgcc atcctgataa ctactgtaac      120
attgcatttc aagcaatatg aattcaactc cccccaaac aaccaagtga tgctgtgtga      180
accaacaata atagaaagaa acataacaga gatagtgtat ctgaccaaca ccaccataga      240
gaaggaaata tgccccaaac tagcagaata cagaaattgg tcaaagccgc aatgtaacat      300
tacaggattt gcaccttttt ctaaggacaa ttcgattcgg ctttccgctg gtggggacat      360
ctgggtgaca agagaacctt atgtgtcatg cgatcctgac aagtgttatc aatttgccct      420
```

```
tggacaggga acaacactaa acaacgtgca ttcaaatgac acagtacatg ataggacccc    480
ttatcggacc ctattgatga atgagttggg tgttccattt catctgggga ccaagcaagt    540
gtgcatagca tggtccagct caagttgtca cgatggaaaa gcatggctgc atgtttgtgt    600
aacgggggat gatgaaaatg caactgctag cttcatttac aatgggaggc ttgtagatag    660
tattgtttca tggtccaaaa aaatcctcag gacccaggag tcagaatgcg tttgtatcaa    720
tggaacttgt acagtagtaa tgactgatgg agtgcttca ggaaaagctg atactaaaat    780
actattcatt gaggagggga aaattgttca tactagcaca ttatcaggaa gtgctcagca    840
tgtcgaggag tgctcctgtt atcctcgata tcctggtgtc agatgtgtct gcagagacaa    900
ctggaaaggc tccaataggc ccatcgtaga tataaacata aaggattata gcattgtttc    960
cagttatgtg tgctcaggac ttgttggaga cacacccaga aaaaacgaca gctccagcag   1020
tagccattgc ttggatccaa acaatgagga aggtggtcat ggagtgaaag gctgggcatt   1080
tgatgatgga aatgacgtgt ggatgggaag aacgatcagc gagaagttac gctcaggata   1140
tgaaaccttc aaagtcattg aaggctggtc caaccctaac tccaaattgc agataaatag   1200
gcaagtcata gttgacagag gtaacaggtc cggttattct ggtattttct ctgttgaagg   1260
caaaagctgc atcaatcggt gctttttatgt ggagttgata aggggaagaa acaggaaac    1320 tgaagtcttg tggaccctcaa acagtattgt tgtgttttgt ggcacctcag gtacatatgg   1380
aacaggctca tggcctgatg gggcggacat caatctcatg cctatataag ctttcgcaat   1440
tttagaaaaa aactccttgt ttctact                                       1467
```

<210> SEQ ID NO 13
<211> LENGTH: 1778
<212> TYPE: DNA
<213> ORGANISM: Influenza A virus

<400> SEQUENCE: 13

```
agcaaaagca ggggaaaata aaaacaacca aaatgaaagc aaaactacta gtcctgttat     60
gtgcatttac agctacatat gcagacacaa tatgtatagg ctaccatgcg aacaactcaa    120
ccgacactgt tgacacagta cttgagaaga acgtgacagt gacacactct gtcaacctac    180
ttgaggacag tcacaacgga aaactatgtc gactaaaggg aatagcccca ctacaattgg    240
gtaattgcag cgttgccgga tggatcttag gaaacccaaa atgcgaatca ctgttttcta    300
aggaatcatg gtcctacatt gcagaaacac caaaccctga gatggaaaca tgttacccag    360
ggtatttcgc cgactatgag gaactgaggg agcaattgag ttcagtatca tcattcgaga    420
gattcgaaat attccccaaa gaaagctcat ggcccaacca caccgtaacc aaaggagtaa    480
cgacatcatg ctcccataat gggaaaagca gttttttacag aaatttgcta tggctgacga    540
agaagaatgg cttgtaccca aatgtgagca agtcctatgt aaacaacaaa gagaagaag    600 tccttgtact atggggtgtt catcacccgt ctaacatagg ggaccaaagg gccatctatc    660
atacagaaaa tgcttatgtc tctgtagtgt cttcacatta tagcagaaga ttcacccag    720 aaatagcaaa aagacccaaa gtaagagatc aagaaggaag aattaactac tactggactc    780
tgctggaacc cggggacaca ataatatttg aggcaaatgg aaatctaata gcgccatggt    840
atgctttcgc actgagtaga ggctttgggt caggaatcat cacctcaaac gcatcaatgg    900
atgaatgtga cgcgaagtgt caaacacccc agggagctat aaacagtagt cttccttttcc    960 agaatgtaca cccagtcaca ataggagagt gtccaaagta tgtcaggagt acaaaattaa   1020
ggatggttac aggactaagg aacatcccat ccattcaatc cagaggtttg tttggagcca   1080
```

-continued

```
ttgccggttt cattgaaggg gggtggactg gaatgataga tggatggtat ggttatcatc    1140
atcagaatga acaaggatct ggctatgctg cggaccaaaa aagcacacaa aatgccatta    1200
acgggattac aaacaaggtg aattctgtaa tcgagaaaat gaacactcaa ttcacagctg    1260
tgggcaaaga attcaacaaa ttagaaagaa ggatggaaaa cttaaataaa aaagttgatg    1320
atggatttct ggacatttgg acatataatg cagaattgtt ggttctactg aaaatggaa     1380 ggactttgga ttttcatgac tcaaatgtga agaatctgta tgagaaagta aaaagccaat    1440
tgaagaataa tgccaaagaa atagggaacg ggtgttttga attctatcac aagtgtaaca    1500
atgaatgcat ggaaagtgtg aaaaatgaa cttatgacta tccaaaatat tccgaagaat     1560
caaagttaaa caggggaaaa attgatggag tgaaattgga atcaatggga gtctatcaga    1620
ttctggcgat ctactcaact gtcgccagtt cactggtgct tttggtctcc ctgggggcaa    1680
tcagcttctg gatgtgttct aatgggtctt tgcagtgtag aatatgcatc tgagaccaga    1740
atttcagaaa ataagaaaaa aacacccttg tttctact                            1778
```

```
<210> SEQ ID NO 14
<211> LENGTH: 1463
<212> TYPE: DNA
<213> ORGANISM: Influenza A virus

<400> SEQUENCE: 14
```

```
agcaaaagca ggagtttaaa atgaatccaa atcaaaaaat aataatcata ggatcaatca      60
gtatggcaat cggaataatt agtctaatat tgcaaatagg aaatattatt tcaatatggg     120
ctagccactc aatccaaact ggaagtcaaa accacactgg aatatgcaac caagaatca     180 ttacatatga aaatagcacc tgggtgaatc aaacatatgt taatattaac aacactaatg     240
ttgttgctgg aaaggacaaa acttcagtga cattggccgg caattcatct ctttgcccta     300
tccgtgggtg ggctatatac acaaaagaca acagcataag aattggttcc aaaggagatg     360 ttttgtcat aagagagcct tttatatcat gttctcactt ggaatgcaga acctttttc       420 tgacccaagg tgctctatta aatgacaagc attcaaatgg accgttaag acagaagcc      480 cttataggc cttaatgagc tgtcctctag gtgaagctcc gtctccatac aattcaagat      540
ttgaatcagt tgcttggtca gcaagcgcat gccatgatgg catgggctgg ctaacaatcg     600
gaatttctgg tccagataat ggagcagtgg ctgtactaaa atacaacggc ataataactg     660
aaaccataaa aagttggaag aagcgaatat taagaacaca agagtctgaa tgtgtctgtg     720
tgaacggttc atgttttacc ataatgaccg atggcccgag taatgggcc gcctcgtaca      780 gaatcttcaa aatcgagaag gggaaggtta ctaaatcaat agagttggat gcacccaatt     840
atcattacga ggaatgttcc tgttacccag acaccggcac agtgatgtgt gtgtgcaggg     900
acaattggca cggttcaaat cgaccttggg tgtctttaa tcaaaacctg gattatcaaa      960
taggatacat ctgcagtggg gtgttcggtg acaatccgcg tcccaaagat ggagaaggca     1020
gctgtaatcc agtgactgtt gatggagcag acggagtaaa ggggttttca tacagatatg     1080
gtaatggtgt ttggataggaa aggactaaaa gtaacagact cagaaaggga tttgagatga     1140
tttgggatcc taatggatgg acagataccg acagtgattt ctctgtgaaa caggatgtcg    1200
tggcaatgac tgattggtca gggtacagcg gaagtttcgt tcaacatcct gagctaacag    1260
gattggactg tatgagacct tgcttctggg ttgaattaat cagagggcga cctagagaaa    1320
atacaacaat ctggactagt gggagcagca tttcttttg tggcgtaaat agcgatactg     1380
```

```
caaactggtc ttggccagac ggtgccgagt tgccattcac cattgacaag tagtccgttg    1440
aaaaaaaact ccttgtttct act                                            1463

<210> SEQ ID NO 15
<211> LENGTH: 1689
<212> TYPE: DNA
<213> ORGANISM: Influenza A virus

<400> SEQUENCE: 15
aaatgaaagc aaaactacta gtcctgttgt gtgcatttac agctacatat gcagacacaa      60
tatgtatagg ctaccatgcg aacaactcaa ccgacactgt tgacacagta cttgagaaga     120
acgtgacagt gacacactct gtcaacctac ttgaggacag tcacaacgga aaactatgcc     180
gactaaaagg aacagcccca ctacaattgg gtaattgcag cgttgccgga tggatcttag     240
gaaacccaga atgcgaatca ctgttttcta aggaatcatg gtcctacatt gcagaaacac     300
caaaccctga gaatggaaca tgttaccagg gtatttcgc cgactatgag gaactgaggg     360
agcaattgag ctcagtatca tcattcgaga gattcgaaat attccccaag gaaagctcat     420
ggcccaaaca caccgtaacc aaggagtgac ggcatcatg ctcccataat gggaaaagca     480
gtttttacaa aaatttgcta tggctgacgg aaaagaatgg cttgtaccca atctgagca     540 agtcctatgt aaacaacaag gagaaagaag tccttgtact atggggtgtt catcacccgt     600
ctaacatagg ggaccaaagg gccatctatc atacagaaaa tgcttatgtc tctgtagtgt     660
cttcacatta tagcagaaga ttcacccag aaatagcaaa aagacccaaa gtaagaggtc     720
aagaagggag aattaactac tactggactc tgctggaacc cggggacaca ataatatttg     780
aggcaaatgg aaatctaata gcgccatggt acgctttcgc actgagtaga ggctttgggt     840
caggaatcat cacctcaacc gcatcaatgg gtgaatgtga cgctaagtgt caaacaccc     900 aaggagctat aaacagtagt cttccttttcc agaatgtaca cccagtcaca ataggagagt     960
gtcccaagta tgtcaggagt acaaaattaa ggatggttac aggactaaga acatccccat    1020
ccattcaatc tagaggtttg ttttggagcca ttgccggttt cattgaaggg ggtggactg    1080 gaatgataga tggatggtat ggttatcatc atcagaatga acaaggatct ggctatgctg    1140
cagaccaaaa aagcacacaa atgccattg atgggattac aaacaaggtg aattctgtaa    1200
tcgagaaaat gaacactcaa ttcacagctg taggcaaaga attcaacaaa ttagagagaa    1260
ggatggaaaa cttaaataag aaagttgatg atggatttct ggacatttgg acatataatg    1320
cagagttgtt ggttctcctg gaaaatggaa ggactttggg ttttcatgac tcaaatgtga    1380
agaatctgta tgagaaagta aaaaaccaat tgaagaataa tgccaaagaa atcgggaacg    1440
ggtgttttga attctatcac aagtgtaaca atgaatgcat ggaaagtgtg aaaaatggaa    1500
cttatgacta tccaaaatat tccgaagaat caaagttaaa cagggaaaaa attgatggag    1560
tgaaattgga atcaatggga gtctatcaga ttctggcgat ctactcaact gtcgccagtt    1620
cactggtgct tttggtctcc ctgggggcaa tcagtttctg gatgtgttct aatgggtctt    1680
tgcagtgta                                                            1689

<210> SEQ ID NO 16
<211> LENGTH: 1447
<212> TYPE: DNA
<213> ORGANISM: Influenza A virus

<400> SEQUENCE: 16
agcaaaagca ggagtttaaa atgaatccaa atcaaaaaat aataaccatt ggatcaatca      60
```

```
gtattgcaat tggaataatt agtctgatat tgcaaatagg aaatattatt tcaatatggg    120
ctagccactc aatccaaact ggaagtcaaa accacactgg aatatgcaac caaagaatca    180
ttacatatga aaatagcacc tgggtaaatc aaacatatgt taatattaac aacactaatg    240
ttgttgctgg aaaggacaaa acctcaatga cattggccgg caattcatct ctttgcccta    300
tccgtggatg ggctatatac acaaaagaca acagcataag aattggttcc aaaggagatg    360
tttttgtcat aagagagcct tttatatcat gttctcactt ggaatgcaga accttttttc    420
tgacccaagg tgctctatta aatgacaagc attcaaatgg gaccgttaag gacagaagcc    480
cttatagggc cttaatgagc tgtcctctag gtgaagctcc gtctccatac aattcaagat    540
ttgaatcagt tgcttggtca gcaagcgcat gccatgatgg cttgggctgg ctaacaatcg    600
gaatttctgg tccagataat ggggcagtgg ctgtactaaa atacaacggc ataataactg    660
aaaccattaa aagttggaag aagcgaatat taagaacaca agagtctgaa tgtgtctgta    720
tgaacggttc atgttttacc ataatgaccg atggcccgag taatggggcc gcatcgtaca    780
gaatcttcaa aatcgagaag ggagagttta ctaaatcaat agagttggat gcacccaatt    840
atcattacga ggaatgttca tgttacccag acaccggcac agtgatgtgt gtgtgcaggg    900
acaattggca cggttcaaat cgaccttggg tgtcttttaa tcaaaacctg gattatcaaa    960
taggatacat ctgcagtggg gtgttcggtg acaatccgcg tcccaaagat ggagaaggca   1020
gctgtaatcc agtgactgtt gatggagcag acggagtaaa ggggttttca tacagatatg   1080
gtaatggtgt ttggatagga aggactaaaa gtaacagact cagaaaggga tttgagatga   1140
tttgggatcc taatggatgg acagataccg acagtgattt ctcaatgaaa caggatatcg   1200
tggcaatgac tgattggtca gggtacagcg gaagttttgt tcaacatcct gagctaacag   1260
gattggactg tatgagacct tgcttttggg ttgaattagt cagagggcta cctagagaaa   1320
atacaacaat ctggactagt gggagcagca tttctttttg tggcgtaaat agcgatactg   1380
caaactggtc ttggccagac ggtgccgagt tgccattcac cattgacaag tagtccgttg   1440
aaaaaaa                                                             1447
```

<210> SEQ ID NO 17
<211> LENGTH: 1775
<212> TYPE: DNA
<213> ORGANISM: Influenza A virus

<400> SEQUENCE: 17

```
agcaaaagca ggggaaaata aaaacaacca aaatgaaagc aaaactacta gtcctgttat     60
gtacatttac agctacatat gcagacacaa tatgtatagg ctaccatgcc aacaactcaa    120
ccgacactgt tgacacagta cttgagaaga atgtgacagt gacacactct gtcaacctac    180
ttgaggacag tcacaatgga aaactatgtc tactaaaagg aatagcccca ctacaattgg    240
gtaattgcag cgttgccgga tggatcttag gaaacccaga atgcgaatca ctgatttcta    300
aggaatcatg gtcctacatt gtagagacac caaaccctga gaatggaaca tgttacccag    360
ggtatttcgc cgactatgag gaactgaggg agcaattgag ttcagtatca tcatttgaga    420
gattcgaaat attccccaaa gaaagctcat ggcccaaaca caccgtaaca ggagtaacgg    480
catcatgctc ccataatggg aaaagcagtt tttacagaaa tttgctatgg ctgacggaga    540
agaatggctt gtacccaaat ctgagcaatt cctatgtgaa caacaaagag aaagaagtcc    600
ttgtactatg ggtgttcat cacccatcta acatagggga ccaaagggcc atctatcata     660
```

```
cagaaaacgc ttatgtctct gtagtgtctt cacattatag cagaagattc accccagaaa      720
tagcaaaaag acccaaagta agaggtcagg aaggaagaat caactactac tggactctgc      780
tggaacccgg ggacacaata atatttgagg caaatggaaa tctaatagcg ccatggtatg      840
ctttcgcact gagtagaggc tttgggtcag gaatcatcac ctcaaatgca ccaatgaatg      900
aatgtgatgc gaagtgtcaa acacctcagg gagctataaa cagtagtctt cctttccaga      960
atgtacaccc agtcacaata ggagagtgtc caaagtatgt caggagtaca aaattaagga     1020
tggttacagg actaaggaat atcccatcca ttcaatccag aggtttgttt ggagccattg     1080
ccggtttcat tgaaggggggg tggactgaaa tgatggatgg gtggtatggt tatcatcatc     1140
agaatgagca aggatctggc tatgctgcag atcaaaaaag cacacaaaat gccattaacg     1200
ggattacaaa taaggtgaat tctgtaattg agaaaatgaa cactcaattc acagctgtgg     1260
gcaaagaatt caacaaatta gaaagaagga tggaaaactt aaataaaaaa gttgatgatg     1320
gatttctaga catttggaca tataatgcag aattgttggt tctactggaa aatgaaagga     1380
ctttggattt ccatgactca aatgtgaaga atctgtatga aaagtgaaaa agccaattaa     1440
agaataatgc caaagaaata gggaacgggt gttttgaatt ctatcacaag tgtaacaatg     1500
aatgcatgga aagtgtgaaa aatggaactt atgactatcc aaaatattcc gaagaatcaa     1560
agttaaacag ggagaaaatt gatgagtga attggaatc aatgggagtc tatcagattc     1620
tggcgatcta ctcaactgtc gccagttcac tggttctttt ggtctccctg ggggcaatca     1680
gcttctggat gtgttccaat gggtctttgc agtgtagaat atgcatctga gaccagaatt     1740
tcagaaatat aagaaaaaac accttgtttt ctact                                1775

<210> SEQ ID NO 18
<211> LENGTH: 1463
<212> TYPE: DNA
<213> ORGANISM: Influenza A virus

<400> SEQUENCE: 18
agcaaaagca ggagtttaaa atgaatccaa atcaaaaaat aataaccatt ggatcaatca       60
gtatagtaat cgggataatt agtctaatgt tgcaaatagg aaatattatt tcaatatggg      120
ctagtcactc aatccaaact ggaagtcaaa accacactgg aatatgcaac caaagaatca      180
tcacatatga aaatagcacc tgggtgaatc acacatatgt taatattaac aacactaatg      240
ttgttgctgg aaaggacaaa acttcagtga cattggccgg caattcatca ctttgttcta      300
tcagtggatg ggctatatac acaaaagaca acagcataag aattggttcc aaaggagatg      360
tttttgtcat aagagagcct tttatatcat gttctcactt ggaatgcaga acctttttc      420 tgacccaagg tgctctatta atgacaaac attcaaatgg accgttaag acagaagtc      480 cttatagggc cttaatgagc tgtcctctag gcgaagctcc gtctccatat aattcaaagt      540
ttgaatcagt tgcttggtca gcaagcgcat gtcatgatgg catgggctgg ttaacaatcg      600
gaatttctgg tccagataat ggagcagtgg ctgtactaaa atacaacggc ataataactg      660
aaaccataaa aagttggaaa aagcgaatat taagaacaca agagtctgaa tgtgtctgtg      720
tgaacgggtc atgttttacc ataatgaccg atggcccgag taatgggggcc gctcgtaca      780 aaatcttcaa gattgagaag gggaaggtta ctaaatcaat agagttgaat gcacccaatt      840
ctcattatga ggaatgttcc tgttacccag acactggcac agtgatgtgt gtatgcaggg      900
acaattggca cggttcaaat cgaccttggg tgtcttttaa tcaaaacctg gattatcaaa      960
taggatacat ctgcagtggg gtgttcggtg acaatccgcg tccccaaagat ggagagggca     1020
```

```
gctgtaatcc agtgactgtt gatggagcag acggagtaaa ggggttttca tacagatatg    1080
gtaatggtgt ttggatagga aggactaaaa gtaacagact cagaaaggga tttgagatga    1140
tttgggatcc taatggatgg acagataccg acagtgattt ctcagtgaaa caggatgttg    1200
tggcaatgac tgattggtca gggtacagcg aagtttcgt tcaacatcct gagctaacag    1260
gattggactg tataagacct tgcttctggg ttgaattagt cagaggacgg cctagagaaa    1320
atacaacaat ctggactagt gggagcagca tttcttttttg tggcgtaaat agtgatactg    1380
caaactggtc ttggccagac ggtgctgagt tgccattcac cattgacaag tagtccgttg    1440
aaaaaaaact ccttgtttct act                                             1463

<210> SEQ ID NO 19
<211> LENGTH: 1775
<212> TYPE: DNA
<213> ORGANISM: Influenza A virus

<400> SEQUENCE: 19
agcaaaagca ggggaaaata aaaacaacca aaatgaaagc aaaactactg gtcctgttat      60
gtacatttac agctacatat gcagacacaa tatgtatagg ctaccatgcc aacaactcaa     120
ccgacactgt tgacacagta cttgagaaga atgtgacagt gacacactct gtcaacctac     180
ttgaggacag tcacaatgga aaactatgtc tactaaaagg aatagcccca ctacaattgg     240
gtaattgcag cgttgccgga tggatcttag gaaacccaga atgcgaatta ctgatttcca     300
aggaatcatg gtcctacatt gtagaaacac caaatcctga atgtgaaca tgttacccag     360 ggtatttcgc cgactatgag gaactgaggg agcaattgag ttcagtatct tcatttgaga     420
gattcgaaat attccccaaa gaaagctcat ggcccaaaca caccgtaacc ggagtatcag     480
catcatgctc ccataatggg aaaaacagtt tttacagaaa tttgctatgg ctgacgggga     540
agaatggttt gtacccaaac ctgagcaagt cctatgtaaa caacaaagag aagaagtcc      600 ttgtactatg gggtgttcat cacccgccta acataggga ccaagggcc ctctatcata      660 cagaaaatgc ttatgtctct gtagtgtctt cacattatag cagaagattc accccagaaa    720
tagccaaaag acccaaagta agagatcagg aaggaagaat caactactac tggactctgc    780
tggaacctgg ggatacaata atatttgagg caaatggaaa tctaatagcg ccatggtatg    840
cttttgcact gagtagaggc tttggatcag gaatcatcac ctcaaatgca ccaatggatg    900
aatgtgatgc gaagtgtcaa acacctcagg gagctataaa cagcagtctt cctttccaga    960
atgtacaccc agtcacaata ggagagtgtc caaagtatgt caggagtgca aaattgagga    1020
tggttacagg actaaggaac atcccatcca ttcaatccag aggtttgttt ggagccattg    1080
ccggtttcat tgaaggggg tggactgaa tggtagatgg gtggtatggt tatcatcatc      1140
agaatgagca aggatctggc tatgctgcag atcaaaaaag tacacaaaat gccattaacg    1200
ggattacaaa caaggtgaat tctgtaattg agaaaatgaa cactcaattc acagctgtgg    1260
gcaaagaatt caacaaattg gaaagaagga tggaaaactt aataaaaaa gttgatgatg    1320 ggtttctaga catttggaca tataatgcag aattgttggt tctactggaa atgaaagga    1380 cttttggattt ccatgactcc aatgtgaaga atctgtatga gaaagtaaaa agccaattaa    1440
agaataatgc caagagaaata ggaaacgggt gttttgaatt ctatcacaag tgtaacaatg    1500
aatgcatgga gagtgtgaaa atgggaactt atgactatcc aaaatattcc gaagaatcaa    1560
agttaaacag ggagaaaatt gatggagtga aattggaatc aatgggagtc tatcagattc    1620
```

-continued

```
tggcgatcta ctcaactgtc gccagttccc tggttctttt ggtctccctg ggggcaatca   1680
gcttctggat gtgttccaat gggtctttgc agtgtagaat atgcatctga gaccagaatt   1740
tcagaagtat aagaaaaaac acccttgttt ctact                              1775

<210> SEQ ID NO 20
<211> LENGTH: 1463
<212> TYPE: DNA
<213> ORGANISM: Influenza A virus

<400> SEQUENCE: 20
agcaaaagca ggagtttaaa atgaatccaa atcaaaaaat aataaccatt ggatcaatca     60
gtatagcaat cggaataatt agtctaatgt tgcaaatagg aaatattatt tcaatatggg    120
ctagtcactc aatccaaact ggaagtcaaa accacactgg agtatgcaac caaagaatca    180
tcacatatga aaacagcacc tgggtgaatc acacatatgt taatattaac aacactaatg    240
ttgttgctgg aaaggacaaa acttcagtga cattggccgg caattcatct ctttgttcta    300
tcagtggatg ggctatatac acaaaagaca acagcataag aattggctcc aaaggagatg    360
tttttgtcat aagagaacct ttcatatcat gttctcactt ggaatgcaga accttttttc    420
tgacccaagg tgctctatta aatgacaaac attcaaatgg gaccgttaag gacagaagtc    480
cttatagggc cttaatgagc tgtcctctag gtgaagctcc gtccccatac aattcaaagt    540
ttgaatcagt tgcatggtca gcaagcgcat gccatgatgg catgggctgg ttaacaatcg    600
gaatttctgg tccagacaat ggagctgtgg ctgtactaaa atacaacggc ataataactg    660
aaaccataaa aagttggaaa aagcgaatat taagaacaca agagtctgaa tgtgtctgtg    720
tgaacgggtc atgtttcacc ataatgaccg atggcccgag taatggggcc gcctcgtaca    780
aaatcttcaa gatcgaaaag gggaaggtta ctaaatcaat agagttgaat gcacccaatt    840
ttcattatga ggaatgttcc tgttacccag acactggcac agtgatgtgt gtatgcaggg    900
acaactggca tggttcaaat cgaccttggg tgtcttttaa tcaaaacctg gattatcaaa    960
taggatacat ctgcagtggg gtgttcggtg acaatccgcg tcccaaagat ggagagggca   1020
gctgtaatcc agtgactgtt gatggagcag acggagtaaa ggggttttca tacaaatatg   1080
gtaatggtgt ttggatagga aggactaaaa gtaacagact tagaaagggg tttgagatga   1140
tttgggatcc taatggatgg acagataccg acagtgattt ctcagtgaaa caggatgttg   1200
tggcaataac tgattggtca gggtacagcg gaagtttcgt tcaacatcct gagttaacag   1260
gattggactg tataagacct tgcttctggg ttgagttagt cagaggactg cctagagaaa   1320
atacaacaat ctggactagt gggagcagca tttctttttg tggcgtaaat agtgatactg   1380
caaactggtc ttggccagac ggtgctgagt tgccgttcac cattgacaag tagttcgttg   1440
aaaaaaaact ccttgtttct act                                           1463

<210> SEQ ID NO 21
<211> LENGTH: 1879
<212> TYPE: DNA
<213> ORGANISM: Influenza B virus

<400> SEQUENCE: 21
agcagaagca gagcattttc taatatccac aaaatgaagg caataattgt actactcatg     60
gtagtaacat ccaacgcaga tcgaatctgc actgggataa catcttcaaa ctcacctcat    120
gtggtcaaaa cagctactca aggggaagtc aatgtgactg gtgtgatacc actgacaaca    180
acaccaacaa aatctcattt tgcaaatctc aaaggaacaa agaccagagg gaaactatgc    240
```

```
ccaaactgtc tcaactgcac agatctggat gtggccttgg gcagaccaat gtgtataggg    300
atcacacctt cggcaaaagc ttcaatactc cacgaagtca gacctgttac atccgggtgc    360
tttcctataa tgcacgacag aacaaaaatc agacagctac ccaatcttct cagaggatat    420
gaacatatca gattatcaac ccataacgtt atcaacgcag aaagggcacc aggaggaccc    480
tacagacttg gaacctcagg atcttgccct aacgttacca gtagaagcgg attcttcgca    540
acaatggctt gggctgtccc aagggacaac aaaacagcaa cgaacccact aacagtagaa    600
gtaccataca tttgtacaaa aggagaagac caaattactg tttgggggtt ccattctgat    660
aacaaaatcc aaatgaaaaa cctctatgga gactcaaatc ctcaaaagtt cacctcatct    720
gccaatggaa taaccacaca ttatgtttct cagattggtg gcttcccaaa tcaaacagaa    780
gacggagggc taccacaaag cggcagaatt gttgttgatt acatggtgca aaaacctggg    840
aaaacaggaa caattgtcta tcaaagaggt gttttgttgc ctcaaaaggt gtggtgtgca    900
agtggcagga gcaaggtaat aaaagggtcc ttgcctttaa ttggtgaagc agattgcctt    960
cacgaaaaat acggtggatt aaacaaaagc aagccttact acacaggaga acatgcaaaa   1020
gccataggaa attgcccaat atgggtgaaa acacctttaa agcttgccaa tggaaccaaa   1080
tatagacctc ccgcaaaact attaaaggaa aagggtttct tcggagctat tgctggtttc   1140
ttagaaggag gatgggaagg aatgattgca ggttggcacg gatacacatc tcatggagca   1200
catggggtgg cagtggcagc agaccttaag agtacgcaag aagccataaa caagataaca   1260
aaaaatctca attctttgag tgagctagaa gtaaagaatc ttcaaagact aagtggtgcc   1320
atggatgaac tccacaacga aatactcgag ctggatgaga aagtggatga tctcagagct   1380
gacacaataa gctcgcaaat agagcttgca gtcttgcttt ccaatgaagg aataataaac   1440
agtgaagatg agcatctatt ggcacttgag agaaaactaa agaaaatgct gggtccctct   1500
gctgtagaca tagggaatgg atgcttcgaa accaaacaca agtgcaacca gacctgctta   1560
gacaggatag ctgctggcac ctttaatgca ggagaatttt ctcttcccac ttttgattca   1620
ctgaatatta ctgctgcatc tttaaatgat gatggattgg ataatcatac tatactgctc   1680
tactactcaa ctgcggcttc tagtttggct gtaacattga tgatagctat ttttattgtt   1740
tatatggtct ccagagacaa tgtttcttgc tccatctgtc tatagggaaa attgagccct   1800
gtattttcct ttattgtggt gcttgtttgc ttgttgccat tacagagaaa cgttattgaa   1860
aaatgctctt gttactact                                                 1879
```

```
<210> SEQ ID NO 22
<211> LENGTH: 1554
<212> TYPE: DNA
<213> ORGANISM: Influenza B virus

<400> SEQUENCE: 22
agcagaagca gagcatcttc tcaaaactga agtaaagagg ccaaaaatga acaatgctac     60
cttcaactat acaaacgtta accctatttc tcacatcagg gggagtgtta ttatcactat    120
atgtgtcagc cttactgtca tacttattgt attcggatat attgctaaaa ttttcaccaa    180
aaataattgc accaacaacg tcgttggact gcgcgaacgc atcaaatgtt caggctgtga    240
accattctgc aacaaaagag atgaaattcc ttcccccaga accggagtgg acatacccc     300
gtttatcttg ccagggttca accttccaga aagcactctt aattagccct catagatttg    360
gagaagccaa aggaaactca gctcccttga taataaggga accttttatt gcttgtggac    420
```

-continued

| | |
|---|---|
| caaaggagtg caaacacttt gctctaaccc attatgcagc tcaaccaggg ggatactaca | 480 |
| atggaacaag agaggacaga aacaagctga ggcatctgat ttcagtcaac ttaggcaaaa | 540 |
| tcccaactgt agaaaactcc attttccata tggcagcttg gagtggatcc gcatgccatg | 600 |
| atggtagaga atggacatat atcggagttg atggtcctga cagtaatgca ttgatcaaaa | 660 |
| taaaatatgg agaagcatac actgacacat accattccta tgcaaacaac atcctaagaa | 720 |
| cacaagaaag tgcctgcaat tgcatcgggg gagattgtta tcttatgata actgatggct | 780 |
| cagcttcagg aattagtaaa tgcagattcc ttaagatccg agagggtcga ataataaaag | 840 |
| aaatatttcc aacaggaagg gtagagcaca ctgaagaatg cacatgcgga tttgccagca | 900 |
| acaaaaccat agaatgtgcc tgtagagata acagttacac agcaaaaaga ccctttgtca | 960 |
| aattaaatgt ggagactgat acagctgaaa taagattgat gtgcacagag acttatttgg | 1020 |
| acaccccag accagatgat ggaagcataa cagggccttg cgaatctaat ggggacaaag | 1080 |
| ggagtggagg tgtcaaggga ggatttgttc atcaaagaat ggcatccaag attggaagat | 1140 |
| ggtactcccg aacgatgtct aaaactaaaa gaatggggat ggaactgtat gtcaagtatg | 1200 |
| atggagaccc atggactgac agtgacgccc ttgctcctag tggagtaatg gtctcaatgg | 1260 |
| aagaacctgg ttggtactct ttcggcttcg aaataaaaga taagaaatgt gatgtcccct | 1320 |
| gtattgggat agagatggta catgatggtg gaaaaaggac ttggcactca gcagcaacag | 1380 |
| ccatttactg tttaatgggc tcaggacagt tgctatggga cactgtcaca ggtgttaata | 1440 |
| tggctctgta atggaggaat ggttgaatct gttctaaacc cttgttcct attttatttg | 1500 |
| aacaattgtc cttactggac ttaattgttt ctgaaaaatg ctcttgttac tact | 1554 |

<210> SEQ ID NO 23
<211> LENGTH: 1881
<212> TYPE: DNA
<213> ORGANISM: Influenza B virus

<400> SEQUENCE: 23

| | |
|---|---|
| agcagaagca gagcattttc taatatccac aaaatgaagg caataattgt actactcatg | 60 |
| gtagtaacat ccaatgcaga tcgaatctgc actgggataa catcgtcaaa ctcacctcat | 120 |
| gtggtcaaaa cagctactca aggggaggtc aatgtgactg gtgtgatacc actgacaaca | 180 |
| acaccaacaa aatctcattt tgcaaatctc aaaggaacaa agaccagagg gaaactatgc | 240 |
| ccaacctgtc tcaactgcac agatctggat gtggccttag cagaccaat gtgtgtgggg | 300 |
| gtcacacctt cggcaaaagc ttcaatactc acgaagtca ggcctgttac atccggatgc | 360 |
| tttcctataa tgcacgacag aacaaaaatc agacagctac ccaatcttct cagaggatat | 420 |
| gaaaaaatca gattatcaac ccaaatcgtt atcaacgcag aaaaggcacc aggaggaccc | 480 |
| tacagacttg gaacctcagg atcttgccct aacgctacca gtagaagcgg attttcgca | 540 |
| acaatggctt gggctgtccc aaaggacaac aacaaaacag caacgaatcc actaacagta | 600 |
| gaagtaccac acatctgtac aaaagaagaa gaccaaatta ctgtttgggg gttccattct | 660 |
| gatgacaaaa cccaaatgaa aaacctctat ggagactcaa atcctcaaaa gttcacctca | 720 |
| tctgctaatg gagtaaccac acattatgtt tctcagattg cggcttccc ggatcaaaca | 780 |
| gaagacggag ggctaccaca aagcggcaga attgttgttg attacatggt gcaaaaacct | 840 |
| gggaaaacag gaacaattgt ctatcaaaga ggtattttgt tgcctcaaaa ggtgtggtgc | 900 |
| gcgagtggca ggagcaaagt aataaaaggg tccttgcctt taattggtga agcagattgc | 960 |
| cttcacgaaa aatacggtgg attaaacaaa agcaagcctt actacacagg agaacatgca | 1020 |

-continued

| | |
|---|---|
| aaagccatag gaaattgccc aatatgggtg aaaacacctt tgaagcttgc caatggaacc | 1080 |
| aaatatagac ctcctgcaaa actattaaag gaaaggggtt tcttcggagc tattgctggt | 1140 |
| ttcttagaag gaggatggga aggaatgatt gcaggttggc acggatacac atctcacgga | 1200 |
| gcacatggag tggcagtggc agcagacctt aagagtacgc aagaagccat aaacaagata | 1260 |
| acaaaaaatc tcaattcttt gagtgagcta aagtaaaga atcttcaaag actaagtggt | 1320 |
| gccatggatg aactccacaa cgaaatactc gagctggatg agaaagtgga tgatctcaga | 1380 |
| gctgacacaa taagctcaca aatagaactt gcagtcttgc tttccaacga aggaataata | 1440 |
| aacagtgaag atgagcatct attggcactt gagagaaaac taagaaaat gctgggtccc | 1500 |
| tctgctgtag acatagggaa tggatgcttc gaaaccaaac acaagtgcaa ccagacctgc | 1560 |
| ttagacagga tagctgctgg caccttaat gcaggagaat tttctcttcc cactttgat | 1620 |
| tcactgaata ttactgctgc atctttaaat gatgatggat tggataacca tactatactg | 1680 |
| ctctactact caactgctgc ttctagtttg gctgtaacat tgatgatagc tattttat | 1740 |
| gtttatatga tctccagaga caatgtttct tgctccatct gtctataggg aaattaagcc | 1800 |
| ctgtatttc ctttattgta gtgcttgttt gcttgttatc attacaaaga aacgttattg | 1860 |
| aaaaatgctc ttgttactac t | 1881 |

<210> SEQ ID NO 24
<211> LENGTH: 1557
<212> TYPE: DNA
<213> ORGANISM: Influenza B virus

<400> SEQUENCE: 24

| | |
|---|---|
| agcagaagca gagcatcttc tcaaaactga ggcaaatagg ccaaaaatga acaatgctac | 60 |
| cttcaactat acaaacgtta accctatttc tcacatcagg gggagtgtta ttatcactat | 120 |
| atgtgtcagc ttcactgtca tacttactat attcggatat attgctaaaa ttttcaccaa | 180 |
| cagaaataac tgcaccaaca atgccattga attgtgcaaa cgcatcaaat gttcaggctg | 240 |
| tgaaccgttc tgcaacaaaa ggggtgacac ttcctctccc agaaccggag tggacatacc | 300 |
| ctcgtttatc ttgcccgggc tcaaccttc agaaagcact cctaattagc cctcatagat | 360 |
| tcggagaaac caaaggaaac tcagctcct tgataataag ggaacctttt attgcttgtg | 420 |
| gaccaaagga atgcagacac tttgctctaa cccattatgc agcccaacca gggggatact | 480 |
| acaatggaac aagagaagac agaaacaagc tgaggcatct aatttcagtc aaattgggca | 540 |
| aaatcccaac agtagaaaac tccatttcc acatggcagc ttggagcggg tccgcatgcc | 600 |
| atgatggtag agaatggaca tatatcggag ttgatggccc tgacagtaat gcattgctca | 660 |
| aaataaaata tggagaagca tatactgaca catacattc ctatgcaaac aacatcctaa | 720 |
| gaacacaaga aagtgcctgc aattgcatcg ggggagattg ttatcttatg ataactgatg | 780 |
| gctcagcttc agggattagt gaatgcagat tcttaagat tcgagagggc cgaataataa | 840 |
| aagaaatatt tccaacagga agagtagaac atactgaaga atgcacatgc ggatttgcca | 900 |
| gcaataaaac catagaatgt gcctgtagag ataacagtta cacagcaaaa agacccttg | 960 |
| tcaaattaaa tgtggagact gatacagcag aaataagatt gatgtgcaca gagacttact | 1020 |
| tggacacccc cagaccagat gatggaagca taacagggcc ttgtgaatct aatgggggata | 1080 |
| aagggagtgg aggcatcaag ggaggatttg ttcatcaaag aatggcatcc aagattggaa | 1140 |
| ggtggtactc tcgaacgatg tctaaaacta aaaggatggg gatgggactg tatgtcaagt | 1200 |

| | |
|---|---|
| atgatggaga cccatggatt gacagtgatg cccttactct tagcggagta atgg cctgtatttt cctttattgt agtgcttgtt tgcttgttat cattacaaag aaacgttatt 1860 gaaaaatgct cttgttacta ct 1882

<210> SEQ ID NO 26
<211> LENGTH: 1557
<212> TYPE: DNA
<213> ORGANISM: Influenza B virus

<400> SEQUENCE: 26
agcagaagca gagcatcttc tcaaaactga ggcaaatagg ccaaaaatga acaatgctac 60
cctcaactat acaaacgtta accctattcc tcacatcagg gggagtgtta ttatcactat 120
atgtgtcagc ttcactgtca tacttactat attcggatat attgctaaaa ttttcaccaa 180
cagaaataac tgcaccagca atgcccttgg attgtgcaaa cgcatcaaat gttcaggctg 240
tgaaccgttc tgcaacaaaa ggggtgacac ttcttctccc agaaccggag tggacatacc 300
cgcgtttatc ttgcccgggc tcaacctttc agaaagcact cctaattagc cctcatagat 360
tcggagaaac caaaggaaac tcagctccct tgataataag ggaacctttt attgcttgtg 420
gaccaaagga atgcaaacac tttgctctaa cccattatgc agcccaacca gggggatact 480
acaatggaac aagagaagac agaaacaagc taaggcatct aatttcagtc aaatttggta 540
aaatcccaac agtagaaaac tccattttcc acatggcagc atggagcggg tccgcatgcc 600
atgatggtaa agaatggaca tatatcggag ttgatggccc tgacagtaat gcattgctca 660
aaataaaata tggagaagca tatactgaca cataccattc ctatgcaaac aacatcctaa 720
gaacacaaga aagtgcctgc aattgcatcg gggaaattgg ttatcttatg ataactgatg 780
gctcagcttc aggtattagt gagtgcagat ttcttaagat tcgagagggc cgaataataa 840
aagaaatatt tccaacagga agagtaaaac atactgaaga atgcacatgc ggatttgcca 900
gcaataaaac catagaatgt gcctgtagag ataacagtta cacagcaaaa agaccctttg 960
tcaaattaaa tgtggagact gatacagcag aaataagatt gatgtgcaca gagacttatt 1020
tggacacccc cagaccagat gatggaagca taacagggcc ttgtgaatct aatgggggata 1080 aagggagtgg aggcatcaag ggaggatttg ttcatcaaag aatggcatcc aagattggaa 1140
ggtggtactc tcgaacaatg tctaaaacta aaaggatggg gatgggactg tatgtcaagt 1200
atgatggaga cccatggact gacagtgatg cccttgctct tagtggagta atggtttcaa 1260
tggaagaacc tggttggtac tcctttggct tcgaaataaa agataagaaa tgtgatgtcc 1320
cctgtattgg gatagagatg gtacatgatg gtggaaagga gacttggcac tcagcagcaa 1380
cagccattta ctgtttaatg ggctcaggac aactgctatg ggacactgtc acaggtgttg 1440
atatggctct gtaatggagg aatggttgag tctgttctaa accctttgtt cctattttgt 1500
ttgaacaatt gtccttactg aacttaattg tttctgaaaa atgctcttgt tactact 1557

<210> SEQ ID NO 27
<211> LENGTH: 1879
<212> TYPE: DNA
<213> ORGANISM: Influenza B virus

<400> SEQUENCE: 27
agcagaagca gagcattttc taatatccac aaaatgaagg caataattgt actactcatg 60
gtagtaacat ccaacgcaga tcgaatctgc actgggataa catcttcaaa ctcacctcat 120
gtggtcaaaa cagctactca aggggaagtc aatgtgactg gtgtgatacc actgacaaca 180

```
acaccaacaa aatctcattt tgcaaatctc aaaggaacaa agaccagagg gaaactatgc    240
ccaaactgtc tcaactgcac agatctggat gtggccttgg gcagaccaat gtgtataggg    300
atcacacctt cggcaaaagc ttcaatactc cacgaagtca gacctgttac atccgggtgc    360
tttcctataa tgcacgacag aacaaaaatc agacagctac ccaatcttct cagaggatat    420
gaacatatca gattatcaac ccataacgtt atcaacgcag aaagggcacc aggaggaccc    480
tacagacttg gaacctcagg atcttgccct aacgttacca gtagaagcgg attcttcgca    540
acaatggctt gggctgtccc aagggacaac aaaacagcaa cgaacccact aacagtagaa    600
gtaccataca tttgtacaaa aggagaagac caaattactg tttgggggtt ccattctgat    660
aacaaaatcc aaatgaaaaa cctctatgga gactcaaatc ctcaaaagtt cacctcatct    720
gccaatggaa taaccacaca ttatgtttct cagattggtg gcttcccaaa tcaaacagaa    780
gacggagggc taccacaaag cggcagaatt gttgttgatt acatggtgca aaaacctggg    840
aaaacaggaa caattgtcta tcaaagaggt gttttgttgc ctcaaaaggt gtggtgtgca    900
agtggcagga gcaaggtaat aaaagggtcc ttgcctttaa ttggtgaagc agattgcctt    960
cacgaaaaat acggtggatt aaacaaaagc aagccttact acacaggaga acatgcaaaa   1020
gccataggaa attgcccaat atgggtgaaa acacctttaa agcttgccaa tggaaccaaa   1080
tatagacctc ccgcaaaact attaaaggaa aagggtttct tcggagctat tgctggtttc   1140
ttagaaggag gatgggaagg aatgattgca ggttggcacg gatacacatc tcatggagca   1200
catggggtgg cagtggcagc agaccttaag agtacgcaag aagccataaa caagataaca   1260
aaaaatctca attctttgag tgagctagaa gtaaagaatc ttcaaagact aagtggtgcc   1320
atggatgaac tccacaacga aatactcgag ctggatgaga aagtggatga tctcagagct   1380
gacacaataa gctcgcaaat agagcttgca gtcttgcttt ccaatgaagg aataataaac   1440
agtgaagatg agcatctatt ggcacttgag agaaaactaa agaaaatgct gggtccctct   1500
gctgtagaca tagggaatgg atgcttcgaa accaaacaca agtgcaacca gacctgctta   1560
gacaggatag ctgctggcac ctttaatgca ggagaatttt ctcttcccac ttttgattca   1620
ctgaatatta ctgctgcatc tttaaatgat gatggattgg ataatcatac tatactgctc   1680
tactactcaa ctgcggcttc tagtttggct gtaacattga tgatagctat ttttattgtt   1740
tatatggtct ccagagacaa tgtttcttgc tccatctgtc tatagggaaa attgagccct   1800
gtattttcct ttattgtggt gcttgtttgc ttgttgccat tacagagaaa cgttattgaa   1860
aaatgctctt gttactact                                                1879
```

<210> SEQ ID NO 28
<211> LENGTH: 1554
<212> TYPE: DNA
<213> ORGANISM: Influenza B virus

<400> SEQUENCE: 28

```
agcagaagca gagcatcttc tcaaaactga agtaaagagg ccaaaaatga acaatgctac     60
cttcaactat acaaacgtta accctatttc tcacatcagg gggagtgtta ttatcactat    120
atgtgtcagc cttactgtca tacttattgt attcggatat attgctaaaa ttttcaccaa    180
aaataattgc accaacaacg tcgttggact gcgcgaacgc atcaaatgtt caggctgtga    240
accattctgc aacaaaagag atgaaattcc ttcccccaga accggagtgg acataccccc    300
gtttatcttg ccagggttca accttccaga aagcactctt aattagccct catagatttg    360
gagaagccaa aggaaactca gctcccttga taataaggga accttttatt gcttgtggac    420
```

| | |
|---|---|
| caaaggagtg caaacacttt gctctaaccc attatgcagc tcaaccaggg ggatactaca | 480 |
| atggaacaag agaggacaga aacaagctga ggcatctgat ttcagtcaac ttaggcaaaa | 540 |
| tcccaactgt agaaaactcc attttccata tggcagcttg gagtggatcc gcatgccatg | 600 |
| atggtagaga atggacatat atcggagttg atggtcctga cagtaatgca ttgatcaaaa | 660 |
| taaaatatgg agaagcatac actgacacat accattccta tgcaaacaac atcctaagaa | 720 |
| cacaagaaag tgcctgcaat tgcatcgggg gagattgtta tcttatgata actgatggct | 780 |
| cagcttcagg aattagtaaa tgcagattcc ttaagatccg agagggtcga ataataaaag | 840 |
| aaatatttcc aacaggaagg gtagagcaca ctgaagaatg cacatgcgga tttgccagca | 900 |
| acaaaaccat agaatgtgcc tgtagagata cagttacaca gcaaaaaga ccctttgtca | 960 |
| aattaaatgt ggagactgat acagctgaaa taagattgat gtgcacagag acttatttgg | 1020 |
| acacccccag accagatgat ggaagcataa cagggccttg cgaatctaat ggggacaaag | 1080 |
| ggagtggagg tgtcaaggga ggatttgttc atcaaagaat ggcatccaag attggaagat | 1140 |
| ggtactcccg aacgatgtct aaaactaaaa gaatggggat ggaactgtat gtcaagtatg | 1200 |
| atggagaccc atggactgac agtgacgccc ttgctcctag tggagtaatg gtctcaatgg | 1260 |
| aagaacctgg ttggtactct ttcggcttcg aaataaaaga taagaaatgt gatgtcccct | 1320 |
| gtattgggat agagatggta catgatggtg gaaaaaggac ttggcactca gcagcaacag | 1380 |
| ccatttactg tttaatgggc tcaggacagt tgctatggga cactgtcaca ggtgttaata | 1440 |
| tggctctgta atgaggaat ggttgaatct gttctaaacc cttttgttcct attttatttg | 1500 |
| aacaattgtc cttactggac ttaattgttt ctgaaaaatg ctcttgttac tact | 1554 |

<210> SEQ ID NO 29
<211> LENGTH: 1885
<212> TYPE: DNA
<213> ORGANISM: Influenza B virus

<400> SEQUENCE: 29
agcagaagca gagcattttc taatatccac aaaatgaagg caataattgt actactcatg 60
gtagtaacat ccaatgcaga tcgaatctgc actggaataa catcgtcaaa ctcaccccat 120
gtggtcaaaa ctgctactca aggggaagtc aatgtgactg gtgtgatacc actgacaaca 180
acacccacca aatctcattt tgcaaatctc aaaggaacaa aaaccagagg gaaactatgc 240
ccaaaatgtc tcaactgcac agatctggac gtggccttgg gcagaccaaa atgcacgggg 300
aacatacctt cggcaaaagt ttcaatactc catgaagtaa gacctgttac atctgggtgc 360
tttcctataa tgcacgacag aacaaaaatt agacagctgc ccaatcttct cagaggatac 420
gaacgtatca ggttatcaaa ccataacgtt atcaatgcag aaaaagcacc aggaggaccc 480
tacaaaattg gaacctcagg gtcttgccct aacgttacca atggaaacgg attcttcgca 540
acaatggctt gggctgtccc aaaaaacgaa aacaacaaaa cagcaacaaa ttcattaaca 600
atagaagtac catacatttg tacagaagga gaagaccaaa ttaccgtttg ggggttccac 660
tctgatagcg aaacccaaat ggcaaaactc tatggagact caaagcctca gaagttcact 720
tcatctgcta acggagtgac cacacattac gtttcacaga ttggtggctt cccaaatcaa 780
acagaagacg gaggactacc acaaagtggt agaattgttg ttgattacat ggtgcaaaaa 840
tctggaaaaa caggaacaat tacctatcaa agaggtattt tattgcctca aaaagtgtgg 900
tgcgcaagtg gcaggagcaa ggtaataaaa ggatccttgc ctttaattgg agaagcagat 960

-continued

```
tgcctccacg aaaaatacgg tggattaaac aaaagcaagc cttactatac aggggaacat    1020
gcaaaagcca taggaaattg cccaatatgg gtgaaaacac ccttgaagct ggccaatgga    1080
accaaatata gacctcctgc aaaactatta aaggaaaggg gtttcttcgg agctattgct    1140
ggtttcttag aaggaggatg ggaaggaatg attgcaggtt ggcacggata cacatcccat    1200
ggagcacatg gagtagcagt ggcagcagac cttaagagta ctcaagaagc cataaacaag    1260
atcacaaaaa atctcaactc tttgagtgag ctggaagtaa agaatcttca aagactaagc    1320
ggagccatgg atgaactcca caacgaaata ctagaactag atgagaaagt ggatgatctc    1380
agagctgata caataagctc gcaaatagaa ctcgcagtct tgctttccaa tgaaggaata    1440
ataaacagtg aagatgagca tctcttggcg cttgaaagaa aactgaagaa aatgctgggc    1500
ccctctgctg tagagatagg gaatggatgc ttcgaaacca acacaagtg caaccagacc    1560 tgcctcgata aatagctgc tggcacctttt aatgcaggag aattttctct ccccacctttt    1620 gattcactaa atattactgc tgcatcttta aatgacgatg gattggataa tcatactata    1680
ctgctttact actcaactgc tgcttccagt ttggctgtaa cattgatgat agctatcttt    1740
gttgtttata tggtctccag agacaatgtt tcttgttcca tctgtctata aggaaagtta    1800
agccccgtat tttcctttat tgtagtactt gtttgcttgt tatcattaca aaaaacgtt    1860 attgaaaaat gctcttgtta ctact                                         1885
```

<210> SEQ ID NO 30
<211> LENGTH: 1544
<212> TYPE: DNA
<213> ORGANISM: Influenza B virus

<400> SEQUENCE: 30

```
agcagagcat cttctcaaaa ctgaagcaaa taggccaaaa tgacaatgc taccctcaac      60 tatacaaaca ttaaccctat ttctcacatc agggggagtg ttattatcac tatatgtgtc    120
agccttactg tcatacttac tgtattcgga tatattgcta aaattttcac caacaaaaat    180
aattgcacca acaacgtcgt tggactccgc gaacgcatca aattttcagg ccgtgaacca    240
ttctgcaaca aaagagatga catttcttct cccagaaccg gagtggacat accctcgttt    300
atcttgccag ggttcaacct ttcaaaaagc actcctaatt agccctcata gattcggaga    360
agccaaagga aactcagctc ccttgataat aagggaacct tttattgctt gtggaccaaa    420
ggagtgtaaa cactttgctc taacccatta tgcagctcaa ccagggggat actacaatgg    480
aacaagagag gacagaaaca agctgaggca tctgatttca gtcaacttag gcaaaatacc    540
aactgtagaa aactccatt tccacatggc agcttggagt gggtccgcat gccatgatgg    600
tagagagtgg acttatatcg gagttgatgg ccctgacagt aatgcattga tcaaaataaa    660
atatggagaa gcatacactg acacatacca ttcctatgca acaacatcc taagaacaca    720 agaaagtgcc tgcaactgca tcgggggaga ttgttatctt atgataactg atggctcagc    780
ttcaggaatt agtaaatgca gattccttaa gattcgagag ggtcgaatag taaagaaat    840 atttccaaca ggaagagtag agcatactga agaatgcaca tgcggatttg ccagcaataa    900
aaccatagaa tgtgcctgta gagataacag ttacacagca aaaagaccct tgtcaaatt    960 aaatgtggaa actgatacag cagaaataag attgatgtgc acagagactt atttggacac    1020
ccccagacca gatgatggaa gcataacagg gccttgcgaa tctaatgggg acaaagggag    1080
tggaggtatc aagggaggat ttgtccatca agaatggca tccaagattg aagatggta    1140 ctctcgaacg atgtctaaaa ctaaaagaat ggggatggaa ctgtatgtca agtatgatgg    1200
```

```
agacccatgg actgacagtg atgcccttgc tcctagtgga gtaatggtct caatagaaga    1260
acctggttgg tattctttcg gcttcgaaat aaaagataag aaatgcgatg tcccctgtat    1320
tgggatagag atggtacacg atggtggaaa acaacttgg cactcagcag caacagccat    1380
ttactgttta atgggctcag acagttgct atgggacact atcacaggtg ttgatatggc    1440
tctgtaatgg aggaatggtt gaatctgttc taaacccttt gttcctattt tgtttgaaca    1500
attgtcctta ctggacttaa ttgtttctga aaaatgctct tgtt                     1544

<210> SEQ ID NO 31
<211> LENGTH: 1885
<212> TYPE: DNA
<213> ORGANISM: Influenza B virus

<400> SEQUENCE: 31
agcagaagca gagcattttc taatatccac aaaatgaagg caataattgt actactcatg     60
gtagtaacat ccaatgcaga tcgaatctgc actgggataa catcgtcaaa ctcaccccat    120
gtggtcaaaa ctgctactca aggggaggtc aatgtgactg gtgtgatacc actgacaaca    180
acacccacca atctcatttt gcaaatctc aaggaacaa aaaccagagg gaaactatgc    240
ccaaaatgcc tcaactgcac agatctggac gtggccttgg gcagaccaaa atgcacgggg    300 aacatacct cggcaaaagt ttcaatactc catgaagtca gacctgttac atctgggtgc    360
tttcctataa tgcacgacag aacaaaaatt agacagctgc ccaatcttct cagaggatac    420
gaacatatca ggttatcaac tcataacgtt atcaatgcag aaaaggcacc aggaggaccc    480
tacaaaattg gaacctcagg gtcttgccct aacgttacca atggaaacgg attttttcgca    540 acaatggctt gggccgtccc aaaaaacgac aacaacaaaa cagcaacaaa ttcattaaca    600
atagaagtac catacatttg tacagaagga gaagaccaaa ttaccgtttg ggggttccac    660
tctgataacg aagcccaaat ggcaaaactc tatgggggact caaagcccca gaagttcacc    720
tcatctgcca acggagtgac cacacattac gttctcacaga ttggtggctt cccaaatcaa    780
acagaagacg gaggactacc acaaagtggt agaattgttg ttgattacat ggtgcaaaaa    840
tctgggaaaa caggaacaat tacctatcaa agaggtattt tattgcctca aaaagtgtgg    900
tgcgcaagtg gcaggagcaa ggtaataaaa ggatccttgc ctttaattgg agaagcagat    960
tgcctccacg aaaaatacgg tggattaaac aaaagcaagc cttactacac aggggaacat    1020
gcaaaggcca taggaaattg cccaatatgg gtgaaaacac ccttgaagct ggccaatgga    1080
accaaatata gacctcctgc aaaactatta aggaaagag gttcttcgg agctattgct    1140 ggtttcttag aaggaggatg ggaaggaatg attgcaggtt ggcacggata cacatcccat    1200
ggggcacatg gagtagcagt ggcagcagac cttaagagta tcaagaagc cataaacaag    1260 ataacaaaaa atctcaactc tttgagtgag ctggaagtaa agaatcttca aagactaagc    1320
ggtgccatgg atgaactcca caacgaaata ctagaactag cgagaaagt ggatgatctc    1380 agagctgata caataagctc acaaatagaa ctcgcagtct tgctttccaa tgaaggaata    1440
ataaacagtg aagatgagca tctcttggcg cttgaaagaa agctgaagaa aatgctgggc    1500
ccctctgctg tagagatagg gaatggatgc ttcgaaacca acacaagtg caaccagacc    1560 tgtctcgaca gaatagctgc tggtacccttt gatgcaggag aatttctct ccccacttttt    1620 gattcactga atattactgc tgcatcttta aatgacgatg gattggataa tcatactata    1680
ctgctttact actcaactgc tgcctccagt ttggctgtaa cattgatgat agctatcttt    1740
```

```
gttgtttata tggtctccag agacaatgtt tcttgctcca tctgtctata aggaaagtta   1800
agccctgtat tttcctttat tgtagtgctt gtttgcttgt taccattaca aaaaaacgtt   1860
attgaaaaat gctcttgtta ctact                                         1885
```

<210> SEQ ID NO 32
<211> LENGTH: 1557
<212> TYPE: DNA
<213> ORGANISM: Influenza B virus

<400> SEQUENCE: 32

```
agcagaagca gagcatcttc tcaaaactga ggcaaatagg ccaaaaatga acaatgctac     60
cttcaactat acaaacgtta accctatttc tcacatcagg gggagtatta ttatcactat    120
atgtgtcagc ttcattgtca tacttactat attcggatat attgctaaaa ttctcaccaa    180
cagaaataac tgcaccaaca atgccattgg attgtgcaaa cgcatcaaat gttcaggctg    240
tgaaccgttc tgcaacaaaa ggggtgacac ttcttctccc agaaccagag tggacatacc    300
cgcgtttatc ttgcccgggc tcaacctttc agaaagcact cctaattagc cctcatagat    360
tcggagaaac caaaggaaac tcagctccct tgataataag ggaacctttt attgcttgtg    420
gaccaaagga atgcaaacac tttgctctaa cccattatgc agcccaacca gggggatact    480
acaatggaac aagaggagac agaaacaagc tgaggcatct aatttcagtc aaattgggca    540
aaatcccaac agtagaaaac tccattttcc acatggcagc atggagcggg tccgcatgcc    600
atgatggtaa agaatggaca tatatcggag ttgatggccc tgacaataat gcattgctca    660
aaataaaata tggagaagca tatactgaca cataccattc ctatgcaaac aacatcctaa    720
gaacacaaga aagtgcctgc aattgcatcg ggggaaattg ttatcttatg ataactgatg    780
gctcagcttc aggtattagt gaatgcagat ttcttaaaat tcgagagggc cgaataataa    840
aagaaatatt tccaacagga agagtaaaac atactgaaga atgcacatgc ggatttgcca    900
gcaataagac catagaatgt gcctgtagag ataacagtta cacagcaaaa agaccctttg    960
tcaaattaaa cgtggagact gatacagcag aaataagatt gatgtgcaca gagacttatt   1020
tggacacccc cagaccagat gatggaagca taacagggcc ttgtgaatct aatggggaca   1080
aagggagtgg aggcatcaag ggaggatttg ttcatcaaag aatggcatcc aagattggaa   1140
ggtggtactc tcgaacgatg tctaaaacta aaaggatggg gatgggactg tatgtcaagt   1200
atgatggaga cccatgggct gacagtgatg cccttgctct tagtggagta atggtttcaa   1260
tggaagaacc tggttggtac tcctttggct tcgaaataaa agataagaaa tgtgatgtcc   1320
cctgtattgg aatagagatg gtacatgatg gtggaaaaga gacttggcac tcagcagcaa   1380
cagccattta ctgtttaatg ggctcaggac agctgctgtg ggacactgtc acaggtgttg   1440
atatggctct gtaatggagg aatggttgag tctgttctaa accctttgtt cctattttgt   1500
ttgaacaatt gtccttactg aacttaattg tttctgaaaa atgctcttgt tactact      1557
```

<210> SEQ ID NO 33
<211> LENGTH: 1853
<212> TYPE: DNA
<213> ORGANISM: Influenza B virus

<400> SEQUENCE: 33

```
tctaatatcc acaaaatgaa ggcaataatt gtactactca tggtagtaac atccaatgca     60
gatcgaatct gcactgggat aacatcttca aactcacctc atgtggtcaa aacagctact    120
caaggggagg tcaatgtgac tggtgtaata ccactgacaa caacaccaac aaaatcttat    180
```

```
tttgcaaatc tcaaaggaac aaggaccaga gggaaactat gtccagactg tctcaactgt    240
acagatctgg atgtggcctt gggcagacca atgtgtgtgg ggaccacacc ttcggcaaaa    300
gcttcaatac tccacgaagt cagacctgtt acatccgggt gctttcctat aatgcacgac    360
agaacaaaaa tcagacaact acccaatctt ctcagaggat atgaaaatat cagattatca    420
acccaaaacg ttatcgatgc agaaaatgca ccaggaggac cctacagact ggaacctca     480 ggatcttgcc ctaacgctac cagtaaaagc ggattttcg caacaatggc ttgggctgtc     540
ccaaaggaca caacaaaaa tgcaacgaac ccactaacag tagaagtacc atacgtttgt     600
acagaagggg aagaccaaat tactgttggg gggttccatt cagataacaa aacccccaatg   660 aagaacctct atggagactc aaatcctcaa aagttcacct catctgctaa tggagtaacc    720
acacattatg tttctcagat tggcggcttc ccagctcaaa cagaagacga aggactacca    780
caaagcggca gaattgttgt tgattacatg gtgcaaaaac ctaggaaaac aggaacaatt    840
gtctatcaaa gaggtgtttt gttgcctcaa aaggtgtggt gcgcgagtgg caggagcaaa    900
gtaataaaag ggtccttgcc tttaattggt gaagcagatt gccttcatga aaaatacggt    960
ggattaaaca aaagcaagcc ttactacaca ggagaacatg caaaagccat aggaaattgc   1020
ccaatatggg tgaaaacacc tttgaagctt gccaatggaa ccaaatatag acctcctgca   1080
aaactattaa aggaaggggg ttcttcgga gctattgctg gtttcctaga aggaggatgg   1140
gaaggaatga ttgcaggttg gcacggatac acatctcacg gagcacatgg agtggcagtg   1200
gcggcagacc ttaagagtac gcaagaagct ataaacaaga taacaaaaaa tctcaattct   1260
ttgagtgagc tagaagtaaa gaatcttcaa agactaagtg gtgccatgga tgaactccac   1320
aacgaaatac tcgagctgga tgagaaagtg gatgatctca gagctgacac tataagctcg   1380
caaatagaac ttgcagtctt gctttccaat gaaggaataa taaacagtga agatgagcat   1440
ctattggcac ttgagagaaa actaaagaaa atgctgggtc cctctgctgt agacataggt   1500
aatggatgct tcgaaaccaa acacaagtgc aaccagacct gcttagacag gatagctgct   1560
ggcaccttta tgcaggaga ttttctctc cccacttttg attcactgaa cattactgct    1620
gcatctttaa atgatgatgg attggataac catactatac tgctctatta ctcaactgct   1680
gcttctagtt tggctgtaac attgatgcta gctattttta ttgttatatt ggtctccaga   1740
gacaacgttt catgctccat ctgtctataa ggaagattaa gccttgtatt ttcctttatt   1800
gtagtgcttg tttgcttgtc atcattacaa agaaacgtta ttgaaaaatg ctc          1853
```

<210> SEQ ID NO 34
<211> LENGTH: 1529
<212> TYPE: DNA
<213> ORGANISM: Influenza B virus

<400> SEQUENCE: 34

```
tctcaaaact gaggcaaata ggccaaaaat gaacaatgct accctcaact atacaaacgt     60
taaccctatt cctcacatca gggggagtgt tattatcact atatgtgtca gcttcactgt    120
catacttact atattcggat atattgctaa aattttcaac aacagaaata actgcaccaa    180
caatgccatt ggattgtgca aacgcatcaa atgttcaggc tgtgaaccgt tctgcaacaa    240 aagggtgac acttcttctc ccagaaccgg agtggacata cccgcgttta tcttgcccgg    300
gctcaacctt tcagaaagca ctcctaatta gccctcatag attcggagaa accaaaggaa    360
actcagctcc cttgataata agggaaccct ttattgcttg tggaccaaag gaatgcaaac    420
```

```
actttgctct aacccattat gcagcccaac caggggGata ctacaatgga acaaaagaag    480
acagaaacaa gctgaggcat ctaatttcag tcaaattggg caaaatccca acagtagaaa    540
actccatttt ccacatggca gcatggagcg ggtccgcatg ccatgatggt aaagaatgga    600
catatatcgg agttgatggc cctgacagta atgcattgct caaaataaaa tatggagaag    660
catatactga cacataccat tcctatgcaa acaacatcct aagaacacaa gaaagtgcct    720
gcaattgcat cggggaaat tgttatctta tgataactga tggctcagct tcaggtatta    780
gtgagtgcag atttcttaag attcgagagg gccgaataat aaaagaaata tttccaacag    840
gaagagtaaa acatactgaa gaatgcacat gcggatttgc cagcaataaa accatagaat    900
gtgcctgtag agataacagt tacacagcaa aaagaccctt tgtcaaatta aatgtggaga    960
ctgatacagc agaaataaga ttgatgtgca cagagactta tttggacacc cccagaccag    1020
atgatggaag cataacaggg ccttgtgaat ctaatgggaa taagggagt ggaggcatca    1080 agggaggatt tgttcatcaa gaatggcat ccaaaattgg aaggtggtac tctcgaacaa    1140
tgtctaaaac caaaaggatg ggaatgggac tgtatgtcaa gtatgatgga gacccatgga    1200
ctgacagtga tgcccttgct cttagtggag taatggtttc aatggaagaa cctggttggt    1260
actcatttgg cttcgaaata aaagataaga atgtgatgt cccctgtatt gggatagaga    1320
tggtacatga tggtggaaag gagacttggc actcagcagc aacagccatt tactgtttaa    1380
tgggctcagg acaactgttg tgggacactg tcacaggtgt tgatatggct ctgtaatggg    1440
ggaatggttg agtctgttct aaacccttg ttcctatttt gtttgaacaa ttgtccttgc    1500
tgaacttaat tgtttctgaa aaatgctct                                      1529
```

<210> SEQ ID NO 35
<211> LENGTH: 566
<212> TYPE: PRT
<213> ORGANISM: Influenza A virus Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Ser Asp Gln Thr
        195                 200                 205

Ser Leu Tyr Val Arg Ala Ser Gly Arg Val Thr Val Ser Thr Lys Arg
210                 215                 220

Ser Gln Gln Thr Val Thr Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Asn Gly Lys Ser Ser Ile Met Arg Ser Asp Ala
        275                 280                 285

Pro Ile Gly Asn Cys Ser Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 36
<211> LENGTH: 436
<212> TYPE: PRT

<213> ORGANISM: Influenza A virus

<400> SEQUENCE: 36

```
Met Gln Ile Ala Ile Leu Val Thr Thr Val Thr Leu His Phe Lys Gln
1               5                   10                  15

Tyr Glu Cys Asn Ser Pro Pro Asn Asn Gln Val Met Leu Cys Glu Pro
            20                  25                  30

Thr Ile Ile Glu Arg Asn Ile Thr Glu Ile Val Tyr Leu Thr Asn Thr
        35                  40                  45

Thr Ile Glu Lys Glu Ile Cys Pro Lys Leu Ala Glu Tyr Arg Asn Trp
    50                  55                  60

Ser Lys Pro Gln Cys Lys Ile Thr Gly Phe Ala Pro Phe Ser Lys Asp
65                  70                  75                  80

Asn Ser Ile Arg Leu Ser Ala Gly Gly Asp Ile Trp Val Thr Arg Glu
                85                  90                  95

Pro Tyr Val Ser Cys Asp Pro Gly Lys Cys Tyr Gln Phe Ala Leu Gly
            100                 105                 110

Gln Gly Thr Thr Leu Asn Asn Arg His Ser Asn Asp Thr Val His Asp
        115                 120                 125

Arg Thr Pro Tyr Arg Thr Leu Leu Met Asn Glu Leu Gly Val Pro Phe
    130                 135                 140

His Leu Gly Thr Lys Gln Val Cys Ile Ala Trp Ser Ser Ser Ser Cys
145                 150                 155                 160

His Asp Gly Lys Ala Trp Leu His Val Cys Val Thr Gly His Asp Glu
                165                 170                 175

Asn Ala Thr Ala Ser Phe Ile Tyr Asp Gly Arg Leu Val Asp Ser Ile
            180                 185                 190

Gly Ser Trp Ser Lys Asn Ile Leu Arg Thr Gln Glu Ser Glu Cys Val
        195                 200                 205

Cys Ile Asn Gly Thr Cys Thr Val Val Met Thr Asp Gly Ser Ala Ser
    210                 215                 220

Glu Arg Ala Asp Thr Lys Ile Leu Phe Ile Glu Glu Gly Lys Ile Val
225                 230                 235                 240

His Ile Ser Pro Leu Ser Gly Ser Ala Gln His Val Glu Glu Cys Ser
                245                 250                 255

Cys Tyr Pro Arg Tyr Pro Gly Val Arg Cys Val Cys Arg Asp Asn Trp
            260                 265                 270

Lys Gly Ser Asn Arg Pro Ile Val Asp Ile Asn Val Lys Asp Tyr Ser
        275                 280                 285

Ile Val Ser Ser Tyr Val Cys Ser Gly Leu Val Gly Asp Thr Pro Arg
    290                 295                 300

Lys Asn Asp Ser Ser Ser Ser Ser Tyr Cys Arg Asn Pro Asn Asn Glu
305                 310                 315                 320

Lys Gly Ser His Gly Val Lys Gly Trp Ala Phe Asp Asp Gly Asn Asp
                325                 330                 335

Val Trp Met Gly Arg Thr Ile Ser Glu Glu Leu Arg Ser Gly Tyr Glu
            340                 345                 350

Thr Phe Lys Val Ile Gly Gly Trp Ser Lys Pro Asn Ser Lys Leu Gln
        355                 360                 365

Ile Asn Arg Gln Val Ile Val Asp Arg Gly Asn Arg Ser Gly Tyr Ser
    370                 375                 380

Gly Ile Phe Ser Val Glu Gly Lys Ser Cys Ile Asn Arg Cys Phe Tyr
385                 390                 395                 400

-continued

```
Val Glu Leu Ile Arg Gly Arg Lys Gln Glu Thr Glu Val Trp Trp Thr
                405                 410                 415

Ser Asn Ser Ile Val Val Phe Cys Gly Thr Ser Gly Thr Tyr Gly Thr
            420                 425                 430

Gly Ser Trp Pro
        435

<210> SEQ ID NO 37
<211> LENGTH: 566
<212> TYPE: PRT
<213> ORGANISM: Influenza A virus

<400> SEQUENCE: 37

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Pro Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Asn Phe Asn Trp Thr
    130                 135                 140

Gly Val Ala Gln Asp Gly Lys Ser Tyr Ala Cys Lys Arg Gly Ser Val
145                 150                 155                 160

Asn Ser Phe Phe Ser Arg Leu Asn Trp Leu His Lys Leu Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Ser Val Gln Thr
        195                 200                 205

Ser Leu Tyr Val Arg Ala Ser Gly Arg Val Thr Val Ser Thr Lys Arg
    210                 215                 220

Ser Gln Gln Thr Val Ile Pro Asp Ile Gly Tyr Arg Pro Trp Val Arg
225                 230                 235                 240

Gly Gln Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Asn Gly Lys Ser Ser Ile Met Arg Ser Asp Ala
        275                 280                 285

Pro Ile Gly Asn Cys Ser Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335
```

-continued

Arg Asn Val Pro Glu Lys Gln Thr Arg Gly Ile Phe Gly Ala Ile Ala
         340                 345                 350

Gly Phe Ile Glu Asn Gly Trp Glu Gly Met Val Asp Gly Trp Tyr Gly
         355                 360                 365

Phe Arg His Gln Asn Ser Glu Gly Thr Gly Gln Ala Ala Asp Leu Lys
         370                 375                 380

Ser Thr Gln Ala Ala Ile Asp Gln Ile Asn Gly Lys Leu Asn Arg Leu
385                 390                 395                 400

Val Glu Lys Thr Asn Glu Lys Phe His Gln Ile Glu Lys Glu Phe Ser
             405                 410                 415

Glu Val Glu Gly Arg Ile Gln Asp Leu Glu Lys Tyr Val Glu Asp Thr
             420                 425                 430

Lys Ile Asp Leu Trp Ser Tyr Asn Ala Glu Leu Leu Val Ala Leu Glu
             435                 440                 445

Asn Gln His Thr Ile Asp Leu Thr Asp Ser Glu Met Asn Lys Leu Phe
     450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
             485                 490                 495

Ile Arg Asn Gly Thr Tyr Asp His Asp Val Tyr Arg Asp Glu Ala Leu
             500                 505                 510

Asn Asn Arg Phe Gln Ile Lys Gly Val Glu Leu Lys Ser Gly Tyr Lys
             515                 520                 525

Asp Trp Ile Leu Trp Ile Ser Phe Ala Ile Ser Cys Phe Leu Leu Cys
     530                 535                 540

Val Val Leu Leu Gly Phe Ile Met Trp Ala Cys Gln Lys Gly Asn Ile
545                 550                 555                 560

Arg Cys Asn Ile Cys Ile
             565

<210> SEQ ID NO 38
<211> LENGTH: 451
<212> TYPE: PRT
<213> ORGANISM: Influenza A virus

<400> SEQUENCE: 38

Lys Met Asn Pro Asn Gln Lys Ile Ile Thr Ile Gly Ser Val Ser Leu
1               5                   10                  15

Thr Ile Ala Thr Ile Cys Phe Leu Met Gln Ile Ala Ile Leu Val Thr
             20                  25                  30

Thr Val Thr Leu His Phe Lys Gln Tyr Glu Cys Asn Ser Pro Pro Asn
             35                  40                  45

Asn Gln Val Met Leu Cys Glu Pro Thr Ile Ile Glu Arg Asn Ile Thr
     50                  55                  60

Glu Ile Val Tyr Leu Thr Asn Thr Thr Ile Glu Lys Glu Ile Cys Pro
65                  70                  75                  80

Lys Leu Ala Glu Tyr Arg Asn Trp Ser Lys Pro Gln Cys Lys Ile Thr
                 85                  90                  95

Gly Phe Ala Pro Phe Ser Lys Asp Asn Ser Ile Arg Leu Ser Ala Gly
             100                 105                 110

Gly Asp Ile Trp Val Thr Arg Glu Pro Tyr Val Ser Cys Asp Pro Gly
             115                 120                 125

Lys Cys Tyr Gln Phe Ala Leu Gly Gln Gly Thr Thr Leu Asn Asn Arg

```
            130                 135                 140
His Ser Asn Asp Thr Val His Asp Arg Thr Pro Tyr Arg Thr Leu Leu
145                 150                 155                 160

Met Asn Glu Leu Gly Val Pro Phe His Leu Gly Thr Lys Gln Val Cys
                165                 170                 175

Ile Ala Trp Ser Ser Ser Cys His Asp Gly Lys Ala Trp Leu His
            180                 185                 190

Val Cys Val Thr Gly His Asp Glu Asn Ala Thr Ala Ser Phe Ile Tyr
            195                 200                 205

Asp Gly Arg Leu Val Asp Ser Ile Gly Ser Trp Ser Lys Asn Ile Leu
        210                 215                 220

Arg Thr Gln Glu Ser Glu Cys Val Cys Ile Asn Gly Thr Cys Thr Val
225                 230                 235                 240

Val Met Thr Asp Gly Ser Ala Ser Glu Arg Ala Asp Thr Lys Ile Leu
                245                 250                 255

Phe Ile Glu Glu Gly Lys Ile Val His Ile Ser Pro Leu Ser Gly Ser
            260                 265                 270

Ala Gln His Val Glu Glu Cys Ser Cys Tyr Pro Arg Tyr Pro Gly Val
        275                 280                 285

Arg Cys Val Cys Arg Asp Asn Trp Lys Gly Ser Asn Arg Pro Ile Val
        290                 295                 300

Asp Ile Asn Val Lys Asp Tyr Ser Ile Val Ser Ser Tyr Val Cys Ser
305                 310                 315                 320

Gly Leu Val Gly Asp Thr Pro Arg Lys Asn Asp Ser Ser Ser Ser Ser
                325                 330                 335

Tyr Cys Trp Asn Pro Asn Asn Glu Lys Gly His Gly Val Lys Gly
            340                 345                 350

Trp Ala Phe Asp Asp Gly Asn Asp Val Trp Met Gly Arg Thr Ile Ser
        355                 360                 365

Glu Glu Leu Arg Ser Gly Tyr Glu Thr Phe Lys Val Ile Gly Gly Trp
    370                 375                 380

Ser Lys Pro Asn Ser Lys Leu Gln Ile Asn Arg Gln Val Ile Val Asp
385                 390                 395                 400

Arg Gly Asn Arg Ser Gly Tyr Ser Gly Ile Phe Ser Val Glu Gly Lys
                405                 410                 415

Ser Cys Ile Asn Arg Cys Phe Tyr Val Glu Leu Ile Arg Gly Arg Lys
            420                 425                 430

Gln Glu Thr Glu Val Trp Trp Thr Ser Asn Ser Ile Val Val Phe Cys
        435                 440                 445

Gly Thr Ser
    450

<210> SEQ ID NO 39
<211> LENGTH: 566
<212> TYPE: PRT
<213> ORGANISM: Influenza A virus

<400> SEQUENCE: 39

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45
```

```
Gln Ile Glu Val Thr Asn Ala Thr Glu Leu Val Gln Ser Ser Thr
     50                  55                  60
Gly Arg Ile Cys Asp Ser Pro His Arg Ile Leu Asp Gly Lys Asn Cys
 65                  70                  75                  80
Thr Leu Ile Asp Ala Leu Leu Gly Asp Pro His Cys Asp Gly Phe Gln
                 85                  90                  95
Asn Lys Glu Trp Asp Leu Phe Val Glu Arg Ser Lys Ala Tyr Ser Asn
            100                 105                 110
Cys Tyr Pro Tyr Asp Val Pro Asp Tyr Ala Ser Leu Arg Ser Leu Val
        115                 120                 125
Ala Ser Ser Gly Thr Leu Glu Phe Thr Asn Glu Gly Phe Asn Trp Thr
130                 135                 140
Gly Val Ala Gln Asp Gly Thr Ser Tyr Ala Cys Lys Arg Gly Ser Val
145                 150                 155                 160
Lys Ser Phe Phe Ser Arg Leu Asn Trp Leu His Lys Leu Glu Tyr Lys
                165                 170                 175
Tyr Pro Ala Leu Asn Val Thr Met Pro Asn Asn Asp Lys Phe Asp Lys
            180                 185                 190
Leu Tyr Ile Trp Gly Val His His Pro Ser Thr Asp Ser Asp Gln Thr
        195                 200                 205
Ser Ile Tyr Val Gln Ala Ser Gly Arg Val Thr Val Ser Thr Lys Arg
210                 215                 220
Ser Gln Gln Thr Val Ile Pro Asn Ile Gly Ser Arg Pro Trp Val Arg
225                 230                 235                 240
Gly Ile Ser Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
        275                 280                 285
Pro Ile Gly Asn Cys Asn Ser Glu Cys Ile Thr Pro Asn Gly Ser Ile
290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Thr Gly Gln Ala Ala Asp Leu Lys
370                 375                 380
Ser Thr Gln Ala Ala Ile Asn Gln Ile Asn Gly Lys Leu Asn Arg Leu
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
450                 455                 460
Glu Arg Thr Arg Lys Gln Leu Arg Glu Asn Ala Glu Asp Met Gly Asn
```

```
            465                 470                 475                 480
        Gly Cys Phe Lys Ile Tyr His Lys Cys Asp Asn Ala Cys Ile Gly Ser
                        485                 490                 495

Ile Arg Asn Gly Thr Tyr Asp His Asp Val Tyr Arg Asp Glu Ala Leu
                        500                 505                 510

Asn Asn Arg Phe Gln Ile Lys Gly Val Glu Leu Lys Ser Gly Tyr Lys
                        515                 520                 525

Asp Trp Ile Leu Trp Ile Ser Phe Ala Ile Ser Cys Phe Leu Leu Cys
                        530                 535                 540

Val Val Leu Leu Gly Phe Ile Met Trp Ala Cys Gln Lys Gly Asn Ile
        545                 550                 555                 560

Arg Cys Asn Ile Cys Ile
                        565

<210> SEQ ID NO 40
<211> LENGTH: 469
<212> TYPE: PRT
<213> ORGANISM: Influenza A virus

<400> SEQUENCE: 40

Met Asn Pro Asn Gln Lys Ile Ile Thr Ile Gly Ser Val Ser Leu Thr
        1               5                   10                  15

Ile Ala Thr Ile Cys Phe Leu Met Gln Ile Ala Ile Leu Val Thr Thr
                        20                  25                  30

Val Thr Leu His Phe Lys Gln Tyr Glu Cys Asn Ser Pro Pro Asn Asn
                        35                  40                  45

Gln Val Met Leu Cys Glu Pro Thr Ile Ile Glu Arg Asn Ile Thr Glu
                        50                  55                  60

Ile Val Tyr Leu Thr Asn Thr Thr Ile Glu Lys Glu Ile Cys Pro Lys
        65                  70                  75                  80

Leu Ala Glu Tyr Arg Asn Trp Ser Lys Pro Gln Cys Lys Ile Thr Gly
                        85                  90                  95

Phe Ala Pro Phe Ser Lys Asp Asn Ser Ile Arg Leu Ser Ala Gly Gly
                        100                 105                 110

Asp Ile Trp Val Thr Arg Glu Pro Tyr Val Ser Cys Asp Pro Asp Lys
                        115                 120                 125

Cys Tyr Gln Phe Ala Leu Gly Gln Gly Thr Thr Leu Asn Asn Arg His
                        130                 135                 140

Ser Asn Asp Thr Val His Asp Arg Thr Pro Tyr Arg Thr Leu Leu Met
        145                 150                 155                 160

Asn Glu Leu Gly Val Pro Phe His Leu Gly Thr Lys Gln Val Cys Ile
                        165                 170                 175

Ala Trp Ser Ser Ser Ser Cys His Asp Gly Lys Ala Trp Leu His Val
                        180                 185                 190

Cys Val Thr Gly His Asp Glu Asn Ala Thr Ala Ser Phe Ile Tyr Asp
                        195                 200                 205

Gly Arg Leu Val Asp Ser Ile Gly Ser Trp Ser Lys Lys Ile Leu Arg
                        210                 215                 220

Thr Gln Glu Ser Glu Cys Val Cys Ile Asn Gly Thr Cys Thr Val Val
        225                 230                 235                 240

Met Thr Asp Gly Ser Ala Ser Gly Arg Ala Asp Thr Lys Ile Leu Phe
                        245                 250                 255

Ile Glu Glu Gly Lys Ile Val His Ile Ser Pro Leu Ser Gly Ser Ala
                        260                 265                 270
```

```
Gln His Val Glu Glu Cys Ser Cys Tyr Pro Arg Tyr Ser Gly Val Arg
            275                 280                 285

Cys Val Cys Arg Asp Asn Trp Lys Gly Ser Asn Arg Pro Ile Val Asp
        290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly His Gly Val Lys Gly Trp
                340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Gly Gly Trp Ser
        370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 41
<211> LENGTH: 566
<212> TYPE: PRT
<213> ORGANISM: Influenza A virus

<400> SEQUENCE: 41

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Arg Ile Cys Asp Ser Pro His Arg Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Tyr Ala Cys Lys Arg Ser Ser Ile
145                 150                 155                 160

Lys Ser Phe Phe Ser Arg Leu Asn Trp Leu His Gln Leu Lys Tyr Lys
                165                 170                 175
```

```
Tyr Pro Ala Leu Asn Val Thr Met Pro Asn Asn Asp Lys Phe Asp Lys
            180                 185                 190

Leu Tyr Ile Trp Gly Val His His Pro Ser Thr Asp Ser Asp Gln Thr
            195                 200                 205

Ser Ile Tyr Ala Gln Ala Ser Gly Arg Val Thr Val Ser Thr Lys Arg
            210                 215                 220

Ser Gln Gln Thr Val Ile Pro Asn Ile Gly Ser Arg Pro Trp Val Arg
225                 230                 235                 240

Gly Ile Ser Ser Arg Ile Ser Ile His Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
            370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 42
<211> LENGTH: 469
```

<212> TYPE: PRT
<213> ORGANISM: Influenza A virus

<400> SEQUENCE: 42

```
Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Ser Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly His Asp Glu Asn Ala Thr Ala Ser Phe Ile Tyr Asp
        195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Phe Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Asp Arg
385                 390                 395                 400
```

```
Gly Asn Arg Ser Gly Tyr Ser Gly Ile Phe Ser Val Glu Lys Ser
            405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 43
<211> LENGTH: 566
<212> TYPE: PRT
<213> ORGANISM: Influenza A virus

<400> SEQUENCE: 43

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Gly Ser Asn
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val Leu His Pro Ser Thr Asp Ser Asp Gln Ile
        195                 200                 205

Ser Leu Tyr Ala Gln Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
```

Pro Asn Asp Lys Pro Phe Gln Asn Val Asn Arg Ile Thr Tyr Gly Ala
305             310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 44
<211> LENGTH: 469
<212> TYPE: PRT
<213> ORGANISM: Influenza A virus

<400> SEQUENCE: 44

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Arg His
130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly His Asp Glu Asn Ala Thr Ala Ser Phe Ile Tyr Asp
            195                 200                 205

Gly Arg Leu Val Asp Ser Ile Gly Ser Trp Ser Lys Lys Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
            245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
            325                 330                 335

Cys Leu Asp Pro Asn Asn Glu Glu Gly His Gly Val Lys Gly Trp
            340                 345                 350

Ala Phe Asp Asp Gly Asn Asp Val Trp Met Gly Arg Thr Ile Ser Glu
        355                 360                 365

Lys Ser Arg Ser Gly Tyr Glu Thr Phe Lys Val Ile Glu Gly Trp Ser
370                 375                 380

Lys Pro Asn Ser Lys Leu Gln Ile Asn Arg Gln Val Ile Val Glu Arg
385                 390                 395                 400

Gly Asn Met Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 45
<211> LENGTH: 566
<212> TYPE: PRT
<213> ORGANISM: Influenza A virus

<400> SEQUENCE: 45

```
Met Lys Thr Ile Ile Ala Leu Ser Tyr Ile Leu Cys Leu Val Phe Ser
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
50                      55                  60

Gly Gly Ile Cys Asp Ser Pro His Gln Ile Leu Asp Gly Glu Asn Cys
65                      70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Ala
130                     135                 140

Gly Val Thr Gln Asn Gly Thr Ser Ser Ala Cys Lys Arg Arg Ser Asn
145                     150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
            195                 200                 205

Ser Leu Tyr Ala Gln Ala Ser Gly Arg Ile Thr Val Ser Thr Lys Arg
210                     215                 220

Ser Gln Gln Thr Val Ile Pro Asn Ile Gly Tyr Arg Pro Arg Val Arg
225                     230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                     310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
            370                 375                 380

Ser Thr Gln Ala Ala Ile Asn Gln Ile Asn Gly Lys Leu Asn Arg Leu
385                     390                 395                 400

Ile Gly Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 46
<211> LENGTH: 469
<212> TYPE: PRT
<213> ORGANISM: Influenza A virus

<400> SEQUENCE: 46

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220
```

```
Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
            245                 250                 255

Ile Glu Glu Gly Lys Ile Val His Thr Ser Thr Leu Ser Gly Ser Ala
        260                 265                 270

Gln His Val Glu Glu Cys Ser Cys Tyr Pro Arg Tyr Pro Gly Val Arg
    275                 280                 285

Cys Val Cys Arg Asp Asn Trp Lys Gly Ser Asn Arg Pro Ile Val Asp
290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
            325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 47
<211> LENGTH: 566
<212> TYPE: PRT
<213> ORGANISM: Influenza A virus

<400> SEQUENCE: 47

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
```

```
            115                 120                 125
Glu Arg Phe Glu Ile Phe Pro Lys Glu Ser Ser Trp Pro Asn His Thr
        130                 135                 140
Val Thr Lys Gly Val Thr Thr Ser Cys Ser His Asn Gly Lys Ser Ser
145                 150                 155                 160
Phe Tyr Arg Asn Leu Leu Trp Leu Thr Lys Asn Gly Leu Tyr Pro
                165                 170                 175
Asn Val Ser Lys Ser Tyr Val Asn Asn Lys Glu Lys Glu Val Leu Val
                180                 185                 190
Leu Trp Gly Val His His Pro Ser Asn Ile Gly Asp Gln Arg Ala Ile
            195                 200                 205
Tyr His Thr Glu Asn Ala Tyr Val Ser Val Val Ser Ser His Tyr Ser
        210                 215                 220
Arg Arg Phe Thr Pro Glu Ile Ala Lys Arg Pro Lys Val Arg Asp Gln
225                 230                 235                 240
Glu Gly Arg Ile Asn Tyr Tyr Trp Thr Leu Leu Glu Pro Gly Asp Thr
                245                 250                 255
Ile Ile Phe Glu Ala Asn Gly Asn Leu Ile Ala Pro Trp Tyr Ala Phe
                260                 265                 270
Ala Leu Ser Arg Gly Phe Gly Ser Gly Ile Ile Thr Ser Asn Ala Ser
            275                 280                 285
Met Asp Glu Cys Asp Ala Lys Cys Gln Thr Pro Gln Gly Ala Ile Asn
        290                 295                 300
Ser Ser Leu Pro Phe Gln Asn Val His Pro Val Thr Ile Gly Glu Cys
305                 310                 315                 320
Pro Lys Tyr Val Arg Ser Thr Lys Leu Arg Met Val Thr Gly Leu Arg
                325                 330                 335
Asn Ile Pro Ser Ile Gln Ser Arg Gly Leu Phe Gly Ala Ile Ala Gly
                340                 345                 350
Phe Ile Glu Gly Gly Trp Thr Gly Met Ile Asp Gly Trp Tyr Gly Tyr
            355                 360                 365
His His Gln Asn Glu Gln Gly Ser Gly Tyr Ala Ala Asp Gln Lys Ser
        370                 375                 380
Thr Gln Asn Ala Ile Asn Gly Ile Thr Asn Lys Val Asn Ser Val Ile
385                 390                 395                 400
Glu Lys Met Asn Thr Gln Phe Thr Ala Val Gly Lys Glu Phe Asn Lys
                405                 410                 415
Leu Glu Arg Arg Met Glu Asn Leu Asn Lys Lys Val Asp Asp Gly Phe
                420                 425                 430
Leu Asp Ile Trp Thr Tyr Asn Ala Glu Leu Leu Val Leu Leu Glu Asn
            435                 440                 445
Gly Arg Thr Leu Asp Phe His Asp Ser Asn Val Lys Asn Leu Tyr Glu
        450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asn Asn Glu Cys Met Glu Ser Val
                485                 490                 495
Lys Asn Gly Thr Tyr Asp Tyr Pro Lys Tyr Ser Glu Glu Ser Lys Leu
                500                 505                 510
Asn Arg Gly Lys Ile Asp Gly Val Lys Leu Glu Ser Met Gly Val Tyr
            515                 520                 525
Gln Ile Leu Ala Ile Tyr Ser Thr Val Ala Ser Ser Leu Val Leu Leu
        530                 535                 540
```

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 48
<211> LENGTH: 470
<212> TYPE: PRT
<213> ORGANISM: Influenza A virus

<400> SEQUENCE: 48

Met Asn Pro Asn Gln Lys Ile Ile Ile Gly Ser Ile Ser Met Ala
1                   5                   10                  15

Ile Gly Ile Ile Ser Leu Ile Leu Gln Ile Gly Asn Ile Ile Ser Ile
                20                  25                  30

Trp Ala Ser His Ser Ile Gln Thr Gly Ser Gln Asn His Thr Gly Ile
                35                  40                  45

Cys Asn Gln Arg Ile Ile Thr Tyr Glu Asn Ser Thr Trp Val Asn Gln
50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Pro Ile Arg Gly
                85                  90                  95

Trp Ala Ile Tyr Thr Lys Asp Asn Ser Ile Arg Ile Gly Ser Lys Gly
                100                 105                 110

Asp Val Phe Val Ile Arg Glu Pro Phe Ile Ser Cys Ser His Leu Glu
                115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
                180                 185                 190

Ile Gly Ile Ser Gly Pro Asp Asn Gly Ala Val Ala Val Leu Lys Tyr
                195                 200                 205

Asn Gly Ile Ile Thr Glu Thr Ile Lys Ser Trp Lys Lys Arg Ile Leu
                210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Arg Ile Phe
                245                 250                 255

Lys Ile Glu Lys Gly Lys Val Thr Lys Ser Ile Glu Leu Asp Ala Pro
                260                 265                 270

Asn Tyr His Tyr Glu Glu Cys Ser Cys Tyr Pro Asp Thr Gly Thr Val
                275                 280                 285

Met Cys Val Cys Arg Asp Asn Trp His Gly Ser Asn Arg Pro Trp Val
                290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Arg

-continued

```
               340                 345                 350
Tyr Gly Asn Gly Val Trp Ile Gly Arg Thr Lys Ser Asn Arg Leu Arg
            355                 360                 365
Lys Gly Phe Glu Met Ile Trp Asp Pro Asn Gly Trp Thr Asp Thr Asp
        370                 375                 380
Ser Asp Phe Ser Val Lys Gln Asp Val Val Ala Met Thr Asp Trp Ser
385                 390                 395                 400
Gly Tyr Ser Gly Ser Phe Val Gln His Pro Glu Leu Thr Gly Leu Asp
                405                 410                 415
Cys Met Arg Pro Cys Phe Trp Val Glu Leu Ile Arg Gly Arg Pro Arg
            420                 425                 430
Glu Asn Thr Thr Ile Trp Thr Ser Gly Ser Ser Ile Ser Phe Cys Gly
        435                 440                 445
Val Asn Ser Asp Thr Ala Asn Trp Ser Trp Pro Asp Gly Ala Glu Leu
    450                 455                 460
Pro Phe Thr Ile Asp Lys
465                 470

<210> SEQ ID NO 49
<211> LENGTH: 562
<212> TYPE: PRT
<213> ORGANISM: Influenza A virus

<400> SEQUENCE: 49

Met Lys Ala Lys Leu Leu Val Leu Leu Cys Ala Phe Thr Ala Thr Tyr
1               5                   10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asp Ser His Asn Gly Lys Leu Cys Arg Leu Lys Gly Thr
    50                  55                  60
Ala Pro Leu Gln Leu Gly Asn Cys Ser Val Ala Gly Trp Ile Leu Gly
65                  70                  75                  80
Asn Pro Glu Cys Glu Ser Leu Phe Ser Lys Glu Ser Trp Ser Tyr Ile
                85                  90                  95
Ala Glu Thr Pro Asn Pro Glu Asn Gly Thr Cys Tyr Pro Gly Tyr Phe
            100                 105                 110
Ala Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Lys His Thr
    130                 135                 140
Val Thr Lys Gly Val Thr Ala Ser Cys Ser His Asn Gly Lys Ser Ser
145                 150                 155                 160
Phe Tyr Lys Asn Leu Leu Trp Leu Thr Glu Lys Asn Gly Leu Tyr Pro
                165                 170                 175
Asn Leu Ser Lys Ser Tyr Val Asn Asn Lys Glu Lys Glu Val Leu Val
            180                 185                 190
Leu Trp Gly Val His His Pro Ser Asn Ile Gly Asp Gln Arg Ala Ile
        195                 200                 205
Tyr His Thr Glu Asn Ala Tyr Val Ser Val Ser Ser His Tyr Ser
    210                 215                 220
Arg Arg Phe Thr Pro Glu Ile Ala Lys Arg Pro Lys Val Arg Gly Gln
225                 230                 235                 240
```

```
Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
        260                 265                 270

Ala Leu Ser Arg Gly Phe Gly Ser Gly Ile Ile Thr Ser Thr Ala Ser
            275                 280                 285

Met Gly Glu Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Gly Arg Thr Leu Gly Phe His Asp Ser Asn Val Lys Asn Leu Tyr Glu
    450                 455                 460

Lys Val Lys Asn Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys

<210> SEQ ID NO 50
<211> LENGTH: 470
<212> TYPE: PRT
<213> ORGANISM: Influenza A virus

<400> SEQUENCE: 50

Met Asn Pro Asn Gln Lys Ile Ile Thr Ile Gly Ser Ile Ser Ile Ala
1               5                   10                  15

Ile Gly Ile Ile Ser Leu Ile Leu Gln Ile Gly Asn Ile Ile Ser Ile
            20                  25                  30

Trp Ala Ser His Ser Ile Gln Thr Gly Ser Gln Asn His Thr Gly Ile
        35                  40                  45
```

```
Cys Asn Gln Arg Ile Ile Thr Tyr Glu Asn Ser Thr Trp Val Asn Gln
     50                  55                  60

Thr Tyr Val Asn Ile Asn Asn Thr Asn Val Val Ala Gly Lys Asp Lys
 65                  70                  75                  80

Thr Ser Met Thr Leu Ala Gly Asn Ser Ser Leu Cys Pro Ile Arg Gly
                 85                  90                  95

Trp Ala Ile Tyr Thr Lys Asp Asn Ser Ile Arg Ile Gly Ser Lys Gly
                100                 105                 110

Asp Val Phe Val Ile Arg Glu Pro Phe Ile Ser Cys Ser His Leu Glu
            115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Val Ala Trp Ser Ala Ser Ala Cys His Asp Gly Leu Gly Trp Leu Thr
            180                 185                 190

Ile Gly Ile Ser Gly Pro Asp Asn Gly Ala Val Ala Val Leu Lys Tyr
            195                 200                 205

Asn Gly Ile Ile Thr Glu Thr Ile Lys Ser Trp Lys Lys Arg Ile Leu
210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Gly Ala Ala Ser Tyr Arg Ile Phe
                245                 250                 255

Lys Ile Glu Lys Gly Arg Val Thr Lys Ser Ile Glu Leu Asp Ala Pro
            260                 265                 270

Asn Tyr His Tyr Glu Glu Cys Ser Cys Tyr Pro Asp Thr Gly Thr Val
            275                 280                 285

Met Cys Val Cys Arg Asp Asn Trp His Gly Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asp Thr Asp
370                 375                 380

Ser Asp Phe Ser Met Lys Gln Asp Ile Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Leu Pro Arg
            420                 425                 430

Glu Asn Thr Thr Ile Trp Thr Ser Gly Ser Ile Ser Phe Cys Gly
            435                 440                 445

Val Asn Ser Asp Thr Ala Asn Trp Ser Trp Pro Asp Gly Ala Glu Leu
450                 455                 460

Pro Phe Thr Ile Asp Lys
```

<210> SEQ ID NO 51
<211> LENGTH: 565
<212> TYPE: PRT
<213> ORGANISM: Influenza A virus

<400> SEQUENCE: 51

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Gl

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 52
<211> LENGTH: 470
<212> TYPE: PRT
<213> ORGANISM: Influenza A virus

<400> SEQUENCE: 52

Met Asn Pro Asn Gln Lys Ile Ile Thr Ile Gly Ser Ile Ser Ile Val
1               5                   10                  15

Ile Gly Ile Ile Ser Leu Met Leu Gln Ile Gly Asn Ile Ile Ser Ile
                20                  25                  30

Trp Ala Ser His Ser Ile Gln Thr Gly Ser Gln Asn His Thr Gly Ile
            35                  40                  45

Cys Asn Gln Arg Ile Ile Thr Tyr Glu Asn Ser Thr Trp Val Asn His
50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
                100                 105                 110

Asp Val Phe Val Ile Arg Glu Pro Phe Ile Ser Cys Ser His Leu Glu
            115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

```
Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asp Thr Asp
    370                 375                 380

Ser Asp Phe Ser Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Arg Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470

<210> SEQ ID NO 53
<211> LENGTH: 565
<212> TYPE: PRT
<213> ORGANISM: Influenza A virus

<400> SEQUENCE: 53

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
```

```
              65                  70                  75                  80
Asn Pro Glu Cys Glu Leu Leu Ile Ser Lys Glu Ser Trp Ser Tyr Ile
                    85                  90                  95

Val Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Ser Ser Trp Pro Lys His Thr
        130                 135                 140

Val Thr Gly Val Ser Ala Ser Cys Ser His Asn Gly Lys Asn Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495
```

```
Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 54
<211> LENGTH: 470
<212> TYPE: PRT
<213> ORGANISM: Influenza A virus

<400> SEQUENCE: 54

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Val
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
```

```
                    290                 295                 300
Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Lys
                    340                 345                 350

Tyr Gly Asn Gly Val Trp Ile Gly Arg Thr Lys Ser Asn Arg Leu Arg
                355                 360                 365

Lys Gly Phe Glu Met Ile Trp Asp Pro Asn Gly Trp Thr Asp Thr Asp
                370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                    405                 410                 415

Cys Ile Arg Pro Cys Phe Trp Val Glu Leu Val Arg Gly Leu Pro Arg
                420                 425                 430

Glu Asn Thr Thr Ile Trp Thr Ser Gly Ser Ser Ile Ser Phe Cys Gly
                435                 440                 445

Val Asn Ser Asp Thr Ala Asn Trp Ser Trp Pro Asp Gly Ala Glu Leu
                    450                 455                 460

Pro Phe Thr Ile Asp Lys
465                 470

<210> SEQ ID NO 55
<211> LENGTH: 583
<212> TYPE: PRT
<213> ORGANISM: Influenza B virus

<400> SEQUENCE: 55

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Lys Thr
        50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Ile Thr Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Arg
        130                 135                 140

Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190
```

Ile Cys Thr Lys Gly Glu Asp Gln Ile Thr Val Trp Gly Phe His Ser
195 200 205

Asp Asn Lys Ile Gln Met Lys Asn Leu Tyr Gly Asp Ser Asn Pro Gln
210 215 220

Lys Phe Thr Ser Ser Ala Asn Gly Ile Thr Thr His Tyr Val Ser Gln
225 230 235 240

Ile Gly Gly Phe Pro Asn Gln Thr Glu Asp Gly Gly Leu Pro Gln Ser
245 250 255

Gly Arg Ile Val Val Asp Tyr Met Val Gln Lys Pro Gly Lys Thr Gly
260 265 270

Thr Ile Val Tyr Gln Arg Gly Val Leu Leu Pro Gln Lys Val Trp Cys
275 280 285

Ala Ser Gly Arg Ser Lys Val Ile Lys Gly Ser Leu Pro Leu Ile Gly
290 295 300

Glu Ala Asp Cys Leu His Glu Lys Tyr Gly Gly Leu Asn Lys Ser Lys
305 310 315 320

Pro Tyr Tyr Thr Gly Glu His Ala Lys Ala Ile Gly Asn Cys Pro Ile
325 330 335

Trp Val Lys Thr Pro Leu Lys Leu Ala Asn Gly Thr Lys Tyr Arg Pro
340 345 350

Pro Ala Lys Leu Leu Lys Glu Lys Gly Phe Phe Gly Ala Ile Ala Gly
355 360 365

Phe Leu Glu Gly Gly Trp Glu Gly Met Ile Ala Gly Trp His Gly Tyr
370 375 380

Thr Ser His Gly Ala His Gly Val Ala Val Ala Ala Asp Leu Lys Ser
385 390 395 400

Thr Gln Glu Ala Ile Asn Lys Ile Thr Lys Asn Leu Asn Ser Leu Ser
405 410 415

Glu Leu Glu Val Lys Asn Leu Gln Arg Leu Ser Gly Ala Met Asp Glu
420 425 430

Leu His Asn Glu Ile Leu Glu Leu Asp Glu Lys Val Asp Asp Leu Arg
435 440 445

Ala Asp Thr Ile Ser Ser Gln Ile Glu Leu Ala Val Leu Leu Ser Asn
450 455 460

Glu Gly Ile Ile Asn Ser Glu Asp Glu His Leu Leu Ala Leu Glu Arg
465 470 475 480

Lys Leu Lys Lys Met Leu Gly Pro Ser Ala Val Asp Ile Gly Asn Gly
485 490 495

Cys Phe Glu Thr Lys His Lys Cys Asn Gln Thr Cys Leu Asp Arg Ile
500 505 510

Ala Ala Gly Thr Phe Asn Ala Gly Glu Phe Ser Leu Pro Thr Phe Asp
515 520 525

Ser Leu Asn Ile Thr Ala Ala Ser Leu Asn Asp Asp Gly Leu Asp Asn
530 535 540

His Thr Ile Leu Leu Tyr Tyr Ser Thr Ala Ala Ser Ser Leu Ala Val
545 550 555 560

Thr Leu Met Ile Ala Ile Phe Ile Val Tyr Met Val Ser Arg Asp Asn
565 570 575

Val Ser Cys Ser Ile Cys Leu
580

<210> SEQ ID NO 56
<211> LENGTH: 465
<212> TYPE: PRT

<213> ORGANISM: Influenza B virus

<400> SEQUENCE: 56

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Pro Lys Ile Ile Ala Pro Thr
        35                  40                  45

Thr Ser Leu Asp Cys Ala Asn Ala Ser Asn Val Gln Ala Val Asn His
    50                  55                  60

Ser Ala Thr Lys Glu Met Lys Phe Leu Pro Glu Pro Glu Trp Thr
65                  70                  75                  80

Tyr Pro Arg Leu Ser Cys Gln Gly Ser Thr Phe Gln Lys Ala Leu Leu
                85                  90                  95

Ile Ser Pro His Arg Phe Gly Glu Ala Lys Gly Asn Ser Ala Pro Leu
            100                 105                 110

Ile Ile Arg Glu Pro Phe Ile Ala Cys Gly Pro Lys Glu Cys Lys His
        115                 120                 125

Phe Ala Leu Thr His Tyr Ala Ala Gln Pro Gly Gly Tyr Tyr Asn Gly
    130                 135                 140

Thr Arg Glu Asp Arg Asn Lys Leu Arg His Leu Ile Ser Val Asn Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
        195                 200                 205

Tyr Thr Asp Thr Tyr His Ser Tyr Ala Asn Asn Ile Leu Arg Thr Gln
    210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
        275                 280                 285

Ala Cys Arg Asp Asn Ser Tyr Thr Ala Lys Arg Pro Phe Val Lys Leu
    290                 295                 300

Asn Val Glu Thr Asp Thr Ala Glu Ile Arg Leu Met Cys Thr Glu Thr
305                 310                 315                 320

Tyr Leu Asp Thr Pro Arg Pro Asp Asp Gly Ser Ile Thr Gly Pro Cys
                325                 330                 335

Glu Ser Asn Gly Asp Lys Gly Ser Gly Val Lys Gly Gly Phe Val
            340                 345                 350

His Gln Arg Met Ala Ser Lys Ile Gly Arg Trp Tyr Ser Arg Thr Met
        355                 360                 365

Ser Lys Thr Lys Arg Met Gly Met Glu Leu Tyr Val Lys Tyr Asp Gly
    370                 375                 380

Asp Pro Trp Thr Asp Ser Asp Ala Leu Ala Pro Ser Gly Val Met Val
385                 390                 395                 400
```

```
Ser Met Glu Glu Pro Gly Trp Tyr Ser Phe Gly Phe Glu Ile Lys Asp
                405                 410                 415
Lys Lys Cys Asp Val Pro Cys Ile Gly Ile Glu Met Val His Asp Gly
            420                 425                 430
Gly Lys Arg Thr Trp His Ser Ala Ala Thr Ala Ile Tyr Cys Leu Met
        435                 440                 445
Gly Ser Gly Gln Leu Leu Trp Asp Thr Val Thr Gly Val Asn Met Ala
    450                 455                 460
Leu
465

<210> SEQ ID NO 57
<211> LENGTH: 584
<212> TYPE: PRT
<213> ORGANISM: Influenza B virus

<400> SEQUENCE: 57

Met Lys Ala Ile Ile Val Leu Leu Met Val Val Thr Ser Asn Ala Asp
1               5                   10                  15
Arg Ile Cys Thr Gly Ile Thr Ser Ser Asn Ser Pro His Val Val Lys
            20                  25                  30
Thr Ala Thr Gln Gly Glu Val Asn Val Thr Gly Val Ile Pro Leu Thr
        35                  40                  45
Thr Thr Pro Thr Lys Ser His Phe Ala Asn Leu Lys Gly Thr Lys Thr
    50                  55                  60
Arg Gly Lys Leu Cys Pro Thr Cys Leu Asn Cys Thr Asp Leu Asp Val
65                  70                  75                  80
Ala Leu Gly Arg Pro Met Cys Val Gly Val Thr Pro Ser Ala Lys Ala
                85                  90                  95
Ser Ile Leu His Glu Val Arg Pro Val Thr Ser Gly Cys Phe Pro Ile
            100                 105                 110
Met His Asp Arg Thr Lys Ile Arg Gln Leu Pro Asn Leu Leu Arg Gly
        115                 120                 125
Tyr Glu Lys Ile Arg Leu Ser Thr Gln Ile Val Ile Asn Ala Glu Lys
    130                 135                 140
Ala Pro Gly Gly Pro Tyr Arg Leu Gly Thr Ser Gly Ser Cys Pro Asn
145                 150                 155                 160
Ala Thr Ser Arg Ser Gly Phe Phe Ala Thr Met Ala Trp Ala Val Pro
                165                 170                 175
Lys Asp Asn Asn Lys Thr Ala Thr Asn Pro Leu Thr Val Glu Val Pro
            180                 185                 190
His Ile Cys Thr Lys Glu Glu Asp Gln Ile Thr Val Trp Gly Phe His
        195                 200                 205
Ser Asp Asp Lys Thr Gln Met Lys Asn Leu Tyr Gly Asp Ser Asn Pro
    210                 215                 220
Gln Lys Phe Thr Ser Ser Ala Asn Gly Val Thr Thr His Tyr Val Ser
225                 230                 235                 240
Gln Ile Gly Gly Phe Pro Asp Gln Thr Glu Asp Gly Gly Leu Pro Gln
                245                 250                 255
Ser Gly Arg Ile Val Val Asp Tyr Met Val Gln Lys Pro Gly Lys Thr
            260                 265                 270
Gly Thr Ile Val Tyr Gln Arg Gly Ile Leu Leu Pro Gln Lys Val Trp
        275                 280                 285
Cys Ala Ser Gly Arg Ser Lys Val Ile Lys Gly Ser Leu Pro Leu Ile
    290                 295                 300
```

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
            325                 330                 335

Ile Trp Val Lys Thr Pro Leu Lys Leu Ala Asn Gly Thr Lys Tyr Arg
        340                 345                 350

Pro Pro Ala Lys Leu Leu Lys Glu Arg Gly Phe Phe Gly Ala Ile Ala
            355                 360                 365

Gly Phe Leu Glu Gly Gly Trp Glu Gly Met Ile Ala Gly Trp His Gly
        370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
            405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
        450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
            485                 490                 495

Gly Cys Phe Glu Thr Lys His Lys Cys Asn Gln Thr Cys Leu Asp Arg
        500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
        530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
            565                 570                 575

Asn Val Ser Cys Ser Ile Cys Leu
            580

<210> SEQ ID NO 58
<211> LENGTH: 466
<212> TYPE: PRT
<213> ORGANISM: Influenza B virus

<400> SEQUENCE: 58

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asn Cys Ala Asn Ala Ser Asn Val Gln Ala Val Asn
        50                  55                  60

Arg Ser Ala Thr Lys Gly Val Thr Leu Pro Leu Pro Glu Pro Glu Trp
65                  70                  75                  80

Thr Tyr Pro Arg Leu Ser Cys Pro Gly Ser Thr Phe Gln Lys Ala Leu

```
                      85                  90                  95
Leu Ile Ser Pro His Arg Phe Gly Glu Thr Lys Gly Asn Ser Ala Pro
                100                 105                 110

Leu Ile Ile Arg Glu Pro Phe Ile Ala Cys Gly Pro Lys Glu Cys Arg
                115                 120                 125

His Phe Ala Leu Thr His Tyr Ala Ala Gln Pro Gly Tyr Tyr Asn
130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
                180                 185                 190

Val Asp Gly Pro Asp Ser Asn Ala Leu Leu Lys Ile Lys Tyr Gly Glu
                195                 200                 205

Ala Tyr Thr Asp Thr Tyr His Ser Tyr Ala Asn Asn Ile Leu Arg Thr
                210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Glu
                260                 265                 270

His Thr Glu Glu Cys Thr Cys Gly Phe Ala Ser Asn Lys Thr Ile Glu
                275                 280                 285

Cys Ala Cys Arg Asp Asn Ser Tyr Thr Ala Lys Arg Pro Phe Val Lys
                290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
                340                 345                 350

Val His Gln Arg Met Ala Ser Lys Ile Gly Arg Trp Tyr Ser Arg Thr
                355                 360                 365

Met Ser Lys Thr Lys Arg Met Gly Met Gly Leu Tyr Val Lys Tyr Asp
                370                 375                 380

Gly Asp Pro Trp Ile Asp Ser Asp Ala Leu Thr Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
                420                 425                 430

Gly Gly Lys Lys Thr Trp His Ser Ala Ala Thr Ala Ile Tyr Cys Leu
                435                 440                 445

Met Gly Ser Gly Gln Leu Leu Trp Asp Thr Val Thr Gly Val Asp Met
450                 455                 460

Ala Leu
465

<210> SEQ ID NO 59
<211> LENGTH: 584
<212> TYPE: PRT
<213> ORGANISM: Influenza B virus
```

<400> SEQUENCE: 59

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Ala Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Thr Cys Leu Asn Cys Thr Asp Leu Asp Val
65                  70                  75                  80

Ala Leu Gly Arg Pro Met Cys Val Gly Ile Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Asn Val Ile Asn Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Arg Asp Asn Asn Lys Thr Ala Thr Asn Pro Leu Thr Val Glu Val Pro
            180                 185                 190

His Ile Cys Thr Lys Glu Glu Asp Gln Ile Thr Val Trp Gly Phe His
        195                 200                 205

Ser Asp Asp Lys Thr Gln Met Lys Asn Leu Tyr Gly Asp Ser Asn Pro
210                 215                 220

Gln Lys Phe Thr Ser Ser Ala Asn Gly Ile Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
```

```
                    405                 410                 415
Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
        450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Ile Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
                565                 570                 575

Asn Val Ser Cys Ser Ile Cys Leu
            580

<210> SEQ ID NO 60
<211> LENGTH: 466
<212> TYPE: PRT
<213> ORGANISM: Influenza B virus

<400> SEQUENCE: 60

Met Leu Pro Ser Thr Ile Gln Thr Leu Thr Leu Phe Leu Thr Ser Gly
1               5

```
Val Asp Gly Pro Asp Ser Asn Ala Leu Leu Lys Ile Lys Tyr Gly Glu
            195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
            290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
                340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
        370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
                420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
        450                 455                 460

Ala Leu
465

<210> SEQ ID NO 61
<211> LENGTH: 583
<212> TYPE: PRT
<213> ORGANISM: Influenza B virus

<400> SEQUENCE: 61

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Lys Thr
        50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Ile Thr Pro Ser Ala Lys Ala
                85                  90                  95
```

```
Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Arg
130                 135                 140

Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
            165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
            195                 200                 205

Asp Asn Lys Ile Gln Met Lys Asn Leu Tyr Gly Asp Ser Asn Pro Gln
            210                 215                 220

Lys Phe Thr Ser Ser Ala Asn Gly Ile Thr Thr His Tyr Val Ser Gln
225                 230                 235                 240

Ile Gly Gly Phe Pro Asn Gln Thr Glu Asp Gly Gly Leu Pro Gln Ser
            245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
            275                 280                 285

Ala Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
            325                 330                 335

Trp Val Lys Thr Pro Leu Lys Leu Ala Asn Gly Thr Lys Tyr Arg Pro
            340                 345                 350

Pro Ala Lys Leu Leu Lys Glu Lys Gly Phe Phe Gly Ala Ile Ala Gly
            355                 360                 365

Phe Leu Glu Gly Gly Trp Glu Gly Met Ile Ala Gly Trp His Gly Tyr
370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
            405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
            435                 440                 445

Ala Asp Thr Ile Ser Ser Gln Ile Glu Leu Ala Val Leu Leu Ser Asn
450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
            485                 490                 495

Cys Phe Glu Thr Lys His Lys Cys Asn Gln Thr Cys Leu Asp Arg Ile
            500                 505                 510
```

```
Ala Ala Gly Thr Phe Asn Ala Gly Glu Phe Ser Leu Pro Thr Phe Asp
            515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 62
<211> LENGTH: 465
<212> TYPE: PRT
<213> ORGANISM: Influenza B virus

<400> SEQUENCE: 62

Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Pro Lys Ile Ala Pro Thr
            35                  40                  45

Thr Ser Leu Asp Cys Ala Asn Ala Ser Asn Val Gln Ala Val Asn His
50                  55                  60

Ser Ala Thr Lys Glu Met Lys Phe Leu Pro Pro Glu Pro Glu Trp Thr
65                  70                  75                  80

Tyr Pro Arg Leu Ser Cys Gln Gly Ser Thr Phe Gln Lys Ala Leu Leu
                85                  90                  95

Ile Ser Pro His Arg Phe Gly Glu Ala Lys Gly Asn Ser Ala Pro Leu
            100                 105                 110

Ile Ile Arg Glu Pro Phe Ile Ala Cys Gly Pro Lys Glu Cys Lys His
            115                 120                 125

Phe Ala Leu Thr His Tyr Ala Ala Gln Pro Gly Gly Tyr Tyr Asn Gly
130                 135                 140

Thr Arg Glu Asp Arg Asn Lys Leu Arg His Leu Ile Ser Val Asn Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
            195                 200                 205

Tyr Thr Asp Thr Tyr His Ser Tyr Ala Asn Asn Ile Leu Arg Thr Gln
            210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
            275                 280                 285

Ala Cys Arg Asp Asn Ser Tyr Thr Ala Lys Arg Pro Phe Val Lys Leu
            290                 295                 300
```

```
Asn Val Glu Thr Asp Thr Ala Glu Ile Arg Leu Met Cys Thr Glu Thr
305                 310                 315                 320

Tyr Leu Asp Thr Pro Arg Pro Asp Gly Ser Ile Thr Gly Pro Cys
            325                 330                 335

Glu Ser Asn Gly Asp Lys Gly Ser Gly Gly Val Lys Gly Gly Phe Val
            340                 345                 350

His Gln Arg Met Ala Ser Lys Ile Gly Arg Trp Tyr Ser Arg Thr Met
            355                 360                 365

Ser Lys Thr Lys Arg Met Gly Met Glu Leu Tyr Val Lys Tyr Asp Gly
    370                 375                 380

Asp Pro Trp Thr Asp Ser Asp Ala Leu Ala Pro Ser Gly Val Met Val
385                 390                 395                 400

Ser Met Glu Glu Pro Gly Trp Tyr Ser Phe Gly Phe Glu Ile Lys Asp
                405                 410                 415

Lys Lys Cys Asp Val Pro Cys Ile Gly Ile Glu Met Val His Asp Gly
            420                 425                 430

Gly Lys Arg Thr Trp His Ser Ala Ala Thr Ala Ile Tyr Cys Leu Met
            435                 440                 445

Gly Ser Gly Gln Leu Leu Trp Asp Thr Val Thr Gly Val Asn Met Ala
    450                 455                 460

Leu
465

<210> SEQ ID NO 63
<211> LENGTH: 585
<212> TYPE: PRT
<213> ORGANISM: Influenza B virus

<400> SEQUENCE: 63

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Arg Ile Arg Leu Ser Asn His Asn Val Ile Asn Ala Glu Lys
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Glu Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
```

```
            195                 200                 205
His Ser Asp Ser Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 64
<211> LENGTH: 466
<212> TYPE: PRT
<213> ORGANISM: Influenza B virus
```

<400> SEQUENCE: 64

| | | | | | | | | | | | | | | |
|---|---|---|---|---|---|---|---|---|---|---|---|---|---|---|
| Met | Leu | Pro | Ser | Thr | Ile | Gln | Thr | Leu | Thr | Leu | Phe | Leu | Thr | Ser | Gly |
| 1 | | | | 5 | | | | | 10 | | | | | 15 | |
| Gly | Val | Leu | Leu | Ser | Leu | Tyr | Val | Ser | Ala | Leu | Leu | Ser | Tyr | Leu | Leu |
| | | | 20 | | | | | 25 | | | | | 30 | | |
| Tyr | Ser | Asp | Ile | Leu | Leu | Lys | Phe | Ser | Pro | Thr | Lys | Ile | Ile | Ala | Pro |
| | | 35 | | | | | 40 | | | | | 45 | | | |
| Thr | Thr | Ser | Leu | Asp | Ser | Ala | Asn | Ala | Ser | Asn | Phe | Gln | Ala | Val | Asn |
| | 50 | | | | | 55 | | | | | 60 | | | | |
| His | Ser | Ala | Thr | Lys | Glu | Met | Thr | Phe | Leu | Leu | Pro | Glu | Pro | Glu | Trp |
| 65 | | | | | 70 | | | | | 75 | | | | | 80 |
| Thr | Tyr | Pro | Arg | Leu | Ser | Cys | Gln | Gly | Ser | Thr | Phe | Gln | Lys | Ala | Leu |
| | | | | 85 | | | | | 90 | | | | | 95 | |
| Leu | Ile | Ser | Pro | His | Arg | Phe | Gly | Glu | Ala | Lys | Gly | Asn | Ser | Ala | Pro |
| | | | 100 | | | | | 105 | | | | | 110 | | |
| Leu | Ile | Ile | Arg | Glu | Pro | Phe | Ile | Ala | Cys | Gly | Pro | Lys | Glu | Cys | Lys |
| | | | 115 | | | | | 120 | | | | | 125 | | |
| His | Phe | Ala | Leu | Thr | His | Tyr | Ala | Ala | Gln | Pro | Gly | Gly | Tyr | Tyr | Asn |
| | | 130 | | | | | 135 | | | | | 140 | | | |
| Gly | Thr | Arg | Glu | Asp | Arg | Asn | Lys | Leu | Arg | His | Leu | Ile | Ser | Val | Asn |
| 145 | | | | | 150 | | | | | 155 | | | | | 160 |
| Leu | Gly | Lys | Ile | Pro | Thr | Val | Glu | Asn | Ser | Ile | Phe | His | Met | Ala | Ala |
| | | | | 165 | | | | | 170 | | | | | 175 | |
| Trp | Ser | Gly | Ser | Ala | Cys | His | Asp | Gly | Arg | Glu | Trp | Thr | Tyr | Ile | Gly |
| | | | 180 | | | | | 185 | | | | | 190 | | |
| Val | Asp | Gly | Pro | Asp | Ser | Asn | Ala | Leu | Ile | Lys | Ile | Lys | Tyr | Gly | Glu |
| | | | 195 | | | | | 200 | | | | | 205 | | |
| Ala | Tyr | Thr | Asp | Thr | Tyr | His | Ser | Tyr | Ala | Asn | Asn | Ile | Leu | Arg | Thr |
| | | 210 | | | | | 215 | | | | | 220 | | | |
| Gln | Glu | Ser | Ala | Cys | Asn | Cys | Ile | Gly | Gly | Asp | Cys | Tyr | Leu | Met | Ile |
| 225 | | | | | 230 | | | | | 235 | | | | | 240 |
| Thr | Asp | Gly | Ser | Ala | Ser | Gly | Ile | Ser | Lys | Cys | Arg | Phe | Leu | Lys | Ile |
| | | | | 245 | | | | | 250 | | | | | 255 | |
| Arg | Glu | Gly | Arg | Ile | Val | Lys | Glu | Ile | Phe | Pro | Thr | Gly | Arg | Val | Glu |
| | | | 260 | | | | | 265 | | | | | 270 | | |
| His | Thr | Glu | Glu | Cys | Thr | Cys | Gly | Phe | Ala | Ser | Asn | Lys | Thr | Ile | Glu |
| | | | 275 | | | | | 280 | | | | | 285 | | |
| Cys | Ala | Cys | Arg | Asp | Asn | Ser | Tyr | Thr | Ala | Lys | Arg | Pro | Phe | Val | Lys |
| | 290 | | | | | 295 | | | | | 300 | | | | |
| Leu | Asn | Val | Glu | Thr | Asp | Thr | Ala | Glu | Ile | Arg | Leu | Met | Cys | Thr | Glu |
| 305 | | | | | 310 | | | | | 315 | | | | | 320 |
| Thr | Tyr | Leu | Asp | Thr | Pro | Arg | Pro | Asp | Asp | Gly | Ser | Ile | Thr | Gly | Pro |
| | | | | 325 | | | | | 330 | | | | | 335 | |
| Cys | Glu | Ser | Asn | Gly | Asp | Lys | Gly | Ser | Gly | Gly | Ile | Lys | Gly | Gly | Phe |
| | | | 340 | | | | | 345 | | | | | 350 | | |
| Val | His | Gln | Arg | Met | Ala | Ser | Lys | Ile | Gly | Arg | Trp | Tyr | Ser | Arg | Thr |
| | | 355 | | | | | 360 | | | | | 365 | | | |
| Met | Ser | Lys | Thr | Lys | Arg | Met | Gly | Met | Glu | Leu | Tyr | Val | Lys | Tyr | Asp |
| | 370 | | | | | 375 | | | | | 380 | | | | |
| Gly | Asp | Pro | Trp | Thr | Asp | Ser | Asp | Ala | Leu | Ala | Pro | Ser | Gly | Val | Met |
| 385 | | | | | 390 | | | | | 395 | | | | | 400 |
| Val | Ser | Ile | Glu | Glu | Pro | Gly | Trp | Tyr | Ser | Phe | Gly | Phe | Glu | Ile | Lys |

```
            405                 410                 415
Asp Lys Lys Cys Asp Val Pro Cys Ile Gly Ile Glu Met Val His Asp
        420                 425                 430

Gly Gly Lys Thr Thr Trp His Ser Ala Ala Thr Ala Ile Tyr Cys Leu
        435                 440                 445

Met Gly Ser Gly Gln Leu Leu Trp Asp Thr Ile Thr Gly Val Asp Met
    450                 455                 460

Ala Leu
465

<210> SEQ ID NO 65
<211> LENGTH: 585
<212> TYPE: PRT
<213> ORGANISM: Influenza B virus

<400> SEQUENCE: 65

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Lys
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Ala Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300
```

-continued

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 66
<211> LENGTH: 466
<212> TYPE: PRT
<213> ORGANISM: Influenza B virus

<400> SEQUENCE: 66

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

```
Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
            115                 120                 125

His Phe Ala Leu Thr His Tyr Ala Ala Gln Pro Gly Gly Tyr Tyr Asn
            130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
                180                 185                 190

Val Asp Gly Pro Asp Asn Asn Ala Leu Leu Lys Ile Lys Tyr Gly Glu
                195                 200                 205

Ala Tyr Thr Asp Thr Tyr His Ser Tyr Ala Asn Asn Ile Leu Arg Thr
            210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
            290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
                340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
370                 375                 380

Gly Asp Pro Trp Ala Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
450                 455                 460

Ala Leu
465

<210> SEQ ID NO 67
<211> LENGTH: 584
<212> TYPE: PRT
<213> ORGANISM: Influenza B virus
```

```
<400> SEQUENCE: 67

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Asn
130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Val Cys Thr Glu Gly Glu Asp Gln Ile Thr Val Trp Gly Phe His
        195                 200                 205

Ser Asp Asn Lys Thr Pro Met Lys Asn Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Gly Phe Pro Ala Gln Thr Glu Asp Glu Gly Leu Pro Gln
                245                 250                 255

Ser Gly Arg Ile Val Val Asp Tyr Met Val Gln Lys Pro Arg Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415
```

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 68
<211> LENGTH: 466
<212> TYPE: PRT
<213> ORGANISM: Influenza B virus

<400> SEQUENCE: 68

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Thr Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Lys Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu

-continued

```
                    195                 200                 205
Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
        290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asn Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465
```

INFLUENZA HEMAGGLUTININ AND NEURAMINIDASE VARIANTS

CROSS-REFERENCE TO RELATED APPLICATIONS

This application is a divisional of U.S. patent application Ser. No. 13/767,749, filed on Feb. 14, 2013, which is a continuation of U.S. patent application Ser. No. 13/538,972, filed on Jun. 29, 2012, which is a continuation of U.S. patent application Ser. No. 13/247,903, filed on Sep. 28, 2011, now abandoned, which is a divisional of U.S. patent application Ser. No. 12/877,000, filed on Sep. 7, 2010, now U.S. Pat. No. 8,048,430, which is a continuation of U.S. patent application Ser. No. 12/399,077, filed on Mar. 6, 2009, which is a division of U.S. patent application Ser. No. 10/870,690, filed Jun. 16, 2004, now U.S. Pat. No. 7,566,458, which claims the benefit under 35 U.S.C. §119(e) of the U.S. Provisional Patent Application Ser. No. 60/479,078, filed on Jun. 16, 2003, the disclosures of each of which are incorporated by reference herein in their entirety for all purposes.

BACKGROUND OF THE INVENTION

Vaccines against various and evolving strains of influenza are important from a community health standpoint, as well as commercially, since each year numerous individuals are infected with different strains and types of influenza virus. Infants, the elderly, those without adequate health care and immuno-compromised persons are at special risk of death from such infections. Compounding the problem of influenza infections is that novel influenza strains evolve readily and can spread between various species, thereby necessitating the continuous production of new vaccines.

Numerous vaccines capable of producing a protective immune response specific for different influenza viruses/virus strains have been produced for over 50 years and include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract. Considerable work in the production of influenza viruses, and fragments thereof, for production of vaccines has been done by the present inventors and co-workers; see, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus."

Because of the continual emergence (or re-emergence) or different influenza strains, new influenza vaccines are continually desired. Such vaccines typically are created using antigenic moieties of the newly emergent virus strains so, therefore, polypeptides and polynucleotides of novel, newly emergent, or newly re-emergent virus strains (especially sequences of antigenic genes) are highly desirable. Furthermore, such sequences within preferred vectors are also quite highly desired.

The present invention provides new and/or newly isolated influenza hemagglutinin and neuraminidase variants, optionally within preferred vectors, that are capable of use in production of numerous types of vaccines as well as in research, diagnostics, etc. Numerous other benefits will become apparent upon review of the following

SUMMARY OF THE INVENTION

In some aspects herein, the invention comprises an isolated or recombinant polypeptide that is selected from: the polypeptides encoded by any one of the sequences of the sequence listing, e.g., SEQ ID NO:1 through SEQ ID NO:34, any one of the polypeptides encoded by the sequence listing, e.g., SEQ ID NO:35 through SEQ ID NO:68; any polypeptide that is encoded by a polynucleotide sequence which hybridizes under highly stringent conditions over substantially the entire length of a polynucleotide sequence of the sequence listing; and, a fragment of any of the above wherein the sequence comprises a hemagglutinin or neuraminidase polypeptide, or a fragment thereof. In various embodiments, the isolated or recombinant polypeptides of the invention are substantially identical to about 300 contiguous amino acid residues of any of the above polypeptides. In yet other embodiments, the invention comprises isolated or recombinant polypeptides (comprising hemagglutinin or fragments thereof), that comprise an amino acid sequence that is substantially identical over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids contiguous of any of the polypeptides of claim of any of the above polypeptides. In yet other embodiments, the invention comprises isolated or recombinant polypeptides (e.g., comprising neuraminidase or fragments thereof), that comprise an amino acid sequence that is substantially identical over at least about 350 amino acids; over at least about 400 amino acids; over at least about 436 amino acids; over at least about 450 amino acids; over at least about 451 amino acids; over at least about 465 amino acids; over at least about 466 amino acids; over at least about 469 amino acids; or over at least about 470 amino acids contiguous of any of the polypeptides of any of the above polypeptides. Of course, in some embodiments, the polypeptide sequence (e.g., as listed in the sequence listing herein, e.g., SEQ ID NO:35 through SEQ ID NO:68) comprises less than 565, 559, etc. amino acids. In such embodiments, the shorter listed polypeptides optionally comprise less than 565, 559, etc. amino acids. In yet other embodiments, the polypeptides of the invention optionally comprise fusion proteins, proteins with a leader sequence, a precursor polypeptide, proteins with a secretion signal or a localization signal, or proteins with an epitope tag, an E-tag, or a H is epitope tag, etc. In still other embodiments, the invention comprises a polypeptide comprising a sequence having at least 95%, at least 96%, at least 97%, at least 98%, at least 98.5%, at least 99%, at least 99.2%, at least 99.4%, at least 99.6%, at least 99.8%, or at least 99.9% sequence identity to at least one polypeptide listed above. In some embodiments, such polypeptides are immunogenic.

In other aspects, the invention comprises a composition with one or more polypeptide listed above, or fragments thereof. The invention also includes polypeptides that are specifically bound by a polyclonal antisera raised against at least 1 antigen that comprises at least one amino acid sequence described above, or a fragment thereof. Such antibodies specific for the polypeptides described above are also features of the invention. The polypeptides of the invention are optionally immunogenic.

The invention also encompasses immunogenic compositions comprising an immunologically effective amount of one or more of any of the polypeptides described above as well as methods for stimulating the immune system of an individual to produce a protective immune response against influenza virus by administering to the individual an immunologically effective amount of any of the above polypeptides in a physiologically acceptable carrier.

Additionally, the invention has reassortant influenza virus that encode one or more of the polypeptides above, in addition to immunogenic compositions comprising an immunologically effective amount of such recombinant influenza virus. Methods for stimulating the immune system of an individual to produce a protective immune response against influenza virus, through administering an immunologically effective amount of such recombinant influenza virus in a physiologically acceptable carrier are also part of the invention. Such virus can optionally comprise a 6:2 reassortant virus with 6 genes encoding regions from one or more donor virus (e.g. A/AA/6/60, B/AnnArbor/1/66, or A/Puerto Rico/8/34, which is more commonly known as PR8) and 2 gene encoding regions (typically and preferably encoding HA and NA or fragments thereof) selected from SEQ ID NO:1 through SEQ ID NO:34 or from similar strains, as defined herein, to those having SEQ ID NO:1-34, etc. Immunogenic compositions comprising such reassortant (recombinant) virus are also features of the invention.

In other aspects, the invention comprises an isolated or recombinant nucleic acid that is selected from: any one of the polynucleotide sequences of the sequence listing, e.g., SEQ ID NO:1 through SEQ ID NO:34 (or complementary sequences thereof), any one of the polynucleotide sequences encoding a polypeptide of the sequence listing, e.g., SEQ ID NO:35 through SEQ ID NO:68 (or complementary polynucleotide sequences thereof), a polynucleotide sequence which hybridizes under highly stringent conditions over substantially the entire length of any of the above polynucleotide sequences, and a polynucleotide sequence comprising all or a fragment of any of the above polynucleotide sequences wherein the sequence encodes a hemagglutinin or neuraminidase polypeptide or a fragment thereof. Such nucleic acids can be DNA, RNA, cRNA, DNA:RNA hybrids, single stranded nucleic acid, double stranded nucleic acid, etc. The invention also includes an isolated or recombinant nucleic acid (e.g., comprising hemagglutinin or fragments thereof), that encodes an amino acid sequence which is substantially identical over at least about 300 amino acids of any of the above nucleic acids, or over at least about 350 amino acids; over at least about 400 amino acids; over at least about 450 amino acids; over at least about 500 amino acids; over at least about 502 amino acids; over at least about 550 amino acids; over at least about 559 amino acids; over at least about 565 amino acids; or over at least about 566 amino acids of any of the above nucleic acids. In yet other embodiments, the invention comprises isolated or recombinant nucleic acids (e.g., comprising neuraminidase or fragments thereof), that encode an amino acid sequence that is substantially identical over at least about 350 amino acids; over at least about 400 amino acids; over at least about 436 amino acids; over at least about 450 amino acids; over at least about 451 amino acids; over at least about 465 amino acids; over at least about 466 amino acids; over at least about 469 amino acids; or over at least about 470 amino acids contiguous of any of the polypeptides above. Again, in situations wherein the amino acid is less than, e.g., 566, 565, 559, etc. in length (e.g., see, Sequence Listing in FIG. 1) then it should be understood that the length is optionally less than 566, 565, 559, etc. The invention also includes any of the above nucleic acids that comprise a hemagglutinin or neuraminidase polypeptide, or fragment thereof. Other aspects of the invention include isolated or recombinant nucleic acids that encode a polypeptide (optionally a hemagglutinin or neuraminidase polypeptide) whose sequence has at least 95% identity, at least 96% identity, at least 97% identity, at least 98% identity, at least 98.5% identity, at least 99% identity, at least 99.2% identity, at least 99.4% identity, at least 99.6% identity, at least 99.8% identity, or at least 99.9% identity to at least one of the above described polynucleotide. The invention also includes isolated or recombinant nucleic acids encoding a polypeptide of hemagglutinin or neuraminidase produced by mutating or recombining one or more above described polynucleotide sequence. The polynucleotide sequences of the invention can optionally comprise one or more of, e.g., a leader sequence, a precursor sequence, or an epitope tag sequence or the like, and can optionally encode a fusion protein (e.g., with one or more additional nucleic acid sequences). Such nucleic acids of the invention can optionally encode immunogenic polypeptides.

In yet other embodiments, the invention comprises a composition of matter having two or more above described nucleic acids or fragments thereof (e.g., a library comprising at least about 2, 5, 10, 50 or more nucleic acids). Such compositions can optionally be produced by cleaving one or more above described nucleic acid (e.g., mechanically, chemically, enzymatically with a restriction endonuclease/RNAse/DNAse, etc.). Other compositions of the invention include, e.g., compositions produced by incubating one or more above described nucleic acid in the presence of deoxyribonucleotide triphosphates and a thermostable nucleic acid polymerase. Immunogenic compositions having an immunologically effective amount of any of the above nucleic acids are also within the current invention.

Also within the invention are reassortant influenza virus comprising any of the above nucleic acids. Such reassortant viruses can (and preferably are) 6:2 reassortant viruses with 6 gene encoding regions from one or more donor virus (e.g., A/AA/6/60, B/AA/1/66 (also sometimes referred to herein as B/Ann Arbor/1/66, or A/Puerto Rico/8/34) and 2 gene encoding regions from two sequences above (e.g., from SEQ ID NO:1-34, from similar strains to those encoded in SEQ ID NO:1-34, etc.). Preferably, such two regions encode hemagglutinin and/or neuraminidase. Immunogenic compositions with immunologically effective amounts of such reassortant/recombinant influenza virus are also within purview of the current invention.

Vectors comprising one or more nucleic acid from SEQ ID NO:1-34 (again, also from similar strains to those of the sequence identification numbers) or fragments thereof are also within the current invention. Such vectors (e.g., expression vectors) can optionally be plasmids, cosmids, phage, viruses, virus fragments, etc. Especially preferred embodiments comprise plasmid vectors useful in plasmid rescue methods to produce virus (e.g., typically reassortant/recombinant virus for use in vaccines). Such plasmid systems are exampled in, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Hoffmann, E., 2000, *PNAS,* 97(10:6108-6113; U.S. Published Patent Application No. 20020164770 to Hoffmann; and U.S. Pat. No. 6,544,785 issued Apr. 8, 2003 to Palese, et al. Cells transduced, transformed, transfected, etc. with such vectors are also within the current invention.

The invention also encompasses cells comprising at least one above described nucleic acid, or a cleaved or amplified fragment or product thereof. Such cells can optionally express a polypeptide encoded by such nucleic acid. Other embodiments of the invention include vectors (e.g., plasmids, cosmids, phage, viruses, virus fragments, etc.) comprising any of above described nucleic acid. Such vectors can optionally comprise an expression vector. Cells transduced by such vectors are also within the current invention.

In some embodiments, the invention encompasses a virus (e.g., an influenza virus) comprising one or more above described nucleic acid (e.g., from SEQ ID NO:1-34 or from similar strains to such and optionally encoding hemagglutinin and/or neuraminidase), or one or more fragments thereof. Typically, such viruses are reassortant/recombinant viruses. Immunogenic compositions comprising such virus are also part of the current invention. Such viruses can comprises a reassortant virus such as a 6:2 reassortment virus (which comprises 6 gene encoding regions from one or more donor virus (e.g., a master donor virus or a backbone virus such as A/AA/6/60, B/AA/1/66, A/Puerto Rico/8/34, etc.) and 2 gene encoding regions from one or more above described nucleotide sequence, or one or more fragment thereof which can optionally comprise hemagglutinin and/or neuraminidase). Other reassortant/recombinant viruses can comprise 7:1 reassortments. Reassortment viruses (optionally live viruses) of the invention can include donor viruses that are one or more of, e.g., temperature-sensitive (ts), cold-adapted (ca), or attenuated (att). For example, reassortment viruses can comprise, e.g., A/Ann Arbor/6/60, B/Ann Arbor/1/66, A/Puerto Rico/8/34, etc. In many embodiments, the produced viruses are live viruses (e.g., to be used in vaccines, etc.). Other embodiments include dead or inactivated viruses (e.g., also capable of use in vaccines, etc.). Cells comprising any of the above viruses are also products of the invention.

Methods of producing reassortant/recombinant influenza virus through culturing a host cell harboring an influenza virus in a suitable culture medium under conditions permitting expression of nucleic acid; and, isolating or recovering the recombinant influenza virus from one or more of the host cell or the medium are also part of the invention. Thus, introducing a plurality of vectors having an influenza virus genome into a population of host cells wherein the vectors comprise at least 6 internal genome segments of a first influenza strain (again, e.g., A/AA/6/60, B/AA/1/66, A/PR/8/34, etc.) and at least one (and preferably two) genome segments are selected from a second influenza strain (e.g., preferably one or more nucleic acid as described above, e.g., from SEQ ID NO:1-34 or from a similar strain to such or optionally comprising a hemagglutinin and/or neuraminidase, etc.). is a feature of the invention. Preferably, the first strain of virus is cold-adapted and/or temperature sensitive and/or attenuated. Also preferably, such viruses are suitable for administration as part of an intranasal vaccine formulation. Of course, other embodiments are suitable for administration as killed or inactivated vaccine formulations, live/attenuated nonnasal vaccine formulations, etc. The vectors in such methods can comprise influenza A viruses and/or influenza B viruses. Host cells for such methods can optionally comprise, e.g., Vero cells, PerC6 cells (ECACC deposit number 96022940), MDCK cells, 293T cells, COS cells, etc. Typical embodiments do not comprise helper viruses in the method and yet other typical embodiments comprise eight plasmid vectors to contain the influenza genome.

In other embodiments herein, the invention comprises immunogenic compositions having an immunologically effective amount of the above described recombinant influenza virus (e.g., a live virus). Other embodiments include methods for stimulating the immune system of an individual to produce a protective immune response against influenza virus by administering to the individual an immunologically effective amount of the recombinant influenza virus of described above (optionally in a physiologically effective carrier).

Other aspects of the invention include methods of producing an isolated or recombinant polypeptide by culturing any host cell above, in a suitable culture medium under conditions permitting expression of nucleic acid and, isolating the polypeptide from one or more of the host cell or the medium in which it is grown.

Immunogenic compositions are also features of the invention. For example, immunogenic compositions comprising one or more of the polypeptides and/or nucleic acids described above (e.g., a sequence from SEQ ID NO:1-68 or from similar strains to such, etc.) and, optionally, an excipient such as a pharmaceutically acceptable excipient or one or more pharmaceutically acceptable administration component. Immunogenic compositions of the invention can also comprise one or more above described virus as well (e.g., along with one or more pharmaceutically acceptable administration component).

Methods of producing an influenza virus vaccine are also included in the invention. For example, the invention includes introducing a plurality of vectors (e.g., plasmid vectors) comprising an influenza genome (e.g., influenza A or B) into a population of host cells that is capable of supporting replication of such virus, culturing the cells, recovering a plurality of influenza viruses and providing one or more pharmaceutically acceptable excipient with such virus to an individual (e.g., one in need of such treatment). Such viruses can optionally be cold-adapted and/or temperature sensitive and/or attenuated and preferably are suitable for administration in an intranasal vaccine formulation. Such methods can include wherein the vectors have at least 6 internal genome segments of a first influenza strain and at least one genome segment (and preferably 2 segments) from another influenza strain (e.g., with sequence selected from SEQ ID NO:1-34 or from similar strains to such, etc.) which segment optionally codes for an immunogenic influenza surface antigen of the second influenza strain.

Methods of producing immunogenic responses in a subject through administration of an effective amount of any of the above viruses to a subject are also within the current invention. Additionally, methods of prophylactic or therapeutic treatment of a viral infection (e.g., viral influenza) in a subject through administration of one or more above described virus in an amount effective to produce an immunogenic response against the viral infection are also part of the current invention. Subjects for such treatment can include mammals (e.g., humans). Such methods can also comprise in vivo administration to the subject as well as in vitro or ex vivo administration to one or more cells of the subject. Additionally, such methods can also comprise administration of a composition of the virus and a pharmaceutically acceptable excipient that is administered to the subject in an amount effect to prophylactically or therapeutically treat the viral infection.

The invention also comprises compositions of matter having one or more sequence selected from SEQ ID NO:1 through SEQ ID NO:34, and a selected master donor virus, typically wherein the selected sequence and the master donor virus comprise a 6:2 reassortment, i.e., the HA and NA herein reassorted with the other six influenza genes from the donor virus. Such donor viruses are typically ca, att, ts influenza strains. For example, typically donor strains can include, e.g., A/Ann Arbor/6/60, B/Ann Arbor/1/66, or A/Puerto Rico/8/34 and variants thereof. Those of skill in the art will appreciate that typically donor strains can vary from reassortant to reassortant. Thus, those variations are also encompassed within the current invention. Another element of the invention comprises one or more live attenuated influenza vaccine comprising the such compositions, e.g., those having sequences herein reassorted in a 6:2 manner with a selected master donor virus.

Other aspects of the invention include, compositions of matter comprising a hemagglutinin polynucleotide and/or a neuraminidase polynucleotide reassorted with one or more master donor virus, again typically a ca, att, ts influenza virus, wherein the polynucleotide comprises a same virus strain as one or more virus strain of SEQ ID NO:1 through SEQ ID NO:34. Such hemagglutinin and/or neuraminidase polynucleotide is typically determined to be "within the same strain" when it produces a titer that is within a four-fold range of another virus (e.g., ones having the sequences listed herein) as measured by a hemagglutinin inhibition assay. As described below, however, other common assays can also be utilized to determine whether polynucleotides (i.e., viruses comprising such) are within the same strain.

These and other objects and features of the invention will become more fully apparent when the following detailed description is read in conjunction with the accompanying figures appendix.

BRIEF DESCRIPTION OF THE FIGURES

FIGS. 1A-1HH display the Sequence Listing of variant hemagglutinin and neuraminidase nucleic acids and polypeptides of the invention.

FIG. 2 displays an alternative organization of variant hemagglutinin and neuraminidase sequences as found in FIG. 1.

DETAILED DESCRIPTION

The present invention includes polypeptide and polynucleotide sequences of influenza hemagglutinin and neuraminidase as well as vectors, viruses, vaccines, compositions and the like comprising such sequences and methods of their use. Additional features of the invention are described in more detail herein.

DEFINITIONS

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. Additional terms are defined and described throughout.

As used in this specification and the appended claims, the singular forms "a," "an," and "the" include plural referents unless the context clearly dictates otherwise. Thus, for example, reference to "a virus" includes a plurality of viruses; reference to a "host cell" includes mixtures of host cells, and the like.

The terms "nucleic acid," "polynucleotide," "polynucleotide sequence," and "nucleic acid sequence" refer to single-stranded or double-stranded deoxyribonucleotide or ribonucleotide polymers, chimeras or analogues thereof, or a character string representing such, depending on context. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences in addition to the sequence explicitly indicated. From any specified polynucleotide sequence, either the given nucleic acid or the complementary polynucleotide sequence (e.g., the complementary nucleic acid) can be determined.

The term "nucleic acid" or "polynucleotide" also encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

A "subsequence" is any portion of an entire sequence, up to and including the complete sequence. Typically, a subsequence comprises less than the full-length sequence. A "unique subsequence" is a subsequence that is not found in any previously determined influenza polynucleotide or polypeptide sequence The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

The "neuraminidase" polypeptides of the invention show immunological cross reactivity with one or more known neuraminidase molecule from an influenza virus. The literature is replete with examples of such known neuraminidases (e.g., in GenBank, in publications from the CDC, etc.). Similarly, the "hemagglutinin" polypeptides of the invention show immunological cross-reactivity with one or more known hemagglutinin molecule from an influenza virus. Again, the literature is replete with examples of such known hemagglutinin molecules.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

"Expression of a gene" or "expression of a nucleic acid" typically means transcription of DNA into RNA (optionally including modification of the RNA, e.g., splicing) or transcription of RNA into mRNA, translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

An "amino acid sequence" is a polymer of amino acid residues (a protein, polypeptide, etc.) or a character string representing an amino acid polymer, depending on context.

A "polypeptide" is a polymer comprising two or more amino acid residues (e.g., a peptide or a protein). The polymer can optionally comprise modifications such as glycosylation or the like. The amino acid residues of the polypeptide can be natural or non-natural and can be unsubstituted, unmodified, substituted or modified.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source. As will be apparent herein, such chimeric viruses are typically reassortant/recombinant viruses. Thus, in some embodiments, a chimera can optionally include, e.g., a sequence (e.g., of HA and/or NA) from an A influenza virus placed into a backbone comprised of, or constructed/derived from a B influenza virus (e.g., B/AA/1/66, etc.) or a B influenza virus sequence placed into an A influenza virus backbone (i.e., donor virus) such as, e.g., A/AA/6/60, etc.

The term "recombinant" indicates that the material (e.g., a nucleic acid or protein) has been artificially or synthetically (non-naturally) altered by human intervention. The alteration can be performed on the material within, or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

The term "reassortant," when referring to a virus (typically herein, an influenza virus), indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding a hemagglutinin or neuraminidase such as those listed in the SEQ ID Table herein. A 6:2 reassortant includes 6 genomic segments, most commonly the 6 internal genes from a first parental virus, and two complementary segments, e.g., hemagglutinin and neuraminidase, from one or more different parental virus. Reassortant viruses can also, depending upon context herein, be termed as "chimeric" and/or "recombinant."

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector or a virus, and supports the replication and/or expression of the nucleic acid. Host cells can be prokaryotic cells such as *E. coli*, or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc. In other embodiments, host cells can optionally include eggs (e.g., hen eggs, embryonated hen eggs, etc.).

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with wild-type influenza virus. In some instances, the wild-type (e.g., naturally circulating) influenza virus can still cause infection, but it cannot cause a serious infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immuno globulin genes include the kappa, lambda, alpha, gamma, delta, epsilon and mu constant region genes, as well as myriad immunoglobulin variable-region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see Fundamental Immunology, W. E. Paul, ed., Raven Press, N.Y. (1999) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention are variants of influenza HA and NA sequences. See, e.g., the Sequence Listing in FIG. 1 below. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA). The hemagglutinin molecule consists of a surface glycoprotein and acts to bind to N-Acetyl-Neuraminic acid (NeuNAc), also known as sialic acid, on host cell surface receptors. In some embodiments herein, the polypeptides of the invention (and polypeptides encoded by the polynucleotides of the invention) can act to bind NeuNAc whether in vitro or in vivo. Such action can in some embodiments also be done by fragments of hemagglutinin which retain hemagglutinin activity. Hemagglutinin is made up of two subunits, HA1 and HA2 and the entire structure is about 550 amino acids in length and about 220 kD. Neuraminidase molecules cleave terminal sialic acid residues from cell surface receptors of influenza virus, thereby releasing virions from infected cells. neuraminidase also removes sialic acid from newly made hemagglutinin and neuraminidase molecules. In some embodiments herein, the polypeptides of the invention (and polypeptides encoded by the polynucleotides of the invention) can act to cleave sialic acid residues whether in vitro or in vivo. This action can also be done in some embodiments by fragments of neuraminidase which retain neuraminidase activity. The neuraminidase polypeptides of the invention show immunological cross reactivity with one or more known neuraminidase molecule from an influenza virus. The literature is replete with examples of such known neuraminidases (e.g., in GenBank, in publications from the CDC, etc.). Similarly, the hemagglutinin polypeptides of the invention show immunological cross-reactivity with one or more known hemagglutinin molecule from an influenza virus. Again, the literature is replete with examples of such known hemagglutinin molecules.

Influenza is commonly grouped into influenza A and influenza B categories, as well as a typically less important C category. Influenza A and influenza B viruses each contain eight segments of single stranded RNA with negative polarity.

The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza types A and B are typically associated with influenza outbreaks in human populations. However, type A influenza also infects other creatures as well, e.g., birds, pigs, and other animals. The type A viruses are categorized into subtypes based upon differences within their hemagglutinin and neuraminidase surface glycoprotein antigens. Hemagglutinin in type A viruses has 14 known subtypes and neuraminidase has 9 known subtypes. In humans, currently only about 3 different hemagglutinin and 2 different neuraminidase subtypes are known, e.g., H1, H2, H3, N1, and N2. In particular, two major subtypes of influenza A have been active in humans, namely, H1N1 and H3N2. H1N2, however has recently been of concern. Influenza B viruses are not divided into subtypes based upon their hemagglutinin and neuraminidase proteins. As will be appreciated, the sequences contained within the sequence listing in FIG. 1 comprise a number of different subtypes of influenza. Thus, for example in the sequence listing A-H3N2 strains are exampled by ca A/Shandong/9/93, ca A/Johannesburg/33/94-like, ca A/Wuhan/395/95, ca A/Sydney/05/97, ca A/Panama/2007/99, ca A/Wyoming/03/2003. A-H1N1 strains are shown in ca A/Texas/36/91, ca A/Shenzhen/227/95, ca A/Beijing/262/95, and ca A/New Caledonia/20/99, while B-HANA strains include ca B/Ann Arbor/1/94, ca B/Yamanashi/166/98, ca B/Johannesburg/5/99, ca B/Victoria/504/2000, ca B/Hong Kong/330/2001, ca B/Brisbane/32/2002, and ca B/Jilin/20/2003.

Different strains of influenza can be categorized based upon, e.g., the ability of influenza to agglutinate red blood cells (RBCs or erythrocytes). Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

Briefly, in typical HI assays, sera to be used for typing or categorization, which is often produced in ferrets, is added to erythrocyte samples in various dilutions, e.g., 2-fold, etc. Optical determination is then made whether the erythrocytes are clumped together (i.e., agglutinated) or are suspended (i.e., non-agglutinated). If the cells are not clumped, then agglutination did not occur due to the inhibition from antibodies in the sera that are specific for that influenza. Thus, the types of influenza are defined as being within the same strain. In some cases, one strain is described as being "like" the other, e.g., strain x is a "y-like" strain, etc. For example, if two samples are within four-fold titer of one another as measured by an HI assay, then they can be described as belonging to the same strain (e.g., both belonging to the "New Caledonia" strain or both being "Moscow-like" strains, etc.). In other words, strains are typically categorized based upon their immunologic or antigenic profile. An HAI titer is typically defined as the highest dilution of a scrum that completely inhibits hemagglutination. See, e.g., Schild, et al., *Bull. Wld Hlth Org.*, 1973, 48:269-278, etc. Again, those of skill in the art will be quite familiar with categorization and classification of influenza into strains and the methods to do so.

From the above it will be appreciated that the current invention not only comprises the specific sequences listed herein, but also such sequences within various vectors (e.g., ones used for plasmid reassortment and rescue, see below) as well as hemagglutinin and neuraminidase sequences within the same strains as the sequences listed herein. Also, such same strains that are within various vectors (e.g., typically ones used for plasmid reassortment and rescue such as A/Ann Arbor/6/60 or B/Ann Arbor/1/66, A/Puerto Rico/8/34, etc.) are also included.

As used herein, the term "similar strain" should be taken to indicate that a first influenza virus is of the same or related strain as a second influenza virus. In typical embodiments such relation is commonly determined through use of an HAI assay. Influenza viruses that fall within a four-fold titer of one another in an HAI assay are, thus, of a "similar strain." Those of skill in the art, however, will be familiar with other assays, etc. to determine similar strains, e.g., FRID, neutralization assays, etc. The current invention also comprises such similar strains (i.e., strains similar to the ones present in the sequence listing herein) in the various plasmids, vectors, viruses, methods, etc. herein. Thus, unless the context clearly dictates otherwise, descriptions herein of particular sequences (e.g., those in the sequence listing) or fragments thereof also should be considered to include sequences from similar strains to those (i.e., similar strains to those strains having the sequences in those plasmids, vectors, viruses, etc. herein). Also, it will be appreciated that the NA and HA polypeptides within such similar strains are, thus, "similar polypeptides" when compared between "similar strains."

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (as in the current invention) are quite useful in constructing influenza vaccines.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and NA sequences herein. See, U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus." Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 or B/Ann Arbor/1/66 or A/Puerto Rico/8/34 influenza strain as a "backbone" upon which to add HA and/or NA genes (e.g., such as those sequences listed herein, etc.) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as A/Puerto Rico/8/34, etc., containing the other influenza genes present in a reassortant, namely, the non-HA and non-NA genes). Live, attenuated influenza A virus vaccines against human influenza viruses were recently licensed in the United States. See above. Such vaccines are reassortant H1N1 and H1N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). In some embodiments herein, the reassortants can also comprise 7:1 reassortants. In other words, only the HA or the NA is not from the backbone or MDV strain. Previous work has been reported with suitable backbone donor virus strains that optionally are within various embodiments of the current invention. See, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Maassab et al., *J. of Inf. Dis.*, 1982, 146:780-790; Cox, et al., *Virology*, 1988, 167:554-567; Wareing et al., *Vaccine*, 2001, 19:3320-3330; Clements, et al., *J Infect Dis.*, 1990, 161(5):869-77, etc., In some embodiments, the sequences herein can optionally have specific regions removed (both or either in the nucleic acid sequence or the amino acid sequence). For example, for those molecules having a polybasic cleavage site, such sites can optionally be removed. Those of skill in the art will be familiar with various methods of removing such specific regions. The resulting shortened sequences are also contained within the current invention. See, e.g., Li et al., *J. of Infectious Diseases*, 179:1132-8, 1999

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Thus, the present invention can utilize growth, e.g., in appropriate culture conditions, of virus strains (both A strain and B strain influenza viruses) with desirable properties relative to vaccine production (e.g., attenuated pathogenicity or phenotype, cold adaptation, temperature sensitivity, etc.) in vitro in cultured cells. Influenza viruses can be produced by introducing a plurality of vectors incorporating cloned viral genome segments into host cells, and culturing the cells at a temperature not exceeding 35° C. When vectors including an influenza virus genome are transfected, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain such as those in the sequence listing herein, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

In such embodiments, typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively.

For example, a selected master donor type A virus (MDV-A), or master donor type B virus (MDV-B), is produced from a plurality of cloned viral cDNAs constituting the viral genome. Embodiments include those wherein recombinant viruses are produced from eight cloned viral cDNAs. Eight viral cDNAs representing either the selected MDV-A or MDV-B sequences of PB2, PB1, PA, NP, HA, NA, M and NS are optionally cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site).

Infectious recombinant MDV-A or MDV-B virus can be then recovered following transfection of plasmids bearing the eight viral cDNAs into appropriate host cells, e.g., Vero cells, co-cultured MDCK/293T or MDCK/COS7 cells. Using the plasmids and methods described herein and, e.g., in U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Hoffmann, E., 2000, *PNAS*, 97(11):6108-6113; U.S. Published Patent Application No. 20020164770 to Hoffmann; and U.S. Pat. No. 6,544,785 issued Apr. 8, 2003 to Palese, et al., the invention is useful, e.g., for generating 6:2 reassortant influenza vaccines by co-transfection of the 6 internal genes (PB 1, PB2, PA, NP, M and NS) of the selected virus (e.g., MDV-A, MDV-B) together with the HA and NA derived from different corresponding type (A or B) influenza viruses e.g., as shown in the sequence listings herein. For example, the HA segment is favorably selected from a pathogenically relevant H1, H3 or B strain, as is routinely performed for vaccine production. Similarly, the HA segment can be selected from a strain with emerging relevance as a pathogenic strain such as those in the sequence listing herein. Reassortants incorporating seven genome segments of the MDV and either the HA or NA gene of a selected strain (7:1 reassortants) can also be produced. It will be appreciated, and as is detailed throughout, that the molecules of the invention can optionally be combined in any desired combination. For example, the HA and/or NA sequences herein can be placed, e.g., into a reassortant backbone such as A/AA/6/60, B/AA/1/66, A/Puerto Rico/8/34 (i.e., PR8), etc., in 6:2 reassortants or 7:1 reassortants, etc. Thus, as explained more fully below, there would be 6 backbone gene regions from the donor virus (again, e.g., A/AA/6/60, etc.) and 2 genes regions from a second strain (e.g., a wild-type strain, not the backbone donor virus). Such 2 gene regions are preferably the HA and NA genes. A similar situation arises for 7:1 reassortants, in which however, there are 7 gene regions from the background donor virus and 1 gene (either HA or NA) from a different virus (typically wild-type or one to which an immune response is desired). Also, it will be appreciated that the sequences herein (e.g., those in the sequence listing of FIG. 1, etc.) can be combined in a number of means in different embodiments herein. Thus, any of the sequences herein can be present singularly in a 7:1 reassortant (i.e., the sequence of the invention present with 7 backbone donor virus gene regions) and/or can be present with another sequence of the invention in a 6:2 reassortant. Within such 6:2 reassortants, any of the sequences of the invention can optionally be present with any other sequence of the invention. Typical, and preferred, embodiments comprise HA and NA from the same original wild-type strains however. For example, typical embodiments can comprise a 6:2 reassortant having 6 gene regions from a backbone donor virus such as A/AA/6/60 and the HA and NA gene regions from the same wild-type strain such as ca A/Shandong/9/93 or both HA and NA from ca A/Wuhan/395/95 or both HA and NA from ca B/Ann Arbor/1/94 (which would typically, but not exclusively, be present within a B influenza backbone donor virus such as B/Ann Arbor/1/66, etc.), etc. Of course, it will again be appreciated that the invention also includes such reassortant viruses wherein the non-background gene regions (i.e., the HA and/or NA regions) are from similar strains (i.e., strains that are similar strains to influenza strains having the sequences found in SEQ ID NO:1-34. The above references are specifically incorporated herein in their entirety for all purposes, e.g., especially for their teachings regarding plasmids, plasmid rescue of virus (influenza virus), multi-plasmid systems for virus rescue/production, etc.

Again, the HA and NA sequences of the current invention are optionally utilized in such plasmid reassortment vaccines (and/or in other ts, cs, ea, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., the sequences of the invention).

FluMist™

As mentioned previously, numerous examples and types of influenza vaccine exist. An exemplary influenza vaccine is FluMist™ (Medimmune Vaccines Inc., Mt. View, Calif.) which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial JAMA* 282:137-44). In typical, and preferred, embodiments, the methods and compositions of the current invention are preferably adapted to/used with production of FluMist™ vaccine. However, it will be appreciated by those skilled in the art that the sequences, methods, compositions, etc. herein are also adaptable to production of similar or even different viral vaccines.

FluMist™ vaccine strains contain, e.g., HA and NA gene segments derived from the wild-type strains to which the vaccine is addressed (or, in some instances, to related strains) along with six gene segments, PB1, PB2, PA, NP, M and NS, from a common master donor virus (MDV). The HA and NA sequences herein, thus, are optionally part of various FluMist™ formulations. The MDV for influenza A strains of FluMist™ (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C. Nature* 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (att, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the ts phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines Viral Immunol* 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children N Engl J Med* 338:1405-12; Boyce et al. (2000) *Safety and immunogenicity of adjuvanted and unadjuvanted subunit influenza vaccines administered intranasally to healthy adults Vaccine* 19:217-26; Edwards et al. (1994) *A randomized controlled trial of cold adapted and inactivated vaccines for the prevention of influenza A disease J Infect Dis* 169:68-76; Nichol et al. (1999) *Effectiveness of live, attenuated intranasal influenza virus vaccine in healthy, working adults: a randomized controlled trial JAMA* 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets J. Infect. Dis.* 146:780-900).

Production of such reassorted virus using B strains of influenza is more difficult, however, recent work (see, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus") has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences, methods, etc. of the current invention, are optionally used in conjunction with, or in combination with, such previous work involving, e.g., reassorted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention (e.g., those comprising polynucleotides of SEQ ID NO:1-34 or polypeptides of SEQ ID NO:35-68, or similar strains of the virus sequences within SEQ ID NO:1-68, or fragments of any of the previous) can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hen eggs (i.e., normal allantoic fluid or NAD), or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., an HA and/or an NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, e.g., U.S. Pat. No. 5,922,326; Wright et al., *Infect. Immun.* 37:397-400 (1982); Kim et al., *Pediatrics* 52:56-63 (1973); and Wright et al., *J. Pediatr.* 88:931-936 (1976). For example, influenza viruses are provided in the range of about 1-1000 HID$_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention) or an expression vector encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences, e.g., as described herein. Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two strains, e.g., each of which represents a different subgroup. Additionally, vaccine combinations can optionally include mixes of pandemic vaccines and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents.

Polynucleotides of the Invention

Probes

The HA and NA polynucleotides of the invention, e.g., as shown in the sequences herein such as SEQ ID NO:1 through SEQ ID NO:34, and fragments thereof, are optionally used in a number of different capacities alternative to, or in addition to, the vaccines described above. Other exemplary uses are described herein for illustrative purpose and not as limitations on the actual range of uses, etc. Different methods of construction, purification, and characterization of the nucleotide sequences of the invention are also described herein.

In some embodiments, nucleic acids including one or more polynucleotide sequence of the invention are favorably used as probes for the detection of corresponding or related nucleic acids in a variety of contexts, such as in nucleic hybridization experiments, e.g., to find and/or characterize homologous influenza variants (e.g., homologues to sequences herein, etc.) infecting other species or in different influenza outbreaks, etc. The probes can be either DNA or RNA molecules, such as restriction fragments of genomic or cloned DNA, cDNAs, PCR amplification products, transcripts, and oligonucleotides, and can vary in length from oligonucleotides as short as about 10 nucleotides in length to full length sequences or cDNAs in excess of 1 kb or more. For example, in some embodiments, a probe of the invention includes a polynucleotide sequence or subsequence selected, e.g., from among SEQ ID NO:1-SEQ ID NO:34, or sequences complementary thereto. Alternatively, polynucleotide sequences that are variants of one of the above-designated sequences are used as probes. Most typically, such variants include one or a few conservative nucleotide variations. For example, pairs (or sets) of oligonucleotides can be selected, in which the two (or more) polynucleotide sequences are conservative variations of each other, wherein one polynucleotide sequence corresponds identically to a first variant or and the other(s) corresponds identically to additional variants. Such pairs of oligonucleotide probes are particularly useful, e.g., for specific hybridization experiments to detect polymorphic nucleotides or to, e.g., detect homologous influenza HA and NA variants, e.g., homologous to the current HA and NA sequences, infecting other species or present in different (e.g., either temporally and/or geographically different) influenza outbreaks. In other applications, probes are selected that are more divergent, that is probes that are at least about 91% (or about 92%, about 93%, about 94%, about 95%, about 96%, about 97%, about 98%, about 98.5%, about 98.7%, about 99%, about 99.1%, about 99.2%, about 99.3%, about 99.4%, about 99.5%, or about 99.6% or more about 99.7%, about 99.8%, about 99.9% or more) identical are selected.

The probes of the invention, e.g., as exemplified by sequences derived from the sequences herein, can also be used to identify additional useful polynucleotide sequences according to procedures routine in the art. In one set of embodiments, one or more probes, as described above, are utilized to screen libraries of expression products or chromosomal segments (e.g., expression libraries or genomic libraries) to identify clones that include sequences identical to, or with significant sequence similarity to, e.g., one or more probe of e.g., SEQ ID NO:1-SEQ ID NO:34, i.e., variants, homologues, etc. It will be understood that in addition to such physical methods as library screening, computer assisted bioinformatic approaches, e.g., BLAST and other sequence homology search algorithms, and the like, can also be used for identifying related polynucleotide sequences. Polynucleotide sequences identified in this manner are also a feature of the invention.

Oligonucleotide probes are optionally produced via a variety of methods well known to those skilled in the art. Most typically, they are produced by well known synthetic methods, such as the solid phase phosphoramidite tricster method described by Beaucage and Caruthers (1981) *Tetrahedron Letts* 22(20):1859-1862, e.g., using an automated synthesizer, or as described in Needham-Van Devanter et al. (1984) *Nucl Acids Res,* 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J Chrom* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560. Custom oligos can also easily be ordered from a variety of commercial sources known to persons of skill.

In other circumstances, e.g., relating to attributes of cells or organisms expressing the polynucleotides and polypeptides of the invention (e.g., those harboring virus comprising the sequences of the invention), probes that are polypeptides, peptides or antibodies are favorably utilized. For example, isolated or recombinant polypeptides, polypeptide fragments and peptides derived from any of the amino acid sequences of the invention and/or encoded by polynucleotide sequences of the invention, e.g., selected from SEQ ID NO:1 through SEQ ID NO:34, are favorably used to identify and isolate antibodies, e.g., from phage display libraries, combinatorial libraries, polyclonal sera, and the like.

Antibodies specific for any a polypeptide sequence or subsequence, e.g., of SEQ ID NO:35 through SEQ ID NO:68, and/or encoded by polynucleotide sequences of the invention, e.g., selected from SEQ ID NO:1 through SEQ ID NO:34, are likewise valuable as probes for evaluating expression products, e.g., from cells or tissues. In addition, antibodies are particularly suitable for evaluating expression of proteins comprising amino acid subsequences, e.g., of those given herein, or encoded by polynucleotides sequences of the invention, e.g., selected from those shown herein, in situ, in a tissue array, in a cell, tissue or organism, e.g., an organism infected by an unidentified influenza virus or the like. Antibodies can be directly labeled with a detectable reagent, or detected indirectly by labeling of a secondary antibody specific for the heavy chain constant region (i.e., isotype) of the specific antibody. Antibodies against specific amino acids sequences herein (e.g., SEQ ID NOs: 35-68) are also useful in determining whether other influenza viruses are within the same strain as the current sequences (e.g., through an HI assay, etc.). Additional details regarding production of specific antibodies are provided below.

Diagnostic Assays

The nucleic acid sequences of the present invention can be used in diagnostic assays to detect influenza (and/or hemagglutinin and/or neuraminidase) in a sample, to detect hemagglutinin-like and/or neuraminidase-like sequences, and to detect strain differences in clinical isolates of influenza using either chemically synthesized or recombinant polynucleotide fragments, e.g., selected from the sequences herein. For example, fragments of the hemagglutinin and/or neuraminidase sequences comprising at least between 10 and 20 nucleotides can be used as primers to amplify nucleic acids using polymerase chain reaction (PCR) methods well known in the art (e.g., reverse transcription-PCR) and as probes in nucleic acid hybridization assays to detect target genetic material such as influenza RNA in clinical specimens.

The probes of the invention, e.g., as exemplified by unique subsequences selected from, e.g., SEQ ID NO:1 through SEQ ID NO:34, can also be used to identify additional useful polynucleotide sequences (such as to characterize additional strains of influenza) according to procedures routine in the art. In one set of preferred embodiments, one or more probes, as described above, are utilized to screen libraries of expression products or cloned viral nucleic acids (i.e., expression libraries or genomic libraries) to identify clones that include sequences identical to, or with significant sequence identity to the sequences herein. In turn, each of these identified sequences can be used to make probes, including pairs or sets of variant probes as described above. It will be understood that in addition to such physical methods as library screening, computer assisted bioinformatic approaches, e.g., BLAST and other sequence homology search algorithms, and the like, can also be used for identifying related polynucleotide sequences.

The probes of the invention are particularly useful for detecting the presence and for determining the identity of influenza nucleic acids in cells, tissues or other biological samples (e.g., a nasal wash or bronchial lavage). For example, the probes of the invention are favorably utilized to determine whether a biological sample, such as a subject (e.g., a human subject) or model system (such as a cultured cell sample) has been exposed to, or become infected with influenza, or particular strain(s) of influenza. Detection of hybridization of the selected probe to nucleic acids originating in (e.g., isolated from) the biological sample or model system is indicative of exposure to or infection with the virus (or a related virus) from which the probe polynucleotide is selected.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the lengths of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Vectors, Promoters and Expression Systems

The present invention includes recombinant constructs incorporating one or more of the nucleic acid sequences described herein. Such constructs optionally include a vector, for example, a plasmid, a cosmid, a phage, a virus, a bacterial artificial chromosome (BAC), a yeast artificial chromosome (YAC), etc., into which one or more of the polynucleotide sequences of the invention, e.g., comprising any of SEQ ID NO:1 through SEQ ID NO:34, or a subsequence thereof etc., has been inserted, in a forward or reverse orientation. For example, the inserted nucleic acid can include a viral chromosomal sequence or cDNA including all or part of at least one of the polynucleotide sequences of the invention. In one embodiment, the construct further comprises regulatory sequences, including, for example, a promoter, operably linked to the sequence. Large numbers of suitable vectors and promoters are known to those of skill in the art, and are commercially available.

The polynucleotides of the present invention can be included in any one of a variety of vectors suitable for generating sense or antisense RNA, and optionally, polypeptide (or peptide) expression products (e.g., a hemagglutinin and/or neuraminidase molecule of the invention, or fragments thereof). Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others (e.g., pCDL). Any vector that is capable of introducing genetic material into a cell, and, if replication is desired, which is replicable in the relevant host can be used.

In an expression vector, the HA and/or NA polynucleotide sequence of interest is physically arranged in proximity and orientation to an appropriate transcription control sequence (e.g., promoter, and optionally, one or more enhancers) to direct mRNA synthesis. That is, the polynucleotide sequence of interest is operably linked to an appropriate transcription control sequence. Examples of such promoters include: LTR or SV40 promoter, $E.$ $coli$ lac or trp promoter, phage lambda $P_L$ promoter, and other promoters known to control expression of genes in prokaryotic or eukaryotic cells or their viruses.

A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like.

Various embodiments of the current invention can comprise a number of different vector constructions. Such constructions are typically and preferably used in plasmid rescue systems to create viruses for use in vaccines (e.g., in live attenuated vaccines, in killed or inactivated vaccines, etc.). Thus, the invention includes recombinant DNA molecules having a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of a mRNA coding sequence of a negative strand RNA virus. Also, the invention includes a recombinant DNA molecule that, upon transcription yields an RNA template that contains an RNA sequence comprising the reverse complement of an mRNA coding sequence of a negative strand RNA virus, and vRNA terminal sequences. The invention also includes a recombinant DNA molecule that upon transcription yields a replicable RNA template comprising the reverse complement of an mRNA coding sequence of a negative strand RNA virus. Such above recombinant DNA molecules typically involve wherein the negative strand RNA virus is influenza (e.g., influenza A or B, etc.). Also, the RNA molecule in such embodiments is typically an influenza genome segment and the RNA template is typically an influenza genome segment. The recombinant DNA molecules typically comprise wherein the RNA template is replicable, wherein the negative strand RNA virus is influenza, and wherein the RNA template is an influenza genome segment. Thus, the nucleic acids influenza segments typically comprise HA and/or NA genes (the corresponding nucleic acid of which is, e.g., in FIG. 1, or within similar strains of the strains having the nucleic acids in, e.g., FIG. 1.

The invention also includes methods of preparing an RNA molecule comprising transcribing a recombinant DNA molecule with a DNA-directed RNA polymerase, wherein the DNA molecule comprises a transcription control element that binds a DNA-directed RNA polymerase that is operatively linked to a DNA sequence that encodes an RNA molecule, wherein the RNA molecule comprises a binding site specific for an RNA-directed RNA polymerase of a negative strand RNA virus, operatively linked to an RNA sequence comprising the reverse complement of an mRNA coding sequence of a negative strand RNA virus. The invention also includes a method of preparing an RNA molecule comprising transcribing a recombinant DNA molecule with a DNA-directed RNA polymerase, wherein the recombinant DNA molecule yields upon transcription an RNA molecule that contains an RNA sequence comprising the reverse complement of an mRNA coding sequence of a negative strand RNA virus, and vRNA terminal sequences. Furthermore, the invention includes a method of preparing an RNA molecule comprising transcribing a recombinant DNA molecule with a DNA-directed RNA polymerase, wherein the recombinant DNA molecule yields upon transcription a replicable RNA molecule comprising the reverse complement of an mRNA coding sequence of a negative strand RNA virus. Such methods typically comprise wherein the negative strand RNA virus is influenza, and wherein the RNA molecule is an influenza genome segment. Such methods preferably include wherein the DNA-directed RNA polymerase is pol I, pol II, T7 polymerase, T3 polymerase, or Sp6 polymerase. Thus, again, the influenza nucleic acid segments typically comprise HA and/or NA genes as described throughout.

Other methods within the invention include methods of constructing a DNA molecule comprising a transcription control element that binds a DNA-directed RNA polymerase that is operatively linked to a DNA sequence that encodes an RNA molecule, wherein the RNA molecule comprises a binding site specific for an RNA-directed RNA polymerase of an influenza virus, operatively linked to an RNA sequence comprising the reverse complement of an mRNA coding sequence of an influenza virus, wherein the DNA sequence comprises a nucleic acid corresponding to one or more of SEQ ID NO:1-34 or a fragment thereof or of one or more nucleic acid sequence of a similar strain (e.g., a strain similar to such strains having the sequences found in the sequences of FIG. 1, etc.). Also, the invention includes a method of constructing a DNA molecule comprising a DNA sequence that upon transcription yields an RNA template that contains an RNA sequence comprising the reverse complement of an mRNA coding sequence of an influenza virus, and vRNA terminal sequences, wherein the DNA sequence comprises a nucleic acid corresponding to one or more of SEQ ID NO:1-34 or a fragment thereof, or of one or more nucleic acid of a similar strain (e.g., a strain similar to such strains that have the sequences found in FIG. 1, etc.). Such methods also include wherein the RNA template is replicable. Other methods of the invention include those of constructing a DNA molecule comprising a DNA sequence that upon transcription yields a replicable RNA template comprising the reverse complement of an mRNA coding sequence of an influenza virus. These methods of the invention typically include wherein the RNA molecule is an influenza genome segment, wherein the DNA-directed RNA polymerase is pol I, pol 11, T7 polymerase, T3 polymerase, or Sp6 polymerase.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) *Heat stress promoters and transcription factors Results Probl Cell Differ* 20:125-62; Kriegler et al. (1990) *Assembly of enhancers, promoters, and splice signals to control expression of transferred genes Methods in Enzymol* 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence. Such sequences are commonly available from the 5' and, occasionally 3', untranslated regions of eukaryotic or viral DNAs or cDNAs. In one embodiment, the SV40 polyadenylation signal sequences can provide a bi-directional polyadenylation site that insulates transcription of (+) strand mRNA molecules from the PolI promoter initiating replication of the (−) strand viral genome.

In addition, as described above, the expression vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The vector containing the appropriate nucleic acid sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, MDCK cell, 293 cells, COS cells, or the like, for the purpose of expression.

As described elsewhere, the HA and NA sequences herein, in various embodiments, can be comprised within plasmids involved in plasmid-rescue reassortment. See, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Hoffmann, E., 2000, *PNAS*, 97(11):6108-6113; U.S. Published Patent Application No. 20020164770 to Hoffmann; and U.S. Pat. No. 6,544,785 issued Apr. 8, 2003 to Palese, et al. The reassortants produced can include the HA and NA genes arranged with the 6 other influenza genes from the A/Ann Arbor/6/60 donor strain, the B/Ann Arbor/1/66 donor strain (and/or derivatives and modifications thereof), the A/Puerto Rico/8/34 donor strain, etc.

Additional Expression Elements

Most commonly, the genome segment encoding the influenza virus HA and/or NA protein includes any additional sequences necessary for its expression, including translation into a functional viral protein. In other situations, a minigene, or other artificial construct encoding the viral proteins, e.g., an HA and/or NA protein, can be employed. Again, in such case, it is often desirable to include specific initiation signals that aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Where translation of a polypeptide encoded by a nucleic acid sequence of the invention is desired, additional translation specific initiation signals can improve the efficiency of translation. These signals can include, e.g., an ATG initiation codon and adjacent sequences, an IRES region, etc. In some cases, for example, full-length cDNA molecules or chromosomal segments including a coding sequence incorporating, e.g., a polynucleotide sequence of the invention (e.g., as in the sequences herein), a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including, e.g., an ATG initiation codon is often provided for expression of the relevant sequence. The initiation codon is put in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) *Results Probl Cell Differ* 20:125-62; Bittner et al. (1987) *Methods in Enzymol* 153:516-544).

Production of Recombinant Virus

Negative strand RNA viruses can be genetically engineered and recovered using a recombinant reverse genetics approach (U.S. Pat. No. 5,166,057 to Palese et al.). Such method was originally applied to engineer influenza viral genomes (Luytjes et al. (1989) Cell 59:1107-1113; Enami et al. (1990) *Proc. Natl. Acad. Sci. USA* 92:11563-11567), and has been successfully applied to a wide variety of segmented and nonsegmented negative strand RNA viruses, e.g., rabies (Schnell et al. (1994) *EMBO J.* 13: 4195-4203); VSV (Lawson et al. (1995) *Proc. Natl. Acad. Sci. USA* 92: 4477-4481); measles virus (Radecke et al. (1995) *EMBO J.* 14:5773-5784); rinderpest virus (Baron & Barrett (1997) *J. Virol.* 71: 1265-1271); human parainfluenza virus (Hoffman & Banerjee (1997) *J. Virol.* 71: 3272-3277; Dubin et al. (1997) *Virology* 235:323-332); SV5 (He et al. (1997) *Virology* 237:249-260); canine distemper virus (Gassen et al. (2000) *J. Virol.* 74:10737-44); and Sendai virus (Park et al. (1991) *Proc. Natl. Acad. Sci. USA* 88: 5537-5541; Kato et al. (1996) Genes to Cells 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention. Of course, as will be appreciated by those of skill in the art, influenza virus in general (and those of the invention as well) are RNA viruses. Thus, when the present invention describes influenza viruses as comprising, e.g., the sequences of FIG. 1, etc., it is to be understood to mean the corresponding RNA version of the sequence. The nucleotide sequences in FIG. 1 comprise DNA versions (e.g., coding plus sense, etc.) of the genes (along with some untranslated regions in the nucleotide sequences). Those of skill in the art can easily convert between RNA and DNA sequences, between complementary nucleotide sequences, a corresponding RNA sequence, etc. Thus, for example, those of skill in the art can easily convert from a nucleotide sequence (e.g., one given in FIG. 1 such as SEQ ID NO:1) to the corresponding amino acid sequence or a corresponding complementary sequence, etc. Also, as will be evident, when such HA and/or NA sequences are described within DNA vectors, e.g., plasmids, etc. then the corresponding DNA version of the sequences are to be used.

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda.*

Most commonly, mammalian cells are used to culture the HA and NA molecules of the invention. Suitable host cells for the replication of influenza virus (e.g., with the HA and/or NA sequences herein) include, e.g., Vero cells, BHK cells, MDCK cells, 293 cells and COS cells, including 293T cells, COST cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences, e.g., through production of viruses. The culture conditions, such as temperature, pH and the like, are typically those previously used with the particular host cell selected for expression, and will be apparent to those skilled in the art and in the references cited herein, including, e.g., Freshney (1994) *Culture of Animal Cells, a Manual of Basic Technique,* 3rd edition, Wiley-Liss, New York and the references cited therein. Other helpful references include, e.g., Paul (1975) *Cell and Tissue Culture,* 5th ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation.* in Cohen and Shafferman (eds.) *Novel Strategies in Design and Production of Vaccines*, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some case, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent multi plasmid systems (see, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 μg of each vector is introduced into a population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, e.g., of the invention) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza genome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) *Proc Natl Acad Sci* 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COST, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); *Methods in Enzymology* 153: 516-544.

Nucleic Acid Hybridization

Comparative hybridization can be used to identify nucleic acids of the invention, including conservative variations of nucleic acids of the invention. This comparative hybridization method is a preferred method of distinguishing nucleic acids of the invention. In addition, target nucleic acids which hybridize to the nucleic acids represented by, e.g., SEQ ID NO:1 through SEQ ID NO:34 under high, ultra-high and ultra-ultra-high stringency conditions are features of the invention. Examples of such nucleic acids include those with one or a few silent or conservative nucleic acid substitutions as compared to a given nucleic acid sequence.

A test target nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 5×–10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. Numerous protocols for nucleic acid hybridization are well known in the art. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, Sambrook, and Berger and Kimmel, all below. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions comprises a 0.2×SSC wash at 65° C. for 15 minutes (see, Sambrook, infra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

After hybridization, unhybridized nucleic acids can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the $T_m$) lower the background signal, typically with primarily the specific signal remaining. See, also, Rapley, R. and Walker, J. M. eds., *Molecular Biomethods Handbook* (Humana Press, Inc. 1998).

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the hybridization and wash conditions are gradually increased until a probe binds to a perfectly matched complementary target with a signal to noise ratio that is at least 5× as high as that observed for hybridization of the probe to an unmatched target.

In general, a signal to noise ratio of at least 2× (or higher, e.g., at least 5×, 10×, 20×, 50×, 100×, or more) than that observed for an unrelated probe in the particular hybridization assay indicates detection of a specific hybridization. Detection of at least stringent hybridization between two sequences in the context of the present invention indicates relatively strong structural similarity to, e.g., the nucleic acids of the present invention provided in the sequence listings herein.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any unmatched target nucleic acids. A target nucleic acid which hybridizes to a probe under such conditions, with a signal to noise ratio of at least one-half that of the perfectly matched complementary target nucleic acid is said to bind to the probe under ultra-high stringency conditions.

In determining stringent or highly stringent hybridization (or even more stringent hybridization) and wash conditions, the hybridization and wash conditions are gradually increased (e.g., by increasing temperature, decreasing salt concentration, increasing detergent concentration and/or increasing the concentration of organic solvents, such as formamide, in the hybridization or wash), until a selected set of criteria are met. For example, the hybridization and wash conditions are gradually increased until a probe comprising one or more polynucleotide sequences of the invention, e.g., sequences or unique subsequences selected from those given herein and/or complementary polynucleotide sequences, binds to a perfectly matched complementary target (again, a nucleic acid comprising one or more nucleic acid sequences or subsequences selected from those given herein and/or complementary polynucleotide sequences thereof), with a signal to noise ratio that is at least 2× (and optionally 5×, 10×, or 100× or more) as high as that observed for hybridization of the probe to an unmatched target (e.g., a polynucleotide sequence comprising one or more sequences or subsequences selected from known influenza sequences present in public databases such as GenBank at the time of filing, and/or complementary polynucleotide sequences thereof), as desired.

Using the polynucleotides of the invention, or subsequences thereof, novel target nucleic acids can be obtained; such target nucleic acids are also a feature of the invention. For example, such target nucleic acids include sequences that hybridize under stringent conditions to a unique oligonucleotide probe corresponding to any of the polynucleotides of the invention.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any unmatched target nucleic acids. The particular signal will depend on the label used in the relevant assay, e.g., a fluorescent label, a colorimetric label, a radioactive label, or the like. A target nucleic acid which hybridizes to a probe under such conditions, with a signal to noise ratio of at least one-half that of the perfectly matched complementary target nucleic acid, is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Cloning, Mutagenesis and Expression of Biomolecules of Interest

General texts which describe molecular biological techniques, which are applicable to the present invention, such as cloning, mutation, cell culture and the like, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., *Nature Biotechnology*, 19:456-460 (2001); Ling et al., *Approaches to DNA mutagenesis: an overview*, Anal Biochem 254(2): 157-178 (1997); Dale et al., *Oligonucleotide-directed random mutagenesis using the phosphorothioate method*, Methods Mol Biol 57:369-374 (1996); I. A. Lorimer, I. Pastan, *Nucleic Acids Res* 23, 3067-8 (1995); W. P. C. Stemmer, *Nature* 370, 389-91 (1994); Arnold, *Protein engineering for unusual environments*, Current Opinion in Biotechnology 4:450-455 (1993); Bass et al., *Mutant Trp repressors with new DNA-binding specificities*, Science 242:240-245 (1988); Fritz et al., *Oligonucleotide-directed construction of mutations: a gapped duplex DNA procedure without enzymatic reactions in vitro*, Nucl Acids Res 16: 6987-6999 (1988); Kramer et al., *Improved enzymatic in vitro reactions in the gapped duplex DNA approach to oligonucleotide-directed construction of mutations*, Nucl Acids Res 16: 7207 (1988); Sakamar and Khorana, *Total synthesis and expression of a gene for the a-subunit of bovine rod outer segment guanine nucleotide-binding protein (transducin)*, Nucl Acids Res 14: 6361-6372 (1988); Sayers et al., *Y-T Exonucleases in phosphorothioate-based oligonucleotide-directed mutagenesis*, Nucl Acids Res 16:791-802 (1988); Sayers et al., *Strand specific cleavage of phosphorothioate-containing DNA by reaction with restriction endonucleases in the presence of ethidium bromide*, (1988) Nucl Acids Res 16: 803-814; Carter, *Improved oligonucleotide-directed mutagenesis using M13 vectors*, Methods in Enzymol 154: 382-403 (1987); Kramer & Fritz *Oligonucleotide-directed construction of mutations via gapped duplex DNA, Methods in Enzymol* 154:350-367 (1987); Kunkel, *The efficiency of oligonucleotide directed mutagenesis, in Nucleic Acids & Molecular Biology* (Eckstein, F. and Lilley, D. M. J. eds., Springer Verlag, Berlin)) (1987); Kunkel et al., *Rapid and efficient site-specific mutagenesis without phenotypic selection, Methods in Enzymol* 154, 367-382 (1987); Zoller & Smith, *Oligonucleotide-directed mutagenesis: a simple method using two oligonucleotide primers and a single-stranded DNA template, Methods in Enzymol* 154:329-350 (1987); Carter, *Site-directed mutagenesis, Biochem J* 237:1-7 (1986); Eghtedarzadeh & Henikoff, *Use of oligonucleotides to generate large deletions, Nucl Acids Res* 14: 5115 (1986); Mandecki, *Oligonucleotide-directed double-strand break repair in plasmids of Escherichia coli: a method for site-specific mutagenesis, Proc Natl Acad Sci USA,* 83:7177-7181 (1986); Nakamaye & Eckstein, *Inhibition of restriction endonuclease Nci I cleavage by phosphorothioate groups and its application to oligonucleotide-directed mutagenesis, Nucl Acids Res* 14: 9679-9698 (1986); Wells et al., *Importance of hydrogen-bond formation in stabilizing the transition state of subtilisin, Phil Trans R Soc Lond* A 317: 415-423 (1986); Botstein & Shortle, *Strategies and applications of in vitro mutagenesis, Science* 229:1193-1201 (1985); Carter et al., Improved oligonucleotide site-directed mutagenesis using M13 vectors, Nucl Acids Res 13: 4431-4443 (1985); Grundström et al., Oligonucleotide-directed mutagenesis by microscale 'shot-gun' gene synthesis, Nucl Acids Res 13: 3305-3316 (1985); Kunkel, Rapid and efficient site-specific mutagenesis without phenotypic selection, Proc Natl Acad Sci USA 82:488-492 (1985); Smith, In vitro mutagenesis, Ann Rev Genet 19:423-462 (1985); Taylor et al., The use of phosphorothioate-modified DNA in restriction enzyme reactions to prepare nicked DNA, Nucl Acids Res 13: 8749-8764 (1985); Taylor et al., The rapid generation of oligonucleotide-directed mutations at high frequency using phosphorothioate-modified DNA, Nucl Acids Res 13: 8765-8787 (1985); Wells et al., Cassette mutagenesis: an efficient method for generation of multiple mutations at defined sites, Gene 34:315-323 (1985); Kramer et al., The gapped duplex DNA approach to oligonucleotide-directed mutation construction, Nucl Acids Res 12: 9441-9456 (1984); Kramer et al., Point Mismatch Repair, Cell 38:879-887 (1984); Nambiar et al., Total synthesis and cloning of a gene coding for the ribonuclease S protein, Science 223: 1299-1301 (1984); Zoller & Smith, Oligonucleotide-directed mutagenesis of DNA fragments cloned into M13 vectors, Methods in Enzymol 100:468-500 (1983); and Zoller & Smith, Oligonucleotide-directed mutagenesis using M13-derived vectors: an efficient and general procedure for the production of point mutations in any DNA fragment, Nucl Acids Res 10:6487-6500 (1982). Additional details on many of the above methods can be found in Methods in Enzymol Volume 154, which also describes useful controls for trouble-shooting problems with various mutagenesis, gene isolation, expression, and other methods.

Oligonucicotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, Tetrahedron Letts 22(20):1859-1862, (1981) e.g., using an automated synthesizer, as described in Needham-VanDevanter et al., Nucleic Acids Res, 12:6159-6168 (1984).

In addition, essentially any nucleic acid can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (available at pkim@ccnet.com), HTI Bio-products, Inc. (www.htibio.com), BMA Biomedicals Ltd. (U.K.), Bio. Synthesis, Inc., and many others.

The present invention also relates to host cells and organisms comprising a HA and/or NA molecule or other polypeptide and/or nucleic acid of the invention or such HA and/or NA or other sequences within various vectors such as 6:2 reassortant influenza viruses, plasmids in plasmid rescue systems, etc. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., Proc Natl Acad Sci USA 82, 5824 (1985), infection by viral vectors, high velocity ballistic penetration by small particles with the nucleic acid either within the matrix of small beads or particles, or on the surface (Klein et al., Nature 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, Gene 8:81 (1979); Roberts, et al., Nature, 328:731 (1987); Schneider, B., et al., Protein Expr Purif 6435:10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are also found in Watson et al. (1992) Recombinant DNA Second Edition Scientific American Books, NY. See, above.

Polypeptide Production and Recovery

In some embodiments, following transduction of a suitable host cell line or strain and growth of the host cells to an appropriate cell density, a selected promoter is induced by appropriate means (e.g., temperature shift or chemical induction) and cells are cultured for an additional period. In some embodiments, a secreted polypeptide product, e.g., a HA and/or NA polypeptide as in a secreted fusion protein form, etc., is then recovered from the culture medium. In other embodiments, a virus particle containing a HA and/or a NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus (e.g., by having HA and/or NA molecules, or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) *Bioseparation of Proteins*, Academic Press, Inc.; and Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. *Vaccine Production*, in Nicholson et al. (eds.) *Textbook of Influenza* pp. 324-332; Merten et al. (1996) *Production of influenza virus in cell cultures for vaccine preparation*, in Cohen & Shafferman (eds.) *Novel Strategies in Design and Production of Vaccines* pp. 141-151, and U.S. Pat. No. 5,690,937. If desired, the recovered viruses can be stored at −80° C. in the presence of sucrose-phosphate-glutamate (SPG) as a stabilizer Alternatively, cell-free transcription/translation systems can be employed to produce polypeptides comprising an amino acid sequence or subsequence of, e.g., SEQ ID NO:35 through SEQ ID NO:68, or encoded by the polynucleotide sequences of the invention. A number of suitable in vitro transcription and translation systems are commercially available. A general guide to in vitro transcription and translation protocols is found in Tymms (1995) *In vitro Transcription and Translation Protocols: Methods in Molecular Biology* Volume 37, Garland Publishing, NY.

In addition, the polypeptides, or subsequences thereof, e.g., subsequences comprising antigenic peptides, can be produced manually or by using an automated system, by direct peptide synthesis using solid-phase techniques (see, Stewart et al. (1969) *Solid-Phase Peptide Synthesis*, WH Freeman Co, San Francisco; Merrifield J (1963) *J Am Chem Soc* 85:2149-2154). Exemplary automated systems include the Applied Biosystems 431A Peptide Synthesizer (Perkin Elmer, Foster City, Calif.). If desired, subsequences can be chemically synthesized separately, and combined using chemical methods to provide full-length polypeptides.

Modified Amino Acids

Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc. Amino acid(s) are modified, for example, co-translationally or post-translationally during recombinant production (e.g., N-linked glycosylation at N-X-S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) *Protein Protocols on CD-ROM* Human Press, Towata, N.J.

Fusion Proteins

The present invention also provides fusion proteins comprising fusions of the sequences of the invention (e.g., encoding HA and/or NA polypeptides) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, e.g., similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of target polypeptides. For example, such antibodies can optionally be utilized to define other viruses within the same strain(s) as the HA/NA sequences herein.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) *Current Protocols in Immunology* Wiley/Greene, NY; Paul (ed.) (1998) *Fundamental Immunology, Fourth Edition*, Lippincott-Raven, Lippincott Williams & Wilkins; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) *Science* 246: 1275-1281; and Ward, et al. (1989) *Nature* 341: 544-546. Specific monoclonal and polyclonal antibodies and antisera will usually bind with a $K_D$ of, e.g., at least about 0.1 µM, at least about 0.01 µM or better, and, typically and at least about 0.001 µM or better.

For certain therapeutic applications, humanized antibodies are desirable. Detailed methods for preparation of chimeric (humanized) antibodies can be found in U.S. Pat. No. 5,482,856. Additional details on humanization and other antibody production and engineering techniques can be found in Borrebaeck (ed.) (1995) *Antibody Engineering, 2$^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul). Additional details regarding specific procedures can be found, e.g., in Ostberg et al. (1983), *Hybridoma* 2: 361-367, Ostberg, U.S. Pat. No. 4,634,664, and Engelman et al., U.S. Pat. No. 4,634,666.

Defining Polypeptides by Immunoreactivity

Because the polypeptides of the invention provide a variety of new polypeptide sequences (e.g., comprising HA and NA molecules), the polypeptides also provide new structural features which can be recognized, e.g., in immunological assays. The generation of antisera which specifically bind the polypeptides of the invention, as well as the polypeptides which are bound by such antisera, are features of the invention.

For example, the invention includes polypeptides (e.g., HA and NA molecules) that specifically bind to or that are specifically immunoreactive with an antibody or antisera generated against an immunogen comprising an amino acid sequence selected from one or more of the sequences given herein, etc. To eliminate cross-reactivity with other homologues, the antibody or antisera is subtracted with the HA and/or NA molecules found in public databases at the time of filing, e.g., the "control" polypeptide(s). Where the other control sequences correspond to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to the sequences herein, etc. or a substantial subsequence thereof (i.e., at least about 30% of the full length sequence provided). The set of potential polypeptide immunogens derived from the present sequences are collectively referred to below as "the immunogenic polypeptides." The resulting antisera is optionally selected to have low cross-reactivity against the control hemagglutinin and/or neuraminidase homologues and any such cross-reactivity is removed, e.g., by immunoabsorbtion, with one or more of the control hemagglutinin and neuraminidase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity). Additional references and discussion of antibodies is also found herein and can be applied here to defining polypeptides by immunoreactivity. Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control hemagglutinin and/or neuraminidase polypeptide(s) to produce subtracted pooled titered polyclonal antisera.

The subtracted pooled titered polyclonal antisera are tested for cross reactivity against the control homologue(s) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptides as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control receptor homologues under discriminatory binding conditions, and at least about a V2 signal to noise ratio as compared to the immunogenic polypeptide(s), shares substantial structural similarity with the immunogenic polypeptide as compared to the known receptor, etc., and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control protein(s) to compete for binding to the pooled subtracted antisera is optionally determined as compared to the ability of the immunogenic polypeptide(s) to compete for binding to the antisera. Again, the percent cross-reactivity for the control polypeptide(s) is calculated, using standard calculations. Where the percent cross-reactivity is at least 5-10× as high for the test polypeptides as compared to the control polypeptide(s) and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptide(s)) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein. However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variation" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Unique Polypeptide and Polynucleotide Subsequences

In one aspect, the invention provides a nucleic acid which comprises a unique subsequence in a nucleic acid selected from the sequence of HA and NA molecules disclosed herein (e.g., SEQ ID NO:1-34). The unique subsequence is unique as compared to a nucleic acids corresponding to nucleic acids such as, e.g., those found in GenBank or other similar public databases at the time of filing (e.g., other known or characterized hemagglutinin and/or neuraminidase nucleic acid molecules). Alignment can be performed using, e.g., BLAST set to default parameters. Any unique subsequence is useful, e.g., as a probe to identify the nucleic acids of the invention. See, above.

Similarly, the invention includes a polypeptide (e.g., from SEQ ID NO:35 through 68) which comprises a unique subsequence in a polypeptide selected from the sequence of HA and NA molecules disclosed herein. Here, the unique subsequence is unique as compared to a polypeptide corresponding to, e.g., the amino acid corresponding to polynucleotide sequences found in, e.g., GenBank or other similar public databases at the time of filing.

The invention also provides for target nucleic acids which hybridize under stringent conditions to a unique coding oligonucleotide which encodes a unique subsequence in a polypeptide selected from the sequences of HA and NA molecules of the invention wherein the unique subsequence is unique as compared to a polypeptide corresponding to any of the control polypeptides (sequences of, e.g., the nucleic acids corresponding to those found in, e.g., GenBank or other similar public databases at the time of filing). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, more preferably over a region of at least about 250 residues, and most preferably the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared when the amino acids are hemagglutinin or hemagglutinin fragments or which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; over at least about 470 amino acids; or over at least about 566 amino acids contiguous when the amino acid is neuraminidase.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol Biol* 48:443 (1970), by the search for similarity method of Pearson & Lipman, *Proc Natl Acad Sci USA* 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., *J Mol Biol* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc Natl Acad Sci USA* 89:10915).

In addition to calculating percent sequence identity, the BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) *Nucl. Acids. Res.* 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) *Proc. Natl. Acad. Sci. USA* 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof. Integrated systems can further include, e.g., gene synthesis equipment for making genes corresponding to the character strings.

Various methods known in the art can be used to detect homology or similarity between different character strings (see above), or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among four principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential gene expression, or other operations.

Kits and Reagents

The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit typically further comprises, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like. Furthermore, the kits can comprise various vaccines (e.g., produced through plasmid rescue protocols) such as live attenuated vaccine (e.g., FluMist™) comprising the HA and/or NA sequences herein.

To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A reassortant influenza A virus comprising six internal genome segments from one or more donor viruses and a surface antigen genome segment encoding a hemagglutinin (HA) polypeptide comprising the amino acid sequence of SEQ ID NO: 45, wherein the six internal genome segments and the HA encoding genome segment are from different influenza A viruses.

2. The reassortant influenza A virus of claim 1, further comprising a surface antigen genome segment encoding a neuraminidase (NA) polypeptide comprising the amino acid sequence of SEQ ID NO:46.

3. The reassortant influenza A virus of claim 1, wherein the surface antigen genome segment encoding the HA polypeptide comprises the polynucleotide of SEQ ID NO:11.

4. The reassortant influenza A virus of claim 2, wherein the surface antigen genome segment encoding the NA polypeptide comprises the polynucleotide of SEQ ID NO:12.

5. The reassortant influenza A virus of claim 1, wherein the one or more donor viruses have one or more phenotypes selected from the group consisting of temperature-sensitive, cold-adapted, and attenuated.

6. The reassortant influenza A virus of claim 5, wherein one or more donor viruses are selected from the group consisting of A/Ann Arbor/6/60 and A/Puerto Rico/8/34.

7. The reassortant influenza A virus of claim 1, wherein the virus is killed or inactivated.

8. An immunogenic composition comprising an immunologically effective amount of the reassortant influenza A virus of claim 1.

9. The immunogenic composition of claim 8, wherein the reassortant influenza A virus is a 6:2 reassortant virus.

10. The immunogenic composition of claim 9, wherein the one or more donor viruses have one or more phenotypes selected from the group consisting of temperature-sensitive, cold-adapted, and attenuated.

11. The immunogenic composition of claim 10, wherein the one or more donor viruses are selected from the group consisting of A/Ann Arbor/6/60 and A/Puerto Rico/8/34.

12. A live attenuated influenza A H3 vaccine comprising the immunogenic composition of claim 8.

13. A method of inducing an immune response against an influenza A viral infection in a subject, the method comprising: administering to the subject the reassortant influenza A virus of claim 1 in an amount effective to produce an immune response against the viral infection.

14. A reassortant influenza A virus produced according to a method comprising:
  i) introducing a plurality of vectors into a population of host cells capable of supporting replication of influenza viruses, which plurality of vectors comprises nucleotide sequences corresponding to at least 6 internal genome segments of one or more donor viruses; and at least one surface antigen genome segment encoding an HA polypeptide comprising the amino acid sequence of SEQ ID NO:45, wherein the six internal genome segments and the HA encoding genome segment are from different influenza A viruses;
  ii) culturing the population of host cells; and
  iii) recovering reassortant influenza A virus, wherein the reassortant influenza virus recovered is suitable for administration in an intranasal vaccine formulation.

15. The method of claim 14, wherein the plurality of vectors further comprises a surface antigen genome segment encoding a NA polypeptide comprising the amino acid sequence of SEQ ID NO:46.

16. The method of claim 14, wherein the surface antigen genome segment encoding the HA polypeptide comprises the polynucleotide of SEQ ID NO:11.

17. The method of claim 15, wherein the surface antigen genome segment encoding the NA polypeptide comprises the polynucleotide of SEQ ID NO:12.

18. The method of claim 14, wherein the one or more donor viruses have one or more phenotypes chosen from temperature-sensitive, cold-adapted, and attenuated.

19. The method of claim 14, wherein the plurality of vectors consists of eight vectors.

* * * * *